(12) United States Patent
Stengel et al.

(10) Patent No.: US 12,077,541 B2
(45) Date of Patent: Sep. 3, 2024

(54) COMPOUNDS FOR ELECTRONIC DEVICES

(71) Applicant: Merck Patent GmbH, Darmstadt (DE)

(72) Inventors: Ilona Stengel, Darmstadt (DE); Florian Maier-Flaig, Weinheim (DE); Philipp Harbach, Muehltal (DE); Elvira Montenegro, Weinheim (DE); Aurélie Ludemann, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 853 days.

(21) Appl. No.: 16/979,259

(22) PCT Filed: Mar. 6, 2019

(86) PCT No.: PCT/EP2019/055541
§ 371 (c)(1),
(2) Date: Sep. 9, 2020

(87) PCT Pub. No.: WO2019/170729
PCT Pub. Date: Sep. 12, 2019

(65) Prior Publication Data
US 2020/0399251 A1  Dec. 24, 2020

(30) Foreign Application Priority Data
Mar. 9, 2018 (EP) .................... 18161099

(51) Int. Cl.
C07D 487/04 (2006.01)
H10K 85/60 (2023.01)
H10K 50/15 (2023.01)

(52) U.S. Cl.
CPC ......... *C07D 487/04* (2013.01); *H10K 85/631* (2023.02); *H10K 85/6572* (2023.02); *H10K 85/6574* (2023.02); *H10K 50/15* (2023.02)

(58) Field of Classification Search
None
See application file for complete search history.

(56) References Cited

U.S. PATENT DOCUMENTS

| | | |
|---|---|---|
| 9,502,664 B2 | 11/2016 | Schaefer et al. |
| 10,135,003 B2 | 11/2018 | Stoessel et al. |
| 2012/0241681 A1 | 9/2012 | Schaefer et al. |

FOREIGN PATENT DOCUMENTS

| | | |
|---|---|---|
| CN | 106467548 A | 3/2017 |
| CN | 106467549 A | 3/2017 |

(Continued)

OTHER PUBLICATIONS

Machine translation of CN-106565720, translation generated Apr. 2023, 10 pages. (Year: 2023).*

Machine translation of CN-106467548, translation generated Apr. 2023, 10 pages. (Year: 2023).*

International Search Report for PCT/EP2019/055472 mailed Apr. 24, 2019.

(Continued)

*Primary Examiner* — Robert S Loewe
(74) *Attorney, Agent, or Firm* — Faegre Drinker Biddle & Reath LLP

(57) ABSTRACT

The present application relates to an amine compound according to formula (I), (II) or (III) which is suitable for use in electronic devices.

formula (I)

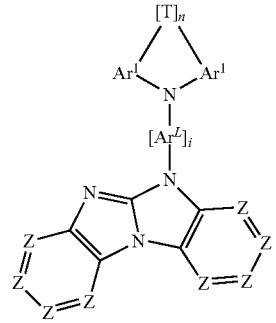

formula (II)

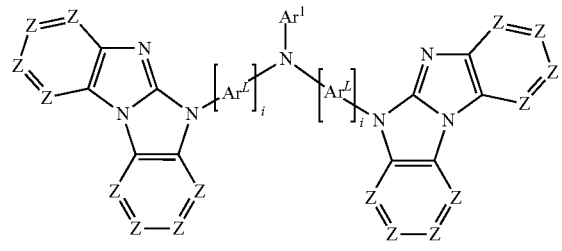

formula (III)

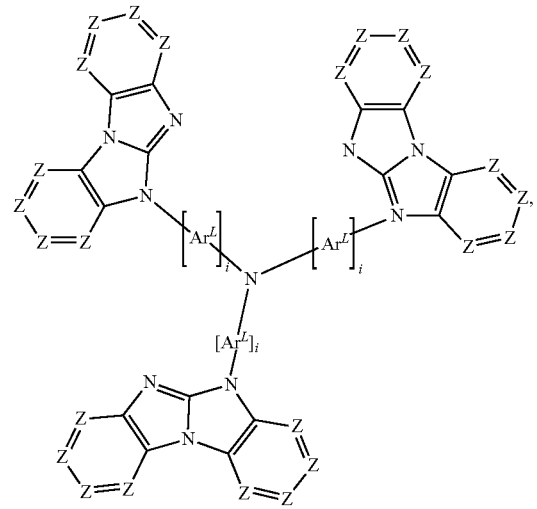

20 Claims, No Drawings

(56) References Cited

FOREIGN PATENT DOCUMENTS

| | | |
|---|---|---|
| CN | 106467552 A | 3/2017 |
| CN | 106565720 A | 4/2017 |
| CN | 106749339 A | 5/2017 |
| WO | WO-11160757 A1 | 12/2011 |
| WO | WO-2013068376 A1 | 5/2013 |
| WO | WO-2014009317 A1 | 1/2014 |
| WO | WO-2016016791 A1 | 2/2016 |
| WO | WO-2016046034 A1 | 3/2016 |
| WO | WO-2016097983 A1 | 6/2016 |
| WO | WO-2019170691 A1 | 9/2019 |

OTHER PUBLICATIONS

International Search Report for PCT/EP2019/055541 mailed Jun. 24, 2019.
Written Opinion of the International Searching Authority for PCT/EP2019/055472 mailed Apr. 24, 2019.
Written Opinion of the International Searching Authority for PCT/EP2019/055541 mailed Jun. 24, 2019.

* cited by examiner

COMPOUNDS FOR ELECTRONIC DEVICES

CROSS-REFERENCE TO RELATED APPLICATIONS

This application is a national stage application (under 35 U.S.C. § 371) of PCT/EP2019/055541, filed Mar. 6, 2019, which claims benefit of European Application No. 18161099.9, filed Mar. 9, 2018, both of which are incorporated herein by reference in their entirety.

The present application relates to an organic compound of a formula defined hereinafter which is suitable for use in electronic devices, especially organic electroluminescent devices (OLEDs).

Electronic devices in the context of this application are understood to mean what are called organic electronic devices, which contain organic semiconductor materials as functional materials. More particularly, these are understood to mean OLEDs.

The construction of OLEDs in which organic compounds are used as functional materials is common knowledge in the prior art. In general, the term OLEDs is understood to mean electronic devices which have one or more layers comprising organic compounds and emit light on application of electrical voltage.

In electronic devices, especially OLEDs, there is great interest in improving the performance data, especially lifetime, efficiency and operating voltage. In these aspects, it has not yet been possible to find any entirely satisfactory solution. Furthermore, for use in electronic devices, there is interest in finding functional materials which have excellent material properties, in particular a high refractive index, because this is required for certain applications of the material in an OLED. Further material properties of high interest are a wide band gap, high HOMO energy level (low ionization potential), high glass transition temperature, high thermal stability, and high charge mobility.

A great influence on the performance data of electronic devices is possessed by layers having a hole-transporting function, for example hole-injecting layers, hole transport layers, electron blocking layers and also emitting layers. For use in these layers, there is a continuous search for new materials having hole-transporting properties.

In the context of studies of novel materials for use in OLEDs, it is found that compounds having the structural element of imidazoimidazole, combined with the structural element of arylamine, are excellent functional materials for electronic devices. They are particularly useful as materials with a hole transporting function, for example for use in hole transporting layers, electron blocking layers and emitting layers.

When used in electronic devices, in particular in OLEDs, they lead to excellent results in terms of lifetime, operating voltage and quantum efficiency of the devices. The compounds also have one or more properties selected from high refractive index, wide band gap, very good hole-conducting properties, very good electron-blocking properties, high glass transition temperature, high oxidation stability, good solubility, high thermal stability, and low sublimation temperature.

The present application thus provides a compound of a formula (I), (II) or (III)

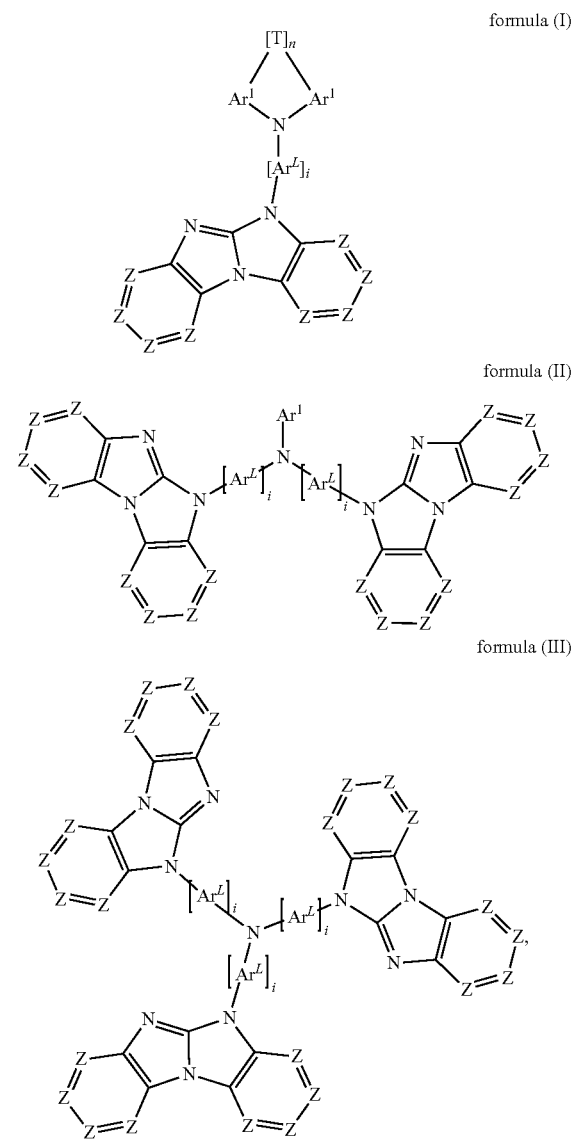

formula (I)

formula (II)

formula (III)

where the following applies to the variables occurring:

Z is on each occurrence, identically or differently, $CR^1$ or N;

$Ar^L$ is on each occurrence, identically or differently, selected from aromatic ring systems having 6 to 40 aromatic ring atoms, which may be substituted by one or more radicals $R^2$, and heteroaromatic ring systems having 5 to 40 aromatic ring atoms, which may be substituted by one or more radicals $R^2$; where the case is excluded that $Ar^L$ comprises at least one heteroaromatic ring having at least one N atom comprised in it, and $Ar^L$ is bonded via at least one of these N atoms to the rest of the structure of formula (I), (II) or (III);

$Ar^1$ is on each occurrence, identically or differently, selected from aromatic ring systems having 6 to 40 aromatic ring atoms, which may be substituted by one or more radicals $R^3$, and heteroaromatic ring systems having 5 to 40 aromatic ring atoms, which may be substituted by one or more radicals $R^3$;

T is a single bond or a divalent group selected from $C(R^3)_2$, C=O, $NR^3$, O, S, S=O and $S(=O)_2$;

$R^1$, $R^2$, $R^3$ is selected, identically or differently at each occurrence, from H, D, F, C(=O)$R^4$, CN, Si($R^4$)$_3$, N($R^4$)$_2$, P(=O)($R^4$)$_2$, O$R^4$, S(=O)$R^4$, S(=O)$_2$$R^4$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^1$, $R^2$ and/or $R^3$ may be connected to each other to form a ring; where the said alkyl, alkoxy, alkenyl and alkynyl groups and the said aromatic and heteroaromatic ring systems may in each case be substituted by one or more radicals $R^4$, and where one or more CH$_2$ groups in the said alkyl, alkoxy, alkenyl and alkynyl groups may in each case be replaced by —$R^4$C=C$R^4$—, —C≡C—, Si($R^4$)$_2$, C=O, C=N$R^4$, —C(=O)O—, —C(=O)N$R^4$—, N$R^4$, P(=O)($R^4$), —O—, —S—, SO or SO$_2$;

with the proviso that in formula (I), a maximum of one group $R^3$ is N($R^4$)$_2$;

$R^4$ is selected, identically or differently at each occurrence, from H, D, F, C(=O)$R^5$, CN, Si($R^5$)$_3$, N($R^5$)$_2$, P(=O)($R^5$)$_2$, O$R^5$, S(=O)$R^5$, S(=O)$_2$$R^5$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^4$ may be connected to each other to form a ring; where the said alkyl, alkoxy, alkenyl and alkynyl groups and the said aromatic and heteroaromatic ring systems may in each case be substituted by one or more radicals $R^5$, and where one or more CH$_2$ groups in the said alkyl, alkoxy, alkenyl and alkynyl groups may in each case be replaced by —$R^5$C=C$R^5$—, —C≡C—, Si($R^5$)$_2$, C=O, C=N$R^5$, —C(=O)O—, —C(=O)N$R^5$—, N$R^5$, P(=O)($R^5$), —O—, —S—, SO or SO$_2$;

$R^5$ is selected, identically or differently at each occurrence, from H, D, F, CN, alkyl groups having 1 to 20 C atoms, aromatic ring systems having 6 to 40 C atoms, or heteroaromatic ring systems having 5 to 40 aromatic ring atoms; where two or more radicals $R^5$ may be connected to each other to form a ring; and where the said alkyl groups, aromatic ring systems and heteroaromatic ring systems may be substituted by one or more radicals selected from F and CN;

i is, identically or differently on each occurrence, 1, 2, 3, 4 or 5;

n is 0 or 1.

The compounds with the definition of $Ar^L$ as given above are well suitable for use in a hole transporting layer or an electron blocking layer. When used in such layers, they contribute to excellent OLED device data. In particular, they are better suitable than otherwise identical compounds which have a heteroaryl group as group $Ar^L$, which is bonded via its N atom to the rest of the formula.

The case of i=2, 3, 4 or 5 means that 2, 3, 4, or 5 groups $Ar^L$ are present in a chain, having the structure —$Ar^L$—$Ar^L$— for the case of i=2, having the structure —$Ar^L$—$Ar^L$—$Ar^L$— for the case of i=3, having the structure —$Ar^L$—$Ar^L$—$Ar^L$—$Ar^L$— for the case of i=4, and having the structure —$Ar^L$—$Ar^L$—$Ar^L$—$Ar^L$—$Ar^L$— for the case of i=5.

The case of n=0 means that the group T is not present, and any bonds which extend from it do not exist.

The following definitions apply to the chemical groups used as general definitions. They apply insofar as no more specific definitions are given.

An aryl group here is taken to mean either a single aromatic ring, for example benzene, or a condensed aromatic polycycle, for example naphthalene, phenanthrene, or anthracene. A condensed aromatic polycycle in the sense of the present application consists of two or more single aromatic rings which are condensed with one another. An aryl group in the sense of this invention contains 6 to 40 aromatic ring atoms, of which none is a heteroatom.

A heteroaryl group here is taken to mean either a single heteroaromatic ring, such as pyridine, pyrimidine or thiophene, or a condensed heteroaromatic polycycle, such as quinoline or carbazole. A condensed heteroaromatic polycycle in the sense of the present application consists of two or more single aromatic or heteroaromatic rings, which are condensed with one another, where at least one of the two or more single aromatic or heteroaromatic rings is a heteroaromatic ring. A heteroaryl group in the sense of this invention contains 5 to 40 aromatic ring atoms, at least one of which is a heteroatom. The heteroatoms are preferably selected from N, O and S.

An aryl or heteroaryl group, which may in each case be substituted by the above-mentioned radicals, is taken to mean, in particular, a group derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, pheno-thiazine, phenoxazine, pyrazole, indazole, imidazole, benzimidazole, benzimidazolo[1,2-a]benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention is a system which does not necessarily contain only aryl groups, but which may additionally contain one or more non-aromatic rings, which are condensed with at least one aryl group. Such non-aromatic rings contain exclusively carbon atoms as ring atoms. Examples of groups embraced by such definition are tetrahydronaphthalene, fluorene, and spirobifluorene. Furthermore, the term aromatic ring system is understood to embrace systems consisting of two or more aromatic ring systems which are connected to each other via single bonds, such as biphenyl, terphenyl, 7-phenyl-2-fluorenyl and quaterphenyl. An aromatic ring system in the sense of this invention contains 6 to 40 C atoms and no heteroatoms as ring atoms of the ring system. An aromatic ring system in the sense of this application does not comprise any heteroaryl groups, as defined above.

A heteroaromatic ring system is defined in analogy to the aromatic ring system above, but with the difference that it must obtain at least one heteroatom as one of the ring atoms. As it is the case for the aromatic ring system, it does not necessarily contain only aryl and heteroaryl groups, but it may additionally contain one or more non-aromatic rings, which are condensed with at least one aryl or heteroaryl group. The non-aromatic rings may contain only carbon atoms as ring atoms, or they may contain additionally one or more heteroatoms, where the heteroatoms are preferably selected from N, O and S. An example for such a heteroaromatic ring system is benzpyranyl. Furthermore, the term heteroaromatic ring system is understood to embrace systems consisting of two or more aromatic or heteroaromatic ring systems, which are connected to each other via single bonds, such as 4,6-diphenyl-2-triazinyl. A heteroaromatic ring system in the sense of this invention contains 5 to 40 ring atoms, which are selected from carbon and heteroatoms, where at least one of the ring atoms is a heteroatom. The heteroatoms are preferably selected from N, O or S.

The terms "heteroaromatic ring system" and "aromatic ring system" according to the definition of the present application differ from each other by the fact that the aromatic ring system cannot comprise any heteroatom as ring atom, whereas the heteroaromatic ring system must comprise at least one heteroatom as ring atom. Such heteroatom may be present as a ring atom of a non-aromatic heterocyclic ring of the system, or as a ring atom of an aromatic heterocyclic ring of the system.

According to the above, any aryl group, as defined above, is embraced by the term "aromatic ring system", as defined above, and any heteroaryl group, as defined above, is embraced by the term "heteroaromatic ring system", as defined above.

An aromatic ring system having 6 to 40 aromatic ring atoms or a heteroaromatic ring system having 5 to 40 aromatic ring atoms is in particular a group which is derived from the above mentioned aryl or heteroaryl groups, or from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, and indenocarbazole, or from any combinations of these groups.

For the purposes of the present invention, a straight-chain alkyl group having 1 to 20 C atoms or a branched or cyclic alkyl group having 3 to 20 C atoms or an alkenyl or alkynyl group having 2 to 20 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, hep-tenyl, cycloheptenyl, octenyl, cyclooctenyl, ethynyl, propynyl, butynyl, pen-tynyl, hexynyl or octynyl.

An alkoxy or thioalkyl group having 1 to 20 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyl-oxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoro-methylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenyl-thio, ethynylthio, propynylthio, butynylthio, pentynylthio, hexynylthio, heptynylthio or octynylthio.

The phrase "two or more radicals may be connected to each other to form a ring" shall be understood to include the case that the two radicals are connected by a chemical bond. Additionally, the phrase shall be understood to include the case that one of the two radicals is H, this radical H is removed, and the other of the two radicals forms a ring by being connected to the position, to which this radical H was initially bonded.

Among the formulae (I) to (III), formula (I) is preferred.

Preferably, the compound of formula (I), (II) or (III) does not comprise more than one triarylamino group. An triarylamino group is understood to be a group which comprises a nitrogen atom having three aromatic groups bonded to it, where aromatic group is meant to embrace both aromatic ring systems and heteroaromatic ring systems. Particularly preferably, none of the groups $R^1$ to $R^5$ in formula (I) or (II) or (III) comprises an arylamino group.

Preferably, the groups $Ar^1$ in formula (I) do not have any groups $N(R^4)_2$ as substituents $R^3$, preferably no groups $N(R^4)_2$ as substituents $R^3$ and no groups $N(R^5)_2$ as substituents $R^4$.

Preferably, the compound of formula (I) is asymmetric. The term "asymmetric" in the context of the structure of formula (I) means that the compound does not have any symmetry, in particular no 03 symmetry.

Preferably, a maximum of three groups Z per cycle is N, more preferably a maximum of two groups Z per cycle, more preferably a maximum of one group Z per cycle. Z is preferably $CR^1$.

According to one preferred embodiment, two groups $R^1$ which each are part of groups Z, where the groups Z are adjacent to each other in the ring, are connected to each other to form an aromatic or heteroaromatic ring which is condensed to the ring to which the two groups $R^1$ are bonded. Preferably, the formed ring is an aromatic ring, more preferably a benzene ring or a pyridine ring, most preferably a benzene ring.

$Ar^L$ is, identically or differently, selected from aromatic ring systems having 6 to 40 aromatic ring atoms, which may be substituted by one or more radicals $R^2$. Furthermore, preferably, $Ar^L$ is selected, identically or differently, from benzene, biphenyl, terphenyl, naphthalene, fluorene, indenofluorene, spirobifluorene, triazine, benzoquinoline, benzoquinazoline, dibenzofuran, dibenzothiophene, and carbazole, where each of the above-mentioned groups may be substituted by one or more radicals $R^1$, and where the case is excluded that $Ar^L$ is carbazole which is bonded via its N atom to the rest of formula (I). Particularly preferably, $Ar^L$ is selected from benzene, biphenyl and fluorene, most preferably from benzene, where the groups may be substituted by one or more radicals $R^1$. The compounds with the definition of $Ar^L$ as given above are particularly well suitable for use in a hole transporting layer or an electron blocking layer. When used in such layers, they contribute to excellent OLED device data.

Index i is, preferably, identically or differently on each occurrence 1, 2 or 3, particularly preferably 1.

Preferred groups $(Ar^L)_i$ are listed in the following table, where the dotted lines are the bonds to the rest of the compound:

Ar^L-1
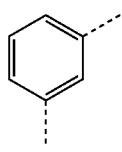
Ar^L-2
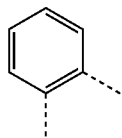
Ar^L-3
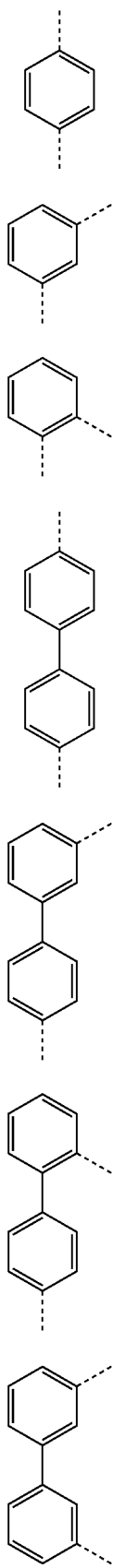
Ar^L-4
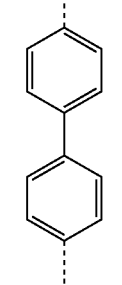
Ar^L-5
Ar^L-6

Ar^L-7

Ar^L-8
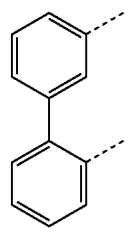
Ar^L-9
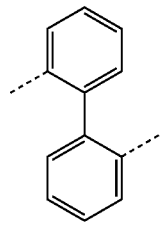
Ar^L-10
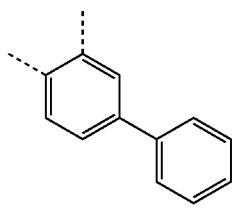
Ar^L-11
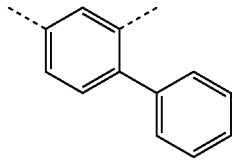
Ar^L-12
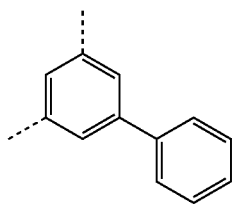
Ar^L-13
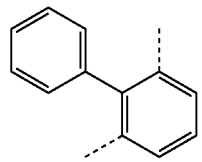
Ar^L-14
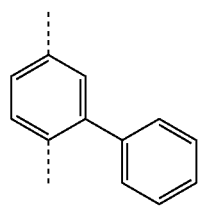
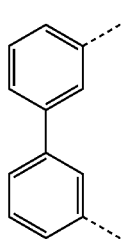

Ar^L-15 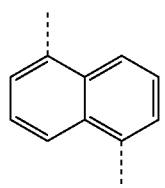
Ar^L-16 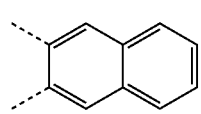
Ar^L-17 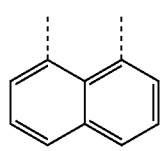
Ar^L-18
Ar^L-19 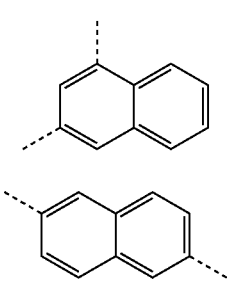
Ar^L-20 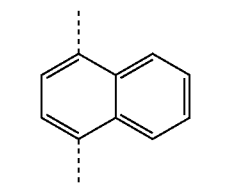
Ar^L-21 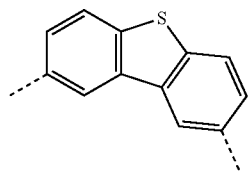
Ar^L-22 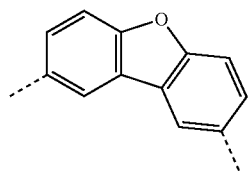
Ar^L-23 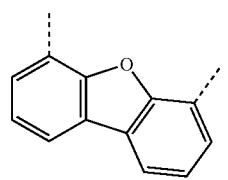
Ar^L-24 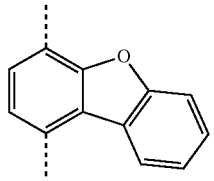
Ar^L-25 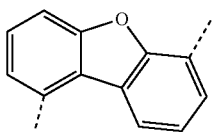
Ar^L-26 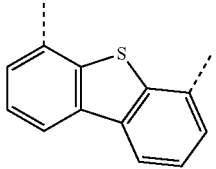
Ar^L-27
Ar^L-28
Ar^L-29
Ar^L-30
Ar^L-31
Ar^L-32

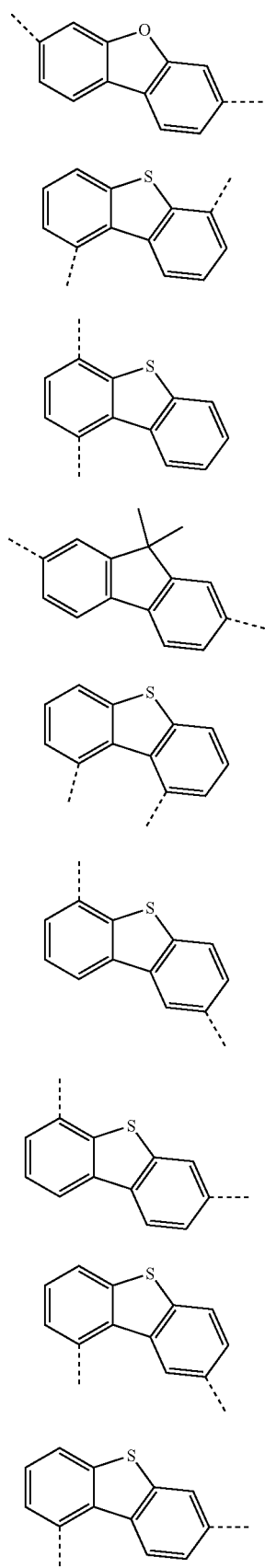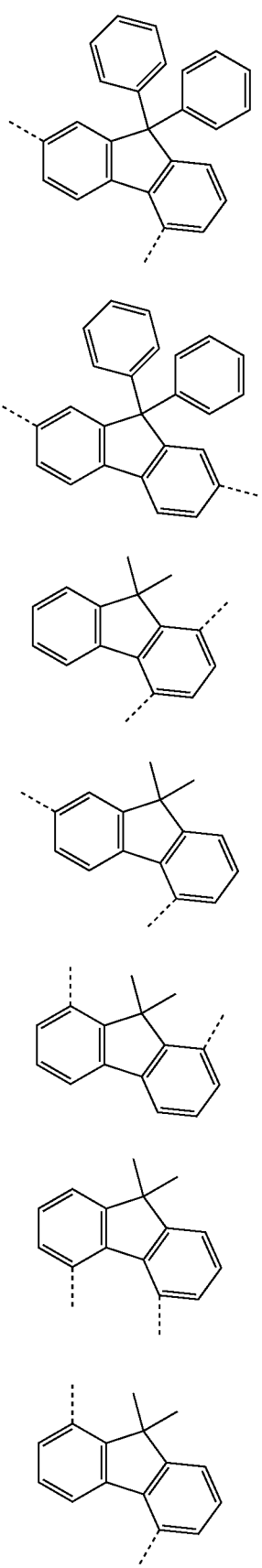

-continued
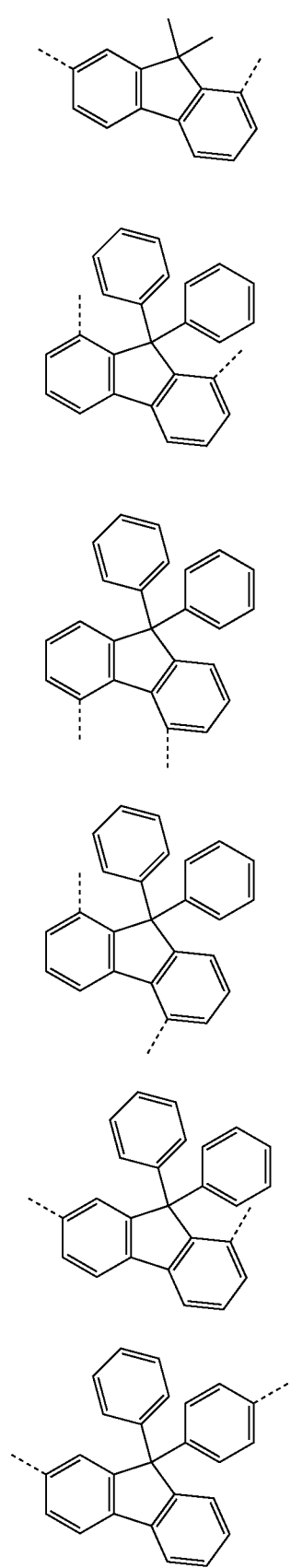
Ar^L-49
Ar^L-50
Ar^L-51
Ar^L-52
Ar^L-53
Ar^L-54
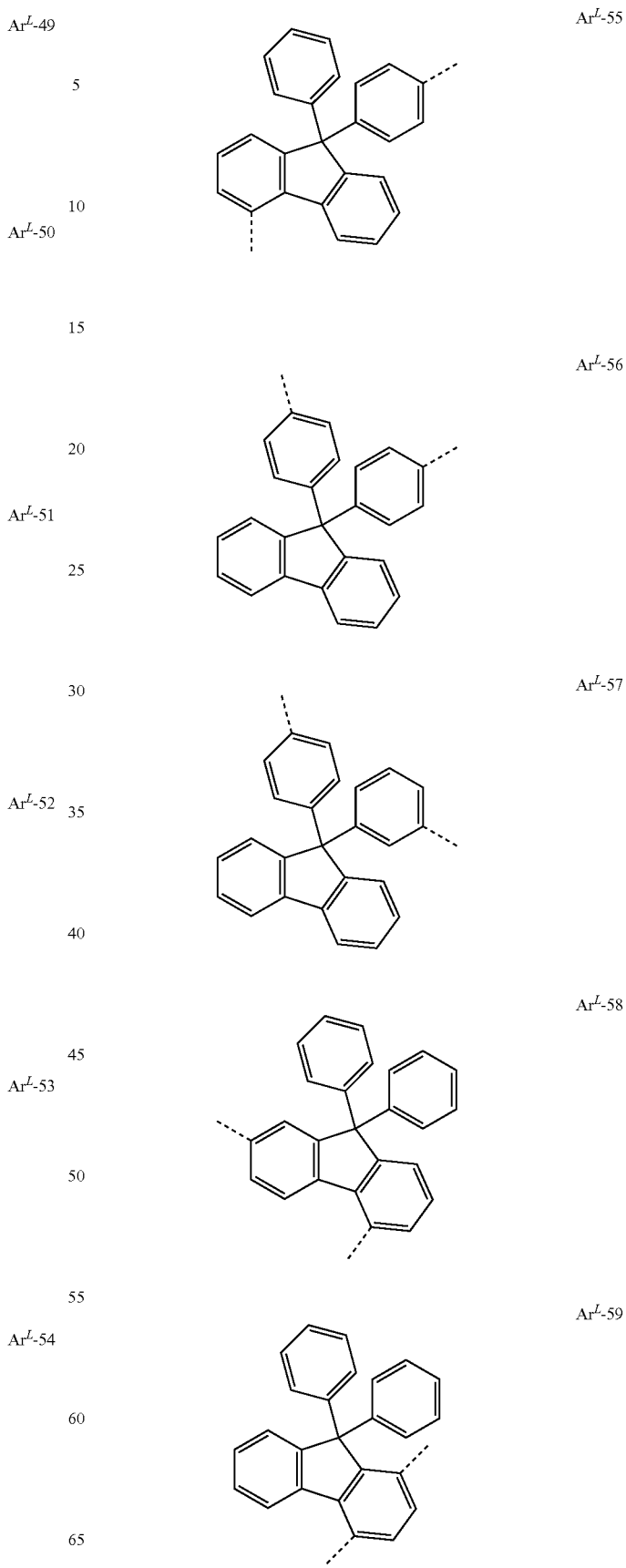
Ar^L-55
Ar^L-56
Ar^L-57
Ar^L-58
Ar^L-59

Ar^L-60
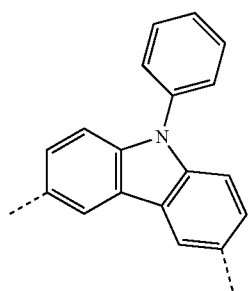
Ar^L-61
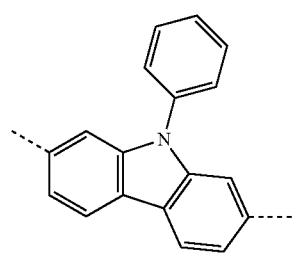
Ar^L-62
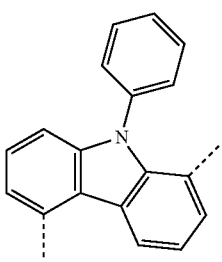
Ar^L-63
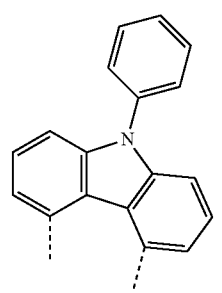
Ar^L-64
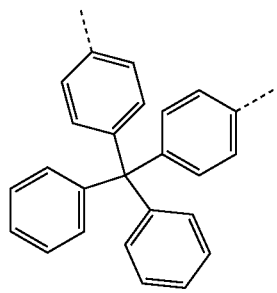
Ar^L-65
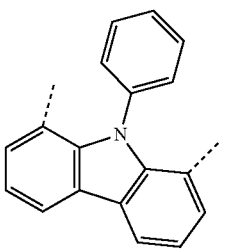
Ar^L-66
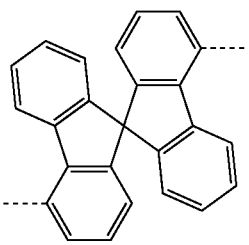
Ar^L-67
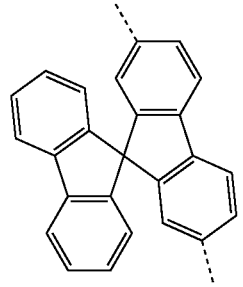
Ar^L-68
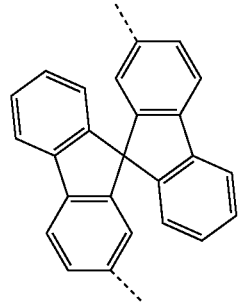
Ar^L-69
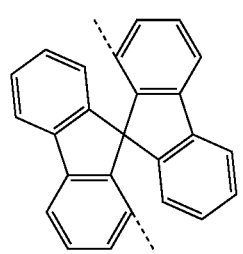
Ar^L-70
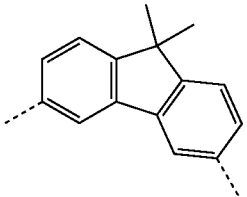

-continued

Ar$^L$-71

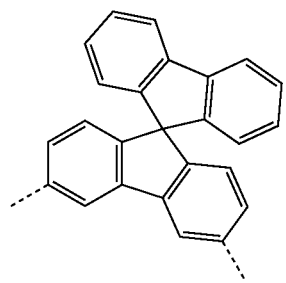

Ar$^L$-72

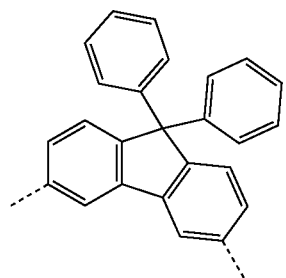

Groups Ar$^1$ are preferably, identically or differently, selected from radicals derived from the following groups, which are each optionally substituted by one or more radicals R$^3$, or from combinations of 2 or 3 radicals derived from the following groups, which are each optionally substituted by one or more radicals R$^3$: phenyl, biphenyl, terphenyl, quaterphenyl, naphthyl, fluorenyl, especially 9,9'-dimethylfluorenyl and 9,9'-diphenylfluorenyl, benzofluorenyl, spirobifluorenyl, indenofluorenyl, dibenzofuranyl, dibenzothiophenyl, carbazolyl, benzofuranyl, benzothiophenyl, indolyl, quinolinyl, pyridyl, pyrimidyl, pyrazinyl, pyridazinyl, triazinyl and benzimidazobenzimidazole. Particularly preferred groups Ar$^1$ are, identically or differently, selected from phenyl, biphenyl, terphenyl, quaterphenyl, naphthyl, fluorenyl, especially 9,9'-dimethylfluorenyl and 9,9'-diphenylfluorenyl, benzofluorenyl, spirobifluorenyl, indenofluorenyl, dibenzofuranyl, dibenzothiophenyl, carbazolyl, benzofuranyl, benzothiophenyl, benzofused dibenzofuranyl, benzofused dibenzothiophenyl, naphthyl-substituted phenyl, fluorenyl-substituted phenyl, spirobifluorenyl-substituted phenyl, dibenzofuranyl-substituted phenyl, dibenzothiophenyl-substituted phenyl, carbazolyl-substituted phenyl, pyridyl-substituted phenyl, pyrimidyl-substituted phenyl, triazinyl-substituted phenyl, benzimidazole and benzimidazoimidazole, each of which may optionally be substituted by one or more radicals R$^3$.

Preferred groups Ar$^1$ are, identically or differently, selected from groups of the following formulae Ar-1

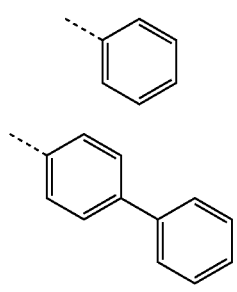

Ar-2

Ar-3

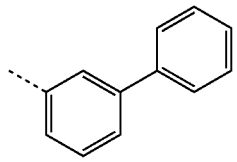

Ar-4

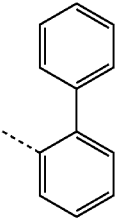

Ar-5

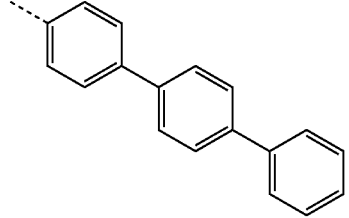

Ar-6

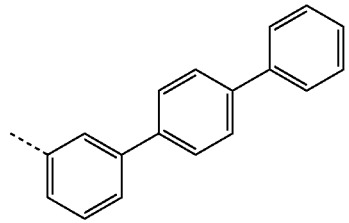

Ar-7

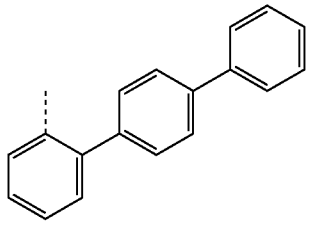

Ar-8

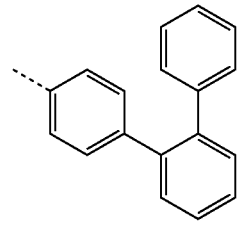

Ar-9

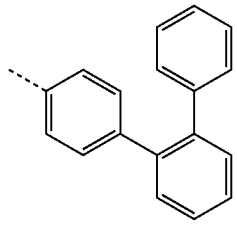

Ar-10
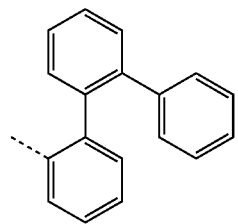
Ar-11
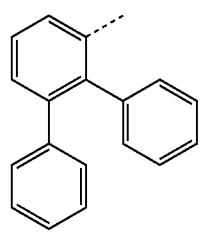
Ar-12
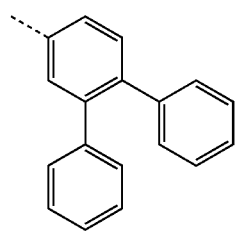
Ar-13
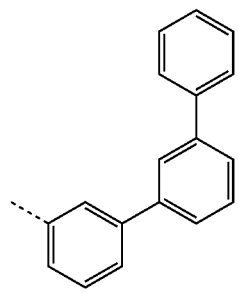
Ar-14
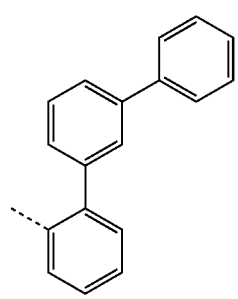
Ar-15
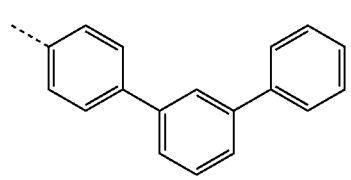
Ar-16
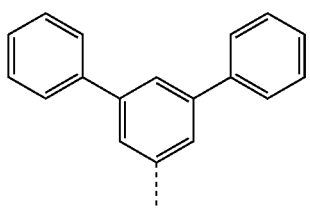
Ar-17
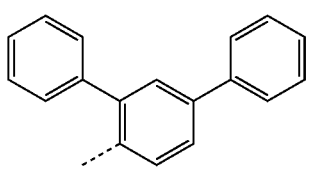
Ar-18
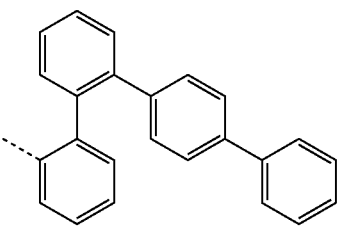
Ar-19
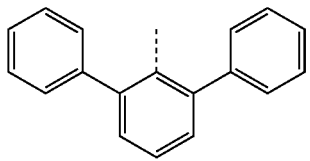
Ar-20
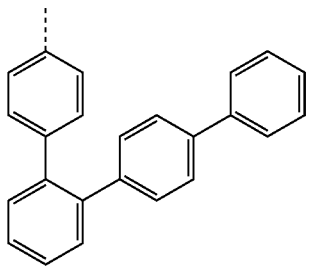
Ar-21
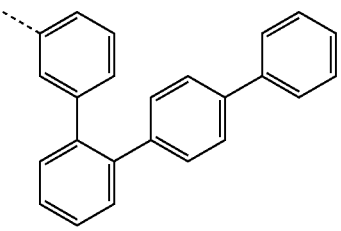
Ar-22
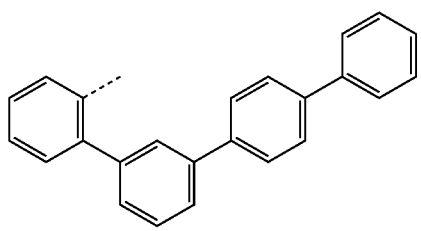

Ar-23
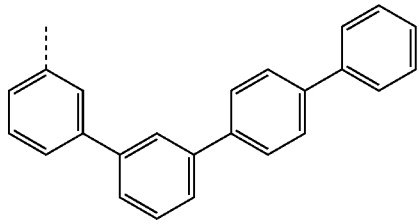
Ar-24
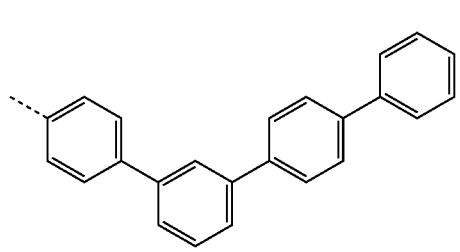
Ar-25
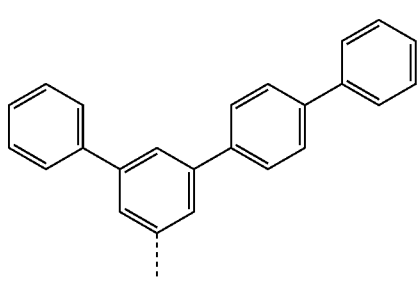
Ar-26
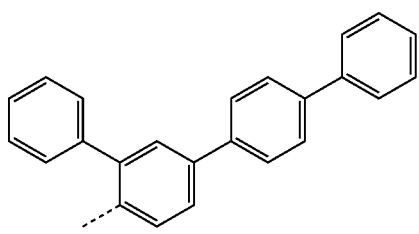
Ar-27
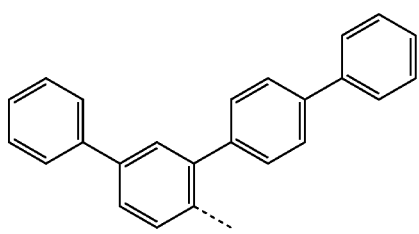
Ar-28
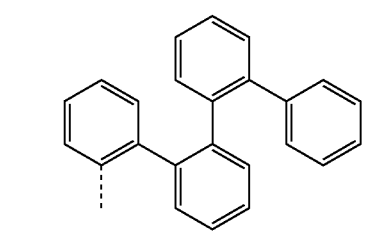
Ar-29
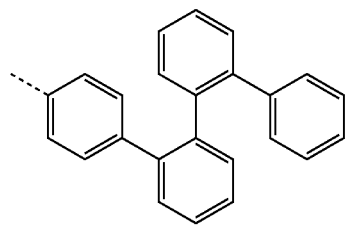
Ar-30
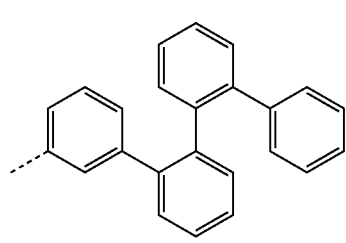
Ar-31
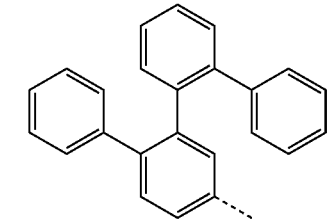
Ar-32
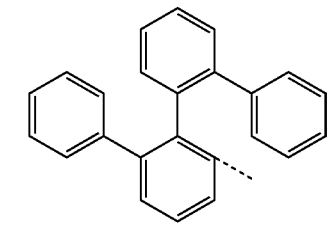
Ar-33
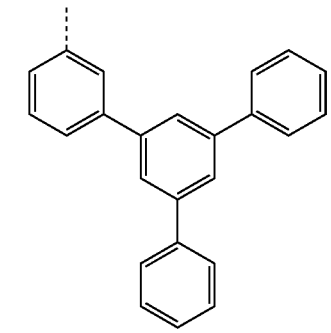
Ar-34
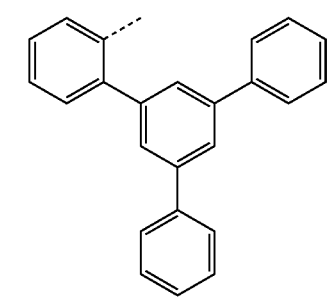

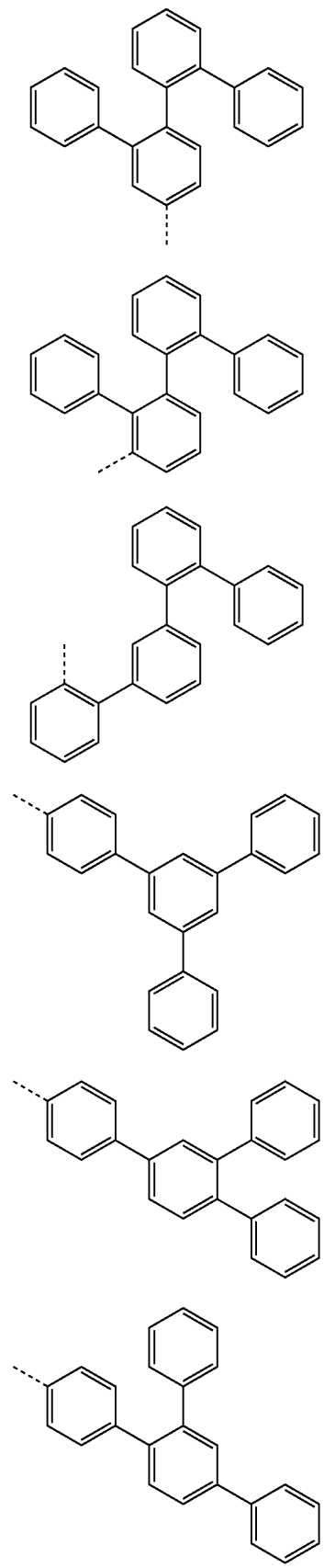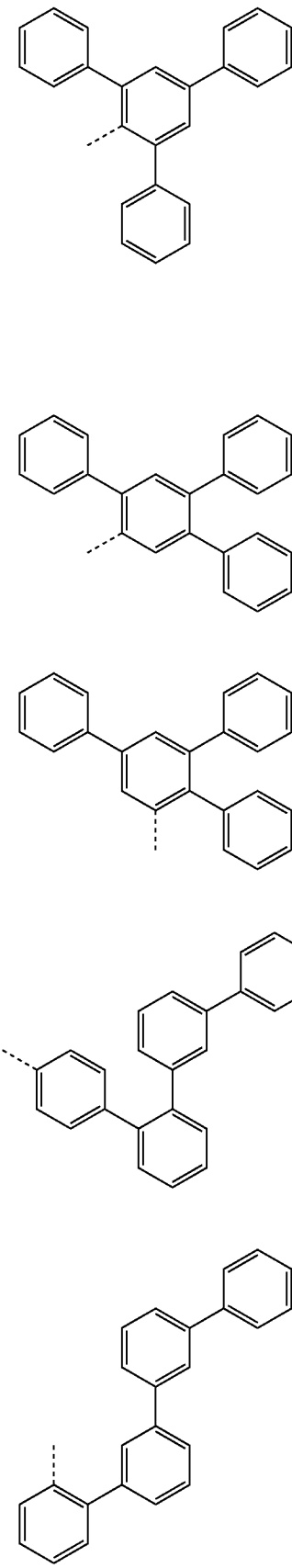

Ar-46
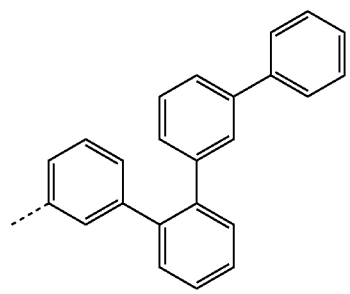
Ar-47
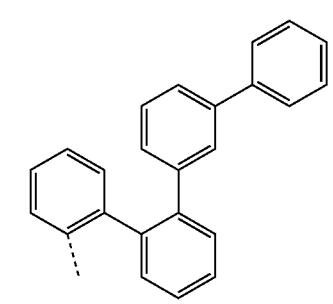
Ar-48
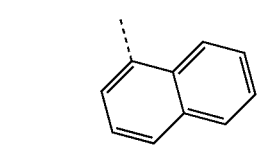
Ar-49
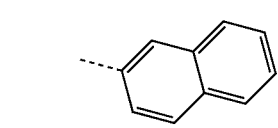
Ar-50
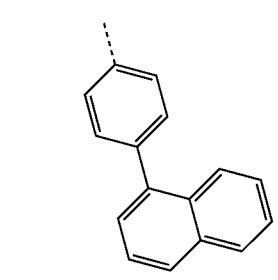
Ar-51
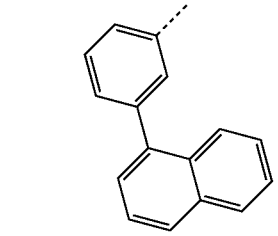
Ar-52
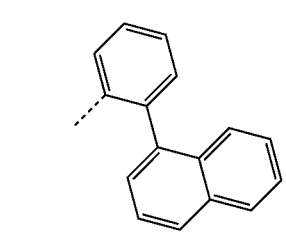
Ar-53
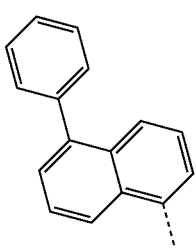
Ar-54
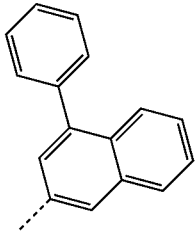
Ar-55
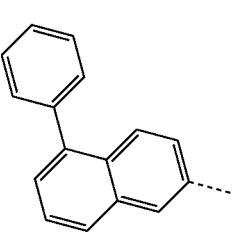
Ar-56
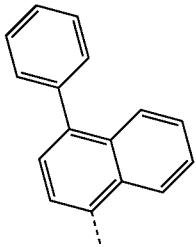
Ar-57
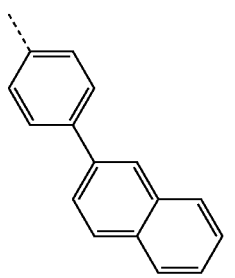
Ar-58
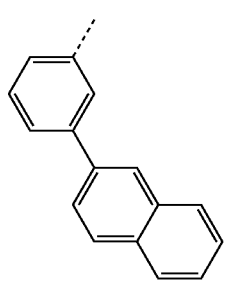

Ar-59
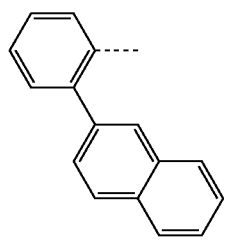
Ar-60
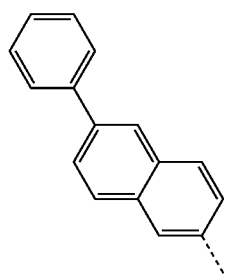
Ar-61
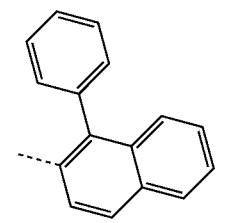
Ar-62
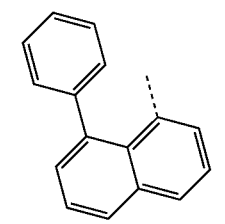
Ar-63
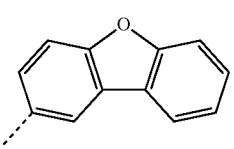
Ar-64
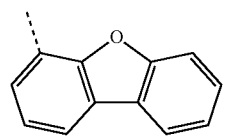
Ar-65
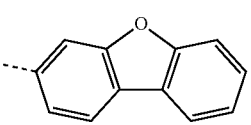
Ar-66
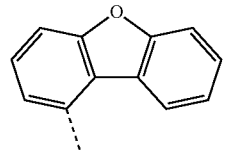
Ar-67
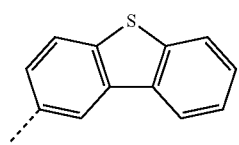
Ar-68
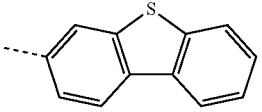
Ar-69
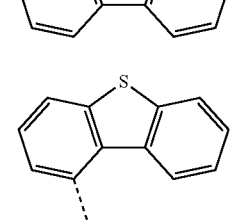
Ar-70
Ar-71
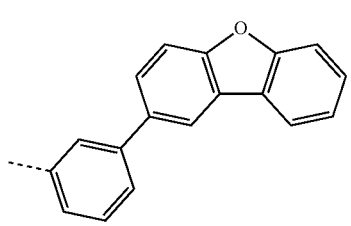
Ar-72
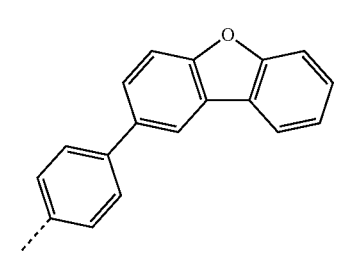
Ar-73
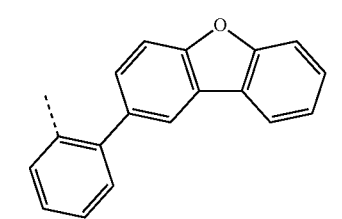
Ar-74
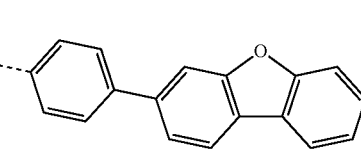
Ar-75
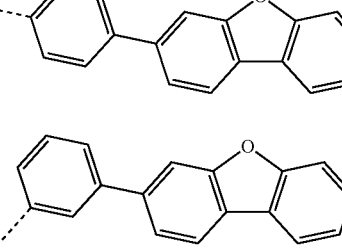

Ar-76
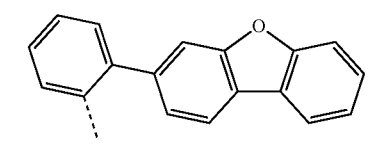
Ar-77
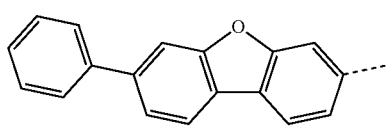
Ar-78
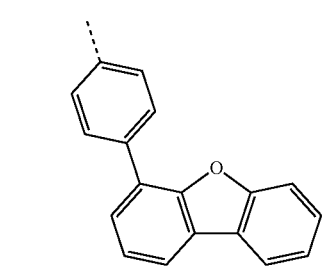
Ar-79
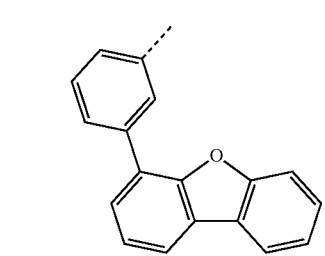
Ar-80
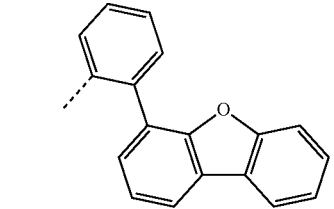
Ar-81
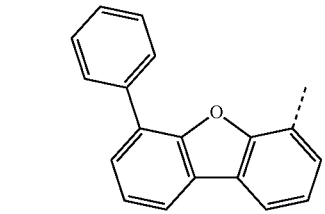
Ar-82
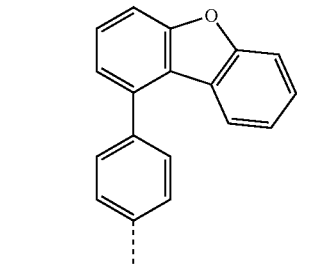
Ar-83
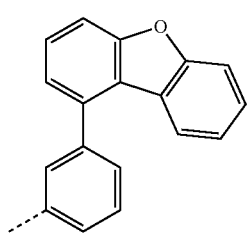
Ar-84
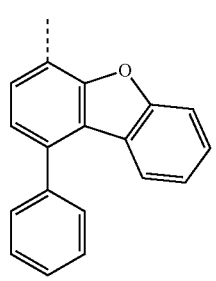
Ar-85
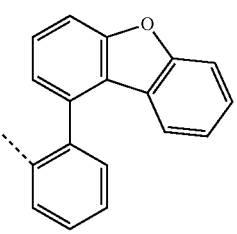
Ar-86
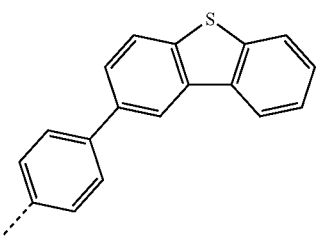
Ar-87
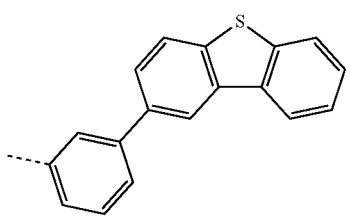
Ar-88
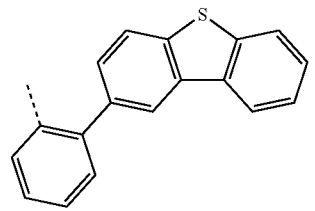

-continued
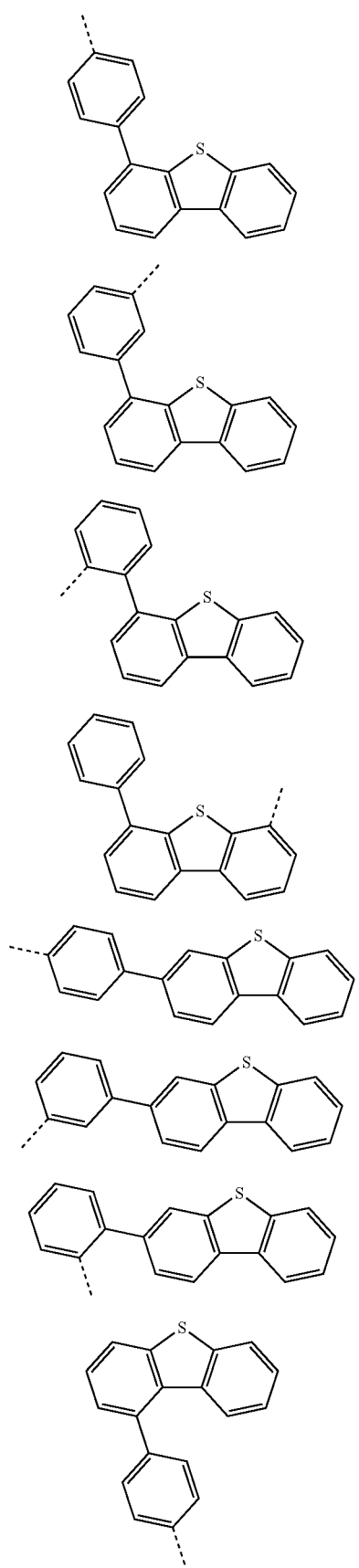
Ar-89
Ar-90
Ar-91
Ar-92
Ar-93
Ar-94
Ar-95
Ar-96
-continued
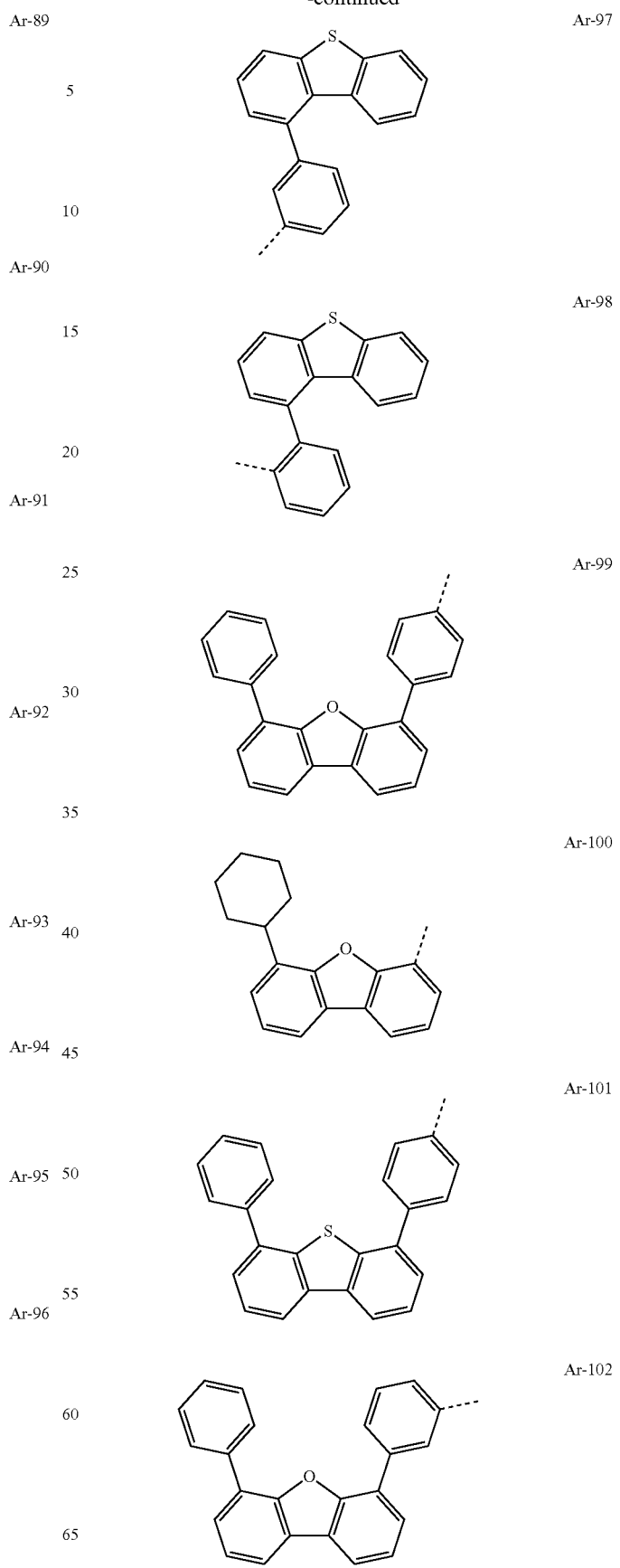
Ar-97
Ar-98
Ar-99
Ar-100
Ar-101
Ar-102

Ar-103
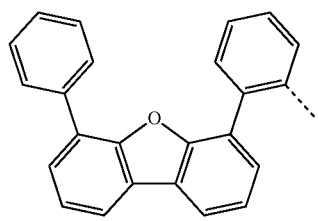
Ar-104
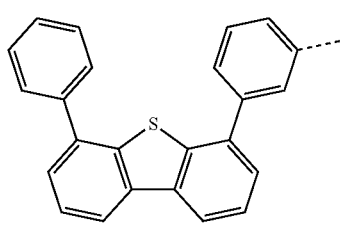
Ar-105
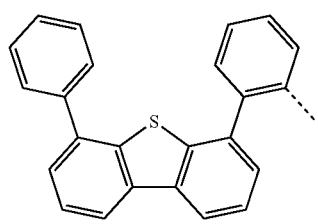
Ar-106
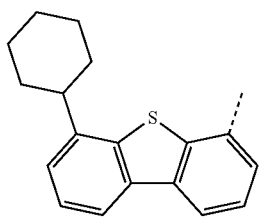
Ar-107
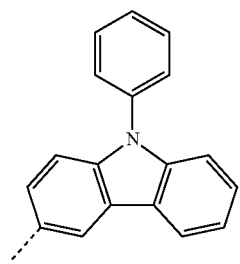
Ar-108
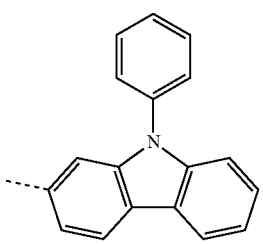
Ar-109
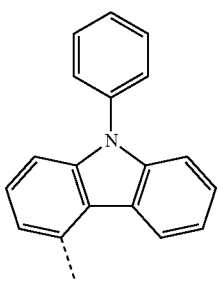
Ar-110
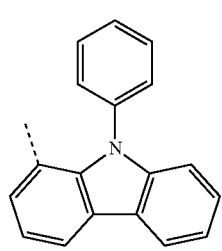
Ar-111
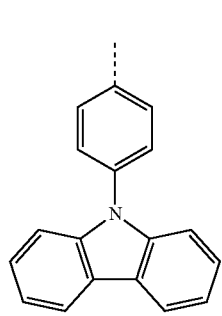
Ar-112
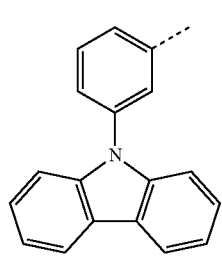
Ar-113
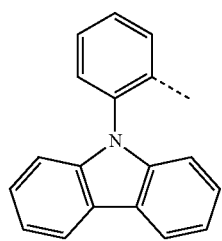
Ar-114
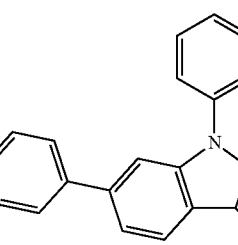

Ar-115 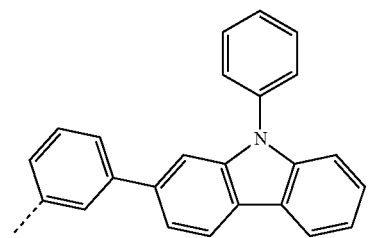
Ar-116 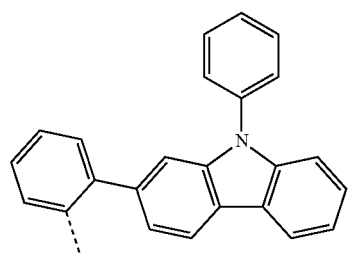
Ar-117 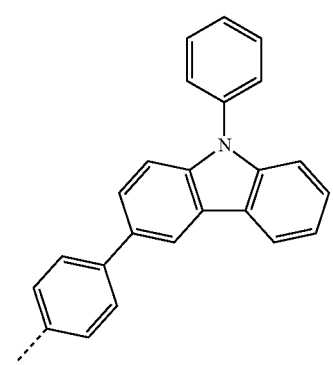
Ar-118 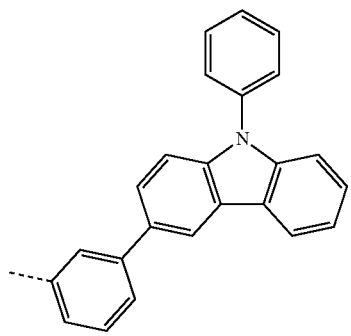
Ar-119 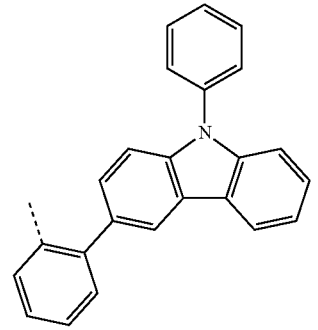
Ar-120 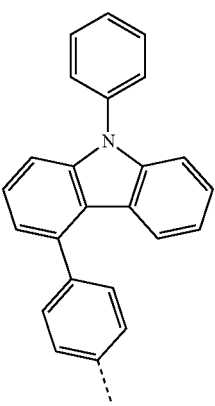
Ar-121 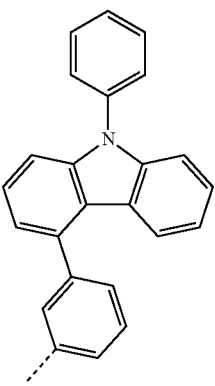
Ar-122 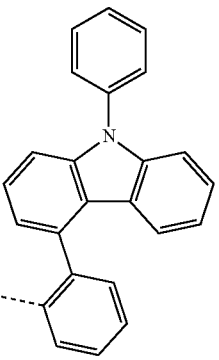
Ar-123 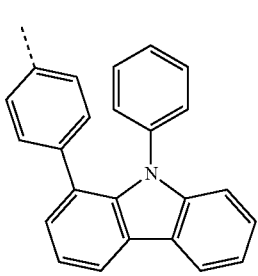

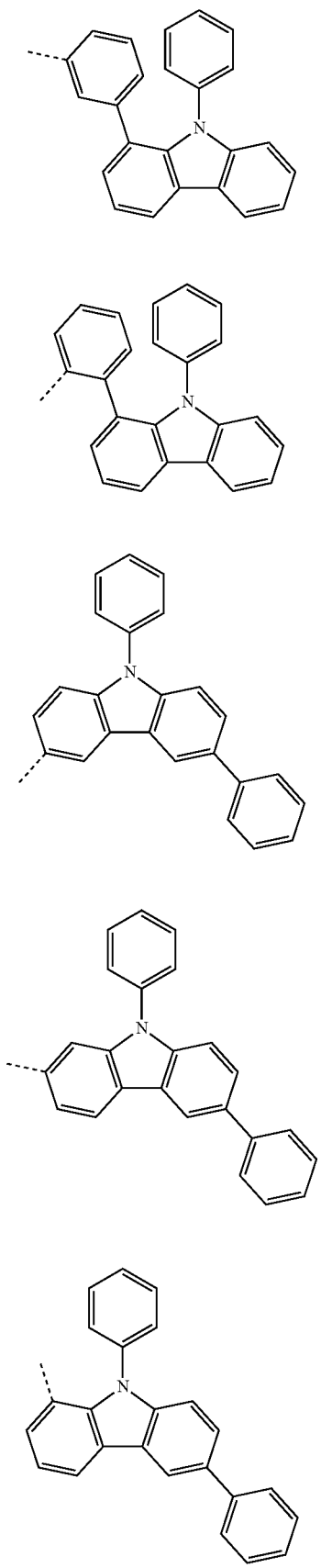
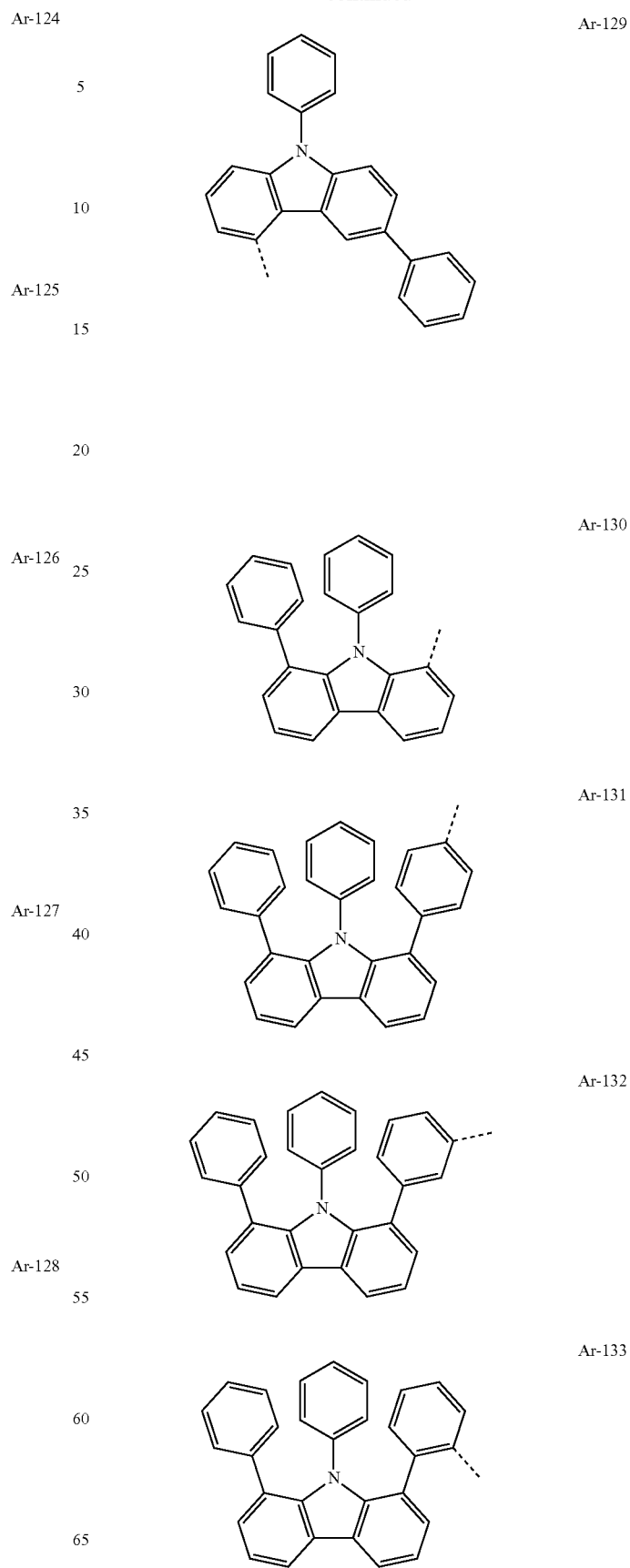

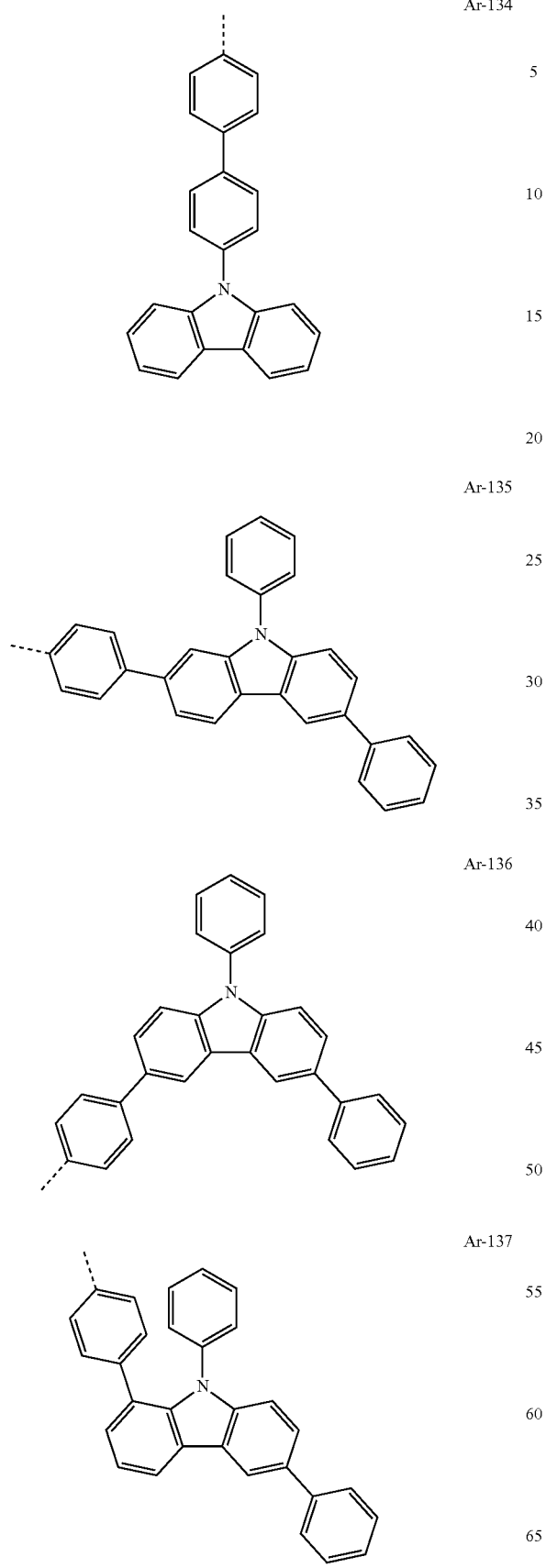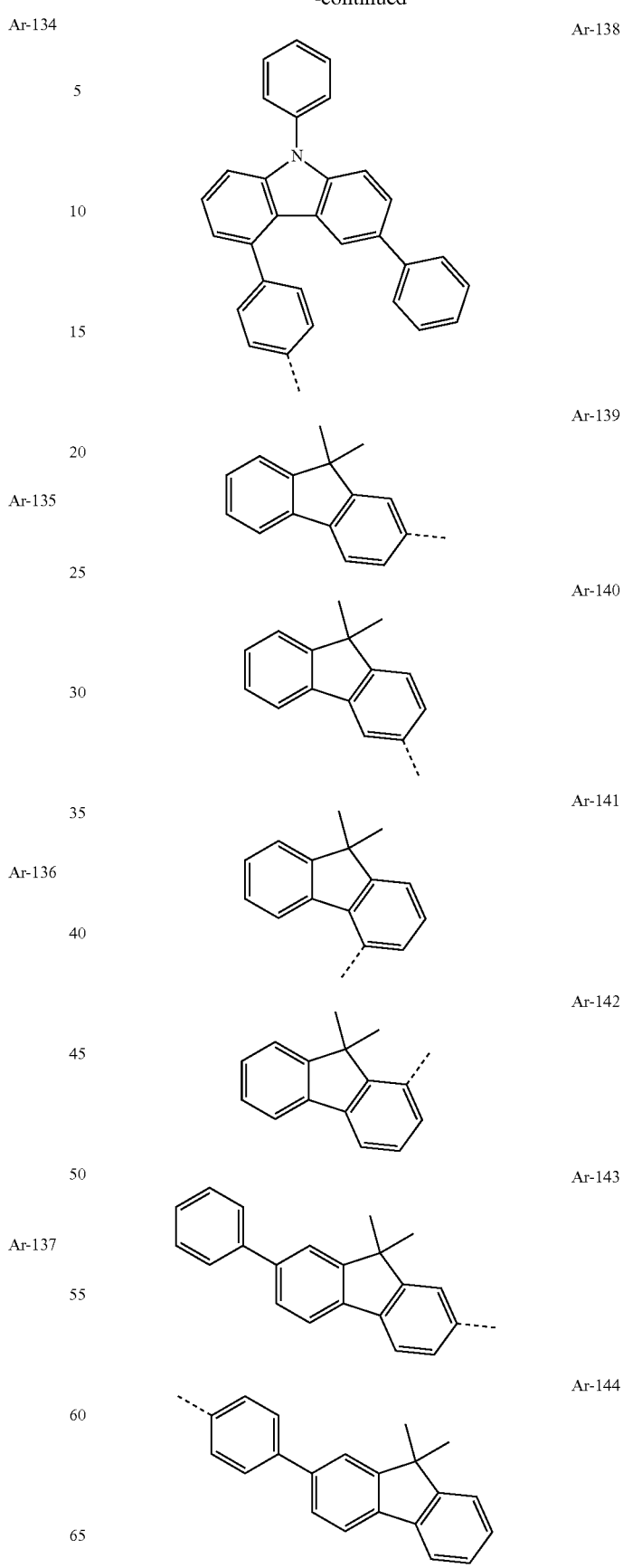

Ar-145
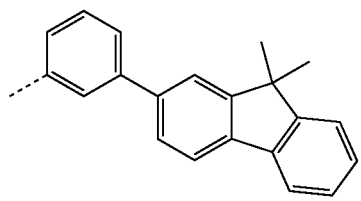
Ar-146
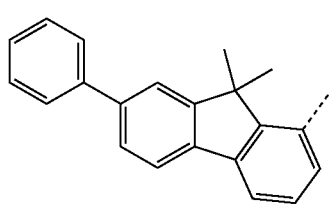
Ar-147
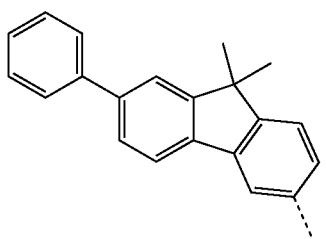
Ar-148
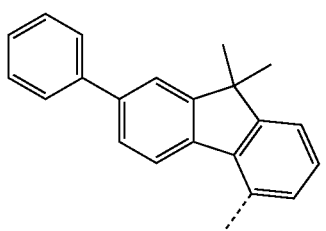
Ar-149
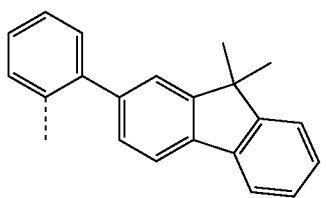
Ar-150
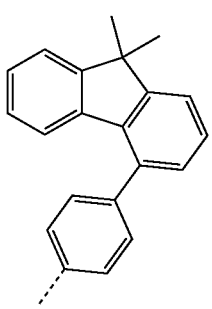
Ar-151
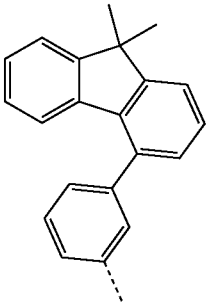
Ar-152
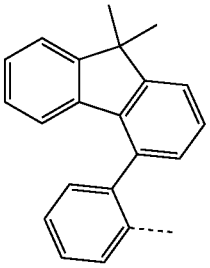
Ar-153
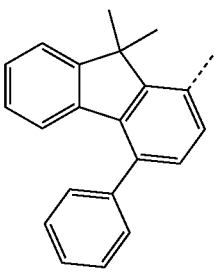
Ar-154
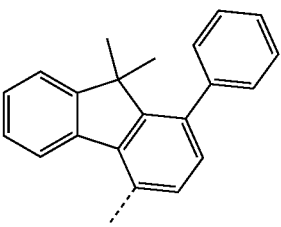
Ar-155
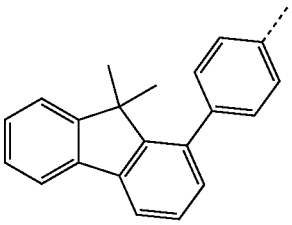
Ar-156
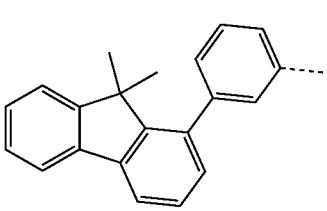

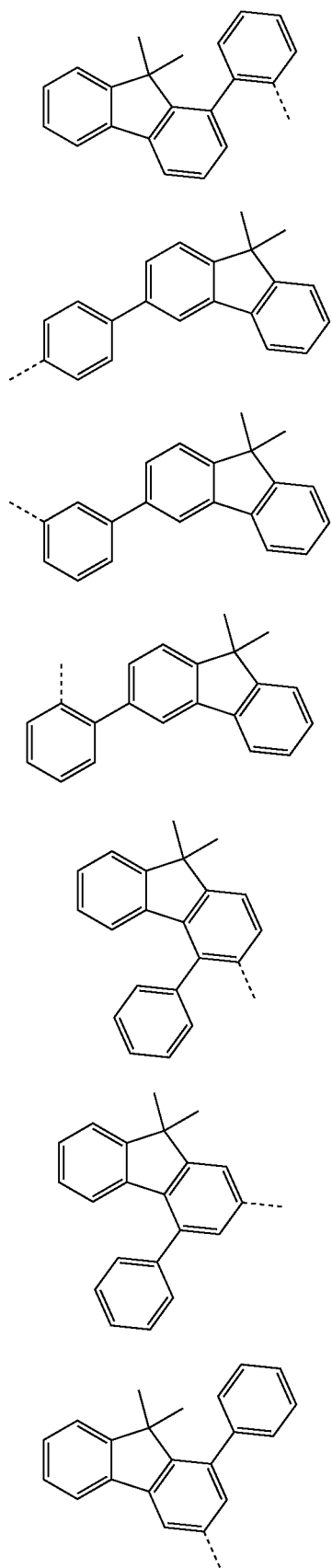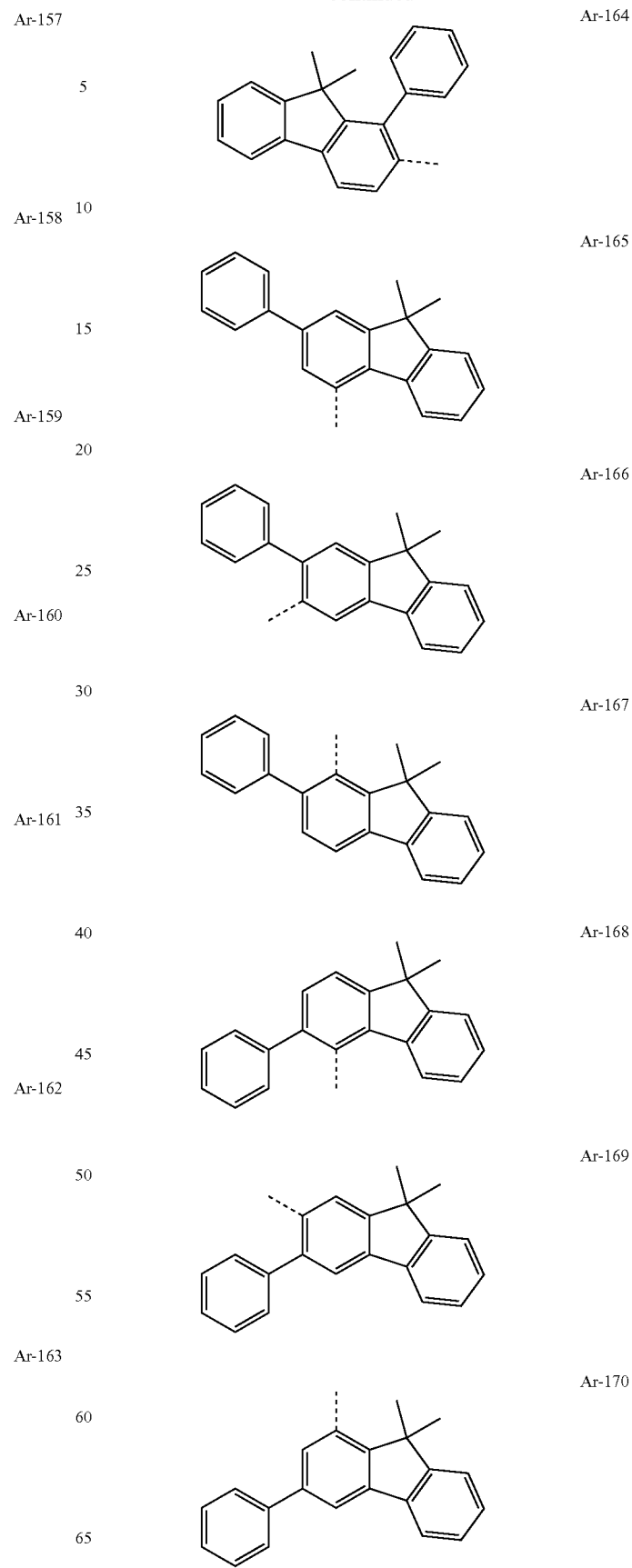

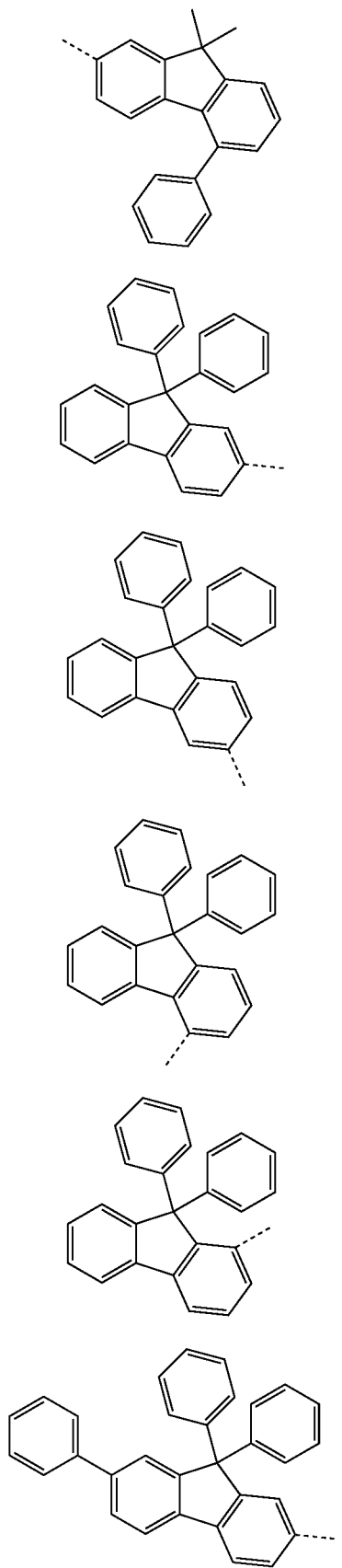
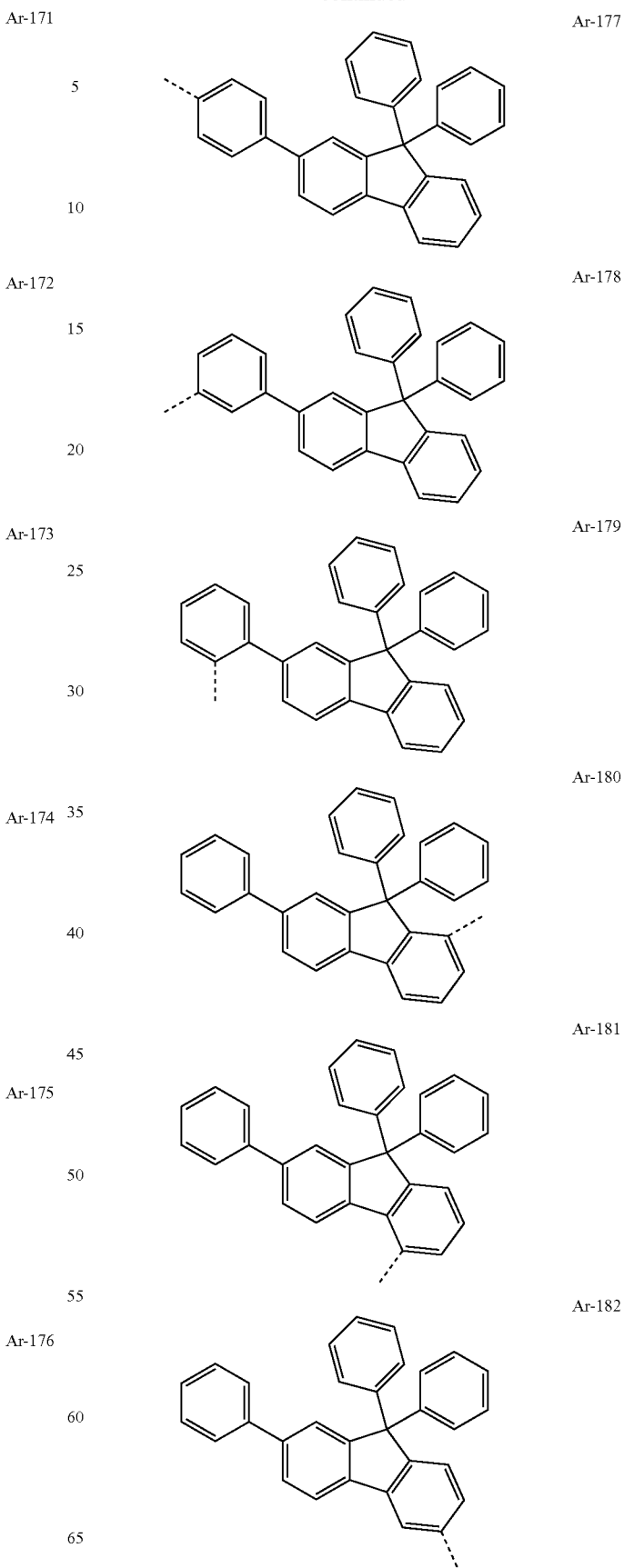

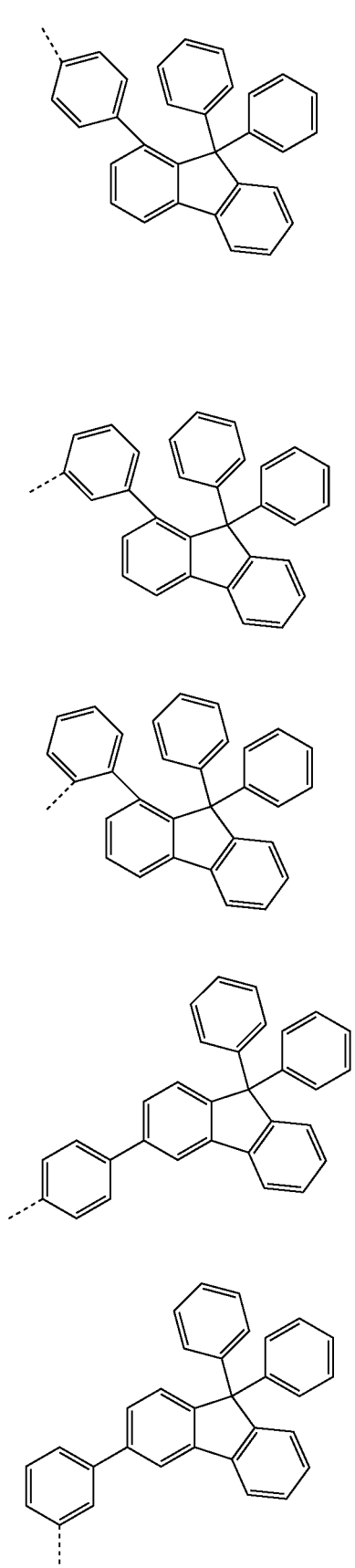
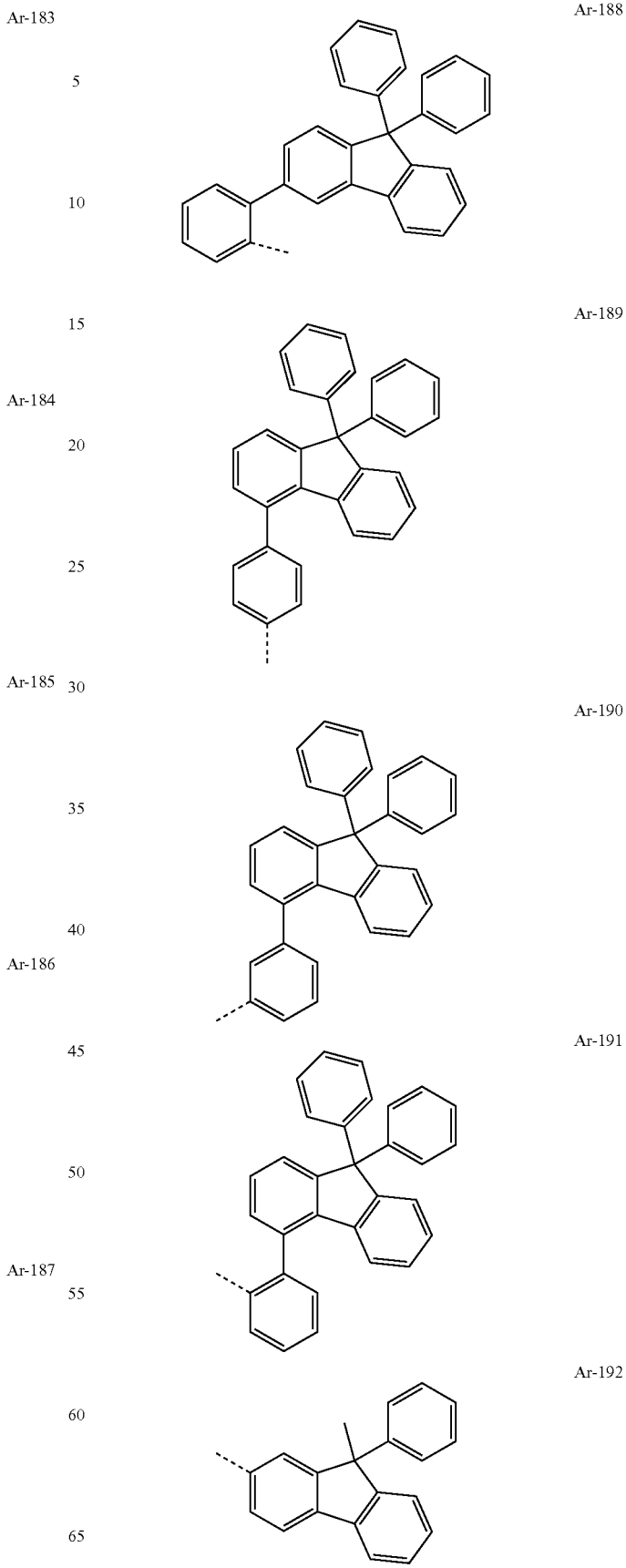

-continued
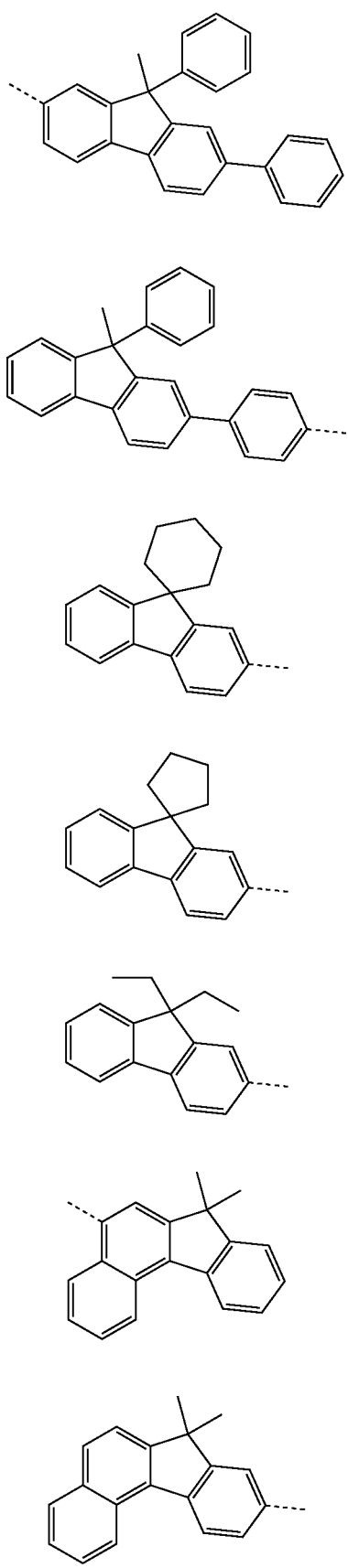
Ar-193
Ar-194
Ar-195
Ar-196
Ar-197
Ar-198
Ar-199
-continued
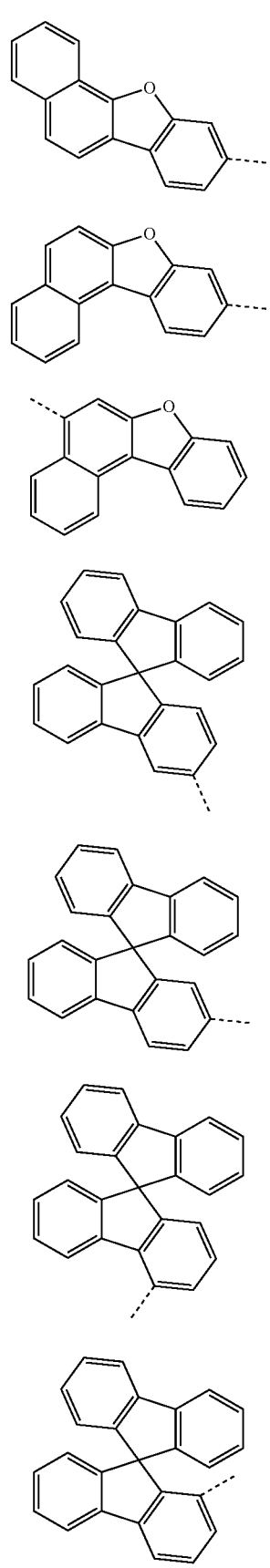
Ar-200
Ar-201
Ar-202
Ar-203
Ar-204
Ar-205
Ar-206

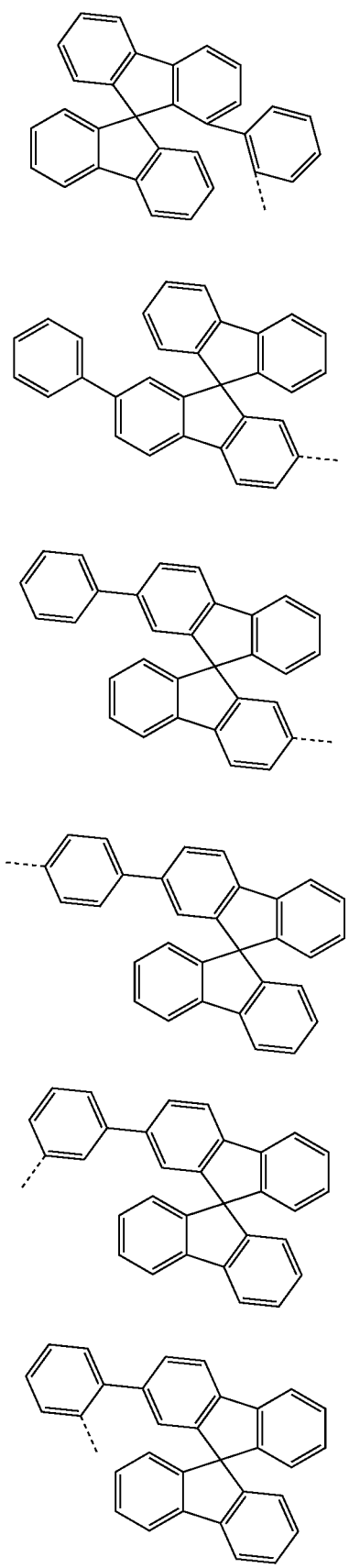
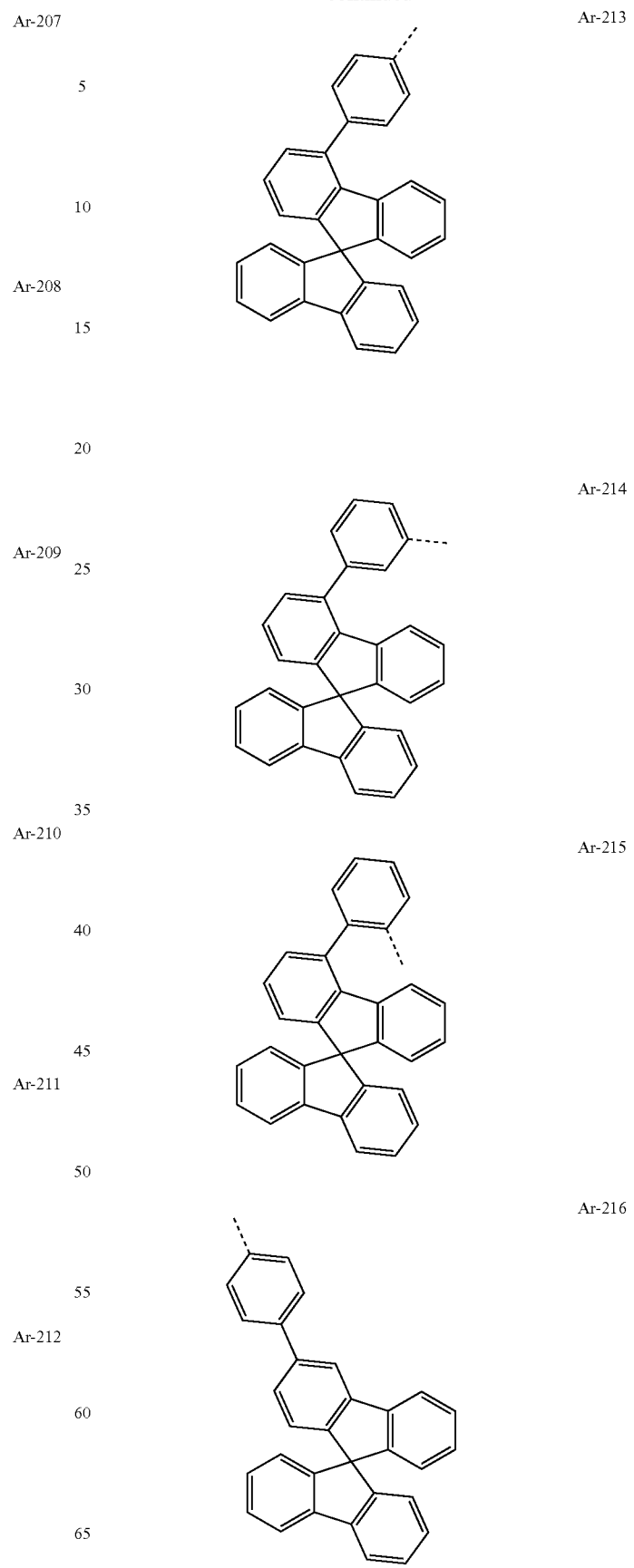

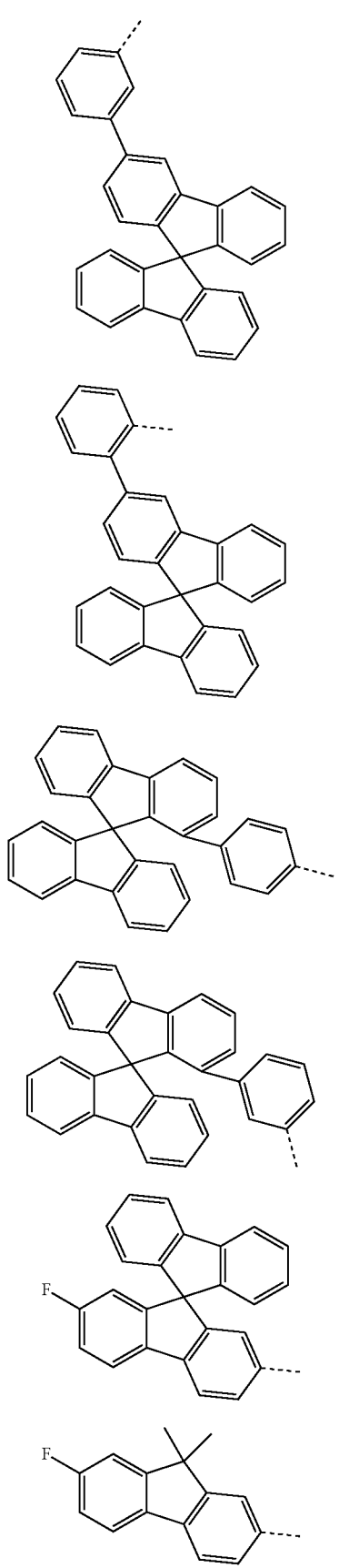
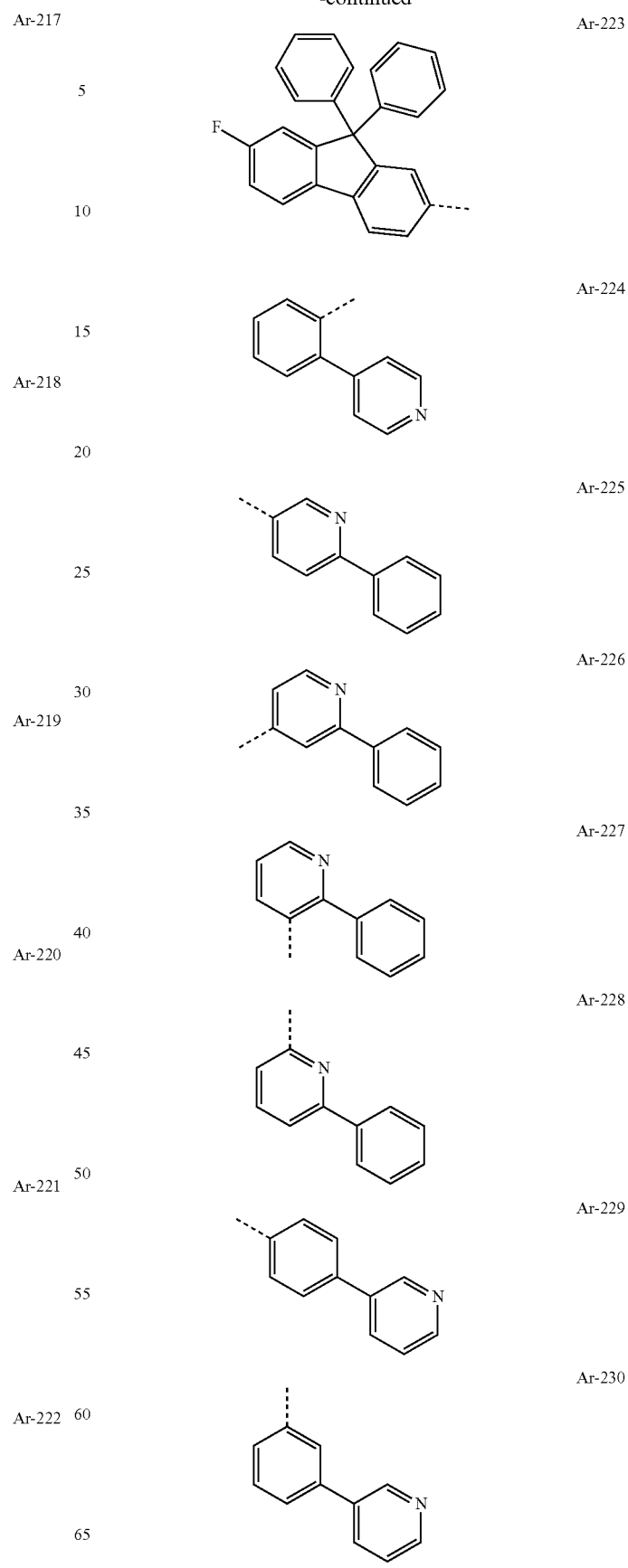

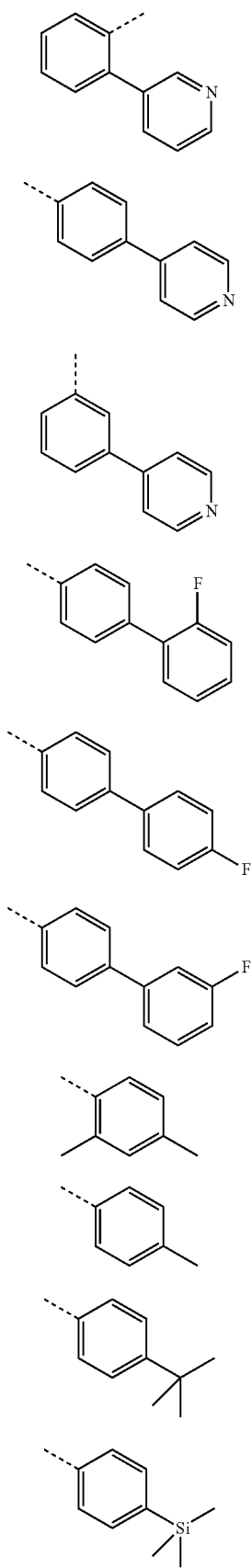
Ar-231
Ar-232
Ar-233
Ar-234
Ar-235
Ar-236
Ar-237
Ar-238
Ar-239
Ar-240
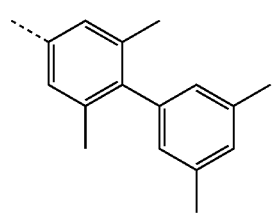
Ar-241
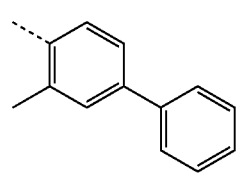
Ar-242
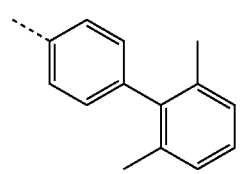
Ar-243
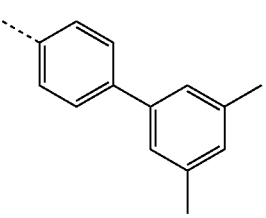
Ar-244
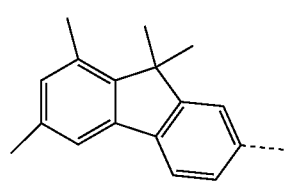
Ar-245
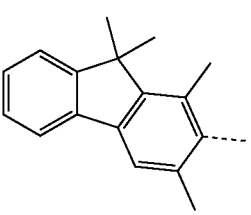
Ar-246
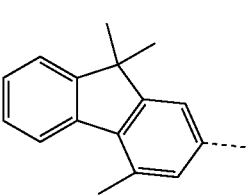
Ar-247

Ar-248 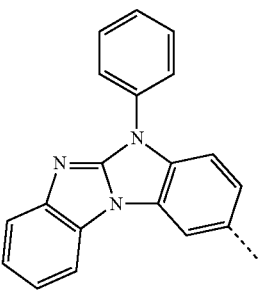

Ar-249 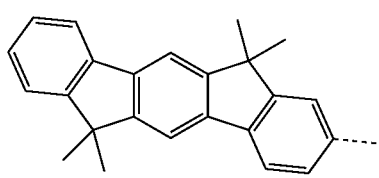

Ar-250 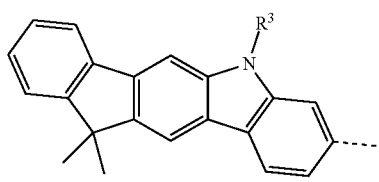

Ar-251 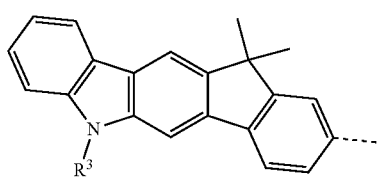

Ar-252 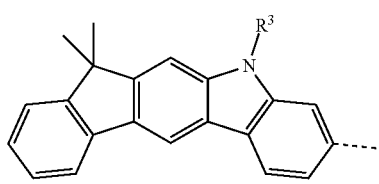

Ar-253 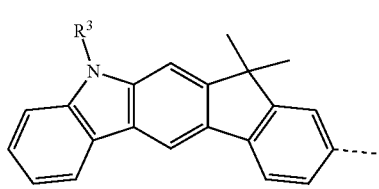

Ar-254 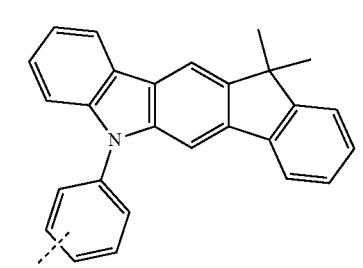

Ar-255 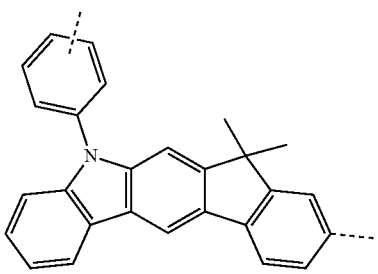

where the groups may be substituted at the free positions with groups $R^3$, but are preferably unsubstituted in these positions, and where the dotted line symbolizes the bonding position to the nitrogen atom.

T is preferably a single bond.

Preferably, n is 0. In case that n=1, the groups $Ar^1$ are preferably phenyl, which is optionally substituted by one or more groups $R^1$. In such case, a carbazolyl group is formed which is connected via its N-atom.

In the case that the two groups $Ar^1$ are connected by a group T, particularly preferred embodiments of the moieties

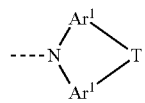

are selected from the following formulae

N-1 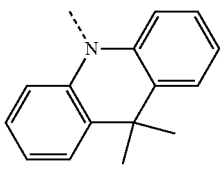

N-2 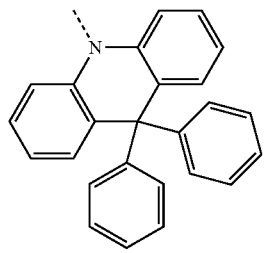

N-3 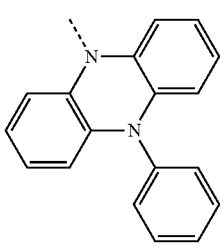

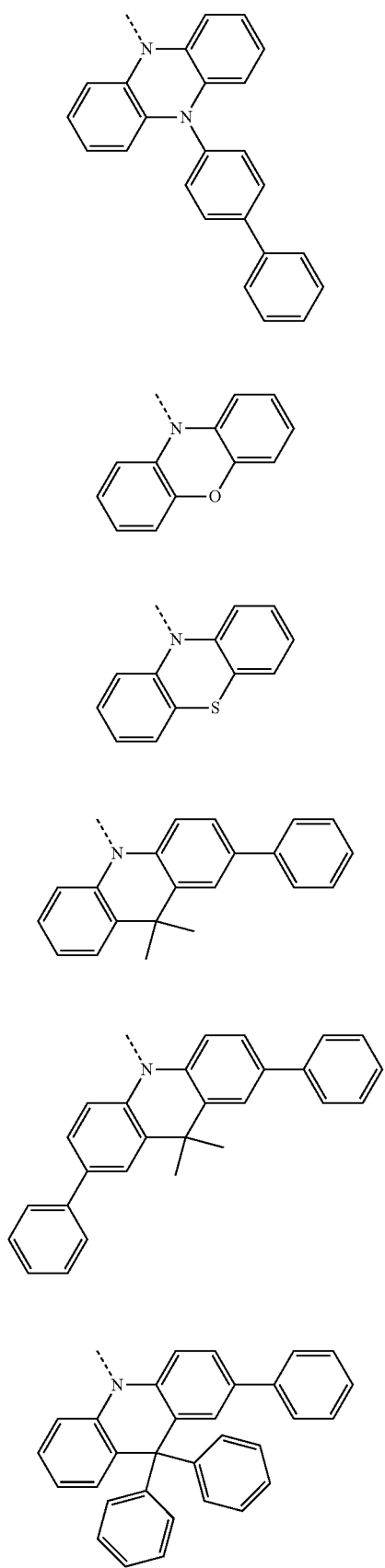
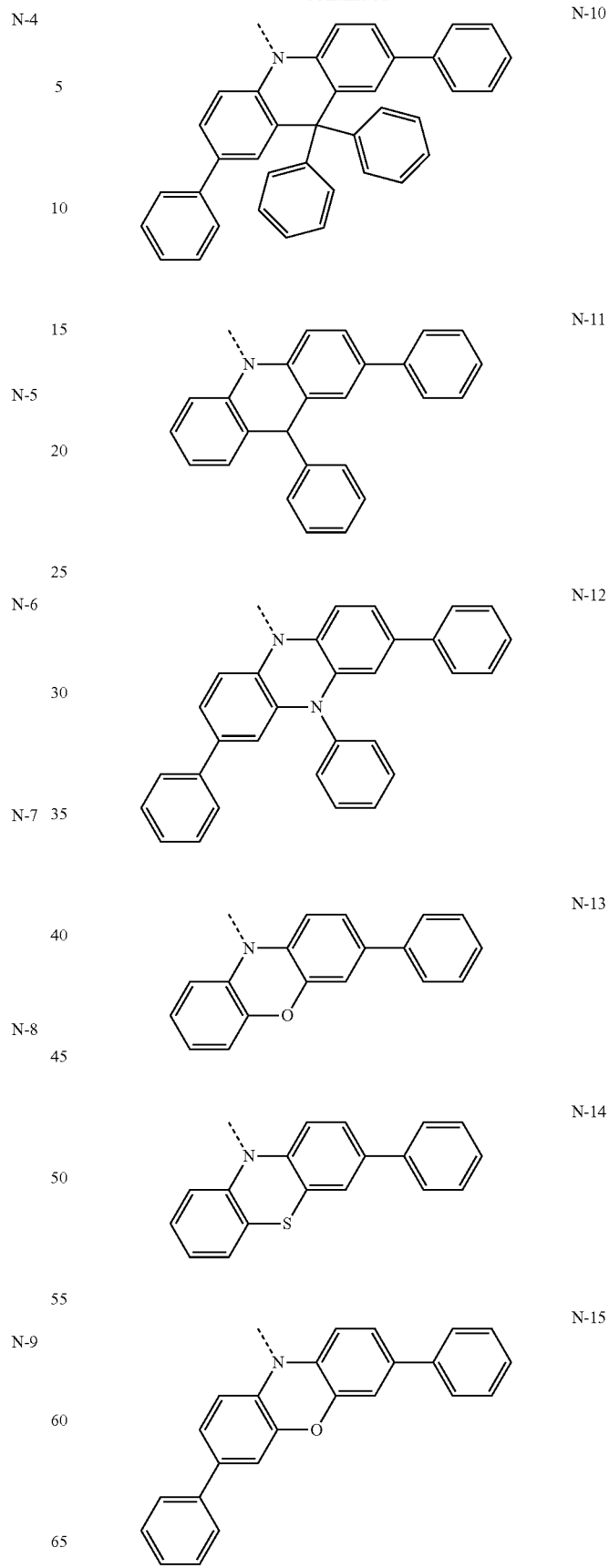

N-16
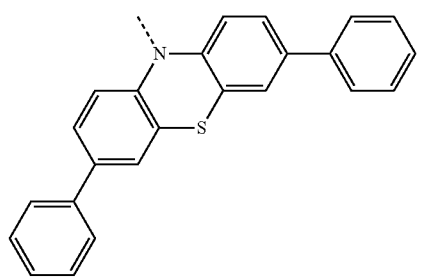
N-17
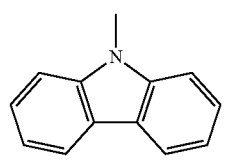
N-18
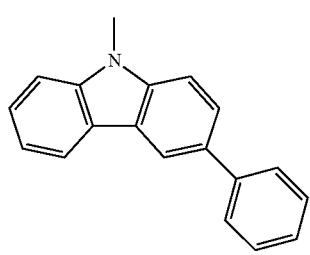
N-19
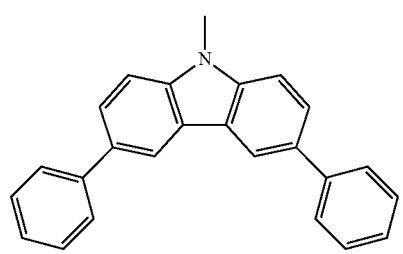
N-20
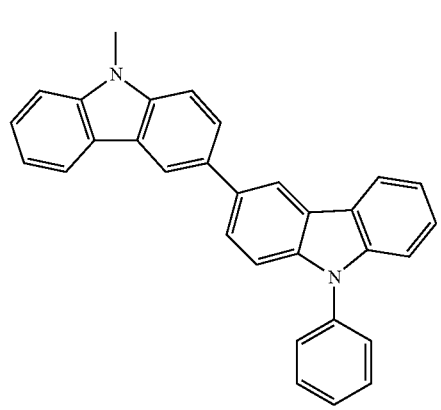
N-21
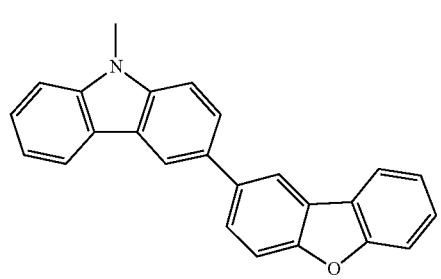
N-22
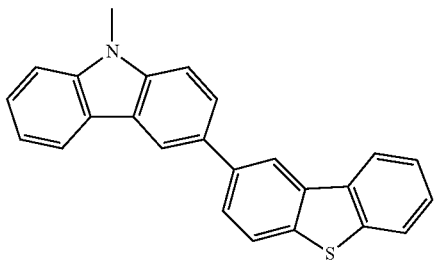
N-23
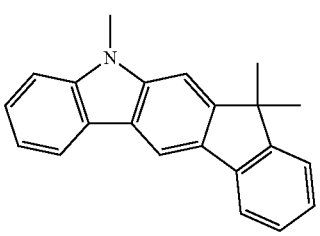
N-24
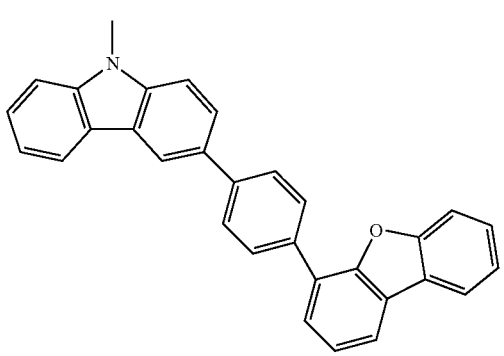
N-25
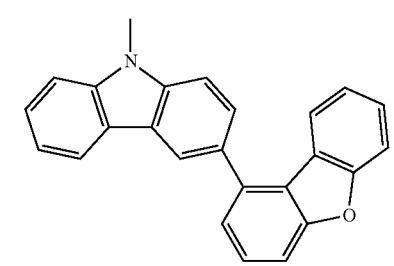
N-26
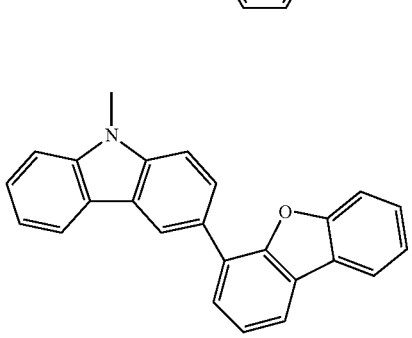

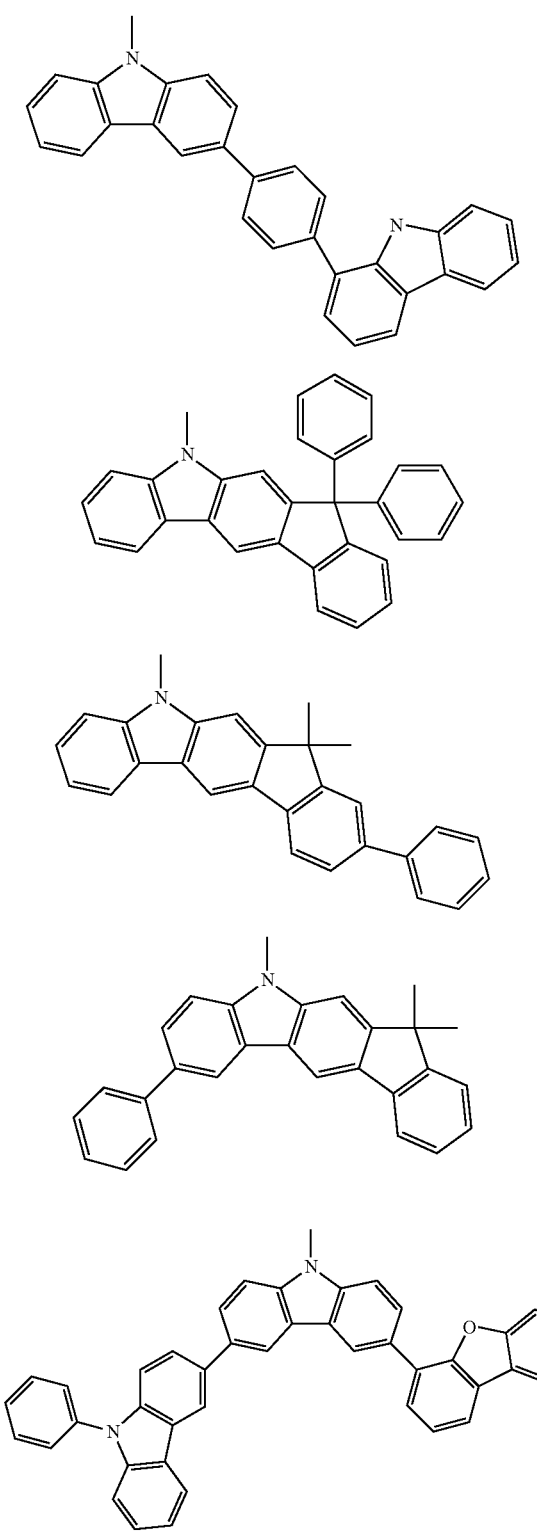

where the groups may be substituted at the free positions with groups R³, but are preferably unsubstituted in these positions, and where the dotted line symbolizes the position in which the group bonds to the rest of the formula.

Preferably, R¹, R² and R³ are selected, identically or differently at each occurrence, from H, D, F, CN, Si(R⁴)₃, N(R⁴)₂, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where two or more radicals R¹ and two or more radicals R² and two or more radicals R³ may be connected to each other to form a ring; and where the said alkyl groups and the said aromatic and heteroaromatic ring systems may in each case be substituted by one or more radicals R⁴.

Particularly preferably, R¹ is H. Particularly preferably, R³ is selected, identically or differently at each occurrence, from H, D, F, CN, Si(R⁴)₃, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where two or more radicals R³ may be connected to each other to form a ring; and where the said alkyl groups and the said aromatic and heteroaromatic ring systems may in each case be substituted by one or more radicals R⁴.

According to one preferable embodiment, at least one group R¹ is a heteroaryl group having 5 to 20 C atoms, which may be substituted by one or more radicals R⁴. The heteroaryl group preferably comprises at least one nitrogen atom in one of its heteroaromatic rings, and is bonded via such nitrogen atom to the rest of formula (I), (II) or (III). Particularly preferable are groups of the following formulae

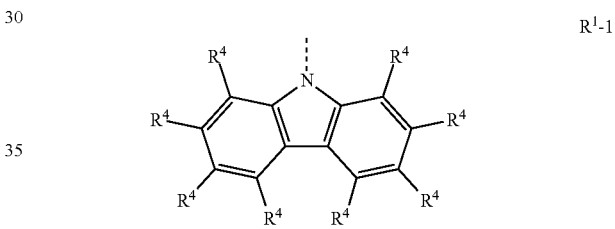

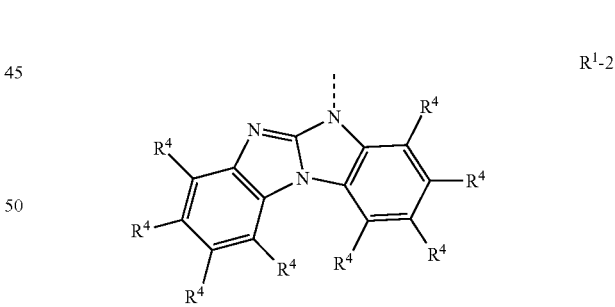

where the dotted bond is the bond connecting the group to the rest of formula (I).

Preferably, R⁴ is selected, identically or differently at each occurrence, from H, D, F, CN, Si(R⁵)₃, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where two or more radicals R⁴ may be connected to each other to form a ring; and where the said alkyl groups and the said aromatic and heteroaromatic ring systems may in each case be substituted by one or more radicals R⁵.

Preferred embodiments of formula (I) are the following formulae:
Formula (I-A)
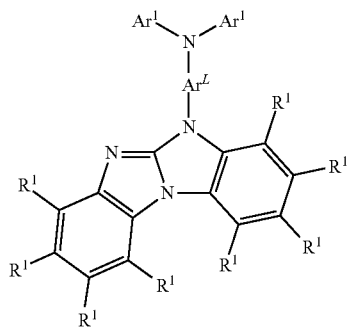
Formula (I-B)
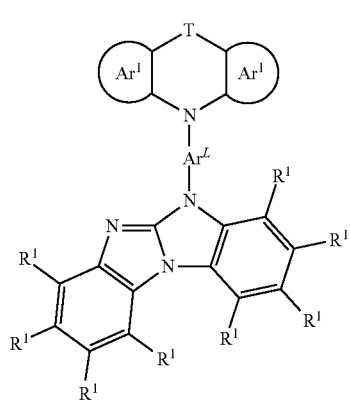
Formula (I-C)
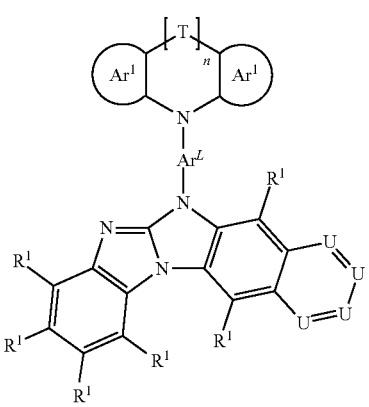
Formula (I-D)
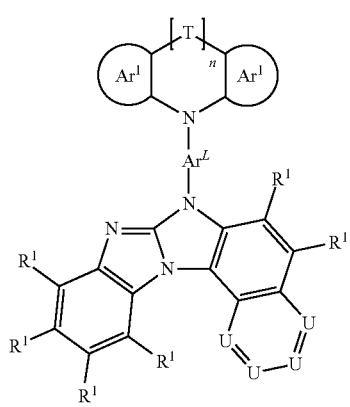
-continued
Formula (I-E)
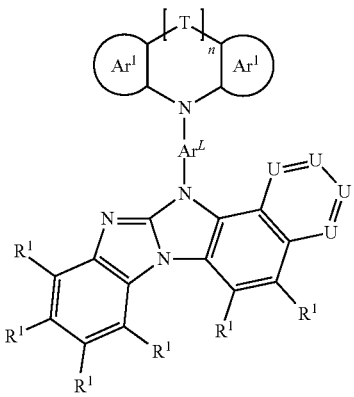
Formula (I-F)
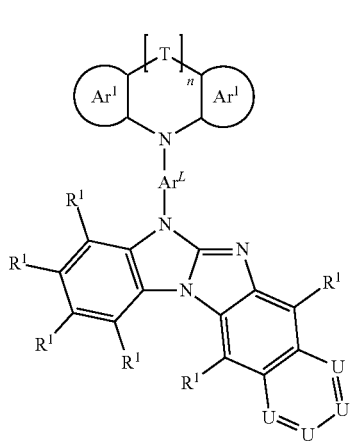
Formula (I-G)
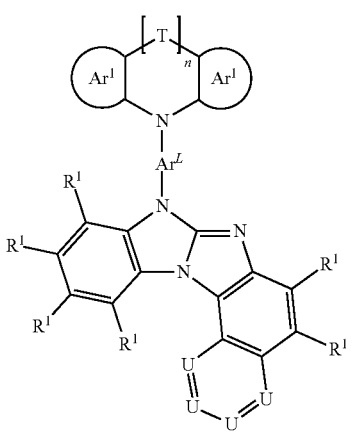

-continued

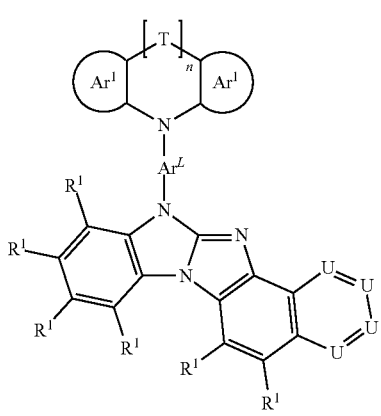

Formula (I-H)

where the variables are defined as above, and preferably correspond to their preferred embodiments mentioned above, and where for formula (I-B) to (I-H), Ar¹ is an aromatic ring system having 6 to 20 aromatic ring atoms, or a heteroaromatic ring system having 5 to 20 aromatic ring atoms, each of which may be substituted by one or more radicals $R^3$; and U is, identically or differently on each occurrence, $CR^1$ or N. According to a preferred embodiment, one group U per ring is N, and the other groups U are $CR^1$. According to another preferred embodiment, U is $CR^1$ at each occurrence. In each of the two groups $Ar^1$ present in formula (I-B) to (I-H), the N atom and the group T are present in ortho-position to each other. In formulae (I-B) to (I-H), T is preferably a single bond. In formulae (I-C) to (I-H), index n is preferably 0.

Preferably, in formula (I-B) and for the case of n=1 in formulae (I-C) to (I-H), $Ar^1$ is selected, identically or differently, from benzene, naphthalene, anthracene, pyridine, pyrimidine, pyridazine, pyrazine, carbazole, fluorene, spirobifluorene, dibenzofuran, and dibenzothiophen, each of which may be substituted by one or more radicals $R^3$. Particularly preferably, $Ar^1$ in formula (I-B), and for the case of n=1 in formulae (I-C) to (I-H), is benzene, which may be substituted by one or more radicals $R^3$. Furthermore preferably, in formula (I-B) and for the case of n=1 in formulae (I-C) to (I-H), $R^3$ is selected, identically or differently at each occurrence, from H, D, F, CN, $Si(R^4)_3$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where two or more radicals $R^3$ may be connected to each other to form a ring; and where the said alkyl groups and the said aromatic and heteroaromatic ring systems may in each case be substituted by one or more radicals $R^4$.

A preferred embodiment of formula (I-A) is formula (I-A-1)

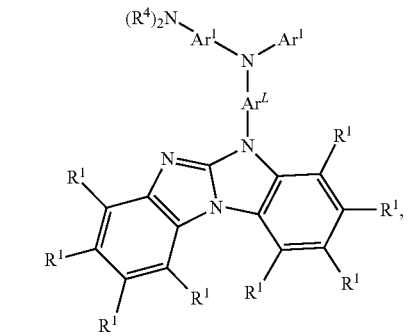

Formula (I-A-1)

where the variables are defined as above, and preferably correspond to their preferred embodiments mentioned above. Preferably, for formula (I-A-1), none of groups $R^3$ to $R^5$ is an amino group, more preferably, none of groups $R^1$ to $R^5$ is an amino group.

A preferred embodiment of formula (I-B) is formula (I-B-1)

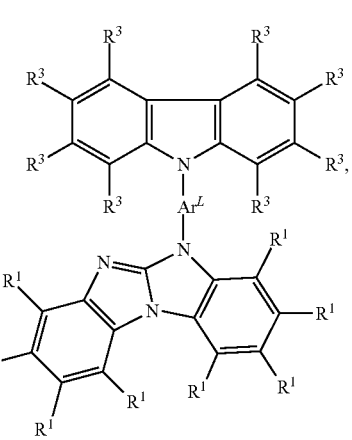

Formula (I-B-1)

where the variables are defined as above, and preferably correspond to their preferred embodiments mentioned above. Preferably, in formula (I-B-1), $R^3$ is selected, identically or differently at each occurrence, from H, D, F, CN, $Si(R^4)_3$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where two or more radicals $R^3$ may be connected to each other to form a ring; and where the said alkyl groups and the said aromatic and heteroaromatic ring systems may in each case be substituted by one or more radicals $R^4$.

Particularly preferably, in formula (I-A), (I-A-1), (I-B), (I-B-1) and (1-0) to (I-H) above, $Ar^L$ is selected from ortho-phenylene, meta-phenylene, para-phenylene, para-biphenylene, meta-biphenylene, ortho-biphenylene, terphenyl, quaterphenyl, and fluorenyl, each of which may be substituted by one or more radicals $R^2$.

A further preferred embodiment of formula (I-A) and (I-B) is represented by the following formulae Formula (I-A-2)

Formula (I-B-2)

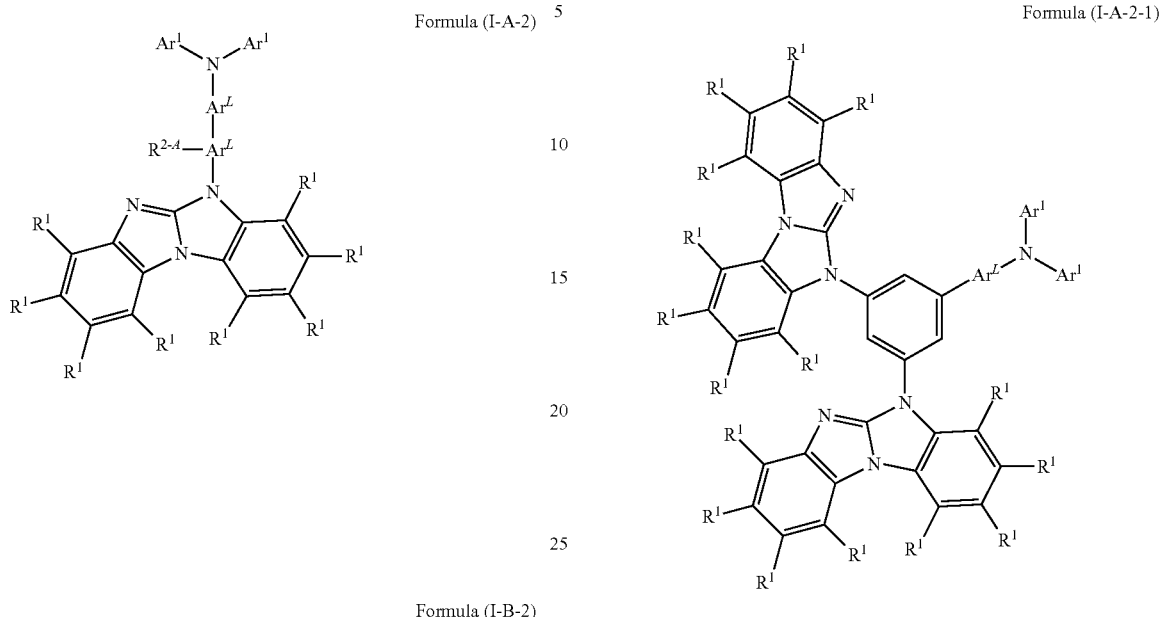

where the variables are defined as above, and preferably correspond to their preferred embodiments mentioned above, and where $R^{2-A}$ is a heteroaryl group having 5 to 20 aromatic ring atoms, which may be substituted by one or more radicals $R^4$, preferably a heteroaryl group which is bonded via a N atom of one of its heteroaromatic rings, more preferably a group of the following formula

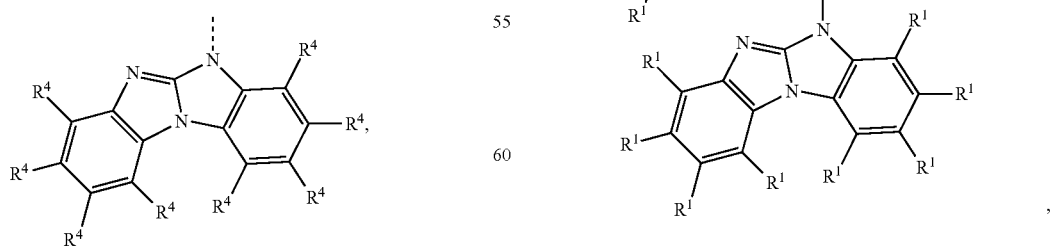

where the dotted bond is the bond connecting the group to the rest of the formula.

Preferred embodiments of formula (I-A-2) and (I-B-2) are represented by the following formulae Formula (I-A-2-1)

Formula (I-B-2-1)

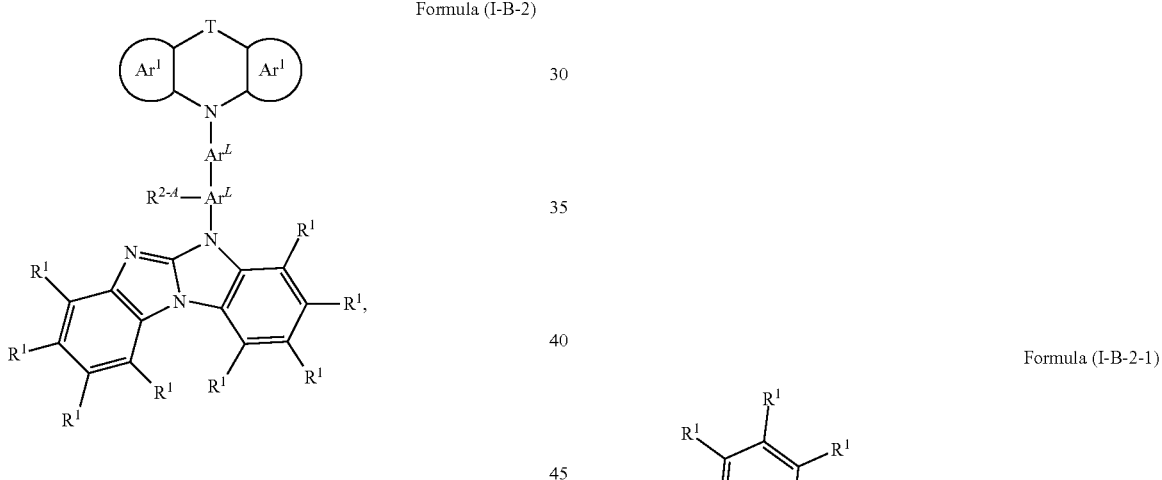

where the variables are defined as above, and preferably correspond to their preferred embodiments mentioned above.

A preferred embodiment of formula (II) is formula (II-A)

A preferred embodiment of formula (III) is formula (III-A)

Formula (II-A)

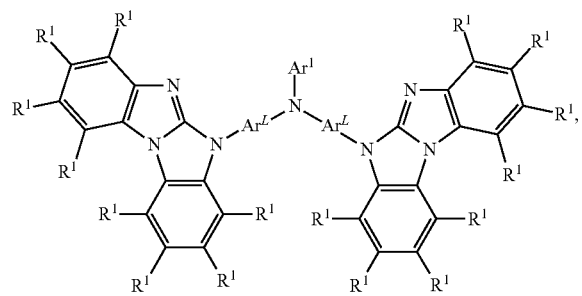

Formula (III-A)

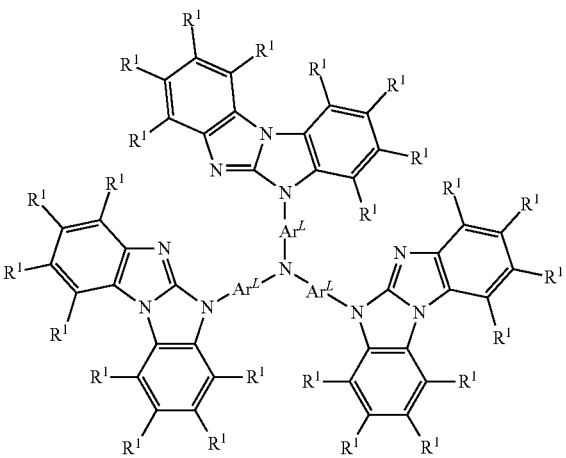

where the variables are defined as above, and preferably correspond to their preferred embodiments mentioned above.

In particular, in formula (II-A), $Ar^1$ is preferably selected from phenyl, biphenyl, terphenyl, quaterphenyl, and fluorenyl, each of which is optionally substituted by one or more radicals $R^3$. Furthermore preferably, $Ar^L$ is selected from ortho-phenylene, meta-phenylene, para-phenylene, para-biphenylene, meta-biphenylene, ortho-biphenylene, terphenyl, quaterphenyl, and fluorenyl, each of which may be substituted by one or more radicals $R^2$.

where the variables are defined as above, and preferably correspond to their preferred embodiments mentioned above.

Preferably, in formula (III-A), $Ar^L$ is selected from ortho-phenylene, meta-phenylene, para-phenylene, para-biphenylene, meta-biphenylene, ortho-biphenylene, terphenyl, quaterphenyl, and fluorenyl, each of which may be substituted by one or more radicals $R^2$.

Preferred compounds according to the invention are shown in the following table:

| 1 |
|---|

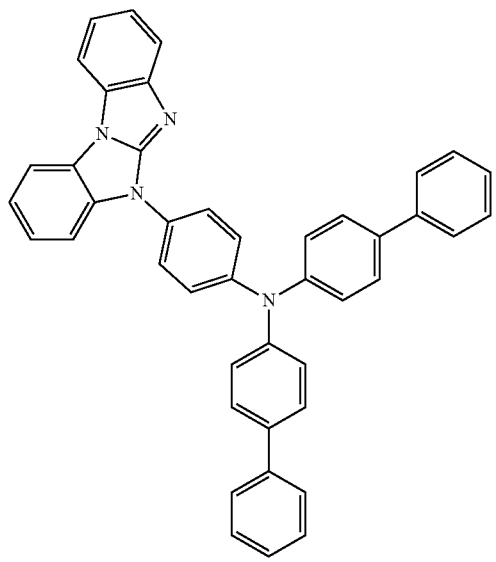 [SMILES: c1ccc(-c2ccc(N(c3ccc(-c4ccccc4)cc3)c3ccc(-n4c5ccccc5n5c6ccccc6nc45)cc3)cc2)cc1]

-continued
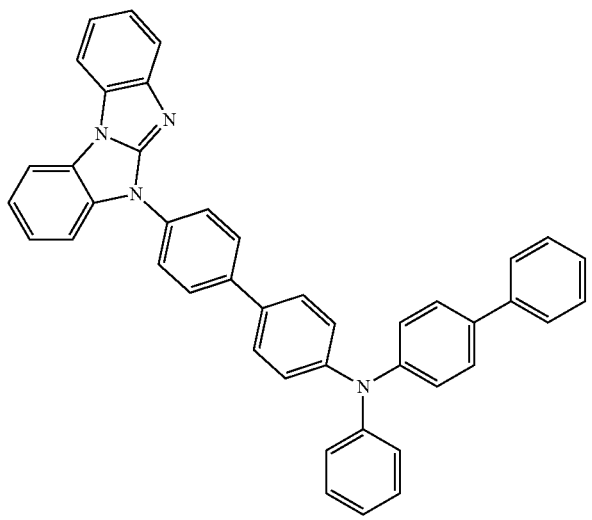 [SMILES: c1ccc(-c2ccc(N(c3ccccc3)c3ccc(-c4ccc(-n5c6ccccc6n6c7ccccc7nc56)cc4)cc3)cc2)cc1]
2
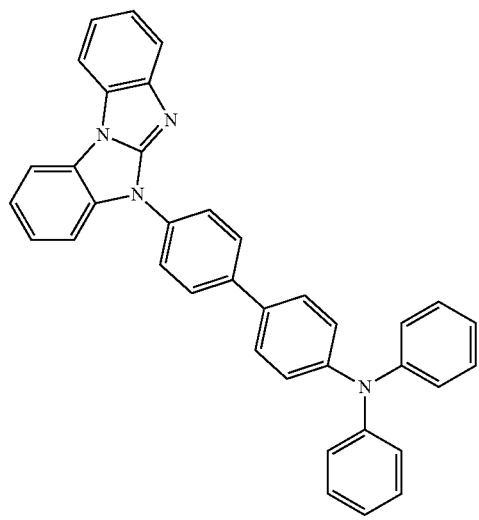 [SMILES: c1ccc(N(c2ccccc2)c2ccc(-c3ccc(-n4c5ccccc5n5c6ccccc6nc45)cc3)cc2)cc1]
3
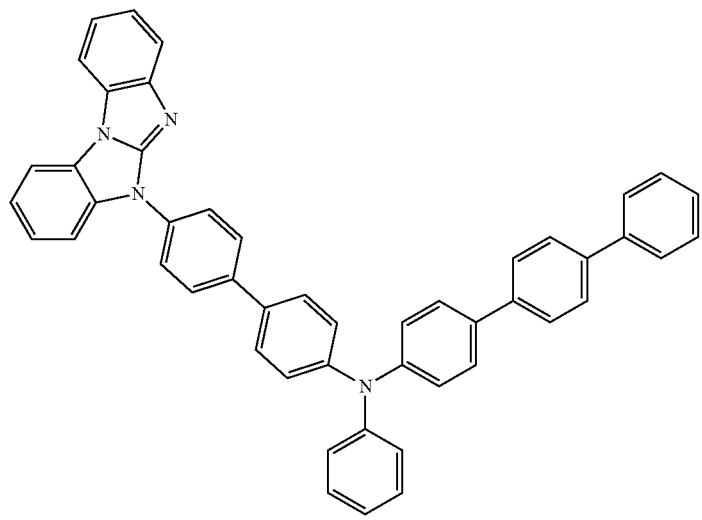 [SMILES: c1ccc(-c2ccc(-c3ccc(N(c4ccccc4)c4ccc(-c5ccc(-n6c7ccccc7n7c8ccccc8nc67)cc5)cc4)cc3)cc2)cc1]
4

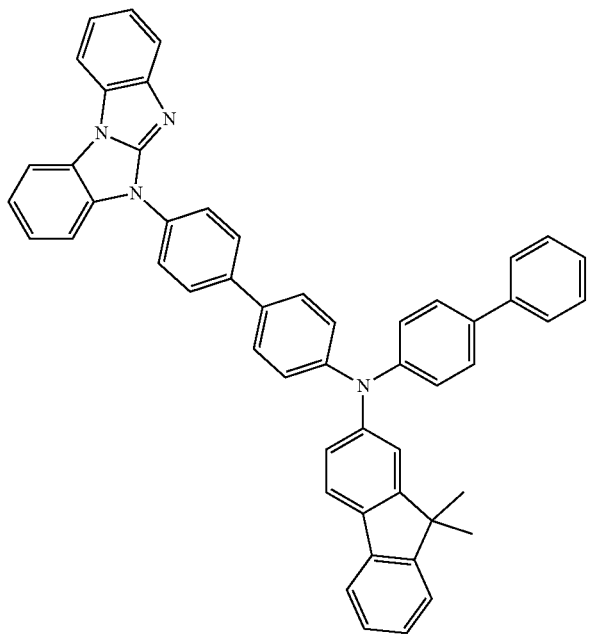 [SMILES: CC1(C)c2ccccc2-c2ccc(N(c3ccc(-c4ccccc4)cc3)c3ccc(-c4ccc(-n5c6ccccc6n6c7ccccc7nc56)cc4)cc3)cc21]
5
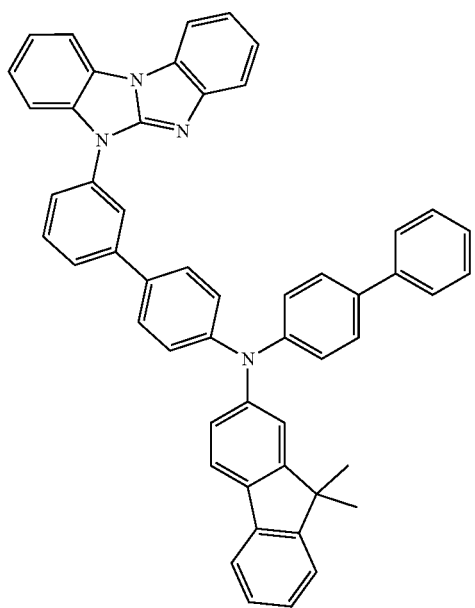 [SMILES: CC1(C)c2ccccc2-c2ccc(N(c3ccc(-c4ccccc4)cc3)c3ccc(-c4cccc(-n5c6ccccc6n6c7ccccc7nc56)c4)cc3)cc21]
6

-continued
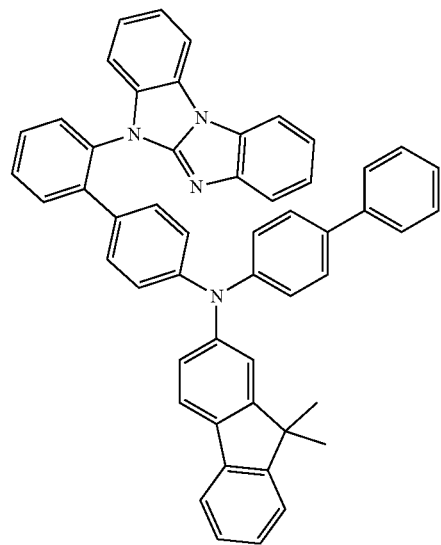 [SMILES: CC1(C)c2ccccc2-c2ccc(N(c3ccc(-c4ccccc4)cc3)c3ccc(-c4ccccc4-n4c5ccccc5n5c6ccccc6nc45)cc3)cc21]
7
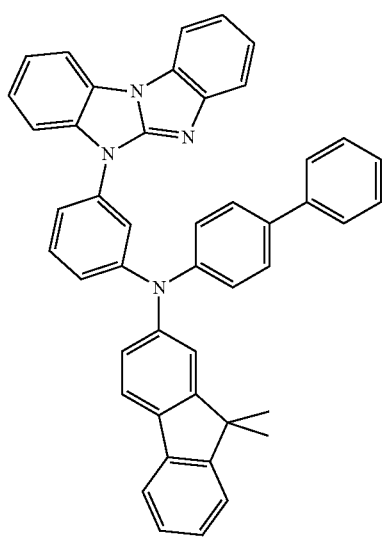 [SMILES: CC1(C)c2ccccc2-c2ccc(N(c3ccc(-c4ccccc4)cc3)c3cccc(-n4c5ccccc5n5c6ccccc6nc45)c3)cc21]
8

-continued
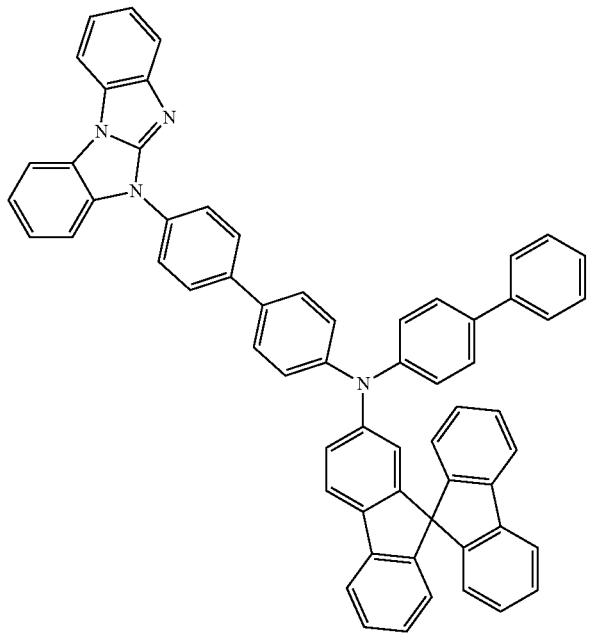 [SMILES: c1ccc(-c2ccc(N(c3ccc(-c4ccc(-n5c6ccccc6n6c7ccccc7nc56)cc4)cc3)c3ccc4c(c3)C3(c5ccccc5-c5ccccc53)c3ccccc3-4)cc2)cc1]
9
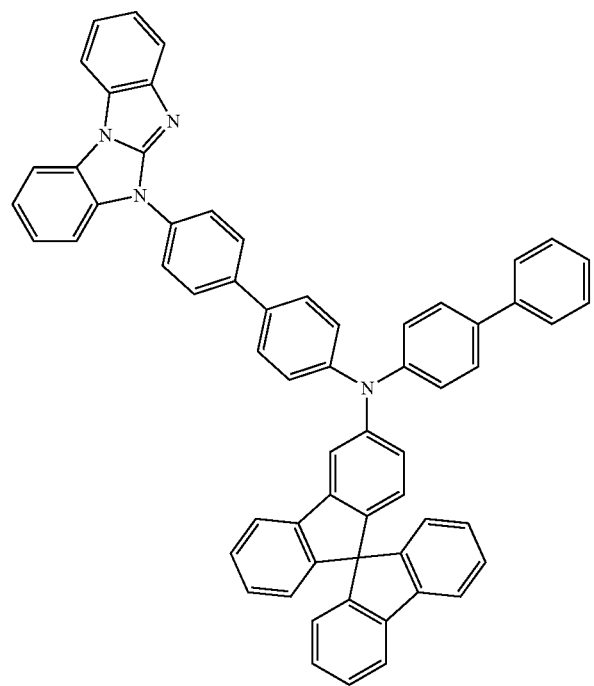 [SMILES: c1ccc(-c2ccc(N(c3ccc(-c4ccc(-n5c6ccccc6n6c7ccccc7nc56)cc4)cc3)c3ccc4c(c3)-c3ccccc3C43c4ccccc4-c4ccccc43)cc2)cc1]
10

-continued
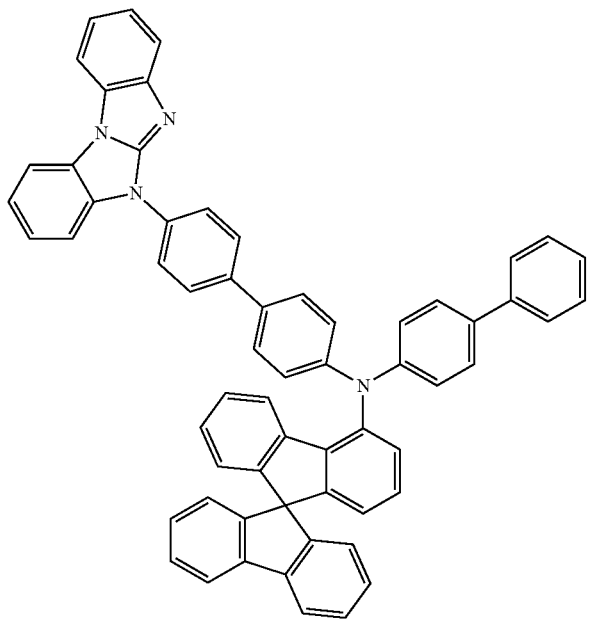 [SMILES: c1ccc(-c2ccc(N(c3ccc(-c4ccc(-n5c6ccccc6n6c7ccccc7nc56)cc4)cc3)c3cccc4c3-c3ccccc3C43c4ccccc4-c4ccccc43)cc2)cc1]
11
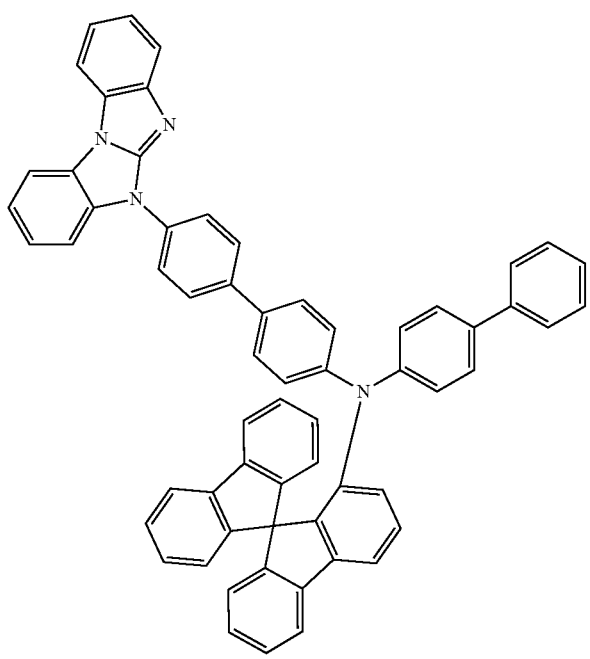 [SMILES: c1ccc(-c2ccc(N(c3ccc(-c4ccc(-n5c6ccccc6n6c7ccccc7nc56)cc4)cc3)c3cccc4c3C3(c5ccccc5-c5ccccc53)c3ccccc3-4)cc2)cc1]
12

-continued
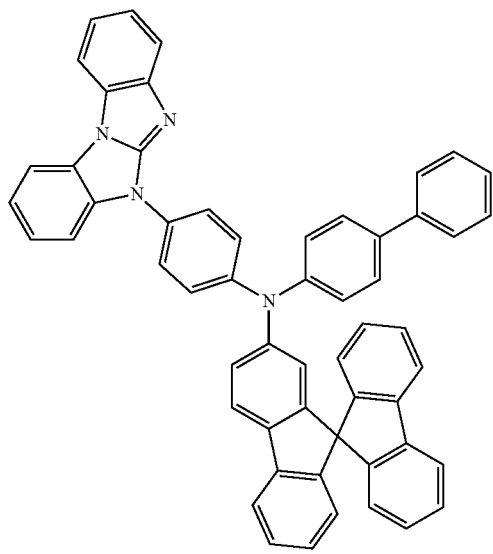 [SMILES: c1ccc(-c2ccc(N(c3ccc(-n4c5ccccc5n5c6ccccc6nc45)cc3)c3ccc4c(c3)C3(c5ccccc5-c5ccccc53)c3ccccc3-4)cc2)cc1]
13
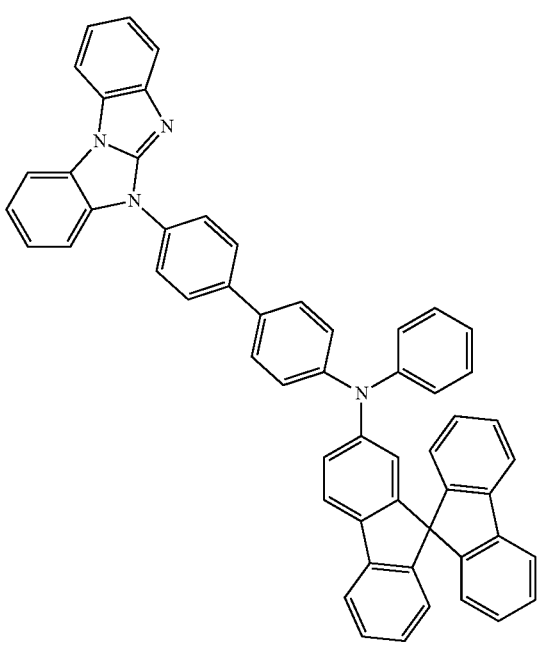 [SMILES: c1ccc(N(c2ccc(-c3ccc(-n4c5ccccc5n5c6ccccc6nc45)cc3)cc2)c2ccc3c(c2)C2(c4ccccc4-c4ccccc42)c2ccccc2-3)cc1]
14

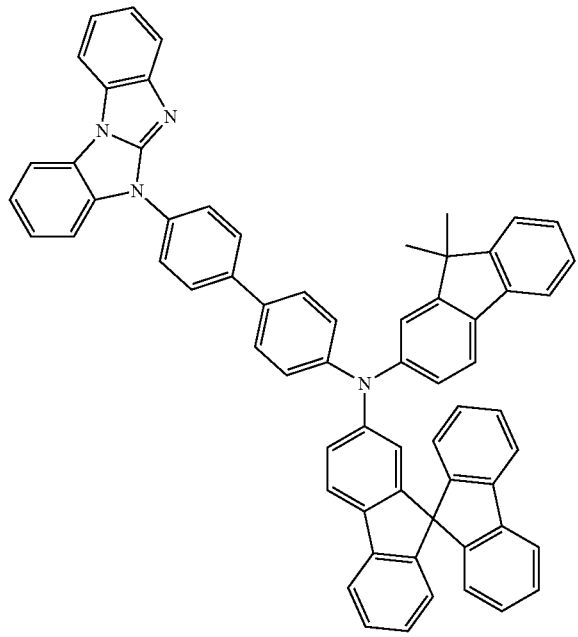 [SMILES: CC1(C)c2ccccc2-c2ccc(N(c3ccc(-c4ccc(-n5c6ccccc6n6c7ccccc7nc56)cc4)cc3)c3ccc4c(c3)C3(c5ccccc5-c5ccccc53)c3ccccc3-4)cc21]
15
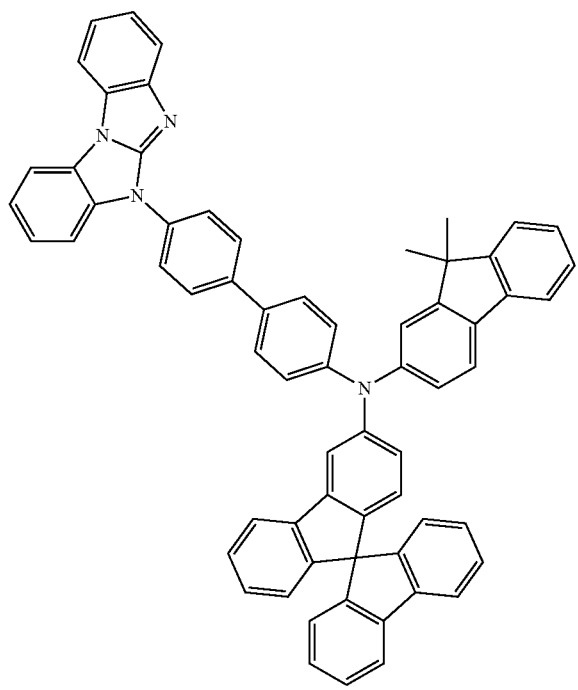 [SMILES: CC1(C)c2ccccc2-c2ccc(N(c3ccc(-c4ccc(-n5c6ccccc6n6c7ccccc7nc56)cc4)cc3)c3ccc4c(c3)-c3ccccc3C43c4ccccc4-c4ccccc43)cc21]
16

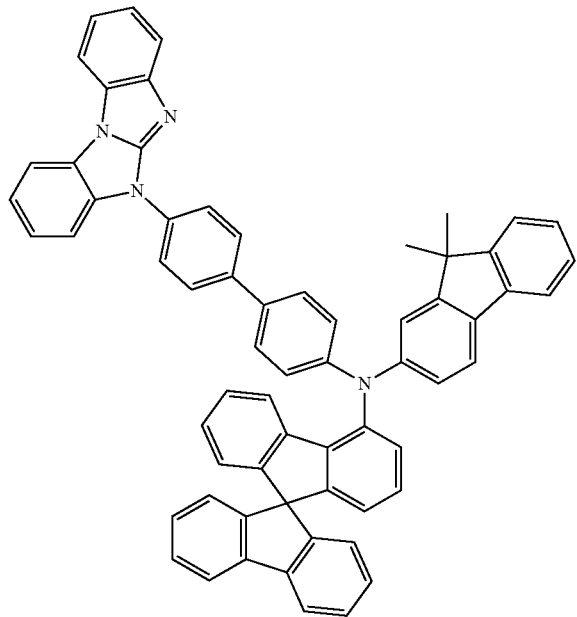 [SMILES: CC1(C)c2ccccc2-c2ccc(N(c3ccc(-c4ccc(-n5c6ccccc6n6c7ccccc7nc56)cc4)cc3)c3cccc4c3-c3ccccc3C43c4ccccc4-c4ccccc43)cc21]
17
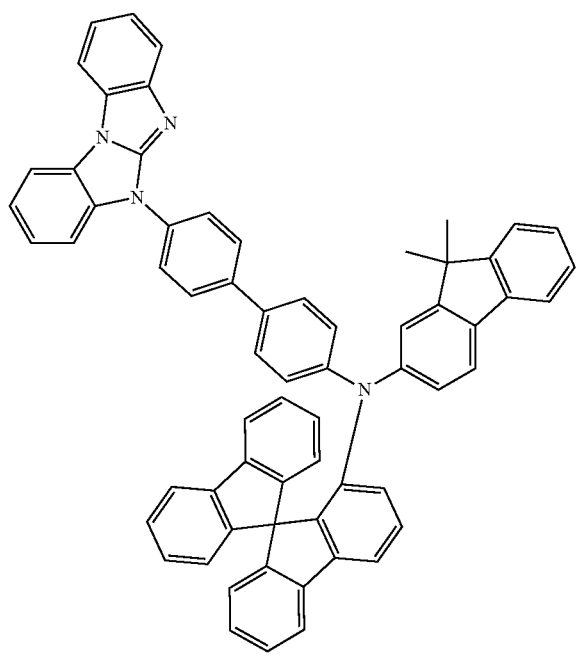 [SMILES: CC1(C)c2ccccc2-c2ccc(N(c3ccc(-c4ccc(-n5c6ccccc6n6c7ccccc7nc56)cc4)cc3)c3cccc4c3C3(c5ccccc5-c5ccccc53)c3ccccc3-4)cc21]
18

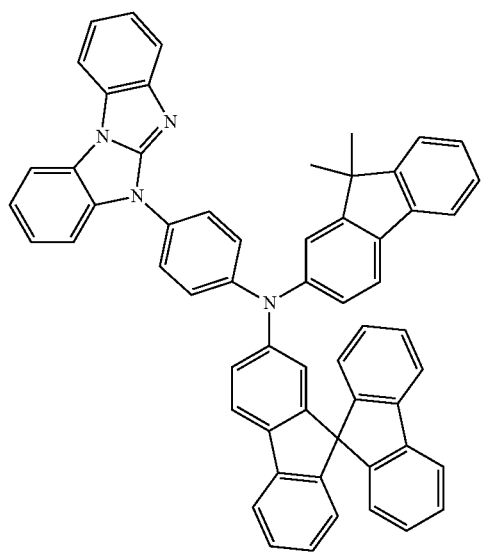 [SMILES: CC1(C)c2ccccc2-c2ccc(N(c3ccc(-n4c5ccccc5n5c6ccccc6nc45)cc3)c3ccc4c(c3)C3(c5ccccc5-c5ccccc53)c3ccccc3-4)cc21]
19
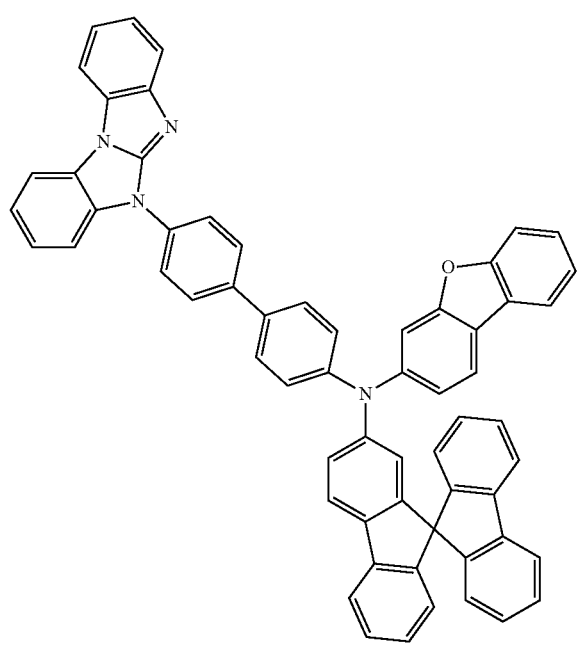 [SMILES: c1ccc2c(c1)-c1ccccc1C21c2ccccc2-c2ccc(N(c3ccc(-c4ccc(-n5c6ccccc6n6c7ccccc7nc56)cc4)cc3)c3ccc4c(c3)oc3ccccc34)cc21]
20

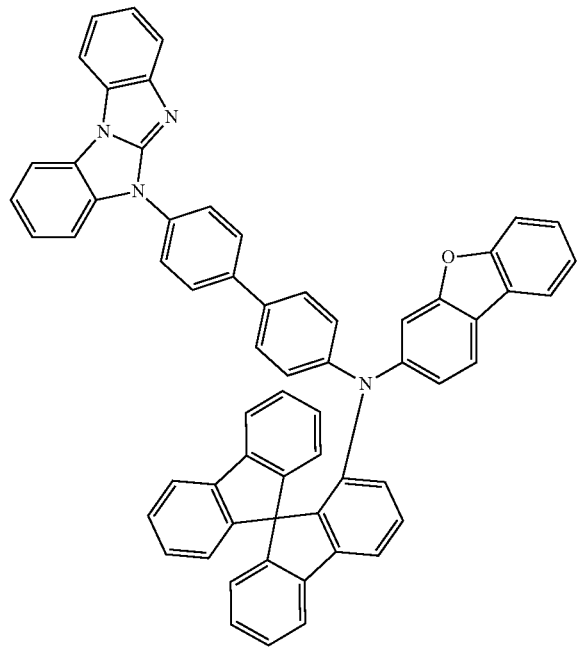 [SMILES: c1ccc2c(c1)-c1ccccc1C21c2ccccc2-c2cccc(N(c3ccc(-c4ccc(-n5c6ccccc6n6c7ccccc7nc56)cc4)cc3)c3ccc4c(c3)oc3ccccc34)c21]
21
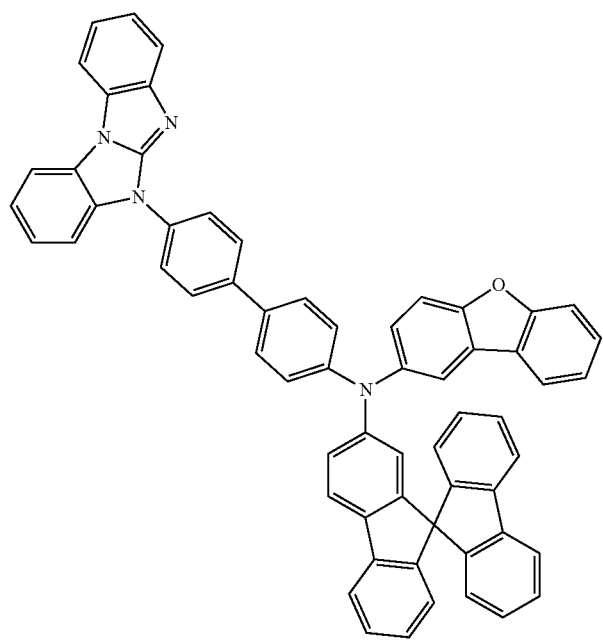
22

-continued
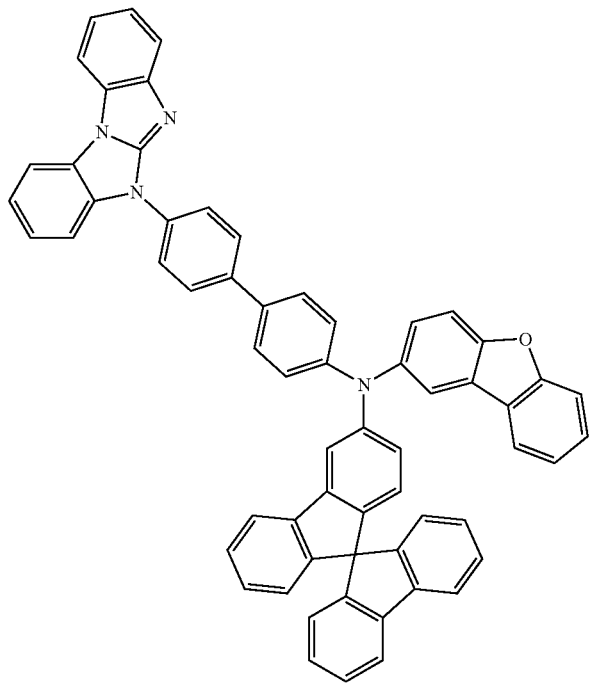 [SMILES: c1ccc2c(c1)-c1ccccc1C21c2ccccc2-c2cc(N(c3ccc(-c4ccc(-n5c6ccccc6n6c7ccccc7nc56)cc4)cc3)c3ccc4oc5ccccc5c4c3)ccc21]
23
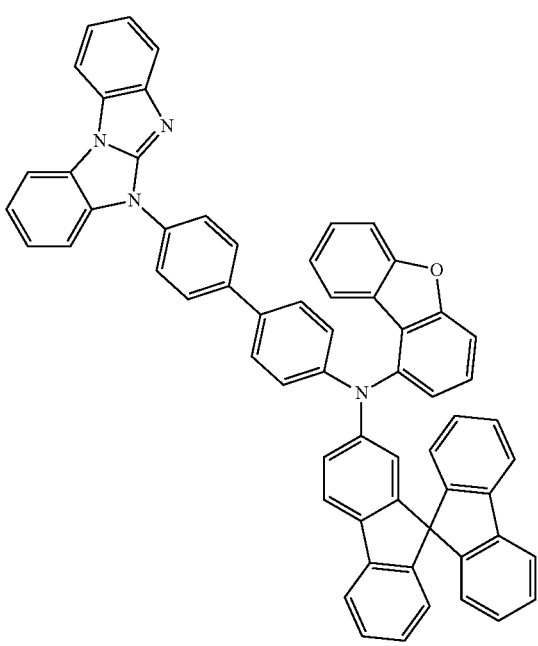 [SMILES: c1ccc2c(c1)-c1ccccc1C21c2ccccc2-c2ccc(N(c3ccc(-c4ccc(-n5c6ccccc6n6c7ccccc7nc56)cc4)cc3)c3cccc4oc5ccccc5c34)cc21]
24

-continued
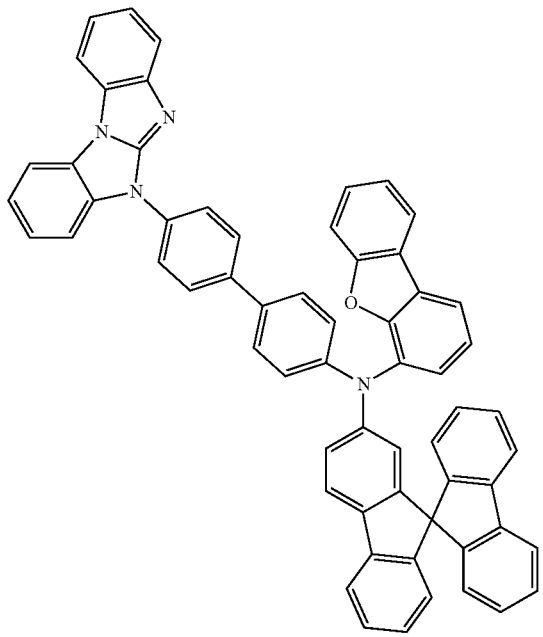 [SMILES: c1ccc2c(c1)-c1ccccc1C21c2ccccc2-c2ccc(N(c3ccc(-c4ccc(-n5c6ccccc6n6c7ccccc7nc56)cc4)cc3)c3cccc4c3oc3ccccc34)cc21]
25
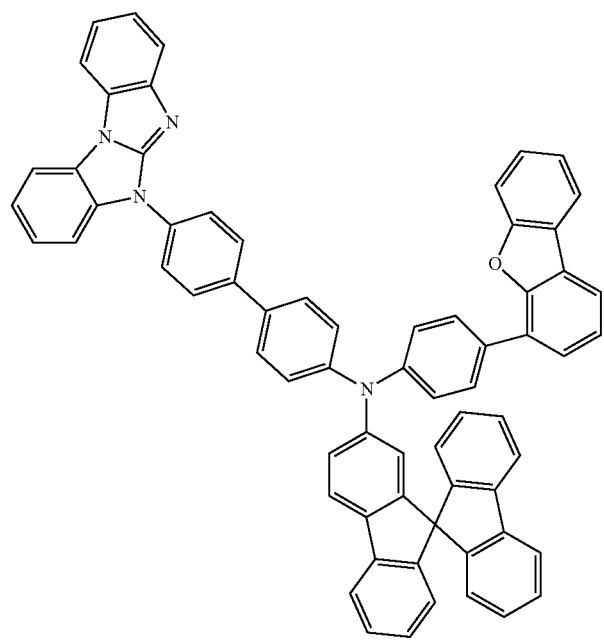 [SMILES: c1ccc2c(c1)-c1ccccc1C21c2ccccc2-c2ccc(N(c3ccc(-c4ccc(-n5c6ccccc6n6c7ccccc7nc56)cc4)cc3)c3ccc(-c4cccc5c4oc4ccccc45)cc3)cc21]
26

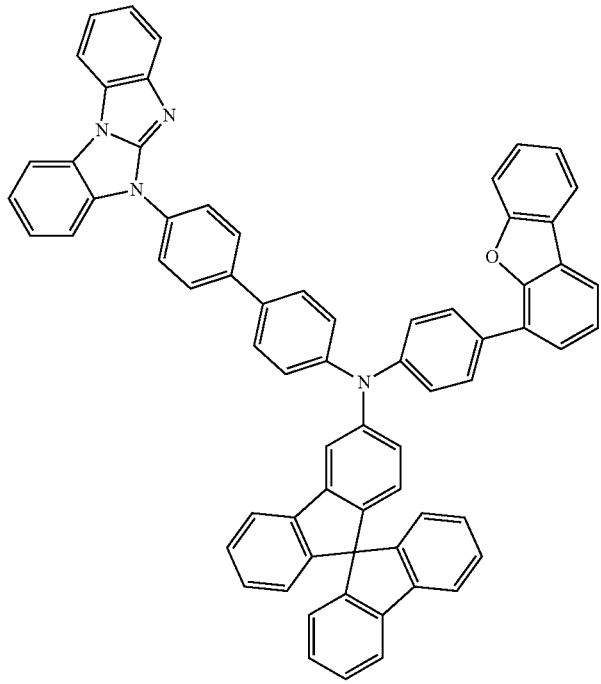 [SMILES: c1ccc2c(c1)-c1ccccc1C21c2ccccc2-c2cc(N(c3ccc(-c4ccc(-n5c6ccccc6n6c7ccccc7nc56)cc4)cc3)c3ccc(-c4cccc5c4oc4ccccc45)cc3)ccc21]
27
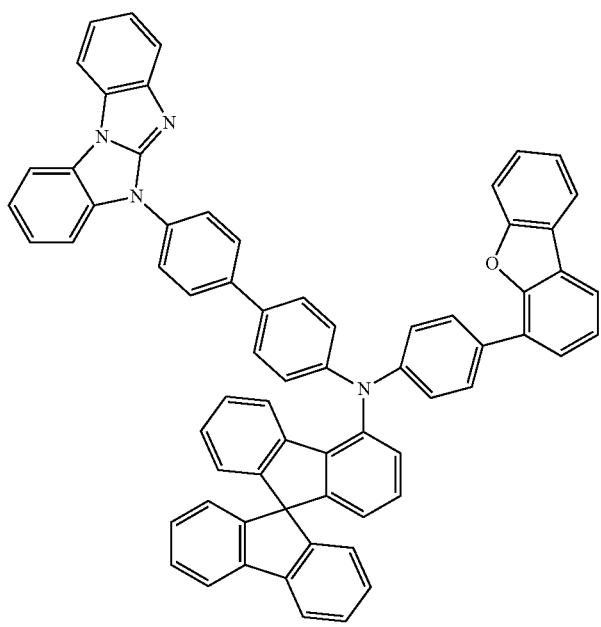 [SMILES: c1ccc2c(c1)-c1ccccc1C21c2ccccc2-c2c(N(c3ccc(-c4ccc(-n5c6ccccc6n6c7ccccc7nc56)cc4)cc3)c3ccc(-c4cccc5c4oc4ccccc45)cc3)cccc21]
28

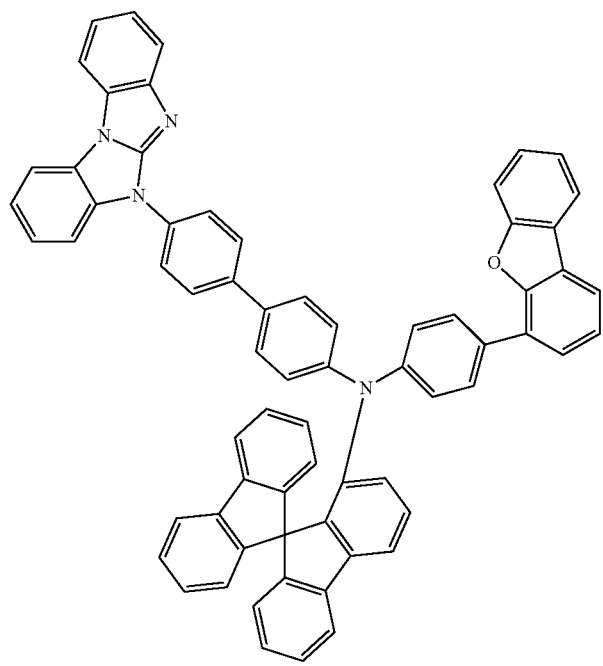 [SMILES: c1ccc2c(c1)-c1ccccc1C21c2ccccc2-c2cccc(N(c3ccc(-c4ccc(-n5c6ccccc6n6c7ccccc7nc56)cc4)cc3)c3ccc(-c4cccc5c4oc4ccccc45)cc3)c21]
29
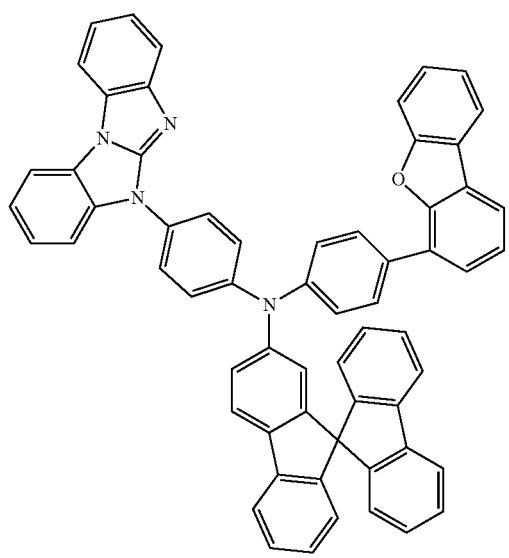 [SMILES: c1ccc2c(c1)-c1ccccc1C21c2ccccc2-c2ccc(N(c3ccc(-c4cccc5c4oc4ccccc45)cc3)c3ccc(-n4c5ccccc5n5c6ccccc6nc45)cc3)cc21]
30

-continued
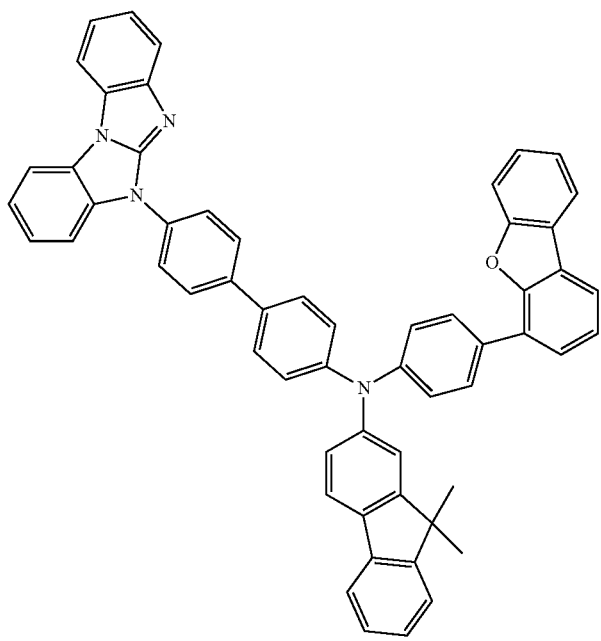
31
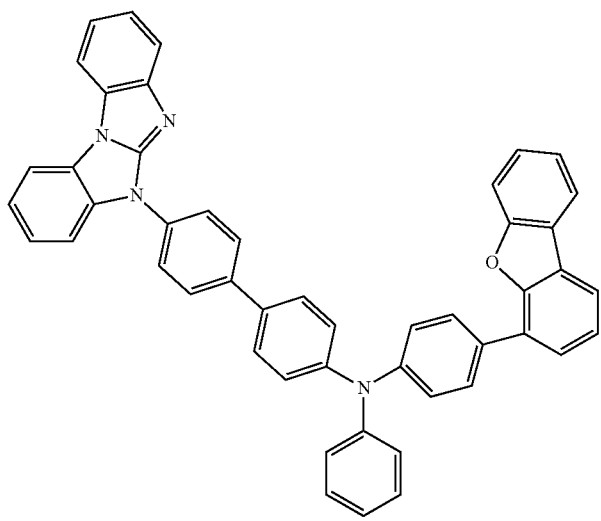 [SMILES: c1ccc(N(c2ccc(-c3ccc(-n4c5ccccc5n5c6ccccc6nc45)cc3)cc2)c2ccc(-c3cccc4c3oc3ccccc34)cc2)cc1]
32

33
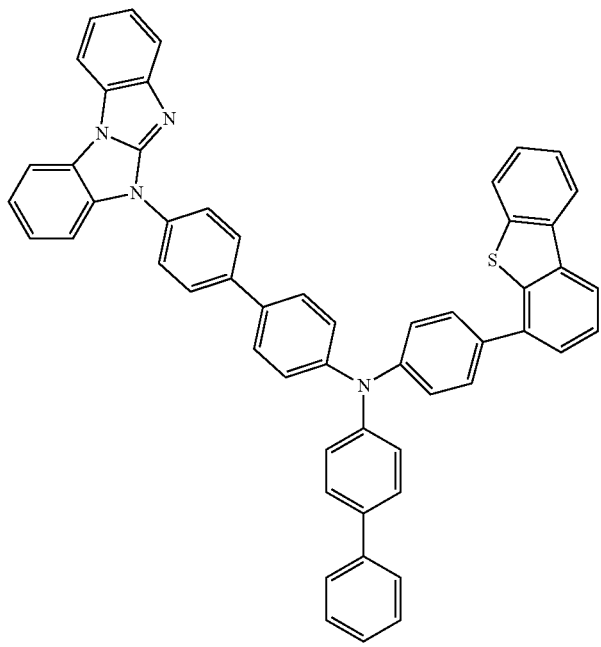 [SMILES: c1ccc(-c2ccc(N(c3ccc(-c4ccc(-n5c6ccccc6n6c7ccccc7nc56)cc4)cc3)c3ccc(-c4cccc5c4sc4ccccc45)cc3)cc2)cc1]
34
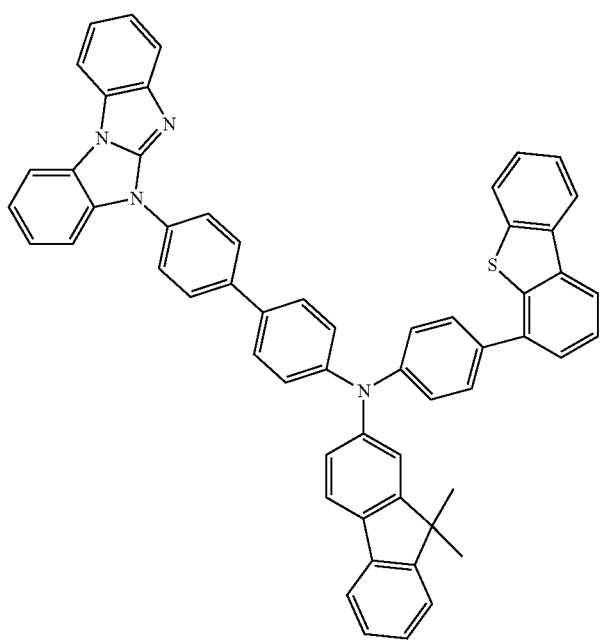 [SMILES: CC1(C)c2ccccc2-c2ccc(N(c3ccc(-c4ccc(-n5c6ccccc6n6c7ccccc7nc56)cc4)cc3)c3ccc(-c4cccc5c4sc4ccccc45)cc3)cc21]

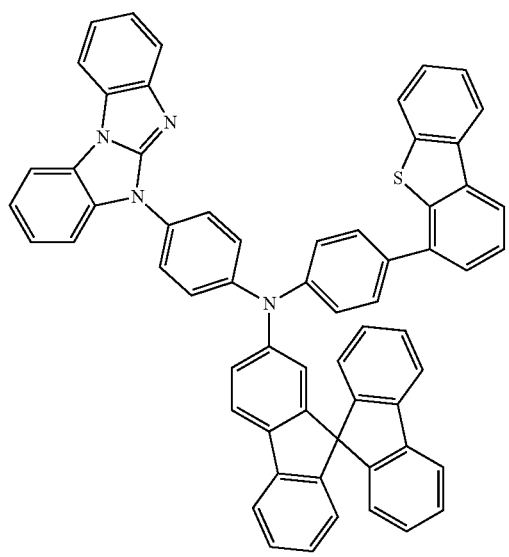 [SMILES: c1ccc2c(c1)-c1ccccc1C21c2ccccc2-c2ccc(N(c3ccc(-c4cccc5c4sc4ccccc45)cc3)c3ccc(-n4c5ccccc5n5c6ccccc6nc45)cc3)cc21]
35
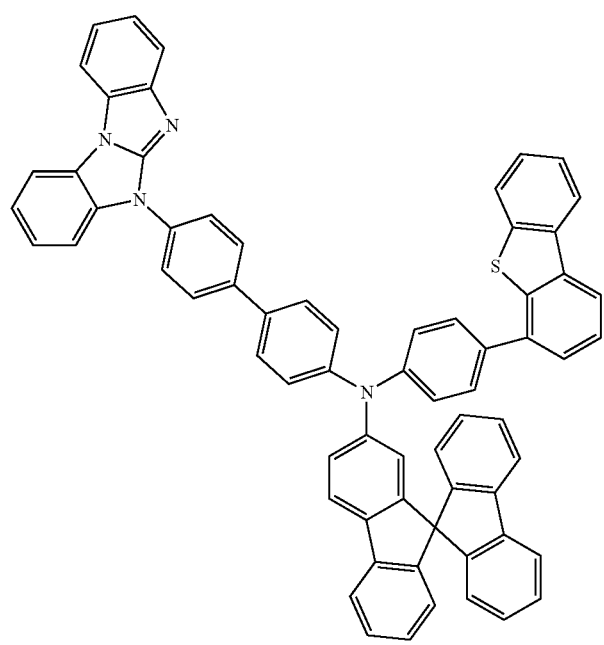
36

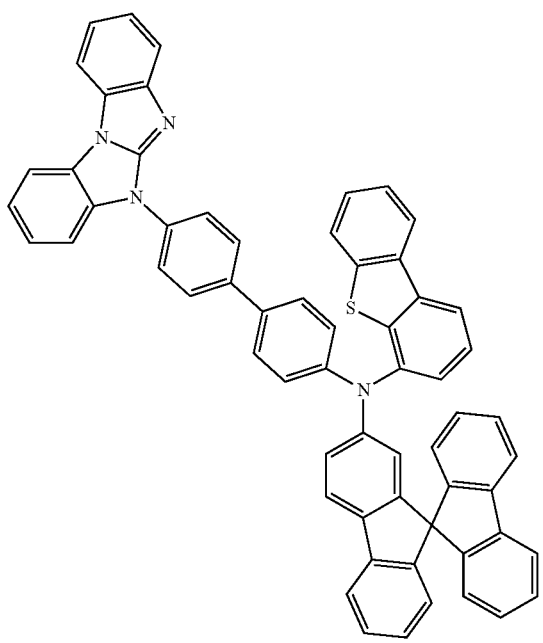 [SMILES: c1ccc2c(c1)-c1ccccc1C21c2ccccc2-c2ccc(N(c3ccc(-c4ccc(-n5c6ccccc6n6c7ccccc7nc56)cc4)cc3)c3cccc4c3sc3ccccc34)cc21]
37
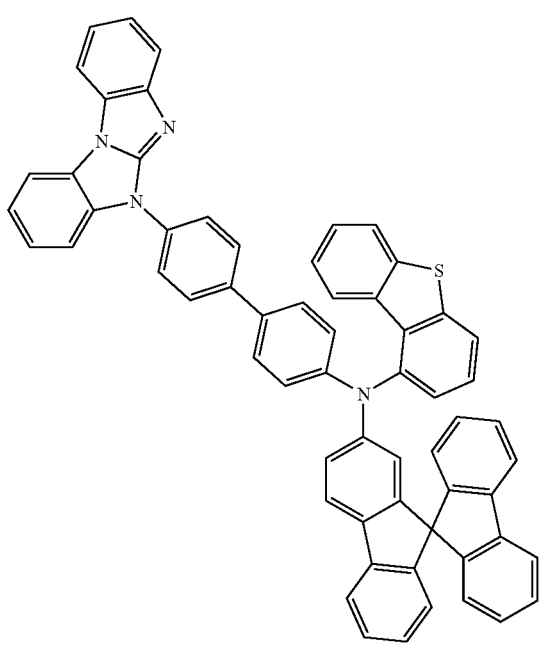
38

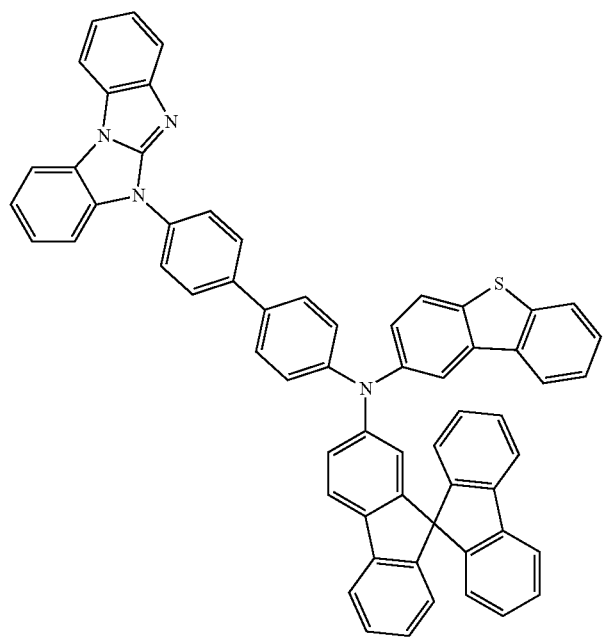 [SMILES: c1ccc2c(c1)-c1ccccc1C21c2ccccc2-c2ccc(N(c3ccc(-c4ccc(-n5c6ccccc6n6c7ccccc7nc56)cc4)cc3)c3ccc4sc5ccccc5c4c3)cc21]
39
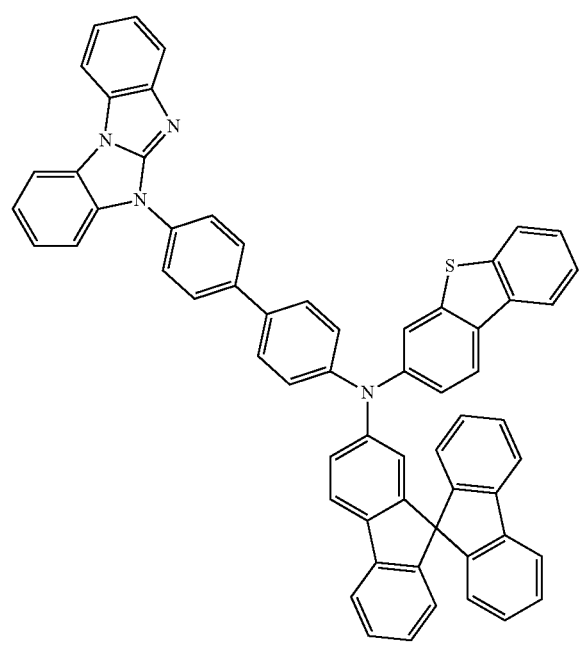
40

-continued
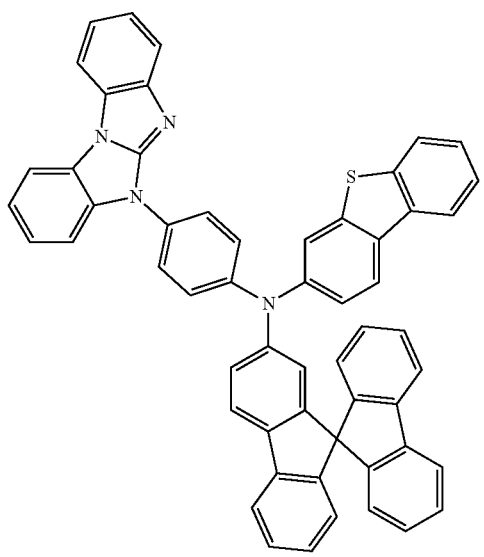 [SMILES: c1ccc2c(c1)-c1ccccc1C21c2ccccc2-c2ccc(N(c3ccc(-n4c5ccccc5n5c6ccccc6nc45)cc3)c3ccc4c(c3)sc3ccccc34)cc21]
41
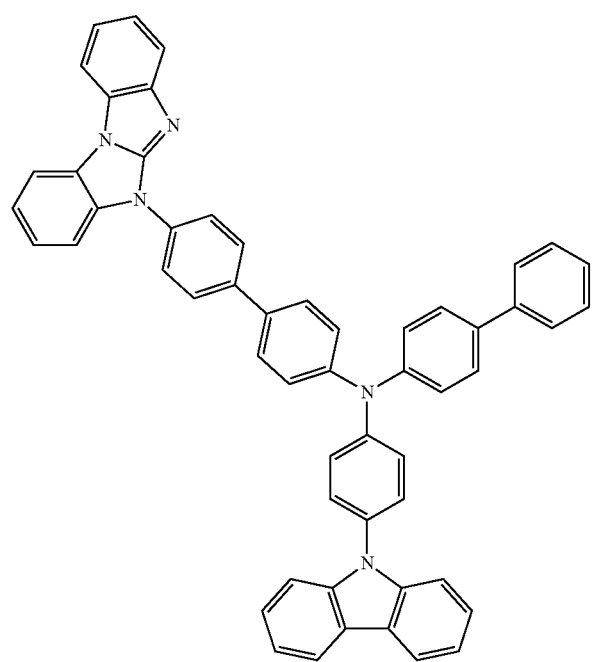 [SMILES: c1ccc(-c2ccc(N(c3ccc(-c4ccc(-n5c6ccccc6n6c7ccccc7nc56)cc4)cc3)c3ccc(-n4c5ccccc5c5ccccc54)cc3)cc2)cc1]
42

-continued
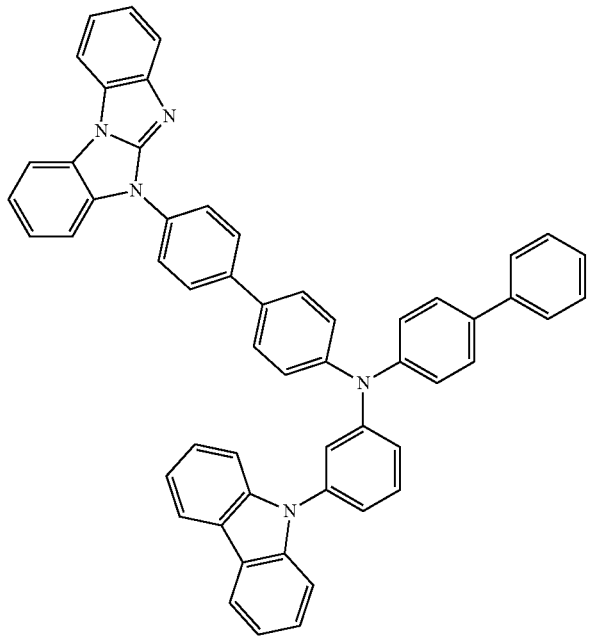 [SMILES: c1ccc(-c2ccc(N(c3ccc(-c4ccc(-n5c6ccccc6n6c7ccccc7nc56)cc4)cc3)c3cccc(-n4c5ccccc5c5ccccc54)c3)cc2)cc1]
43
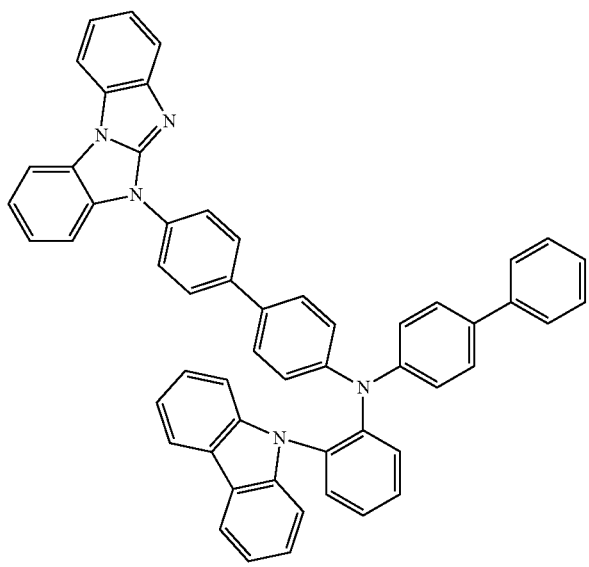 [SMILES: c1ccc(-c2ccc(N(c3ccc(-c4ccc(-n5c6ccccc6n6c7ccccc7nc56)cc4)cc3)c3ccccc3-n3c4ccccc4c4ccccc43)cc2)cc1]
44

-continued
45
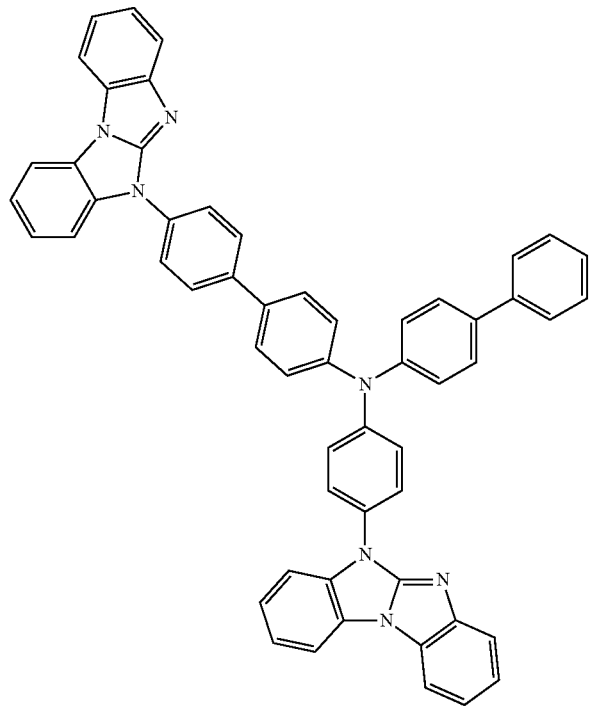 [SMILES: c1ccc(-c2ccc(N(c3ccc(-c4ccc(-n5c6ccccc6n6c7ccccc7nc56)cc4)cc3)c3ccc(-n4c5ccccc5n5c6ccccc6nc45)cc3)cc2)cc1]
46
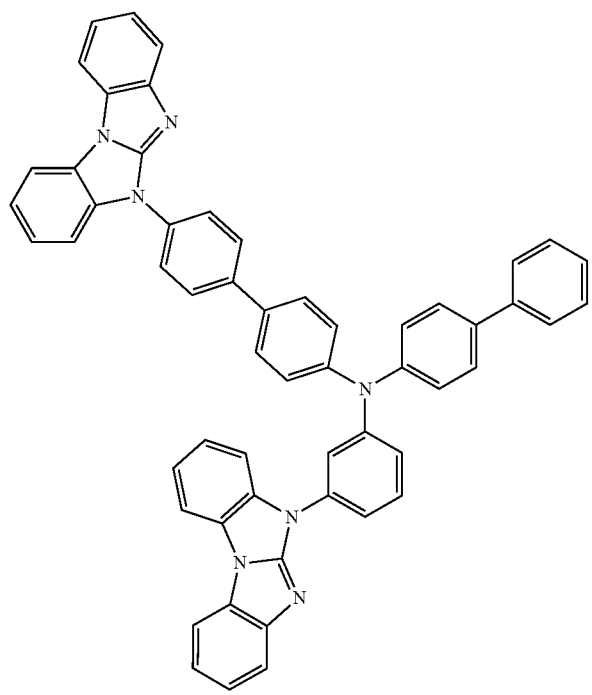 [SMILES: c1ccc(-c2ccc(N(c3ccc(-c4ccc(-n5c6ccccc6n6c7ccccc7nc56)cc4)cc3)c3cccc(-n4c5ccccc5n5c6ccccc6nc45)c3)cc2)cc1]

-continued
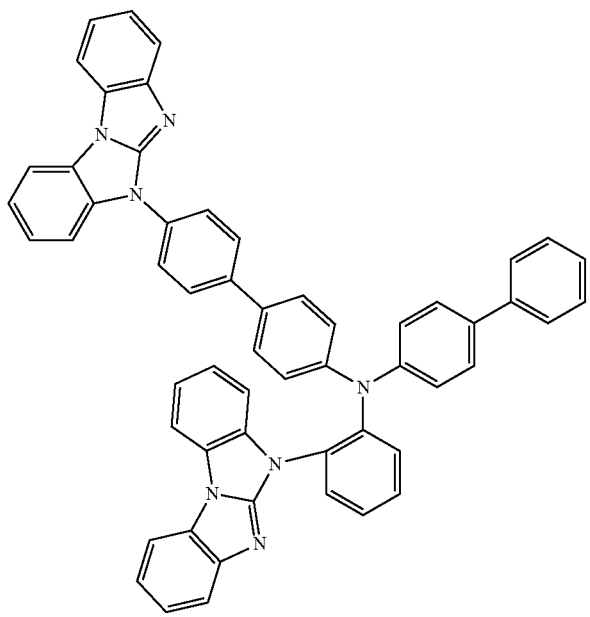 [SMILES: c1ccc(-c2ccc(N(c3ccc(-c4ccc(-n5c6ccccc6n6c7ccccc7nc56)cc4)cc3)c3ccccc3-n3c4ccccc4n4c5ccccc5nc34)cc2)cc1]
47
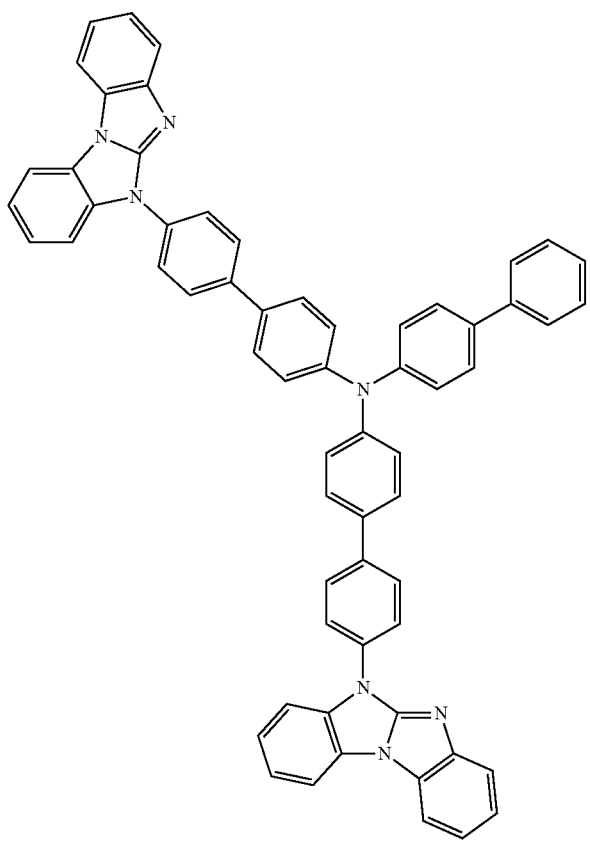 [SMILES: c1ccc(-c2ccc(N(c3ccc(-c4ccc(-n5c6ccccc6n6c7ccccc7nc56)cc4)cc3)c3ccc(-c4ccc(-n5c6ccccc6n6c7ccccc7nc56)cc4)cc3)cc2)cc1]
48

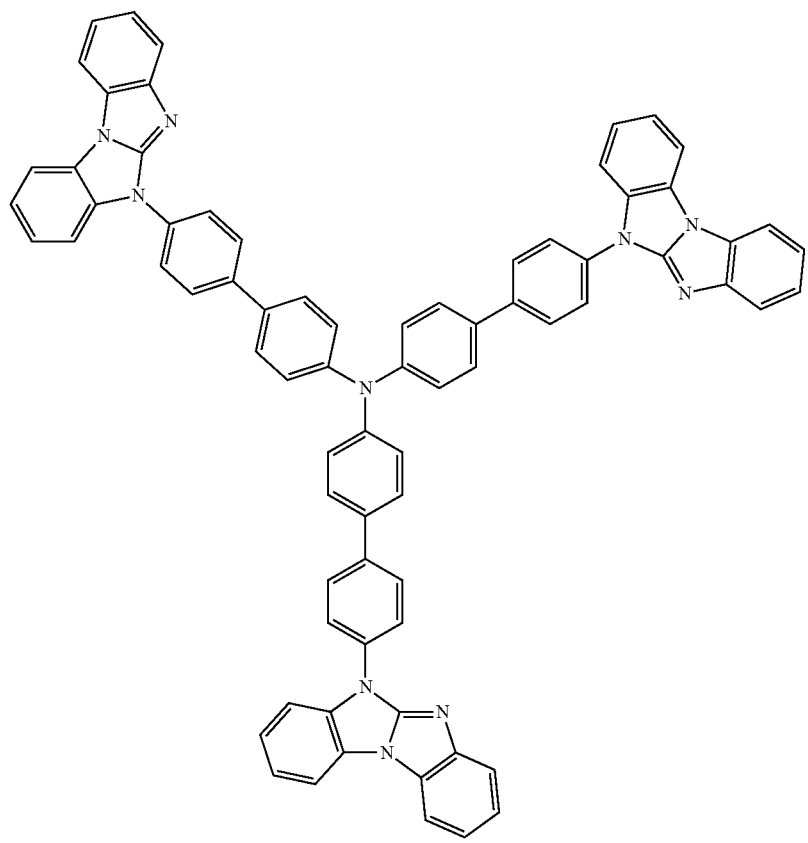 [SMILES: c1ccc2c(c1)nc1n(-c3ccc(-c4ccc(N(c5ccc(-c6ccc(-n7c8ccccc8n8c9ccccc9nc78)cc6)cc5)c5ccc(-c6ccc(-n7c8ccccc8n8c9ccccc9nc78)cc6)cc5)cc4)cc3)c3ccccc3n21]
49
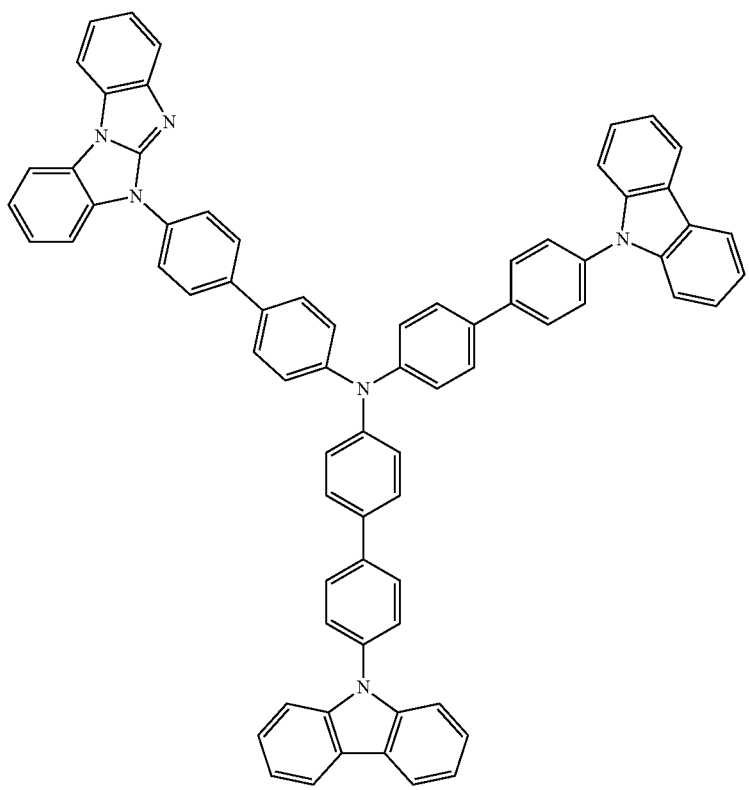 [SMILES: c1ccc2c(c1)nc1n(-c3ccc(-c4ccc(N(c5ccc(-c6ccc(-n7c8ccccc8c8ccccc87)cc6)cc5)c5ccc(-c6ccc(-n7c8ccccc8c8ccccc87)cc6)cc5)cc4)cc3)c3ccccc3n21]
50

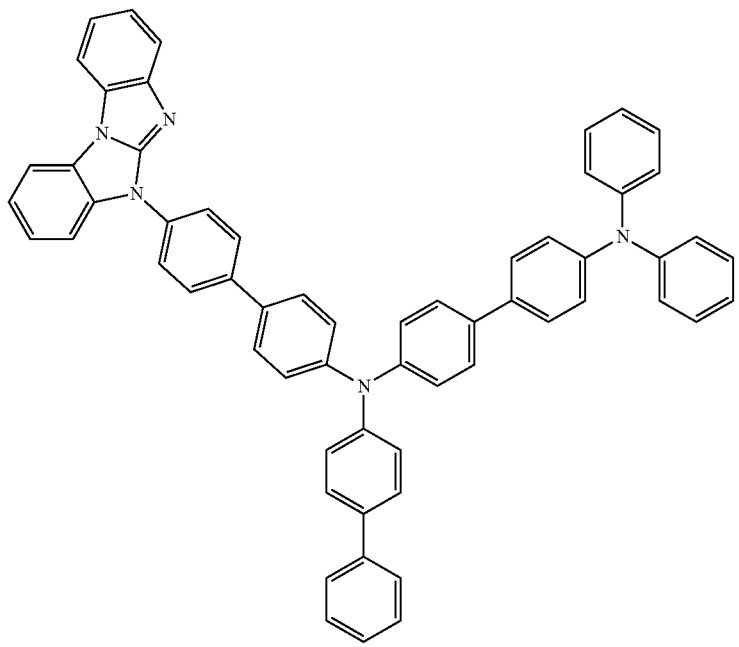 [SMILES: c1ccc(-c2ccc(N(c3ccc(-c4ccc(N(c5ccccc5)c5ccccc5)cc4)cc3)c3ccc(-c4ccc(-n5c6ccccc6n6c7ccccc7nc56)cc4)cc3)cc2)cc1]
51
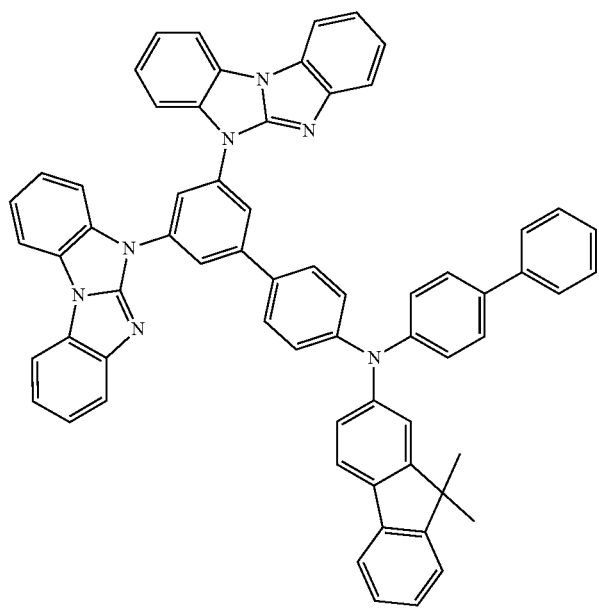 [SMILES: CC1(C)c2ccccc2-c2ccc(N(c3ccc(-c4ccccc4)cc3)c3ccc(-c4cc(-n5c6ccccc6n6c7ccccc7nc56)cc(-n5c6ccccc6n6c7ccccc7nc56)c4)cc3)cc21]
52

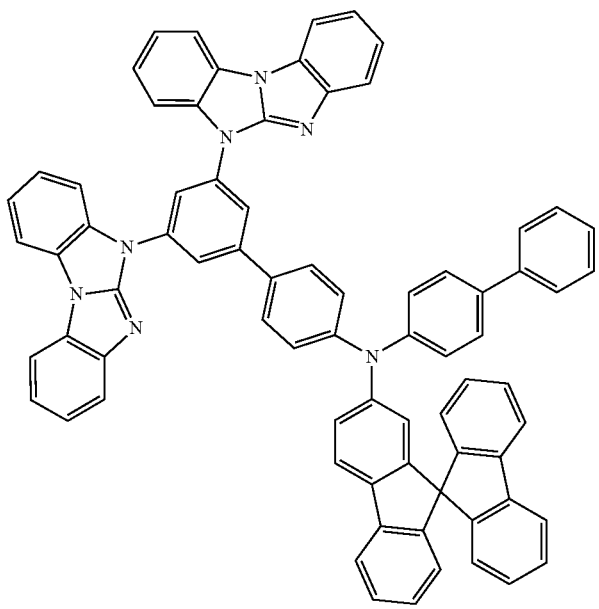 [SMILES: c1ccc(-c2ccc(N(c3ccc(-c4cc(-n5c6ccccc6n6c7ccccc7nc56)cc(-n5c6ccccc6n6c7ccccc7nc56)c4)cc3)c3ccc4c(c3)C3(c5ccccc5-c5ccccc53)c3ccccc3-4)cc2)cc1]
53
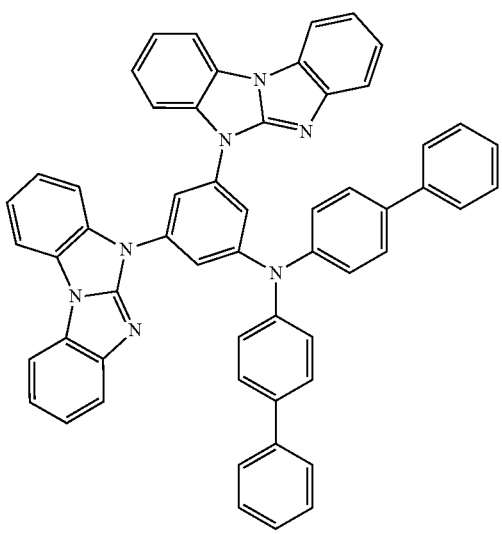 [SMILES: c1ccc(-c2ccc(N(c3ccc(-c4ccccc4)cc3)c3cc(-n4c5ccccc5n5c6ccccc6nc45)cc(-n4c5ccccc5n5c6ccccc6nc45)c3)cc2)cc1]
54
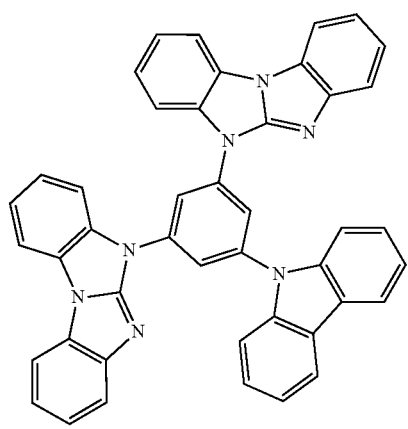 [SMILES: c1ccc2c(c1)nc1n(-c3cc(-n4c5ccccc5c5ccccc54)cc(-n4c5ccccc5n5c6ccccc6nc45)c3)c3ccccc3n21]
55

-continued
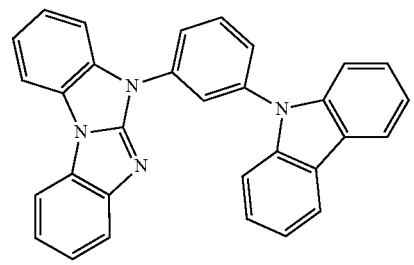 [SMILES: c1cc(-n2c3ccccc3c3ccccc32)cc(-n2c3ccccc3n3c4ccccc4nc23)c1]
56
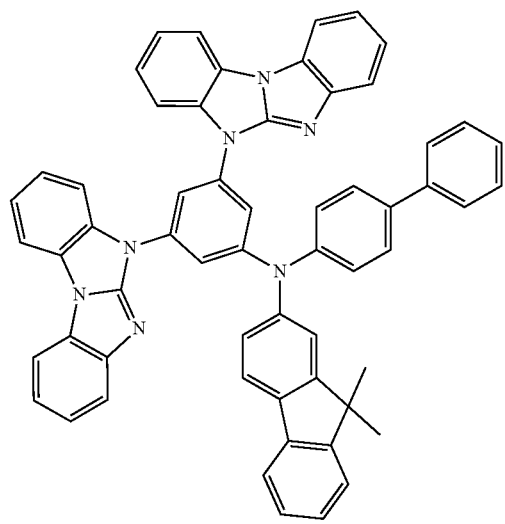 [SMILES: CC1(C)c2ccccc2-c2ccc(N(c3ccc(-c4ccccc4)cc3)c3cc(-n4c5ccccc5n5c6ccccc6nc45)cc(-n4c5ccccc5n5c6ccccc6nc45)c3)cc21]
57
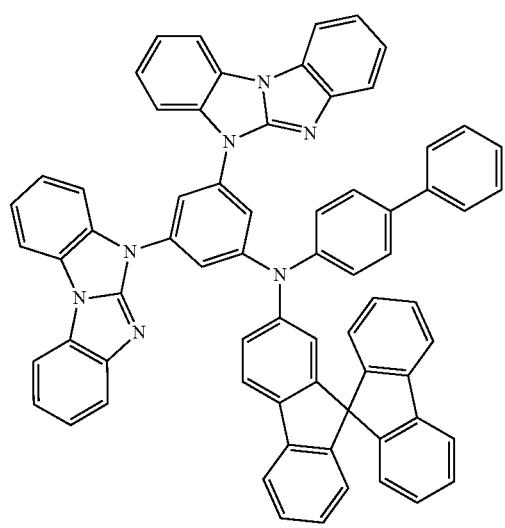 [SMILES: c1ccc(-c2ccc(N(c3cc(-n4c5ccccc5n5c6ccccc6nc45)cc(-n4c5ccccc5n5c6ccccc6nc45)c3)c3ccc4c(c3)C3(c5ccccc5-c5ccccc53)c3ccccc3-4)cc2)cc1]
58

-continued
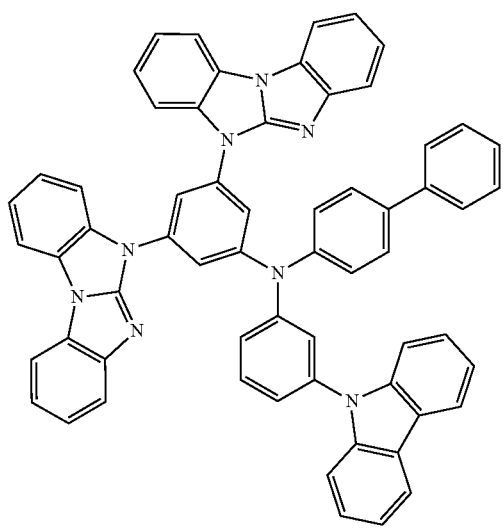 [SMILES: c1ccc(-c2ccc(N(c3cccc(-n4c5ccccc5c5ccccc54)c3)c3cc(-n4c5ccccc5n5c6ccccc6nc45)cc(-n4c5ccccc5n5c6ccccc6nc45)c3)cc2)cc1]
59
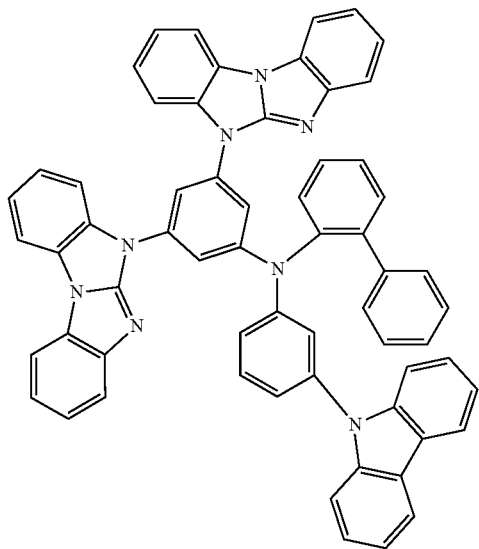 [SMILES: c1ccc(-c2ccccc2N(c2cccc(-n3c4ccccc4c4ccccc43)c2)c2cc(-n3c4ccccc4n4c5ccccc5nc34)cc(-n3c4ccccc4n4c5ccccc5nc34)c2)cc1]
60

-continued
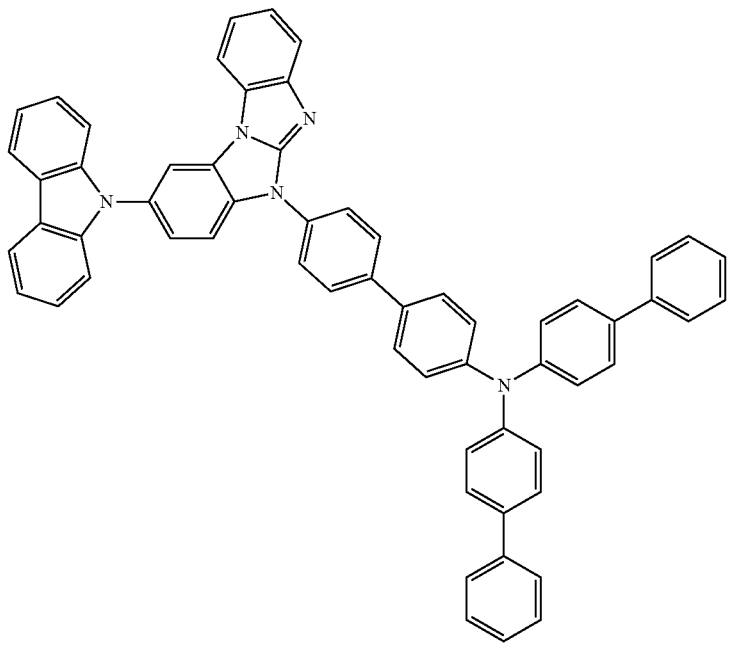 [SMILES: c1ccc(-c2ccc(N(c3ccc(-c4ccccc4)cc3)c3ccc(-c4ccc(-n5c6ccc(-n7c8ccccc8c8ccccc87)cc6n6c7ccccc7nc56)cc4)cc3)cc2)cc1]
61
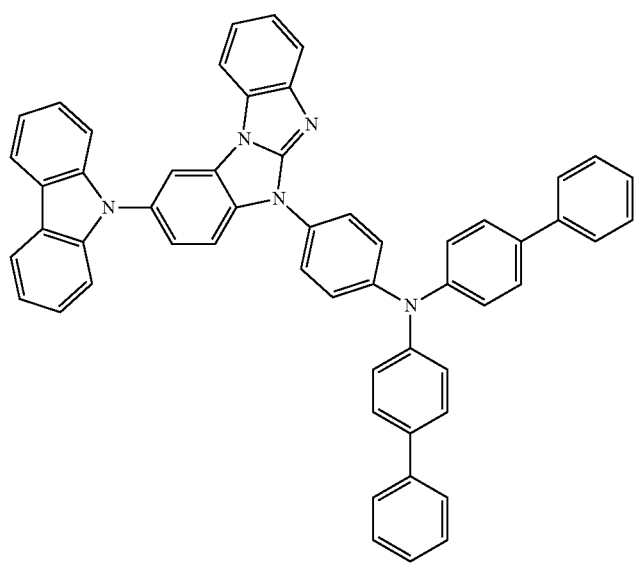 [SMILES: c1ccc(-c2ccc(N(c3ccc(-c4ccccc4)cc3)c3ccc(-n4c5ccc(-n6c7ccccc7c7ccccc76)cc5n5c6ccccc6nc45)cc3)cc2)cc1]
62
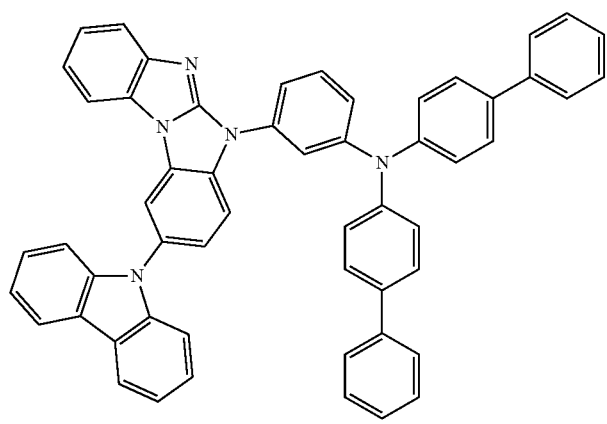 [SMILES: c1ccc(-c2ccc(N(c3ccc(-c4ccccc4)cc3)c3cccc(-n4c5ccc(-n6c7ccccc7c7ccccc76)cc5n5c6ccccc6nc45)c3)cc2)cc1]
63

-continued
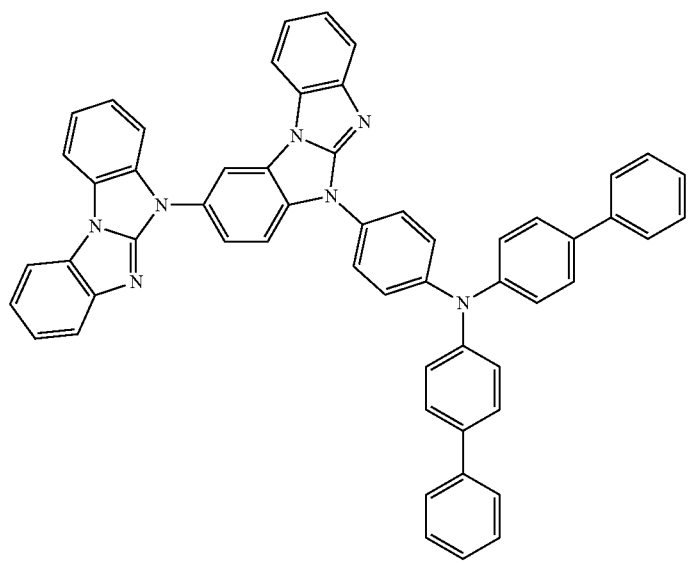 [SMILES: c1ccc(-c2ccc(N(c3ccc(-c4ccccc4)cc3)c3ccc(-n4c5ccc(-n6c7ccccc7n7c8ccccc8nc67)cc5n5c6ccccc6nc45)cc3)cc2)cc1]
64
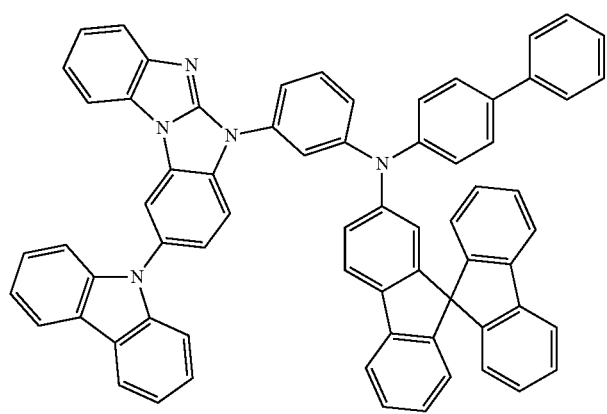 [SMILES: c1ccc(-c2ccc(N(c3cccc(-n4c5ccc(-n6c7ccccc7c7ccccc76)cc5n5c6ccccc6nc45)c3)c3ccc4c(c3)C3(c5ccccc5-c5ccccc53)c3ccccc3-4)cc2)cc1]
65
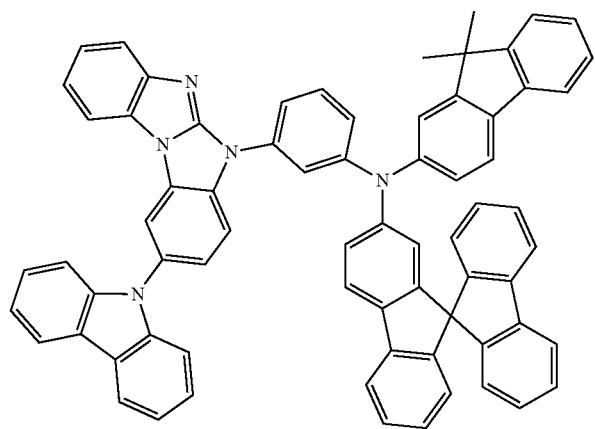 [SMILES: CC1(C)c2ccccc2-c2ccc(N(c3cccc(-n4c5ccc(-n6c7ccccc7c7ccccc76)cc5n5c6ccccc6nc45)c3)c3ccc4c(c3)C3(c5ccccc5-c5ccccc53)c3ccccc3-4)cc21]
66

-continued
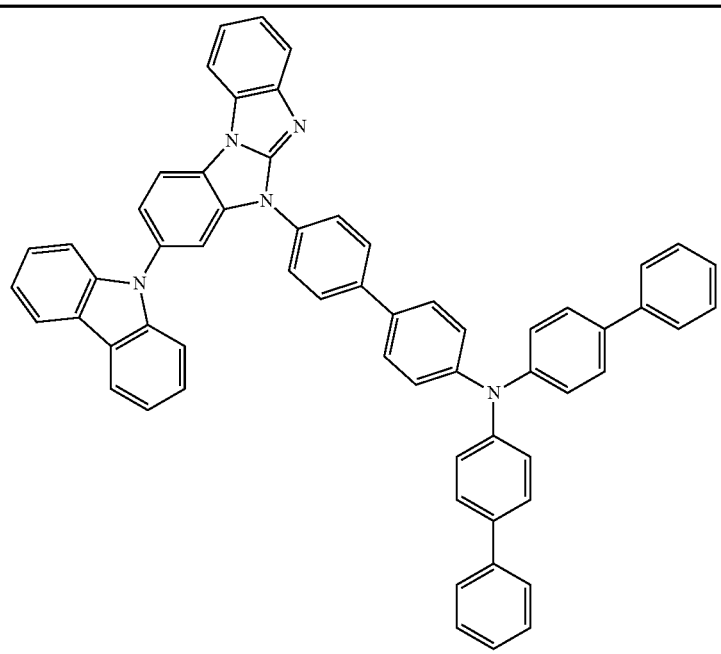
67
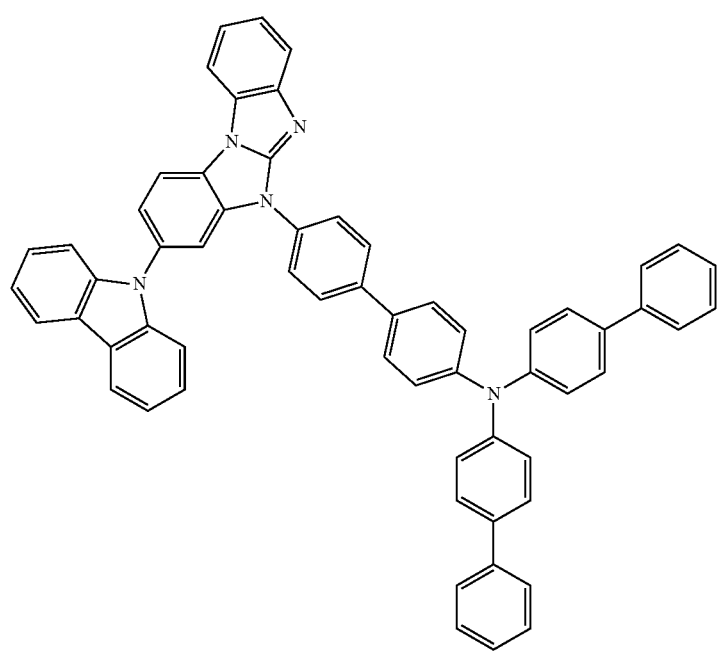 [SMILES: c1ccc(-c2ccc(N(c3ccc(-c4ccccc4)cc3)c3ccc(-c4ccc(-n5c6cc(-n7c8ccccc8c8ccccc87)ccc6n6c7ccccc7nc56)cc4)cc3)cc2)cc1]
68

-continued
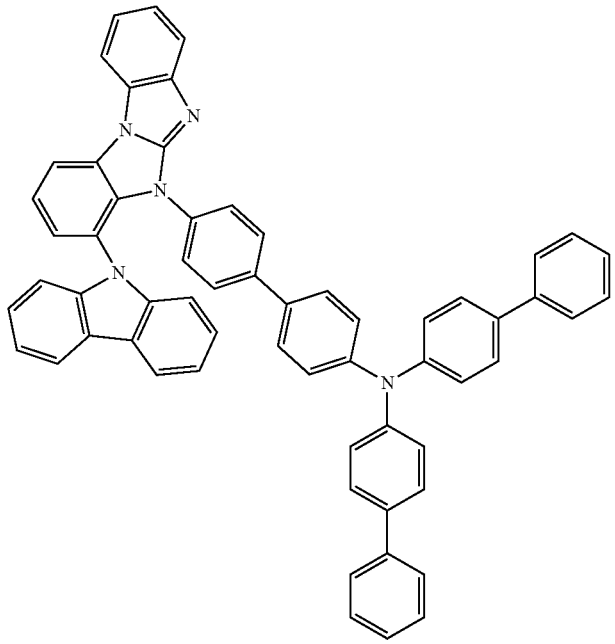 [SMILES: c1ccc(-c2ccc(N(c3ccc(-c4ccccc4)cc3)c3ccc(-c4ccc(-n5c6c(-n7c8ccccc8c8ccccc87)cccc6n6c7ccccc7nc56)cc4)cc3)cc2)cc1]
69
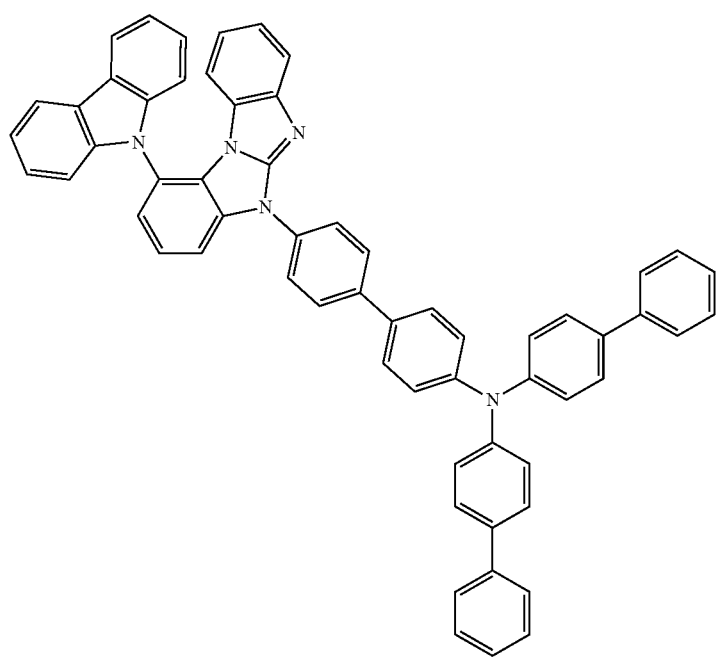 [SMILES: c1ccc(-c2ccc(N(c3ccc(-c4ccccc4)cc3)c3ccc(-c4ccc(-n5c6cccc(-n7c8ccccc8c8ccccc87)c6n6c7ccccc7nc56)cc4)cc3)cc2)cc1]
70

-continued
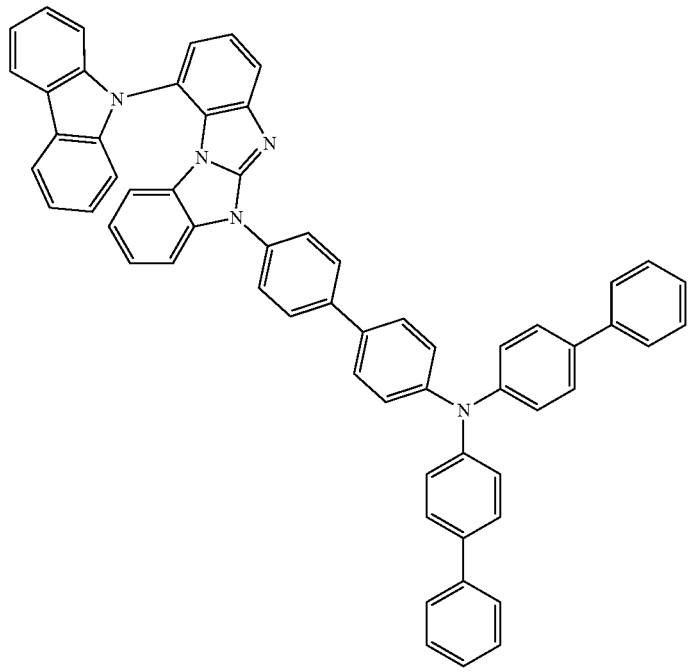 [SMILES: c1ccc(-c2ccc(N(c3ccc(-c4ccccc4)cc3)c3ccc(-c4ccc(-n5c6ccccc6n6c7c(-n8c9ccccc9c9ccccc98)cccc7nc56)cc4)cc3)cc2)cc1]
71
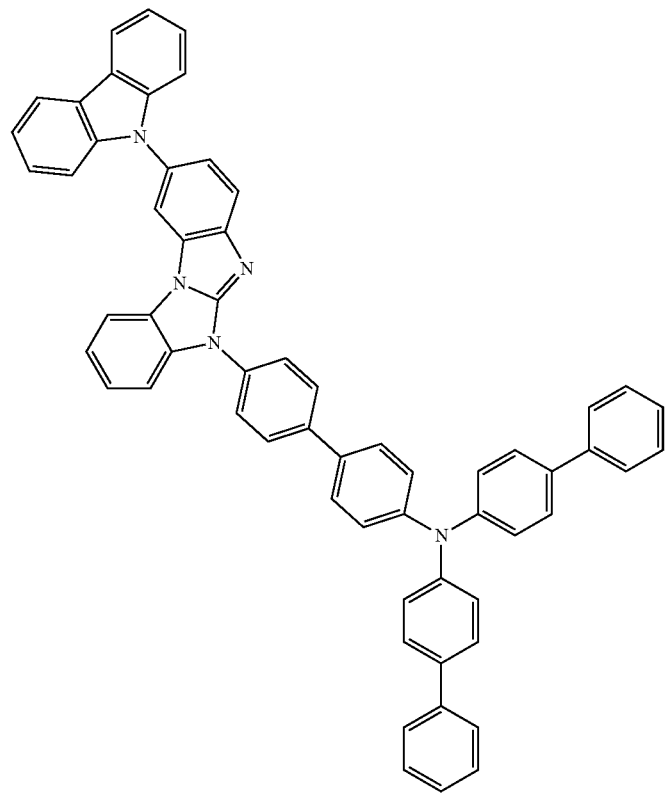 [SMILES: c1ccc(-c2ccc(N(c3ccc(-c4ccccc4)cc3)c3ccc(-c4ccc(-n5c6ccccc6n6c7cc(-n8c9ccccc9c9ccccc98)ccc7nc56)cc4)cc3)cc2)cc1]
72

-continued
73
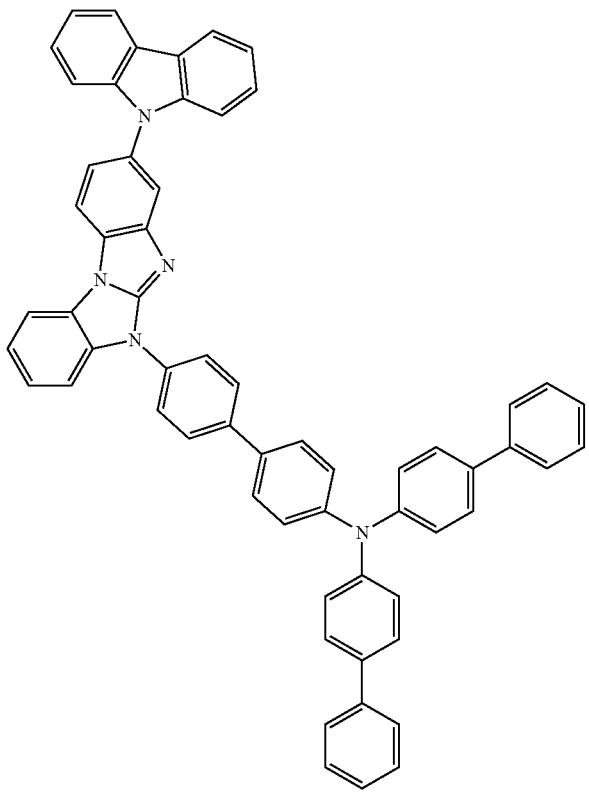 [SMILES: c1ccc(-c2ccc(N(c3ccc(-c4ccccc4)cc3)c3ccc(-c4ccc(-n5c6ccccc6n6c7ccc(-n8c9ccccc9c9ccccc98)cc7nc56)cc4)cc3)cc2)cc1]
74
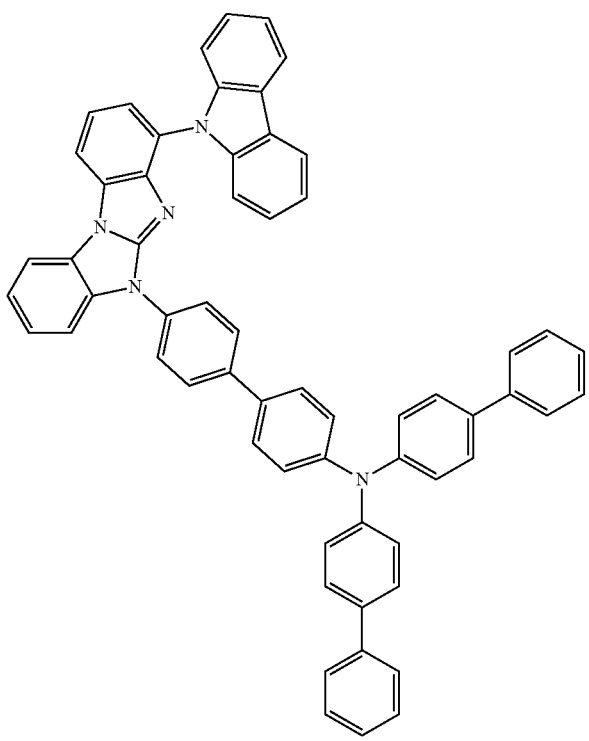 [SMILES: c1ccc(-c2ccc(N(c3ccc(-c4ccccc4)cc3)c3ccc(-c4ccc(-n5c6ccccc6n6c7cccc(-n8c9ccccc9c9ccccc98)c7nc56)cc4)cc3)cc2)cc1]

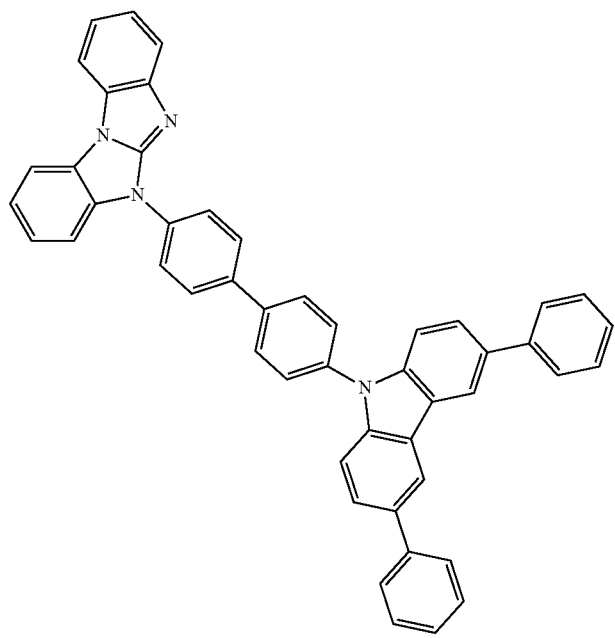 [SMILES: c1ccc(-c2ccc3c(c2)c2cc(-c4ccccc4)ccc2n3-c2ccc(-c3ccc(-n4c5ccccc5n5c6ccccc6nc45)cc3)cc2)cc1]
75
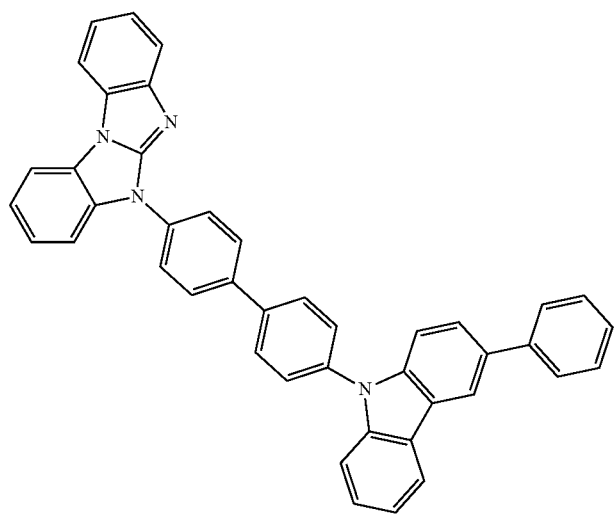 [SMILES: c1ccc(-c2ccc3c(c2)c2ccccc2n3-c2ccc(-c3ccc(-n4c5ccccc5n5c6ccccc6nc45)cc3)cc2)cc1]
76

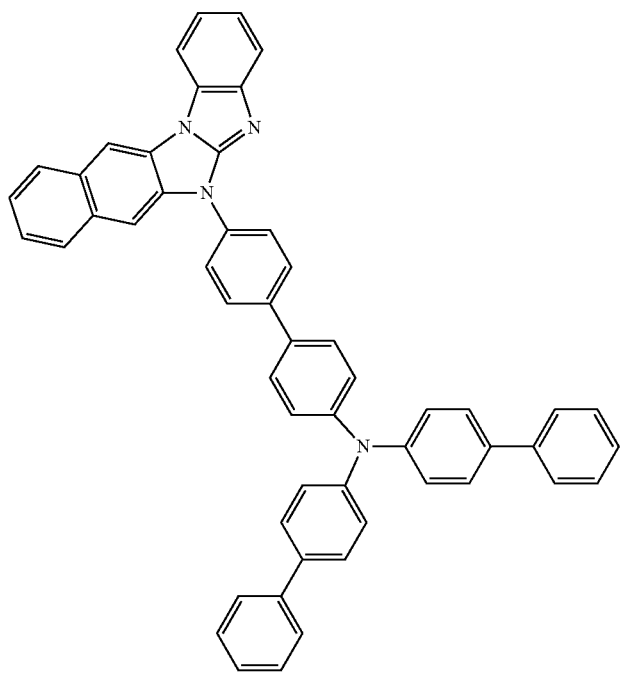 [SMILES: c1ccc(-c2ccc(N(c3ccc(-c4ccccc4)cc3)c3ccc(-c4ccc(-n5c6cc7ccccc7cc6n6c7ccccc7nc56)cc4)cc3)cc2)cc1]
77
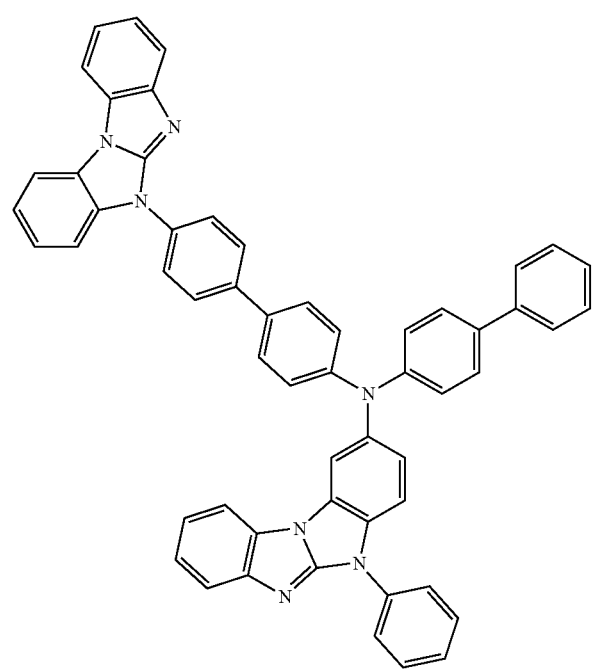 [SMILES: c1ccc(-c2ccc(N(c3ccc(-c4ccc(-n5c6ccccc6n6c7ccccc7nc56)cc4)cc3)c3ccc4c(c3)n3c5ccccc5nc3n4-c3ccccc3)cc2)cc1]
78

-continued
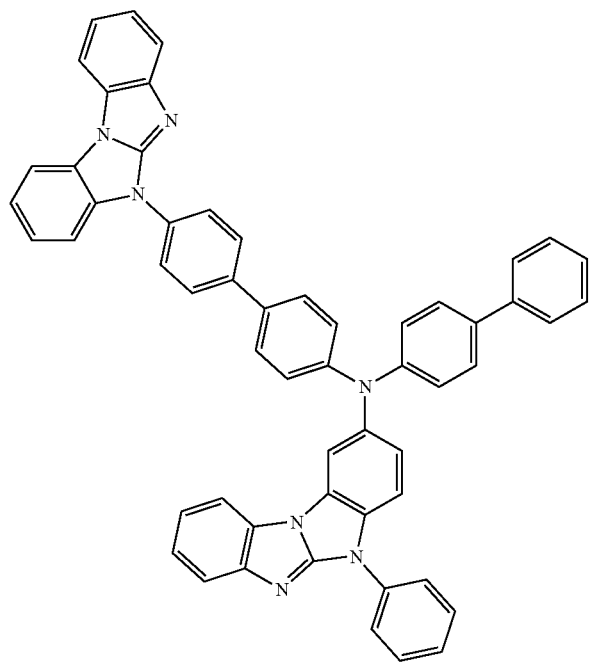 [SMILES: c1ccc(-c2ccc(N(c3ccc(-c4ccc(-n5c6ccccc6n6c7ccccc7nc56)cc4)cc3)c3ccc4c(c3)n3c5ccccc5nc3n4-c3ccccc3)cc2)cc1]
79
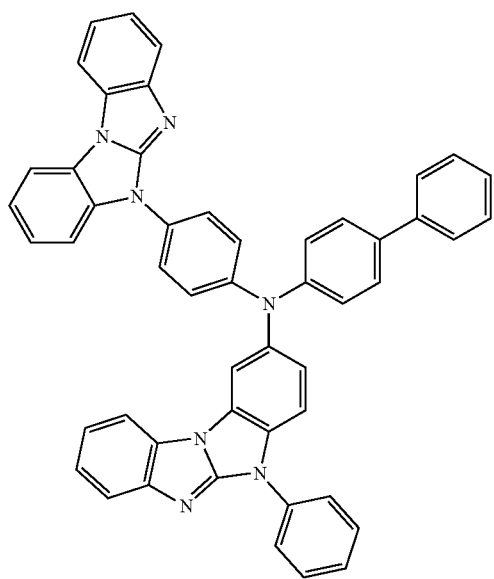 [SMILES: c1ccc(-c2ccc(N(c3ccc(-n4c5ccccc5n5c6ccccc6nc45)cc3)c3ccc4c(c3)n3c5ccccc5nc3n4-c3ccccc3)cc2)cc1]
80

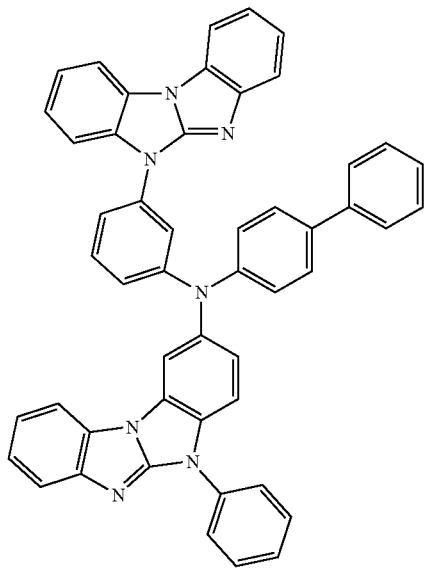 [SMILES: c1ccc(-c2ccc(N(c3cccc(-n4c5ccccc5n5c6ccccc6nc45)c3)c3ccc4c(c3)n3c5ccccc5nc3n4-c3ccccc3)cc2)cc1]
81
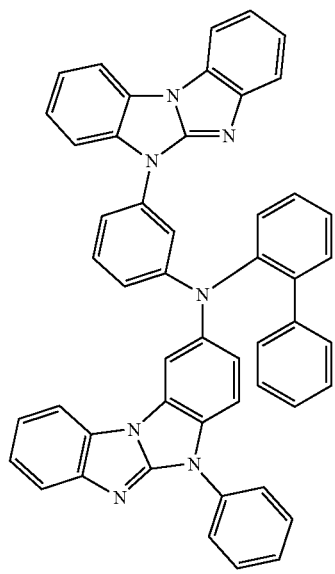 [SMILES: c1ccc(-c2ccccc2N(c2cccc(-n3c4ccccc4n4c5ccccc5nc34)c2)c2ccc3c(c2)n2c4ccccc4nc2n3-c2ccccc2)cc1]
82

-continued
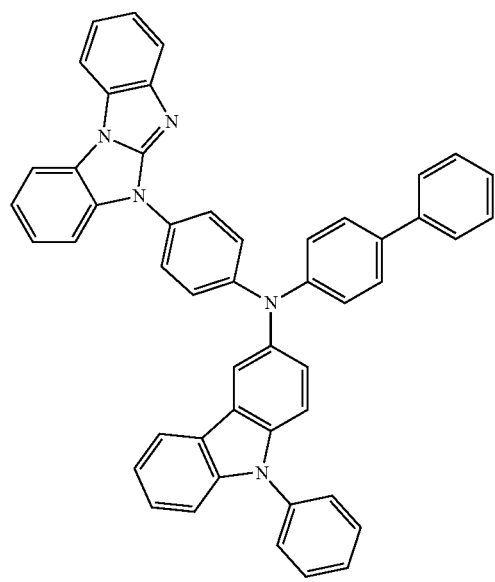 [SMILES: c1ccc(-c2ccc(N(c3ccc(-n4c5ccccc5n5c6ccccc6nc45)cc3)c3ccc4c(c3)c3ccccc3n4-c3ccccc3)cc2)cc1]
83
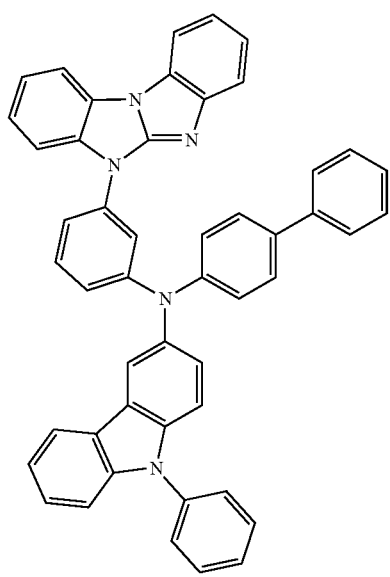 [SMILES: c1ccc(-c2ccc(N(c3cccc(-n4c5ccccc5n5c6ccccc6nc45)c3)c3ccc4c(c3)c3ccccc3n4-c3ccccc3)cc2)cc1]
84

-continued
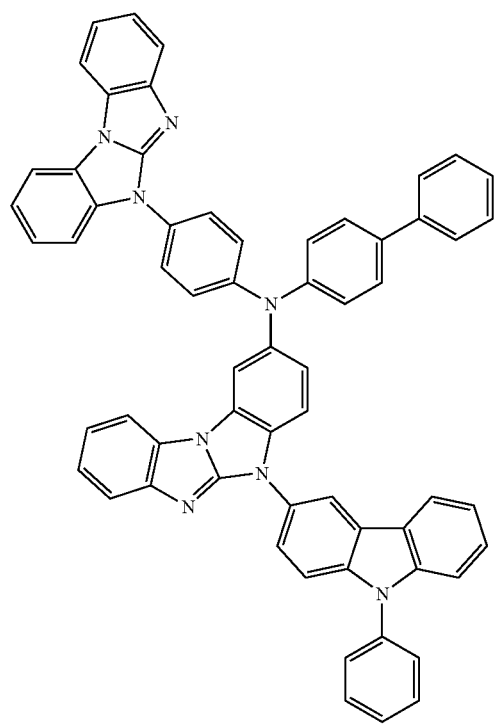 [SMILES: c1ccc(-c2ccc(N(c3ccc(-n4c5ccccc5n5c6ccccc6nc45)cc3)c3ccc4c(c3)n3c5ccccc5nc3n4-c3ccc4c(c3)c3ccccc3n4-c3ccccc3)cc2)cc1]
85
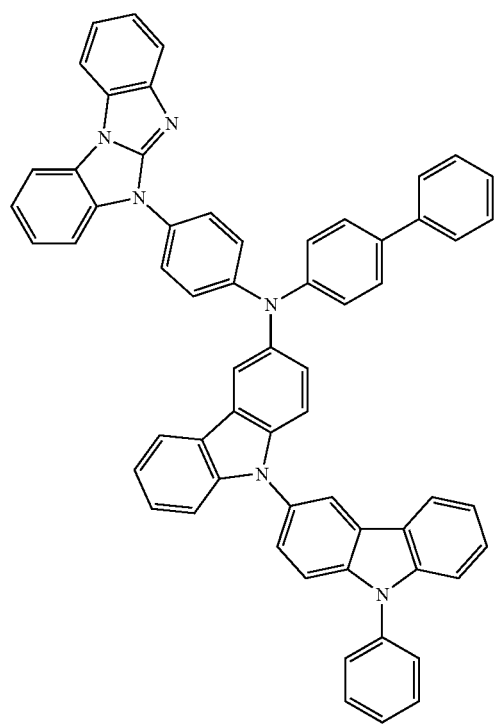 [SMILES: c1ccc(-c2ccc(N(c3ccc(-n4c5ccccc5n5c6ccccc6nc45)cc3)c3ccc4c(c3)c3ccccc3n4-c3ccc4c(c3)c3ccccc3n4-c3ccccc3)cc2)cc1]
86

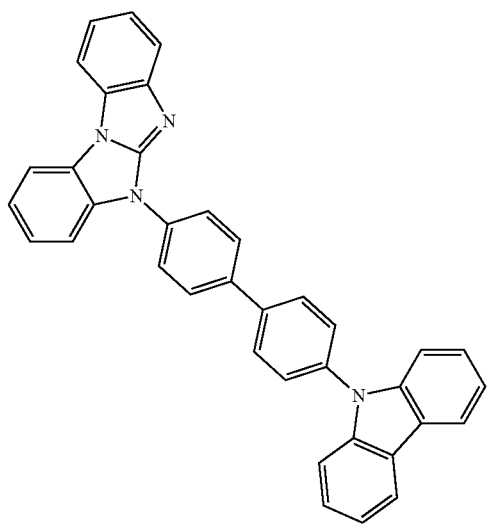 [SMILES: c1ccc2c(c1)nc1n(-c3ccc(-c4ccc(-n5c6ccccc6c6ccccc65)cc4)cc3)c3ccccc3n21]
87
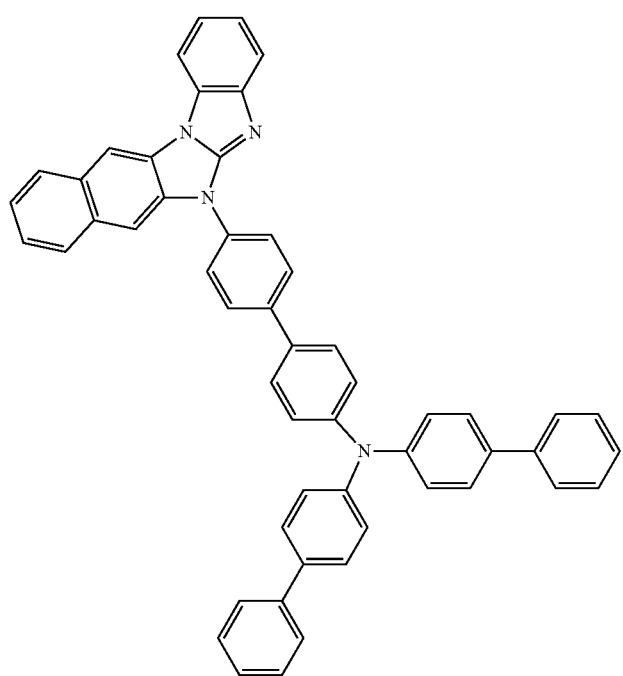 [SMILES: c1ccc(-c2ccc(N(c3ccc(-c4ccccc4)cc3)c3ccc(-c4ccc(-n5c6cc7ccccc7cc6n6c7ccccc7nc56)cc4)cc3)cc2)cc1]
88

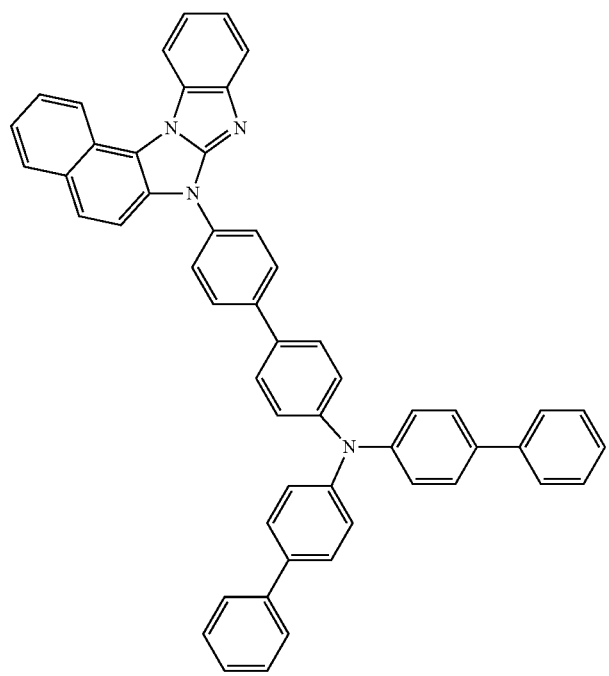 [SMILES: c1ccc(-c2ccc(N(c3ccc(-c4ccccc4)cc3)c3ccc(-c4ccc(-n5c6ccc7ccccc7c6n6c7ccccc7nc56)cc4)cc3)cc2)cc1]
89
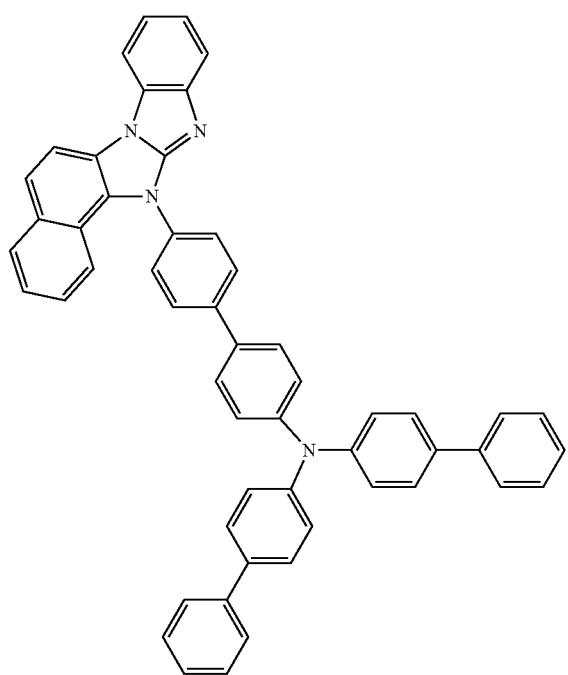 [SMILES: c1ccc(-c2ccc(N(c3ccc(-c4ccccc4)cc3)c3ccc(-c4ccc(-n5c6c7ccccc7ccc6n6c7ccccc7nc56)cc4)cc3)cc2)cc1]
90

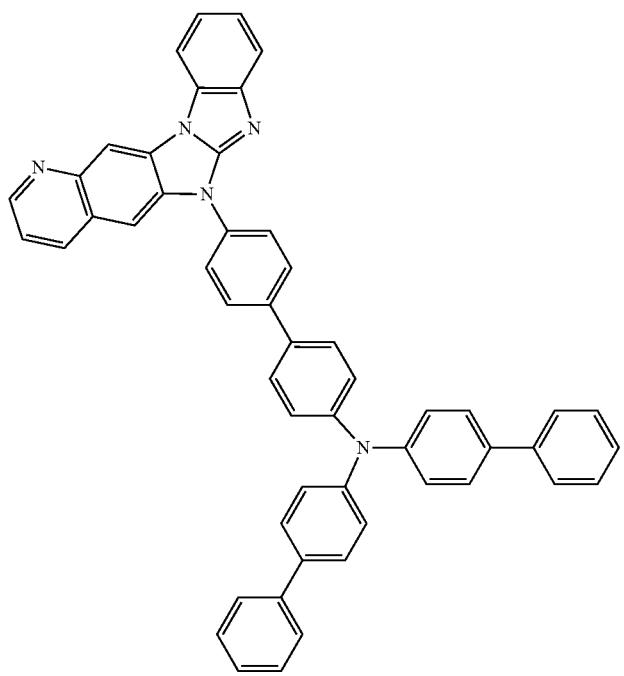 [SMILES: c1ccc(-c2ccc(N(c3ccc(-c4ccccc4)cc3)c3ccc(-c4ccc(-n5c6cc7cccnc7cc6n6c7ccccc7nc56)cc4)cc3)cc2)cc1]
91
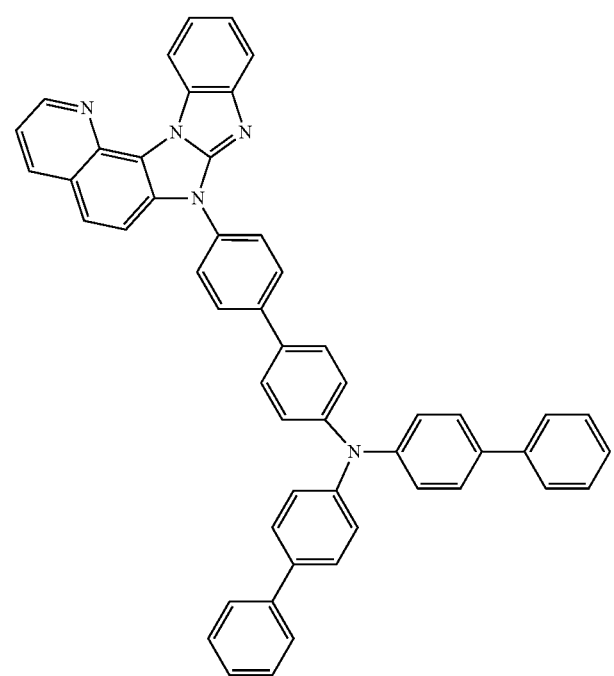 [SMILES: c1ccc(-c2ccc(N(c3ccc(-c4ccccc4)cc3)c3ccc(-c4ccc(-n5c6ccc7cccnc7c6n6c7ccccc7nc56)cc4)cc3)cc2)cc1]
92

-continued
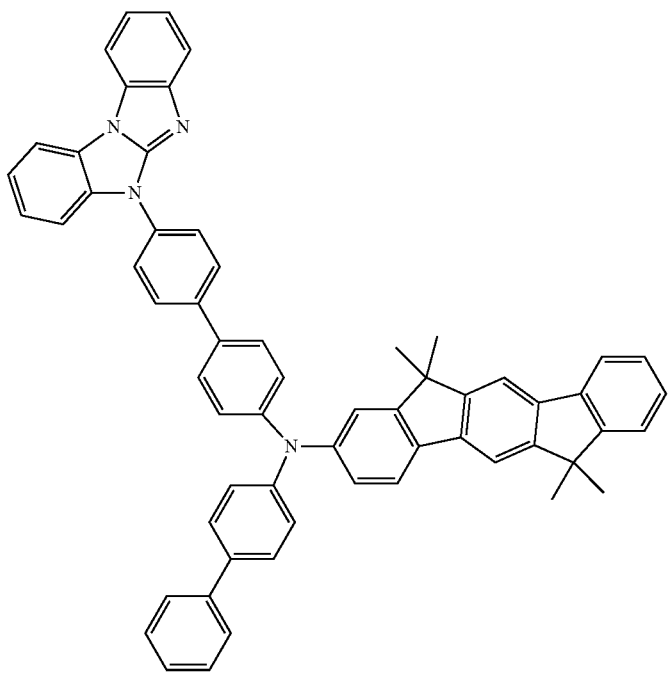 [SMILES: CC1(C)c2ccccc2-c2cc3c(cc21)-c1ccc(N(c2ccc(-c4ccccc4)cc2)c2ccc(-c4ccc(-n5c6ccccc6n6c7ccccc7nc56)cc4)cc2)cc1C3(C)C]
93
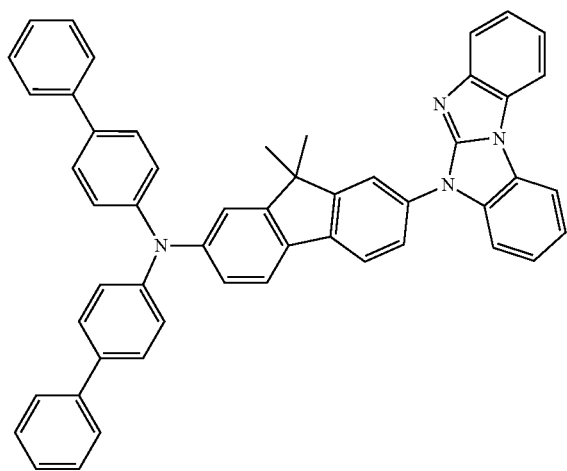 [SMILES: CC1(C)c2cc(N(c3ccc(-c4ccccc4)cc3)c3ccc(-c4ccccc4)cc3)ccc2-c2ccc(-n3c4ccccc4n4c5ccccc5nc34)cc21]
94
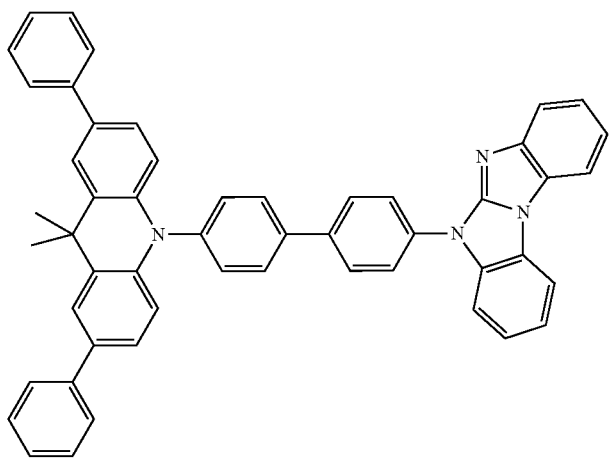 [SMILES: CC1(C)c2cc(-c3ccccc3)ccc2N(c2ccc(-c3ccc(-n4c5ccccc5n5c6ccccc6nc45)cc3)cc2)c2ccc(-c3ccccc3)cc21]
95

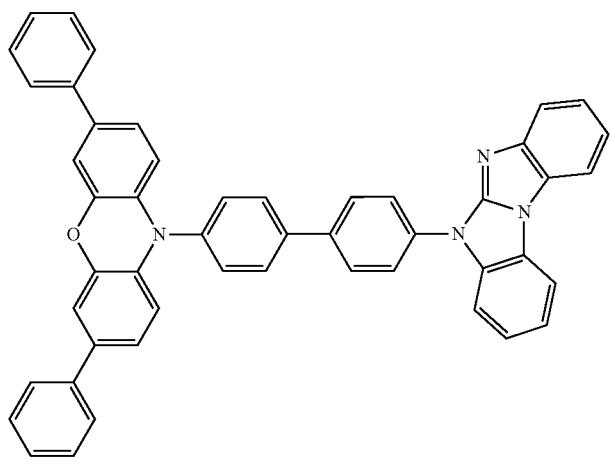 [SMILES: c1ccc(-c2ccc3c(c2)Oc2cc(-c4ccccc4)ccc2N3c2ccc(-c3ccc(-n4c5ccccc5n5c6ccccc6nc45)cc3)cc2)cc1]
96
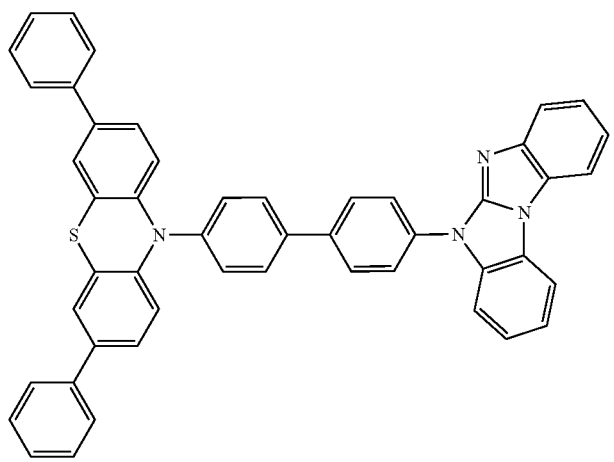
97
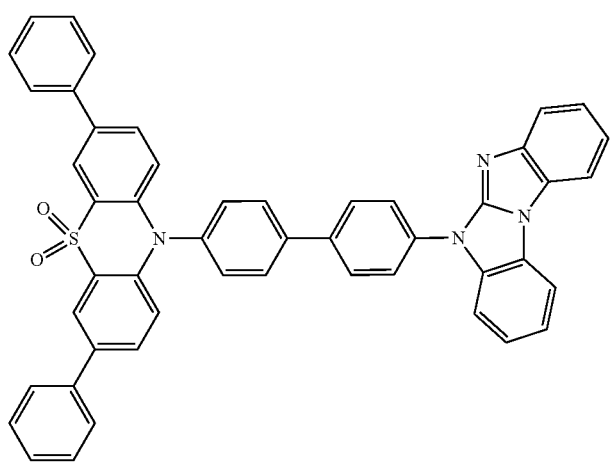 [SMILES: O=S1(=O)c2cc(-c3ccccc3)ccc2N(c2ccc(-c3ccc(-n4c5ccccc5n5c6ccccc6nc45)cc3)cc2)c2ccc(-c3ccccc3)cc21]
98

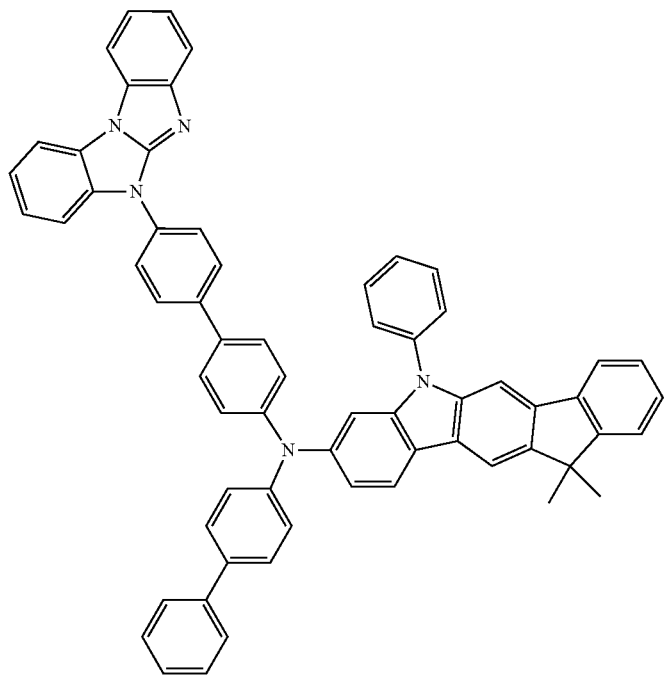 [SMILES: CC1(C)c2ccccc2-c2cc3c(cc21)c1ccc(N(c2ccc(-c4ccccc4)cc2)c2ccc(-c4ccc(-n5c6ccccc6n6c7ccccc7nc56)cc4)cc2)cc1n3-c1ccccc1]
99
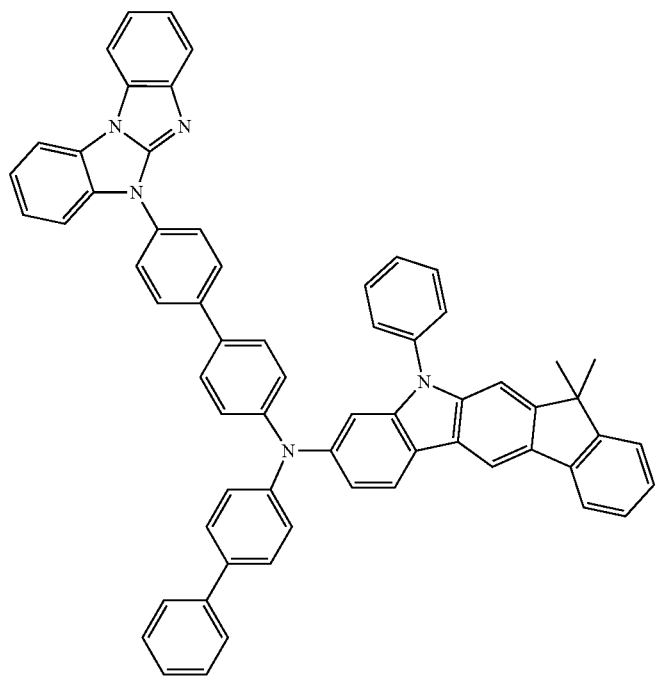 [SMILES: CC1(C)c2ccccc2-c2cc3c4ccc(N(c5ccc(-c6ccccc6)cc5)c5ccc(-c6ccc(-n7c8ccccc8n8c9ccccc9nc78)cc6)cc5)cc4n(-c4ccccc4)c3cc21]
100

-continued
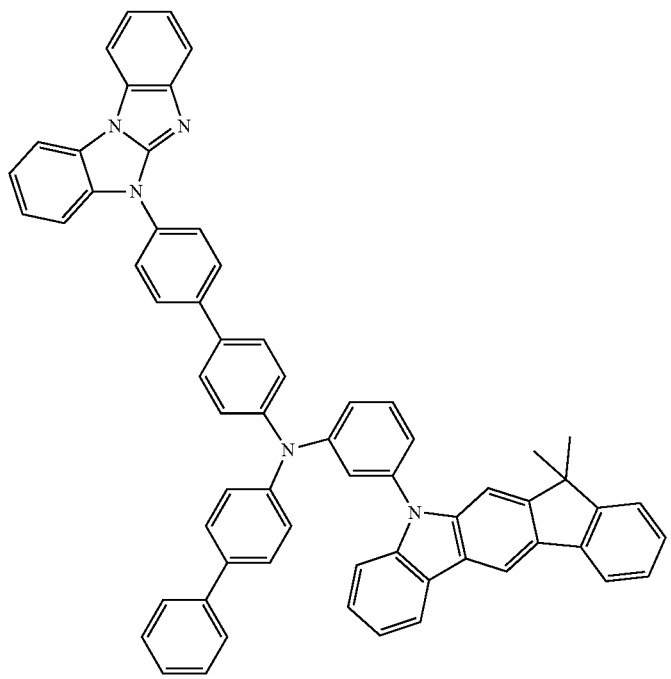 [SMILES: CC1(C)c2ccccc2-c2cc3c4ccccc4n(-c4cccc(N(c5ccc(-c6ccccc6)cc5)c5ccc(-c6ccc(-n7c8ccccc8n8c9ccccc9nc78)cc6)cc5)c4)c3cc21]
101
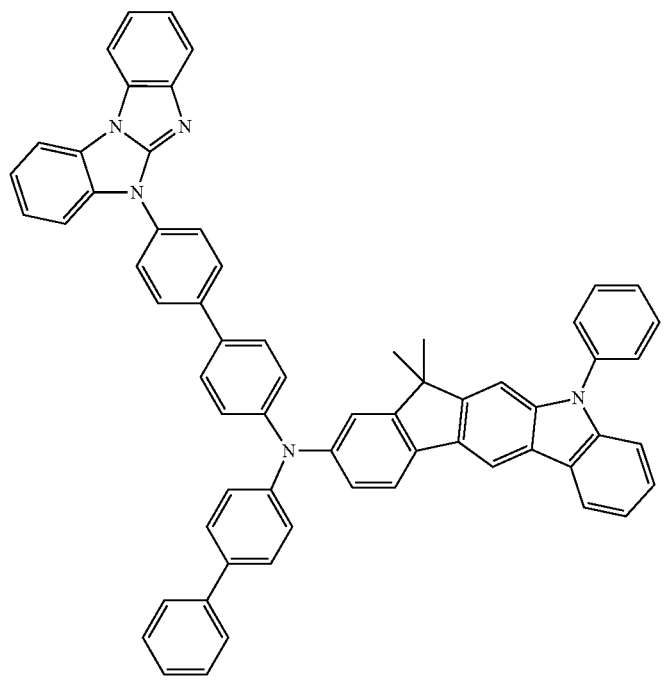 [SMILES: CC1(C)c2cc(N(c3ccc(-c4ccccc4)cc3)c3ccc(-c4ccc(-n5c6ccccc6n6c7ccccc7nc56)cc4)cc3)ccc2-c2cc3c4ccccc4n(-c4ccccc4)c3cc21]
102

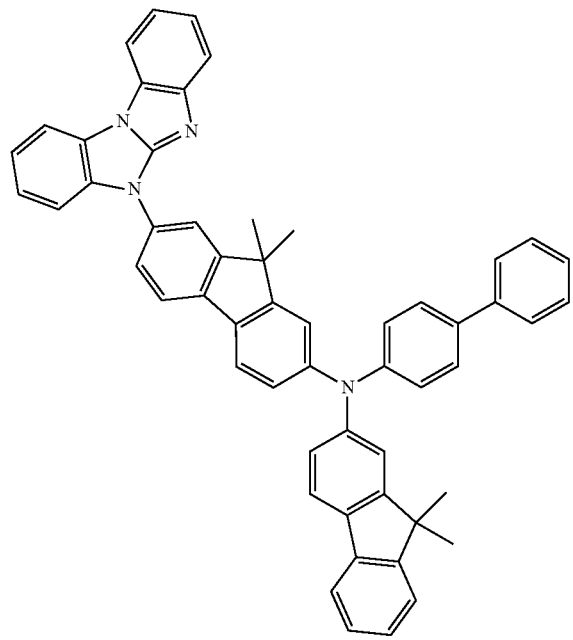 [SMILES: CC1(C)c2ccccc2-c2ccc(N(c3ccc(-c4ccccc4)cc3)c3ccc4c(c3)C(C)(C)c3cc(-n5c6ccccc6n6c7ccccc7nc56)ccc3-4)cc21]
103
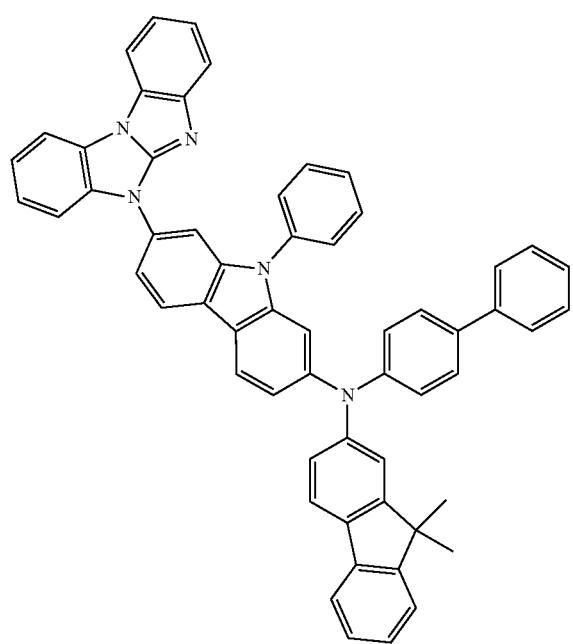 [SMILES: CC1(C)c2ccccc2-c2ccc(N(c3ccc(-c4ccccc4)cc3)c3ccc4c5ccc(-n6c7ccccc7n7c8ccccc8nc67)cc5n(-c5ccccc5)c4c3)cc21]
104

-continued
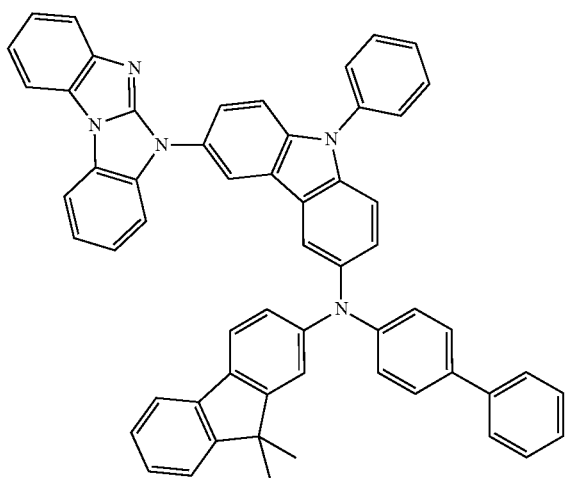 [SMILES: CC1(C)c2ccccc2-c2ccc(N(c3ccc(-c4ccccc4)cc3)c3ccc4c(c3)c3cc(-n5c6ccccc6n6c7ccccc7nc56)ccc3n4-c3ccccc3)cc21]
105
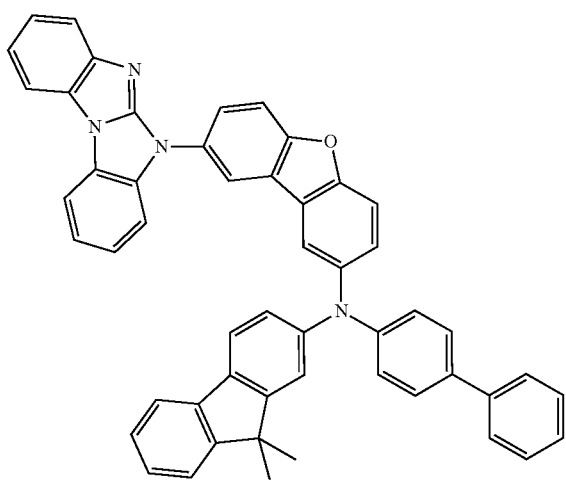 [SMILES: CC1(C)c2ccccc2-c2ccc(N(c3ccc(-c4ccccc4)cc3)c3ccc4oc5ccc(-n6c7ccccc7n7c8ccccc8nc67)cc5c4c3)cc21]
106
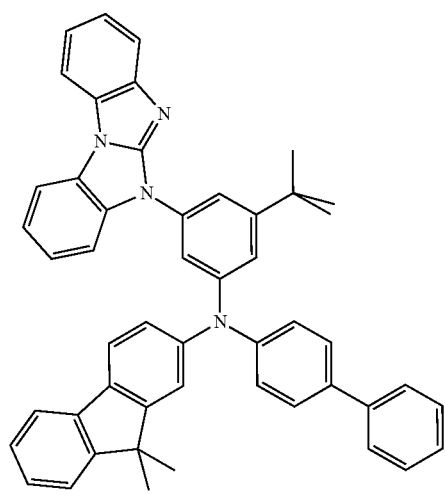 [SMILES: CC(C)(C)c1cc(N(c2ccc(-c3ccccc3)cc2)c2ccc3c(c2)C(C)(C)c2ccccc2-3)cc(-n2c3ccccc3n3c4ccccc4nc23)c1]
107

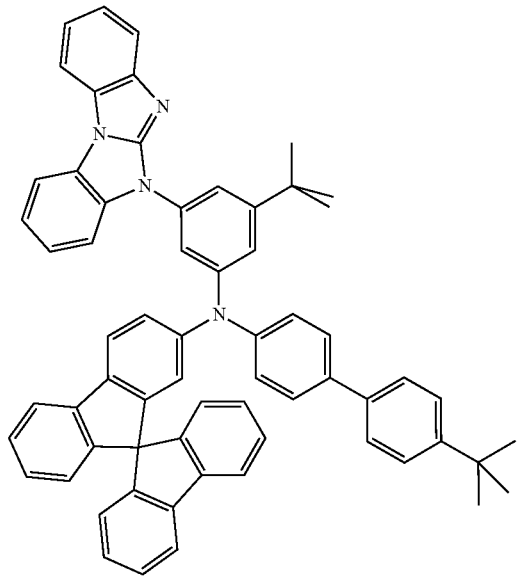 [SMILES: CC(C)(C)c1ccc(-c2ccc(N(c3cc(-n4c5ccccc5n5c6ccccc6nc45)cc(C(C)(C)C)c3)c3ccc4c(c3)C3(c5ccccc5-c5ccccc53)c3ccccc3-4)cc2)cc1]
108
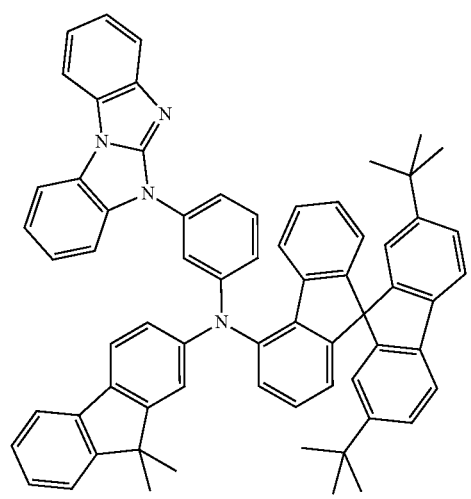 [SMILES: CC(C)(C)c1ccc2c(c1)C1(c3cc(C(C)(C)C)ccc3-2)c2ccccc2-c2c(N(c3cccc(-n4c5ccccc5n5c6ccccc6nc45)c3)c3ccc4c(c3)C(C)(C)c3ccccc3-4)cccc21]
109

-continued
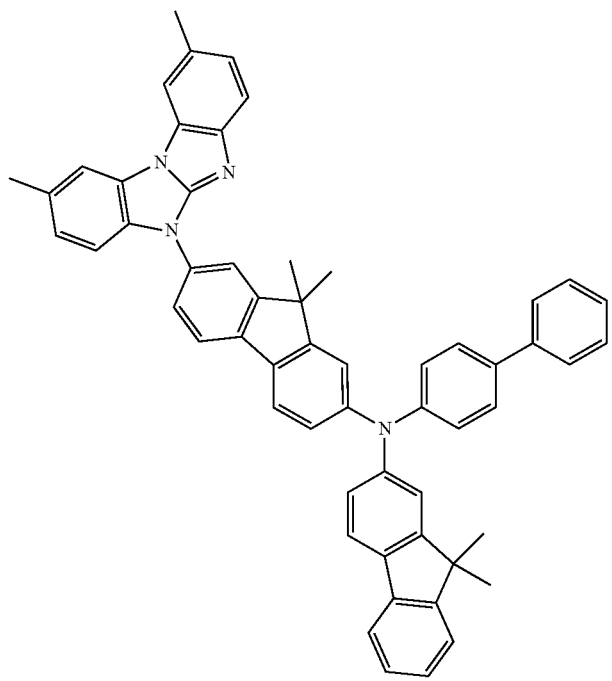 [SMILES: Cc1ccc2nc3n(-c4ccc5c(c4)C(C)(C)c4cc(N(c6ccc(-c7ccccc7)cc6)c6ccc7c(c6)C(C)(C)c6ccccc6-7)ccc4-5)c4ccc(C)cc4n3c2c1]
110
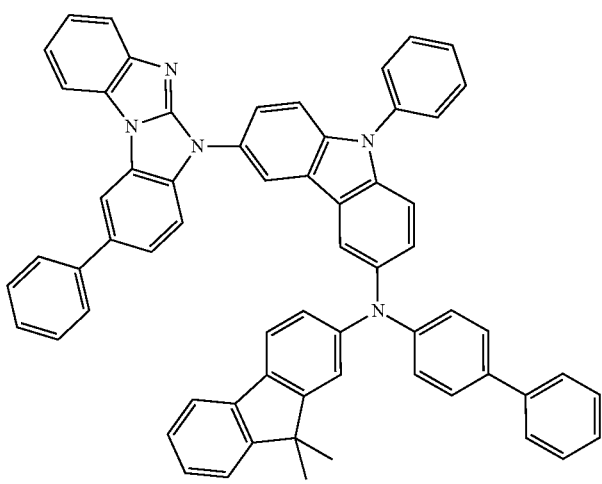 [SMILES: CC1(C)c2ccccc2-c2ccc(N(c3ccc(-c4ccccc4)cc3)c3ccc4c(c3)c3cc(-n5c6ccc(-c7ccccc7)cc6n6c7ccccc7nc56)ccc3n4-c3ccccc3)cc21]
111
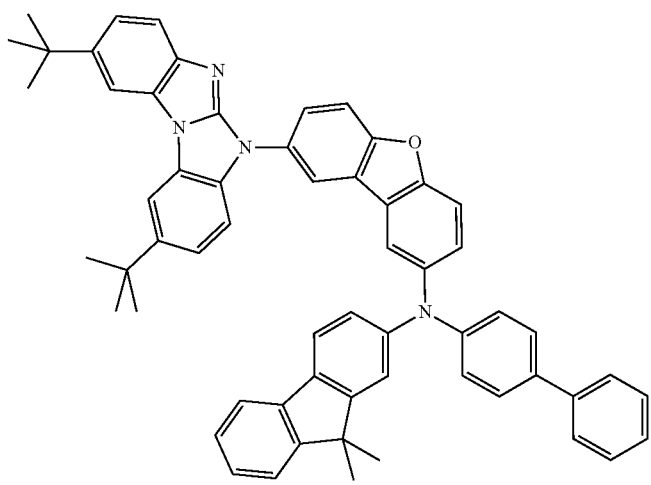 [SMILES: CC(C)(C)c1ccc2nc3n(-c4ccc5oc6ccc(N(c7ccc(-c8ccccc8)cc7)c7ccc8c(c7)C(C)(C)c7ccccc7-8)cc6c5c4)c4ccc(C(C)(C)C)cc4n3c2c1]
112

-continued
113
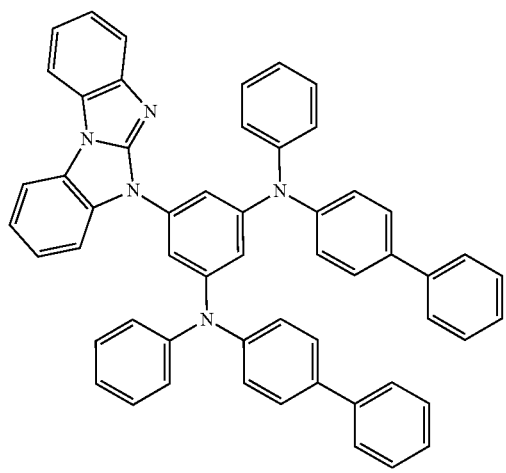 [SMILES: c1ccc(-c2ccc(N(c3ccccc3)c3cc(N(c4ccccc4)c4ccc(-c5ccccc5)cc4)cc(-n4c5ccccc5n5c6ccccc6nc45)c3)cc2)cc1]
114
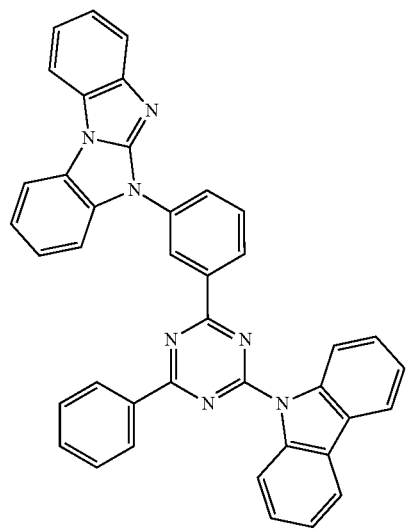 [SMILES: c1ccc(-c2nc(-c3cccc(-n4c5ccccc5n5c6ccccc6nc45)c3)nc(-n3c4ccccc4c4ccccc43)n2)cc1]
115
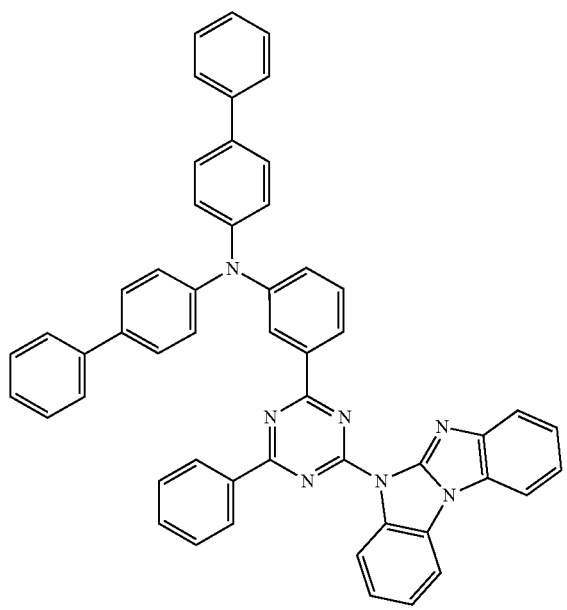 [SMILES: c1ccc(-c2ccc(N(c3ccc(-c4ccccc4)cc3)c3cccc(-c4nc(-c5ccccc5)nc(-n5c6ccccc6n6c7ccccc7nc56)n4)c3)cc2)cc1]

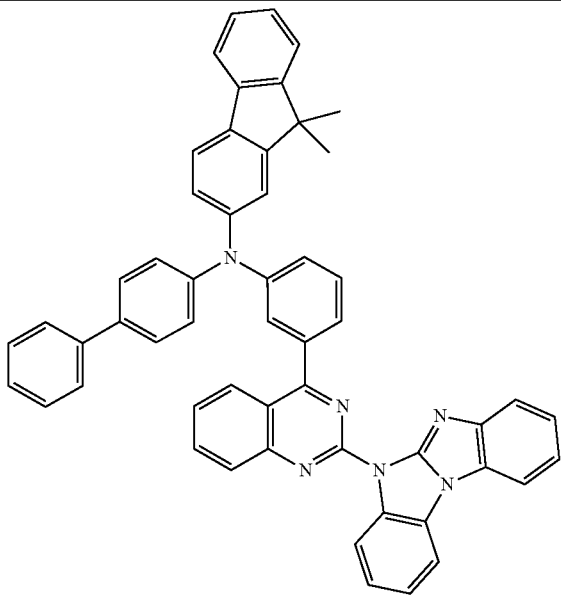

116

The compounds of the present application can be synthesized by making use of established methods of organic synthesis, such as Ullmann-type coupling and Buchwald coupling.

A preferred general synthetic process for preparation of the compounds of formula (I) is shown below (Scheme 1). It is understood that this process can be adapted and varied by the skilled person, as needed.

Scheme 1

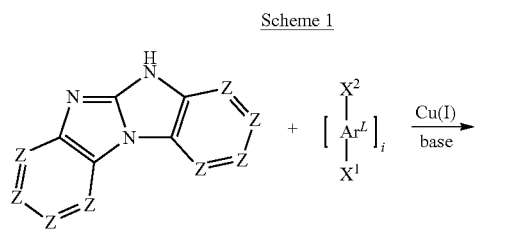

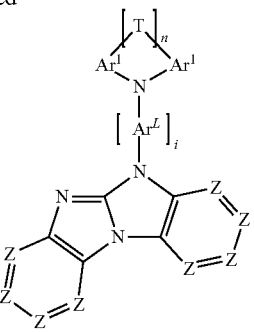

In Scheme 1, the variables used are defined as for formula (I) above. $X^1$ and $X^2$ are reactive groups, preferably halogen atoms, most preferably Cl, Br or I. Preferably, $X^1$ and $X^2$ are selected differently.

In the process of Scheme 1, a benzimidazobenzimidazole precursor compound is reacted with an aromatic group $(Ar^L)_i$, having two reactive groups $X^1$ and $X^2$, preferably in an Ullmann type reaction, more preferably with a copper (I) salt and base. In this reaction, the aromatic group $(Ar^L)_i$ is bonded to the N atom of the NH group of the benzimidazobenzimidazole precursor compound. In a second step, preferably in a Buchwald reaction, the resulting intermediate is reacted with a diaryl amine compound or a carbazole compound. In this reaction, the amine group or carbazole group is bonded to the benzimidazobenzimidazole precursor compound via its N atom, resulting in a compound of formula (I).

A preferred general synthetic process for compounds according to formula (II) is shown in Scheme 2.

Scheme 2

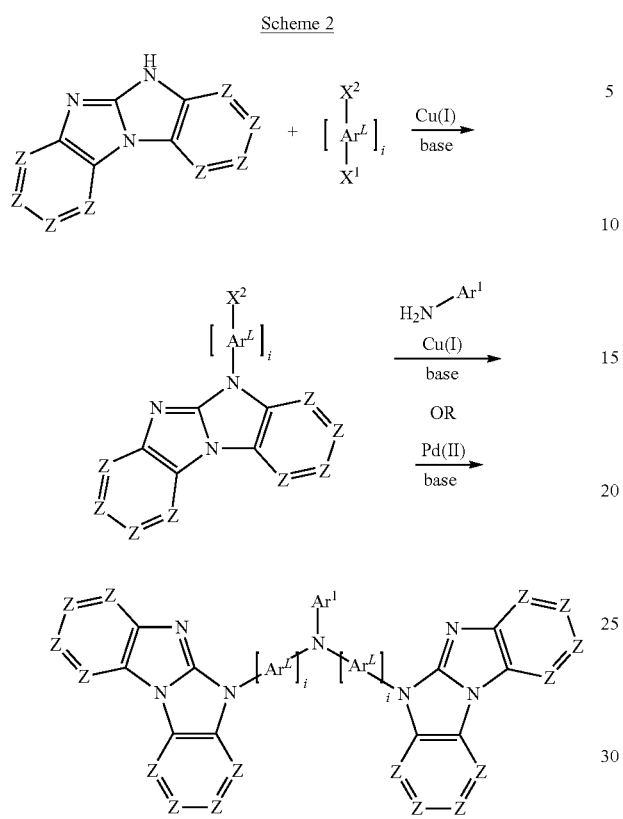

In this process, the first reaction step is the same as in Scheme 1. In the second step, two equivalents of the intermediate obtained in the first reaction step are reacted with a primary amine $Ar^1$—$NH_2$ in the presence of transition metal, preferably Cu(I) or Pd(II), to give the compound of formula (II).

A preferred general synthetic process for compounds according to formula (III) is shown in Scheme 3.

Scheme 3

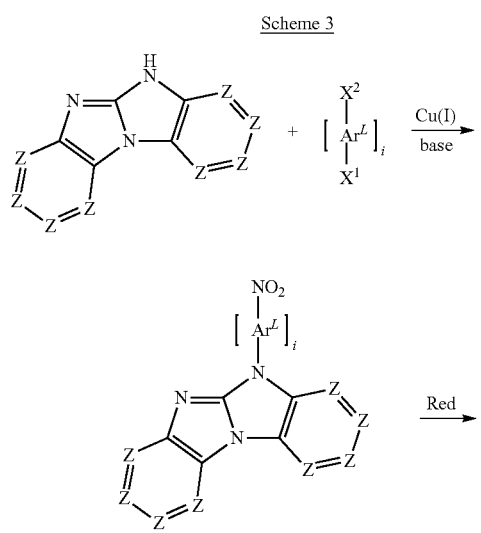

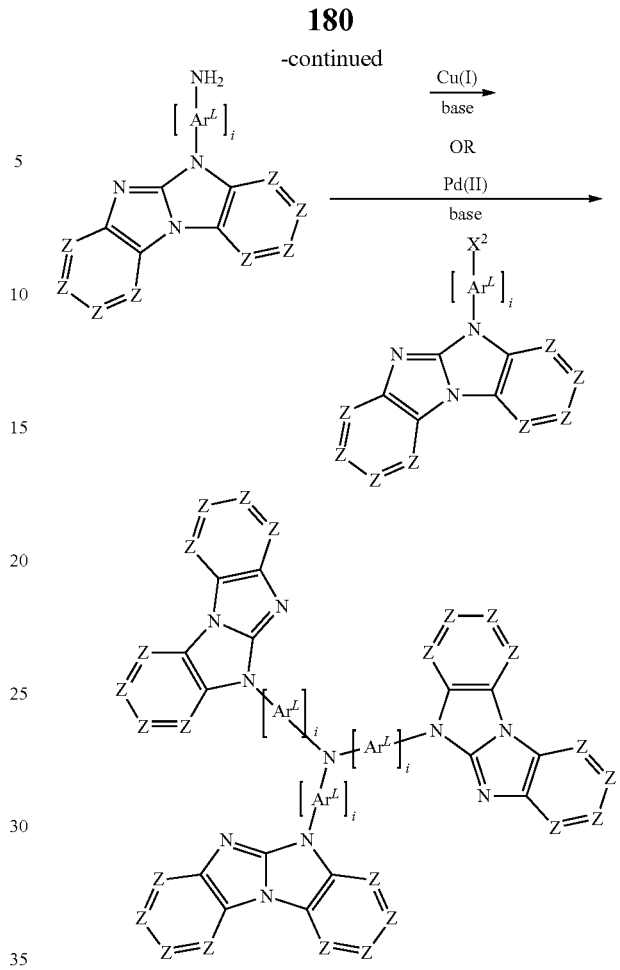

In this process, a benzimidazoimidazole precursor is reacted with a compound $X^1$—$[Ar^L]_i$—$NO_2$ in the presence of transition metal, preferably Cu(I), and a base. The $NO_2$ group of the resulting coupling product is then reduced to a primary amine group. To this primary amine group, in the presence of transition metal, preferably Cu(I) or Pd(II), two equivalents of the intermediate of the first reaction step in Scheme 1 are coupled, yielding the compound of formula (III).

A further subject of the present application is thus a process for preparation of a compound according to formula (I), (II) or (III), characterized in that benzimidazobenzimidazole is reacted with an aromatic group having a reactive group, with a transition metal and base as reagents.

Preferably, the resulting intermediate is further reacted with an amine or carbazole group, under formation of a C—N-bond.

Preferably, in the first reaction step, the transition metal is a copper salt, most preferably a copper (I) salt. Preferably, in the second reaction step, the transition metal is a palladium, copper or platinum salt, preferably a palladium (II) salt.

The above-described compounds, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), (II) or (III), wherein the bond(s) to the polymer, oligomer or dendrimer may be localized at any desired positions substituted by $R^1$, $R^2$ or $R^3$ in the formulae. According to the linkage of the compound, the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of the above formulae may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of the above formulae to be joined via a trivalent or higher-valency group, for example via a trivalent or higher-valency aromatic or heteroaromatic group, to give a branched or dendritic oligomer or polymer.

For the repeat units of the above formulae in oligomers, dendrimers and polymers, the same preferences apply as described above for the compounds of the above formulae.

For preparation of the oligomers or polymers, the monomers of the invention are homopolymerized or copolymerized with further monomers. Suitable and preferred comonomers are chosen from fluorenes, spirobifluorenes, paraphenylenes, carbazoles, thiophenes, dihydrophenanthrenes, cis- and trans-indenofluorenes, ketones, phenanthrenes or else a plurality of these units. The polymers, oligomers and dendrimers typically contain still further units, for example emitting (fluorescent or phosphorescent) units, for example vinyltriarylamines or phosphorescent metal complexes, and/or charge transport units, especially those based on triarylamines.

The polymers and oligomers of the invention are generally prepared by polymerization of one or more monomer types, of which at least one monomer leads to repeat units of the above formulae in the polymer. Suitable polymerization reactions are known to those skilled in the art and are described in the literature. Particularly suitable and preferred polymerization reactions which lead to formation of C—C or C—N bonds are the Suzuki polymerization, the Yamamoto polymerization, the Stille polymerization and the Hartwig-Buchwald polymerization.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (I), (II) or (III) and at least one solvent, preferably an organic solvent. The way in which such solutions can be prepared is known to those skilled in the art and is described, for example, in WO 2002/072714, WO 2003/019694 and the literature cited therein.

The compounds of the invention are suitable for use in electronic devices, especially in organic electroluminescent devices (OLEDs). Depending on the substitution, the compounds are used in different functions and layers.

The invention therefore further provides for the use of the compound in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides, as already set out above, an electronic device comprising at least one compound of formula (I), (II) or (III). This electronic device is preferably selected from the abovementioned devices.

It is more preferably an organic electroluminescent device (OLED) comprising anode, cathode and at least one emitting layer, characterized in that at least one organic layer, which may be an emitting layer, a hole transport layer or another layer, preferably an emitting layer or a hole transport layer, particularly preferably a hole transport layer, comprises at least one compound of formula (I), (II) or (III).

Apart from the cathode, anode and emitting layer, the organic electroluminescent device may also comprise further layers. These are selected, for example, from in each case one or more hole injection layers, hole transport layers, hole blocking layers, electron transport layers, electron injection layers, electron blocking layers, exciton blocking layers, interlayers, charge generation layers and/or organic or inorganic p/n junctions.

The sequence of the layers of the organic electroluminescent device comprising the compound of the above formulae is preferably as follows: anode-hole injection layer-hole transport layer-optionally further hole transport layer(s)-optionally electron blocking layer-emitting layer-optionally hole blocking layer-electron transport layer-electron injection layer-cathode. It is additionally possible for further layers to be present in the OLED.

The organic electroluminescent device of the invention may contain two or more emitting layers. More preferably, these emission layers in this case have several emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, where the three layers show blue, green and orange or red emission. The compounds of the invention are preferably present in the hole transport layer, hole injection layer, electron blocking layer and emitting layer. In case they are present in the emitting layer, they are preferably present as host materials.

It is preferable in accordance with the invention when the compound of formula (I), (II) or (III) is used in an electronic device comprising one or more phosphorescent emitting compounds. In this case, the compound may be present in different layers, preferably in a hole transport layer, an electron blocking layer, a hole injection layer or in an emitting layer.

The term "phosphorescent emitting compounds" typically encompasses compounds where the emission of light is effected through a spin-forbidden transition, for example a transition from an excited triplet state or a state having a higher spin quantum number, for example a quintet state.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds. In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the compounds of formula (I), (II) or (III) in organic electroluminescent devices. Further examples are listed in a table which follows.

It is also possible in accordance with the invention to use the compound of formula (I), (II) or (III) in an electronic device comprising one or more fluorescent emitting compounds.

In a preferred embodiment of the invention, the compounds of formula (I), (II) or (III) are used as hole-transporting material. In that case, the compounds are preferably present in a hole transport layer, an electron blocking layer or a hole injection layer. Particular preference is given to use in an electron blocking layer or in a hole transport layer.

A hole transport layer according to the present application is a layer having a hole-transporting function between the anode and emitting layer.

Hole injection layers and electron blocking layers are understood in the context of the present application to be specific embodiments of hole transport layers. A hole injection layer, in the case of a plurality of hole transport layers between the anode and emitting layer, is a hole transport layer which directly adjoins the anode or is separated therefrom only by a single coating of the anode. An electron blocking layer, in the case of a plurality of hole transport layers between the anode and emitting layer, is that hole transport layer which directly adjoins the emitting layer on the anode side. Preferably, the OLED of the invention comprises two, three or four hole-transporting layers between the anode and emitting layer, at least one of which preferably contains a compound of formula (I), (II) or (III), and more preferably exactly one or two contain a such compound.

If the compound of formula (I), (II) or (III) is used as hole transport material in a hole transport layer, a hole injection layer or an electron blocking layer, the compound can be used as pure material, i.e. in a proportion of 100%, in the hole transport layer, or it can be used in combination with one or more further compounds. In a preferred embodiment, the organic layer comprising the compound of one of the above-mentioned formulae then additionally contains one or more p-dopants. p-Dopants used according to the present invention are preferably those organic electron acceptor compounds capable of oxidizing one or more of the other compounds in the mixture.

Particularly preferred p-dopants are quinodimethane compounds, azaindenofluorenediones, azaphenalenes, azatriphenylenes, $I_2$, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as bonding site. Preference is further given to transition metal oxides as dopants, preferably oxides of rhenium, molybdenum and tungsten, more preferably $Re_2O_7$, $MoO_3$, $WO_3$ and $ReO_3$. Further preferable p-dopants are selected from Bi(III)-containing metal complexes, in particular Bi(III) complexes of benzoic acid or benzoic acid derivatives.

The p-dopants are preferably in substantially homogeneous distribution in the p-doped layers. This can be achieved, for example, by coevaporation of the p-dopant and the hole transport material matrix.

Preferred p-dopants are especially the following compounds:

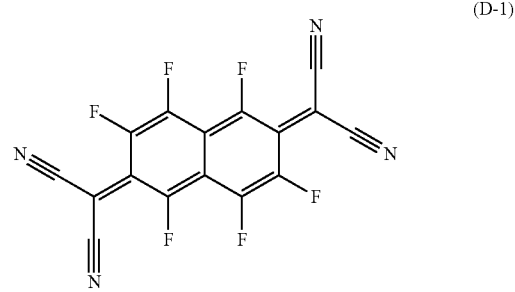
(D-1)

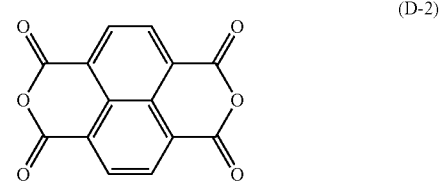
(D-2)

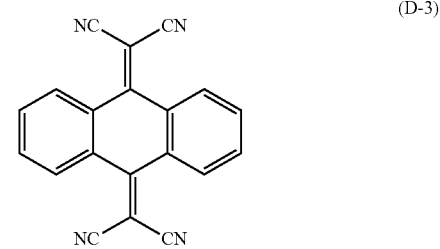
(D-3)

(D-4)
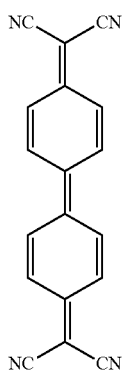
(D-5)
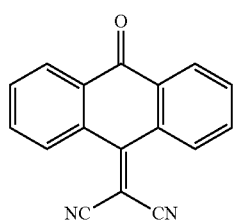
(D-6)
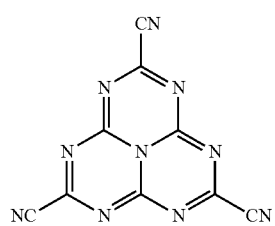
(D-7)
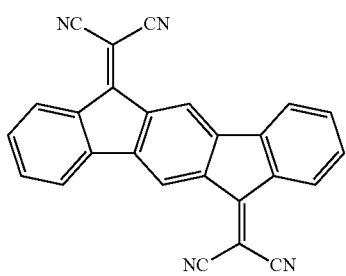
(D-8)
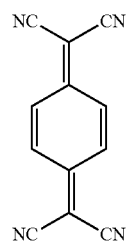
(D-9)
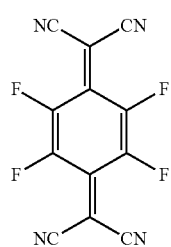
(D-10)
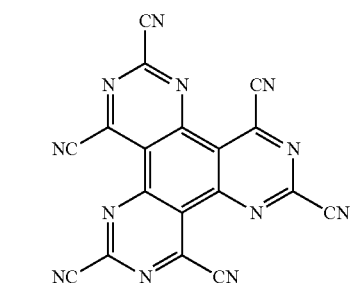
(D-11)
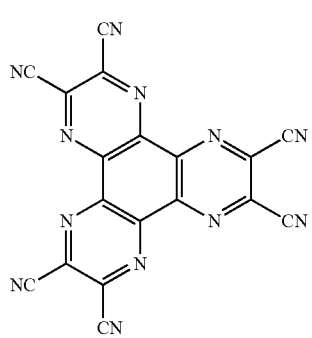
(D-12)
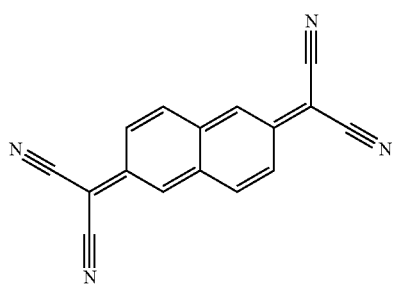
(D-13)
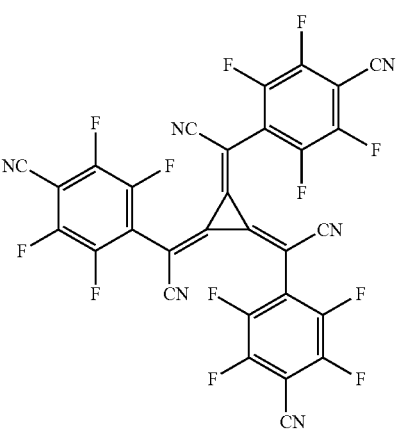

(D-14)

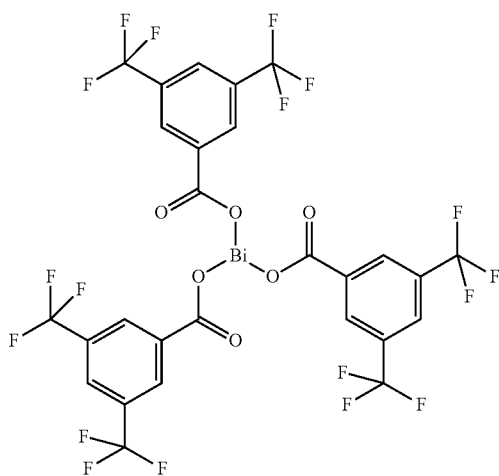

In a further preferred embodiment of the invention, the compound is used as hole transport material in a hole transporting layer, and there is a layer (called hole injection layer) present between anode and this hole transporting layer, which comprises an electron accepting material. Preferably, this electron accepting material is selected from the compound classes mentioned above for use as p-dopants, particularly preferably from the compounds (D-1) to (D-14) mentioned above, most preferably from the compounds (D-6), (D-7) and (D-14). Preferably, the above-mentioned hole injection layer comprises one of the above-mentioned compounds in non-doped form, and with no other compounds admixed. Most preferably, it consists of only one of the above-mentioned compounds and comprises no other compound.

In a further embodiment of the present invention, the compound is used in an emitting layer as matrix material in combination with one or more emitting compounds, preferably phosphorescent emitting compounds.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the emitting compound is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of emitting compounds. In this case too, the emitting compounds are generally those compounds having the smaller proportion in the system and the matrix materials are those compounds having the greater proportion in the system. In individual cases, however, the proportion of a single matrix material in the system may be less than the proportion of a single emitting compound.

It is preferable that the compound is used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The compound is preferably the matrix material having hole-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices.

The mixed matrix systems may comprise one or more emitting compounds, preferably one or more phosphorescent emitting compounds. In general, mixed matrix systems are preferably used in phosphorescent organic electroluminescent devices.

Particularly suitable matrix materials which can be used in combination with the compounds of the invention as matrix components of a mixed matrix system are selected from the preferred matrix materials specified below for phosphorescent emitting compounds or the preferred matrix materials for fluorescent emitting compounds, according to what type of emitting compound is used in the mixed matrix system.

Preferred phosphorescent emitting compounds for use in mixed matrix systems are the same as detailed further up as generally preferred phosphorescent emitter materials.

Preferred embodiments of the different functional materials in the electronic device are listed hereinafter.

Preferred phosphorescent emitting compounds are the following ones:

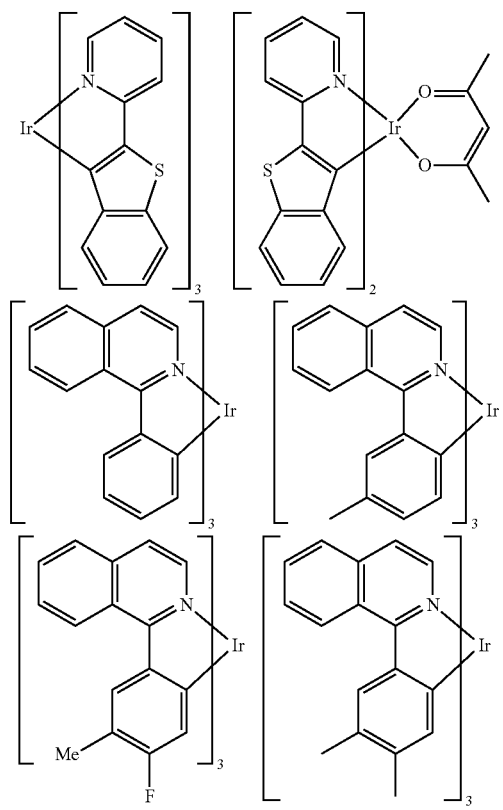

189
-continued
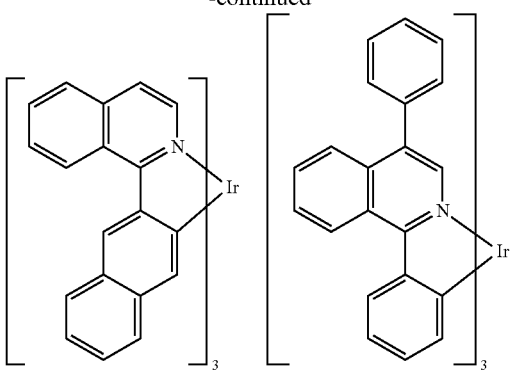
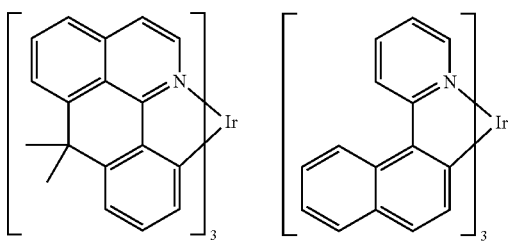
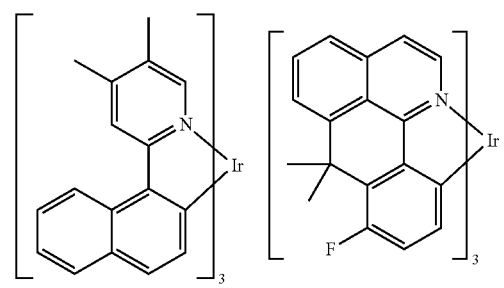
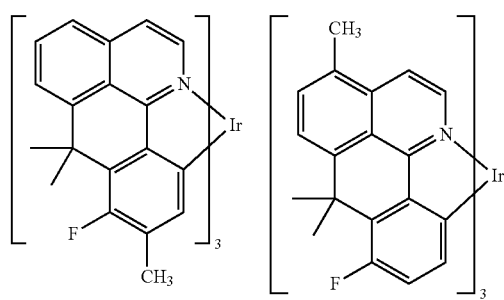
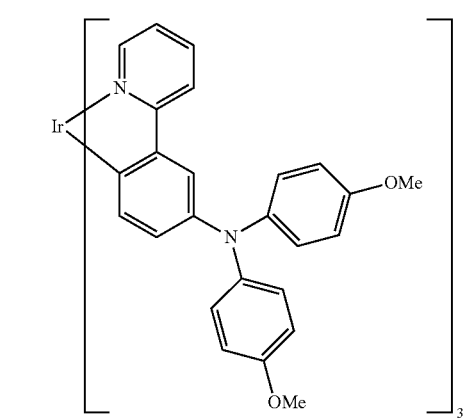
190
-continued
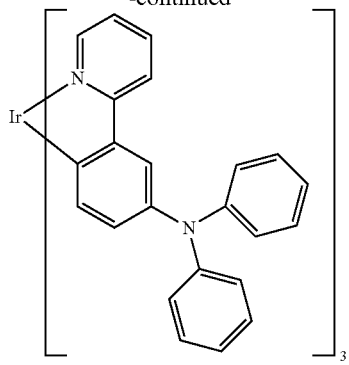
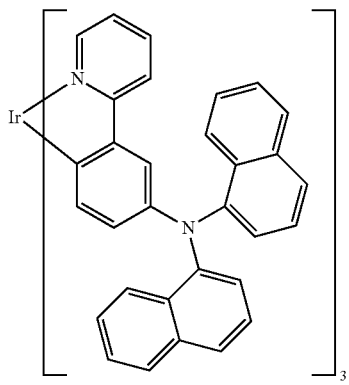
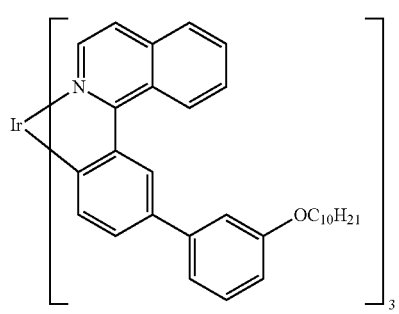
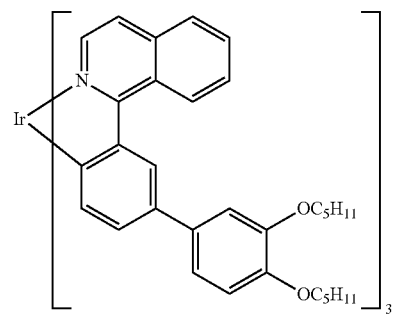

191
-continued
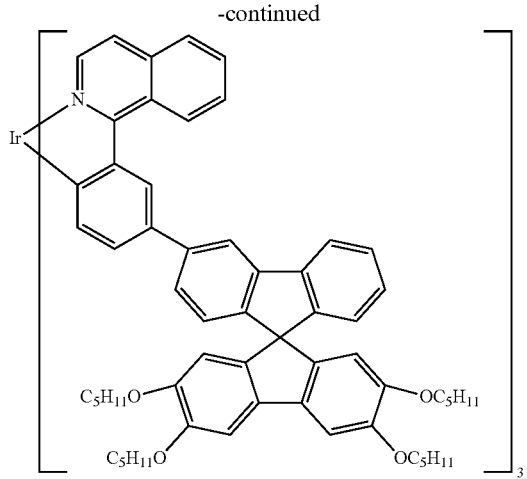
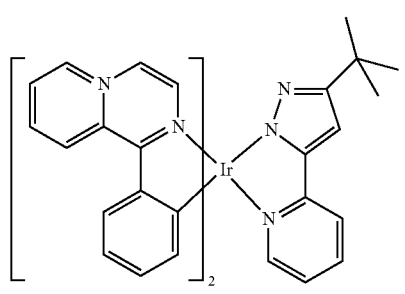
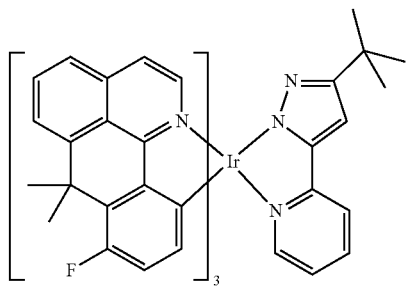
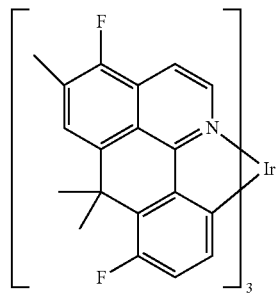
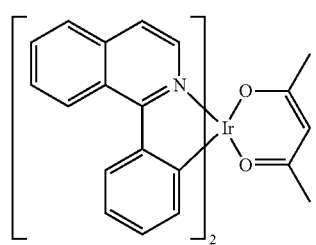
192
-continued
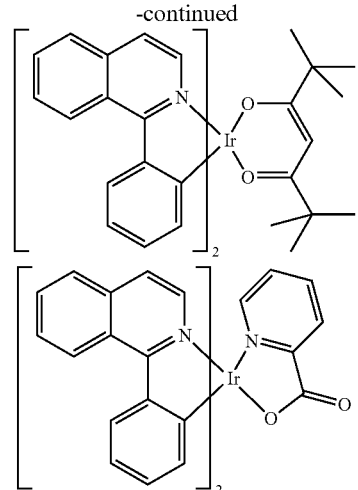
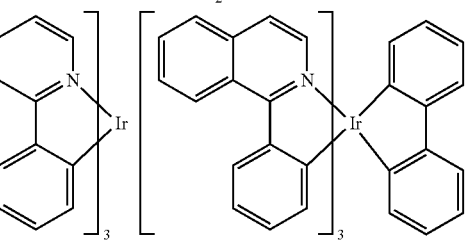
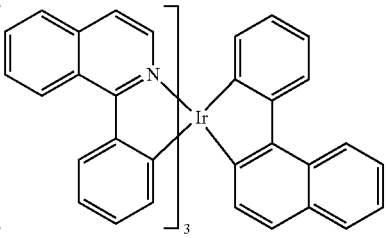
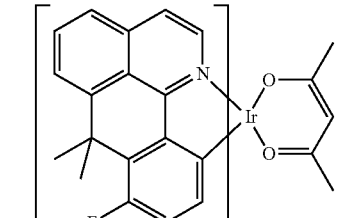
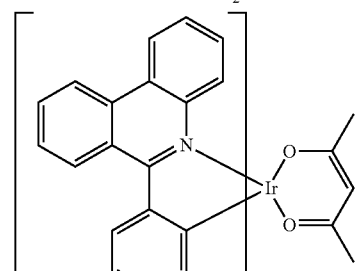
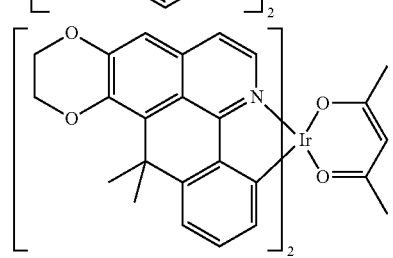

193
-continued
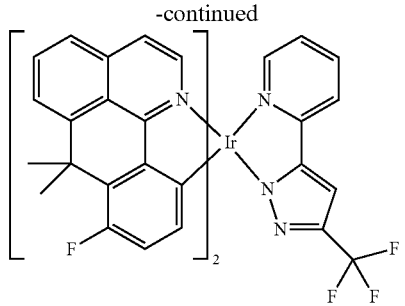
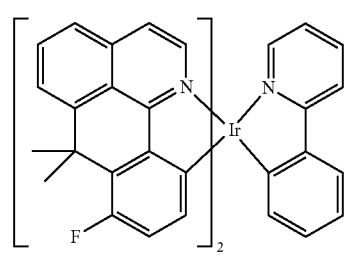
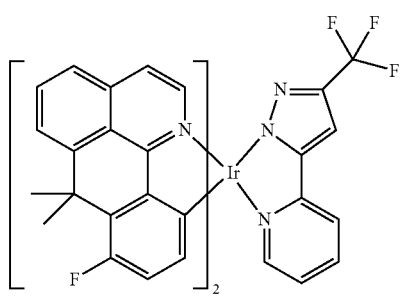
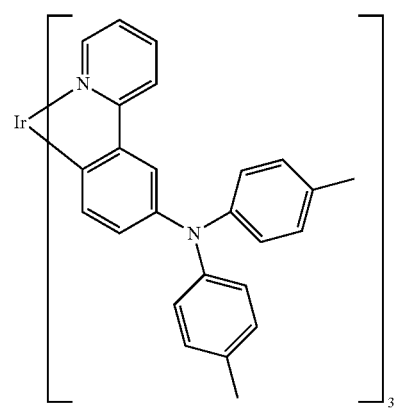
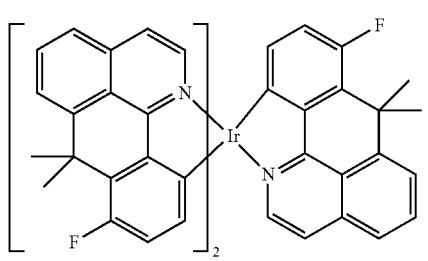
194
-continued
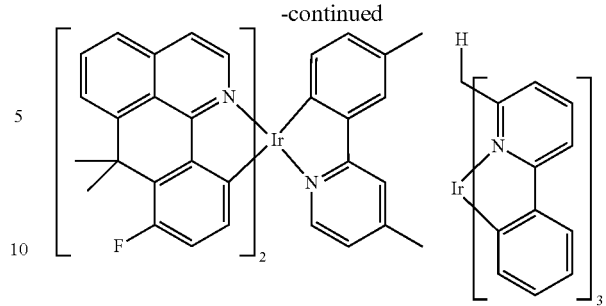
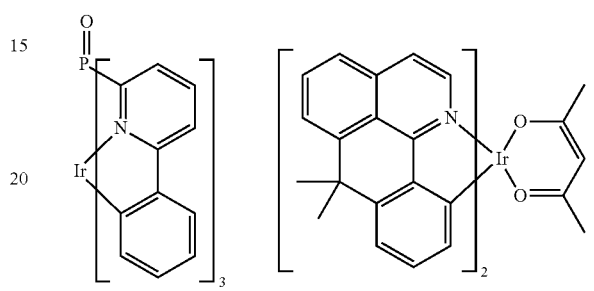
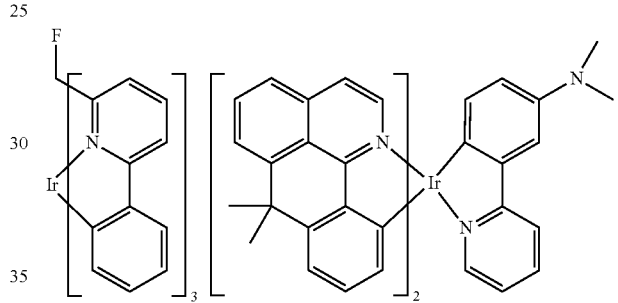
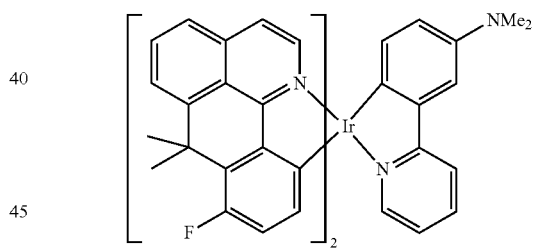
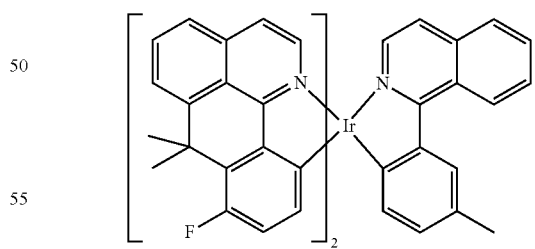
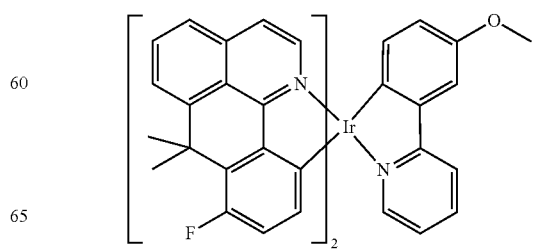

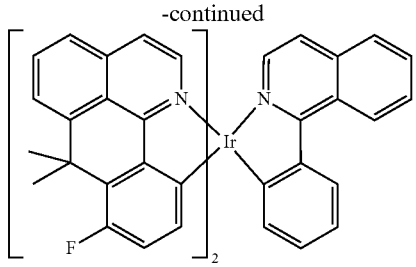
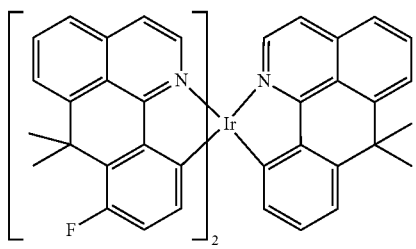
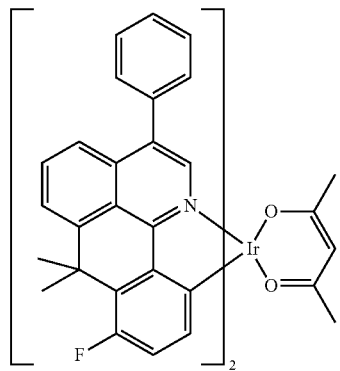
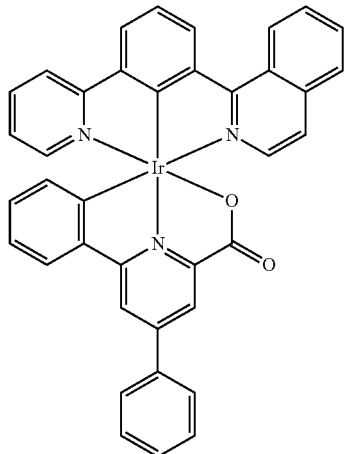
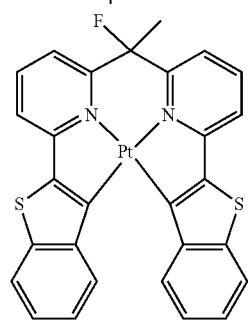
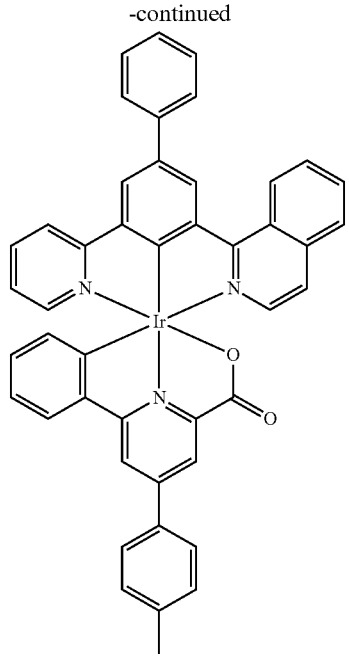
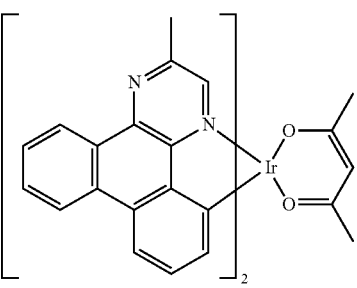
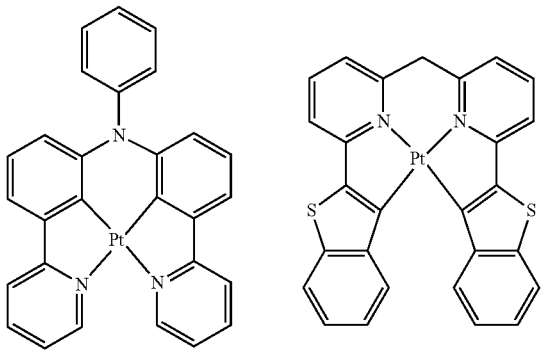
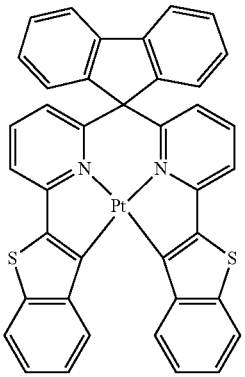
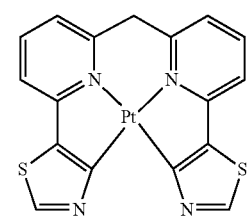

-continued
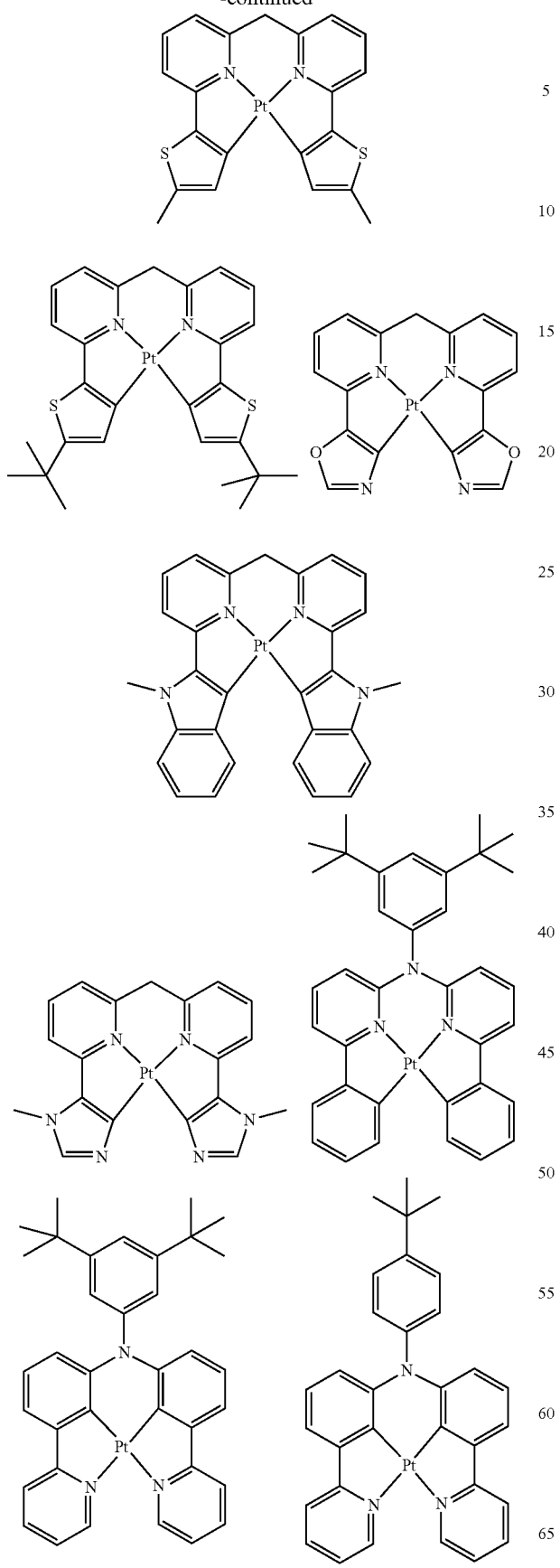
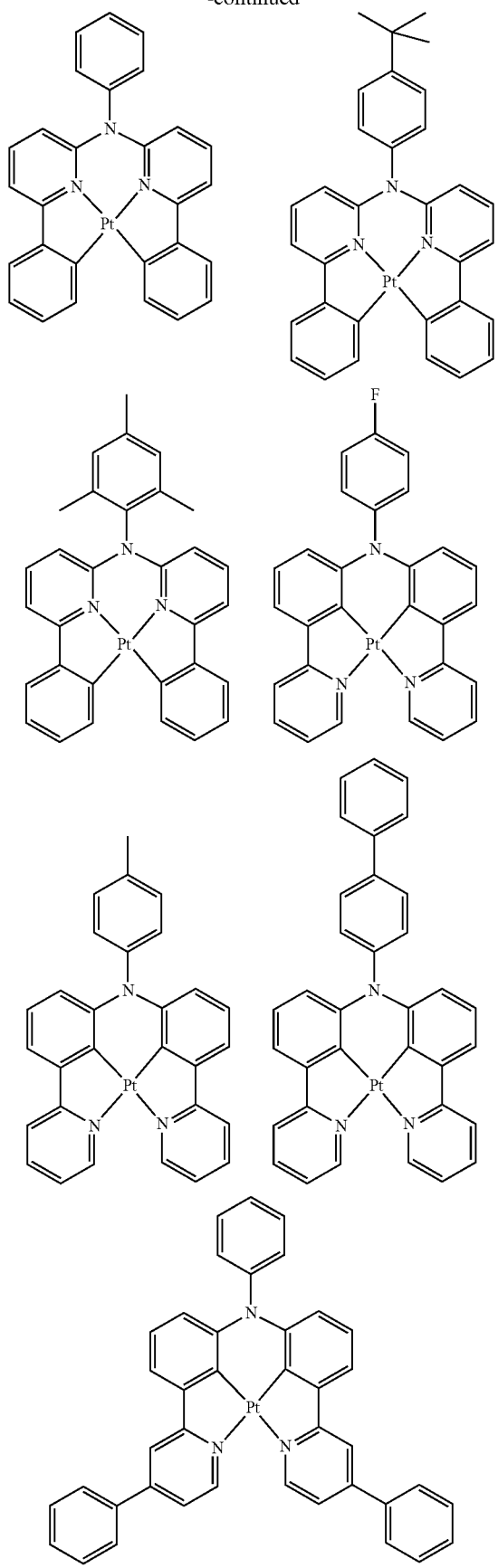

199
-continued
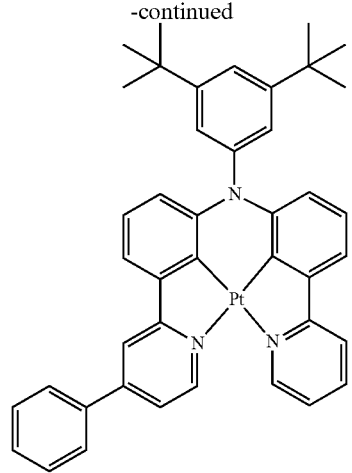
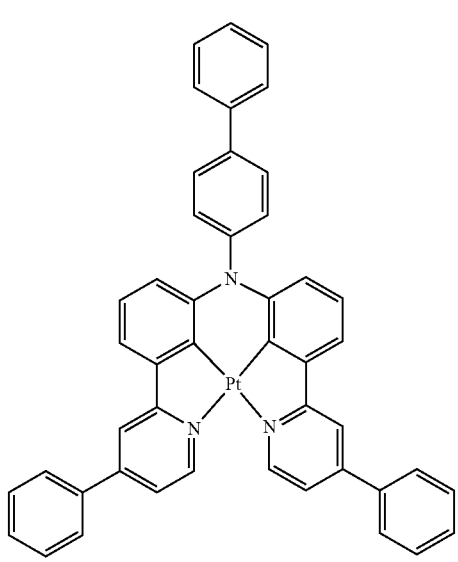
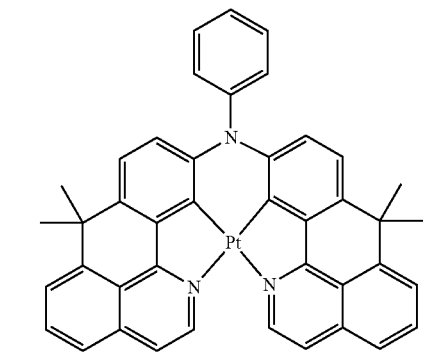
200
-continued
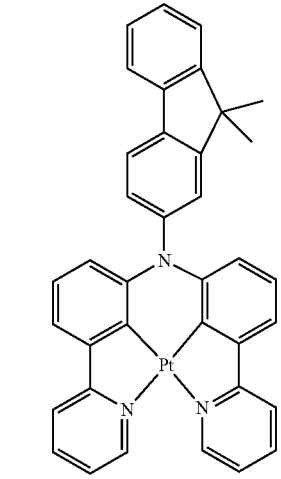
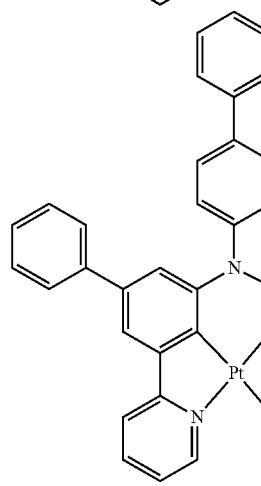
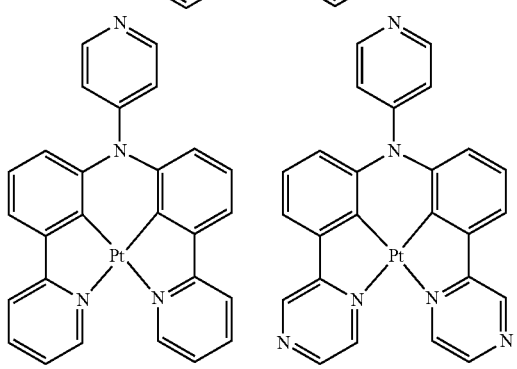
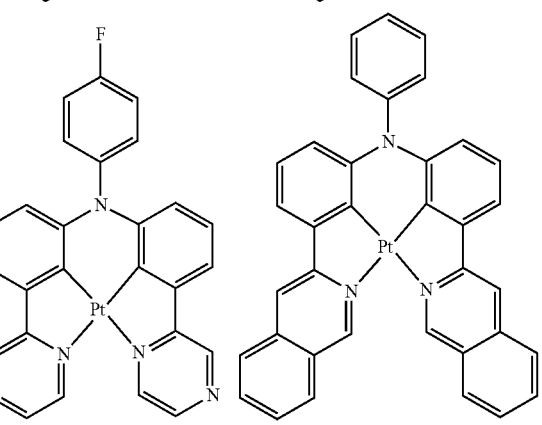

201
-continued
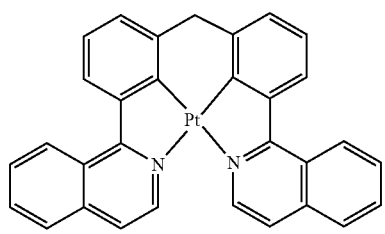
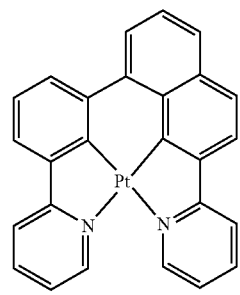
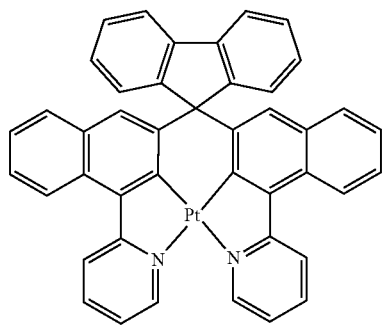
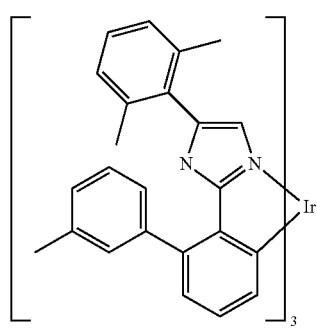
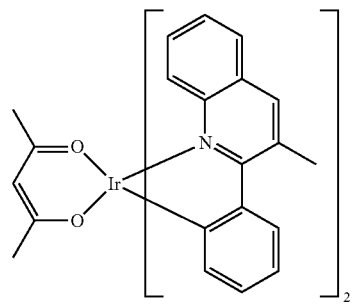
202
-continued
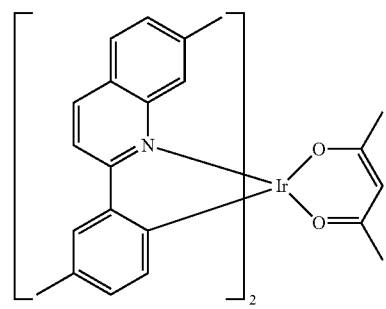
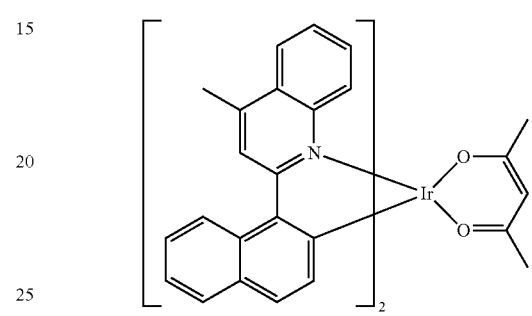
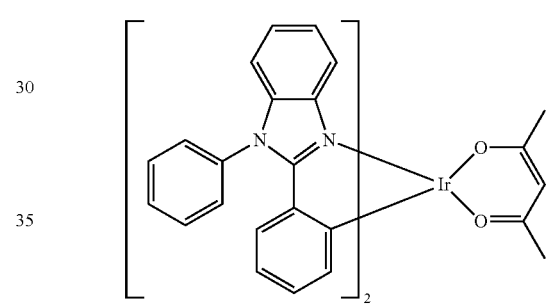
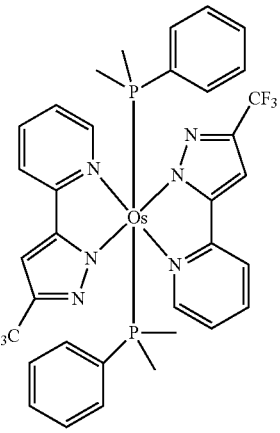 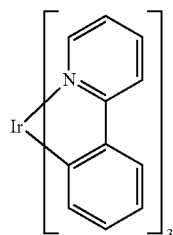
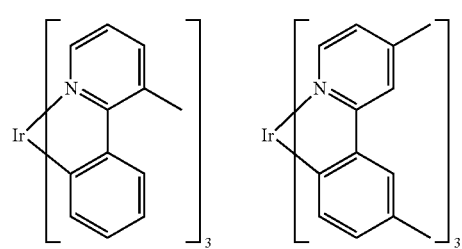

203
-continued
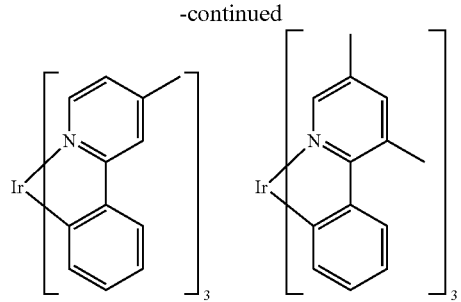
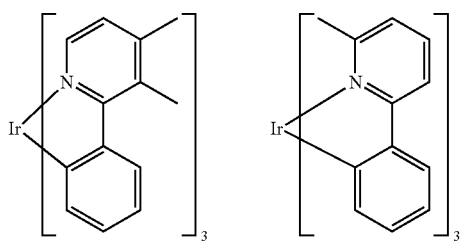
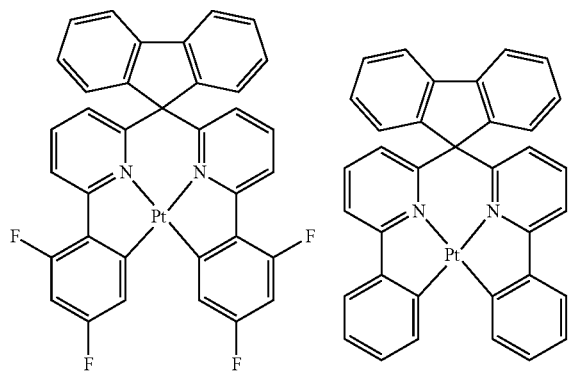
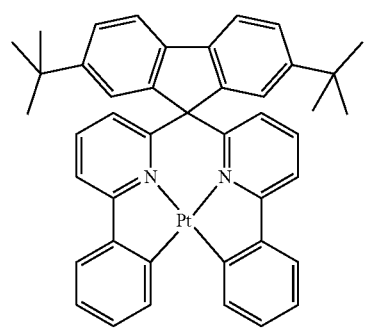
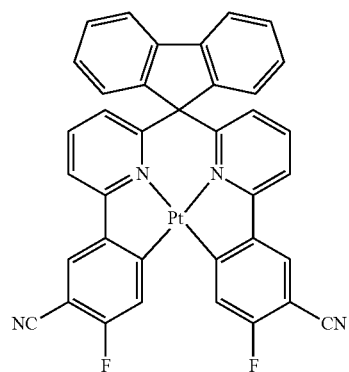
204
-continued
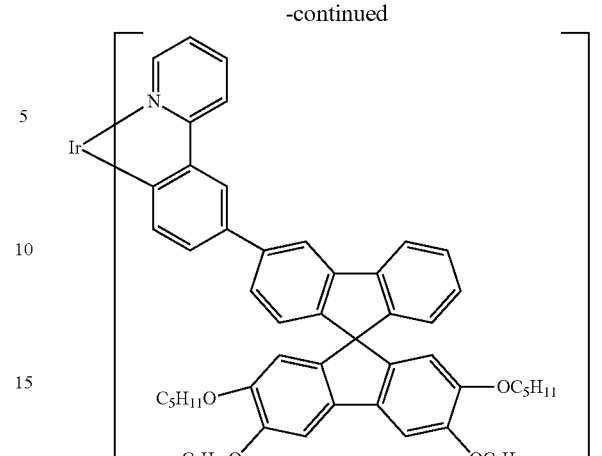
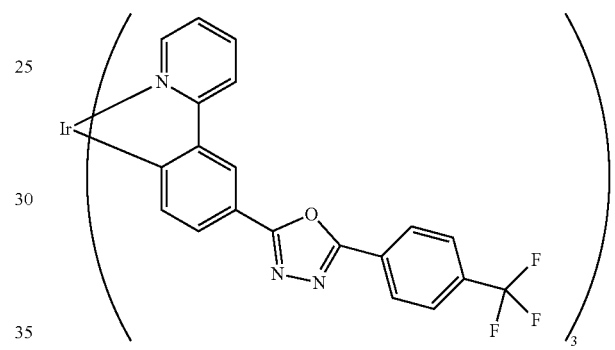
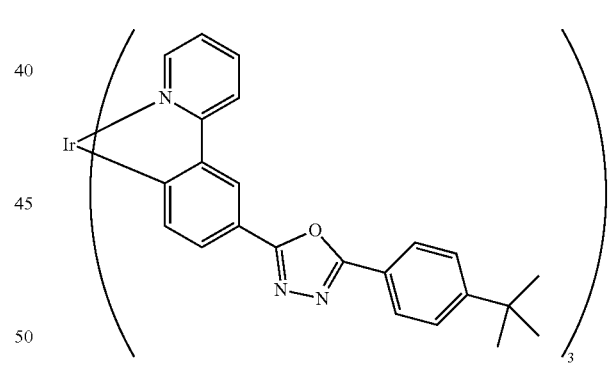
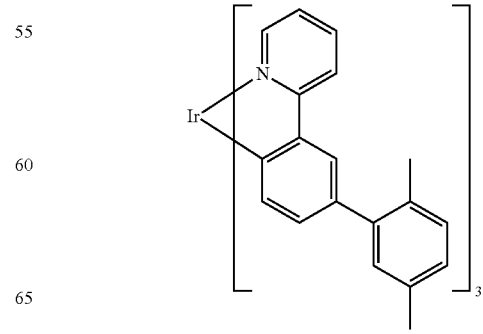

205
-continued
206
-continued
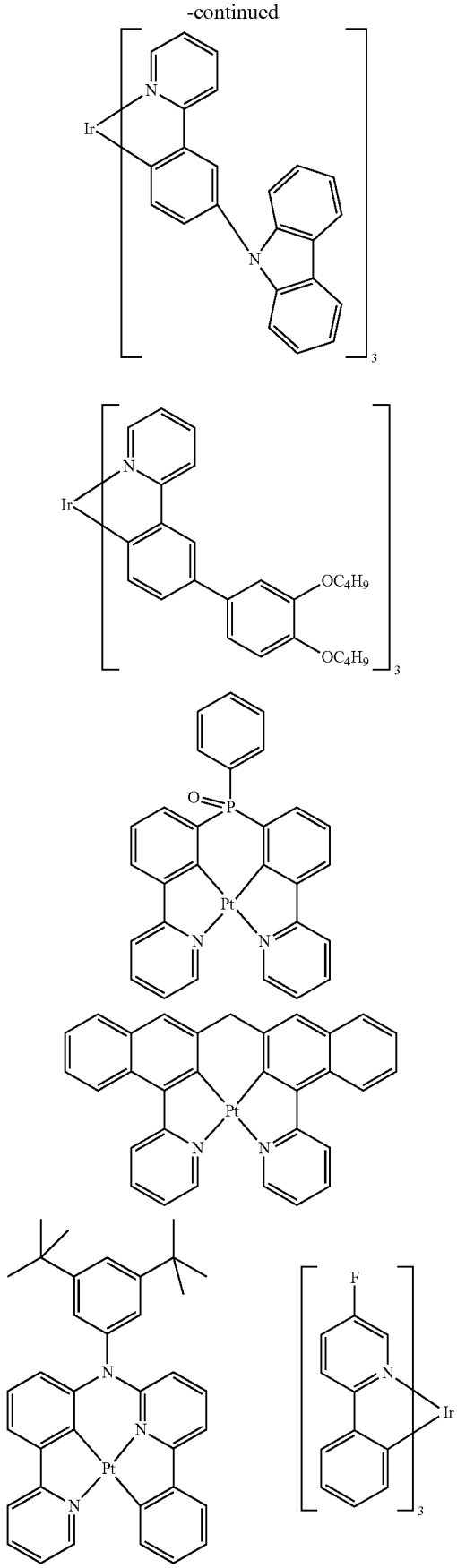

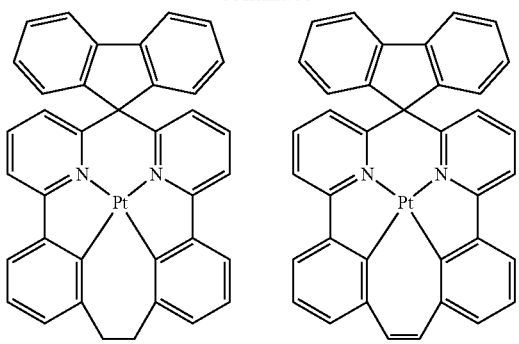
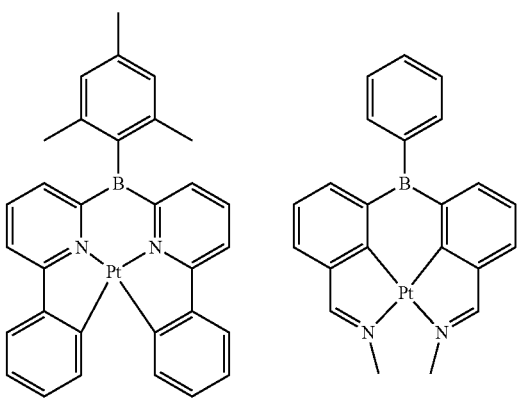
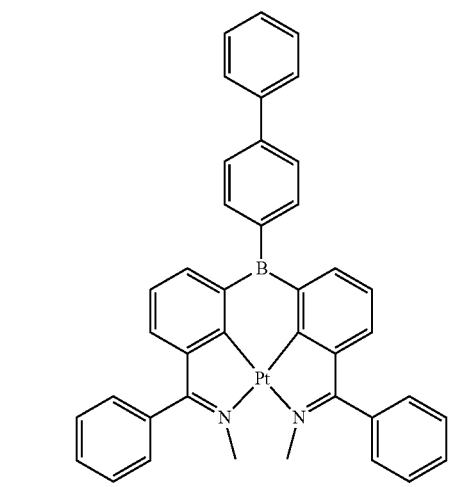
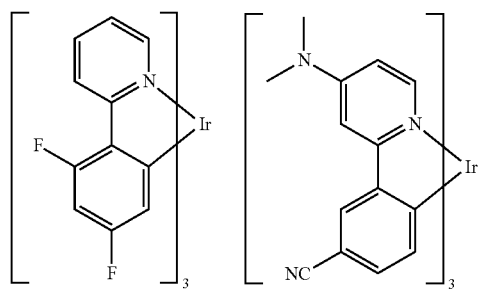
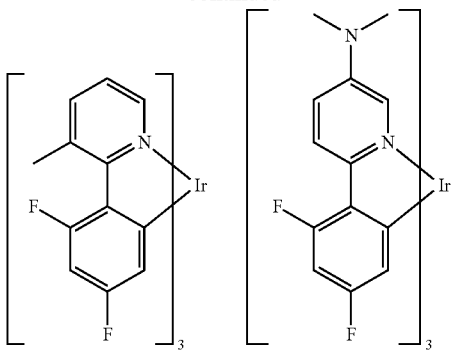
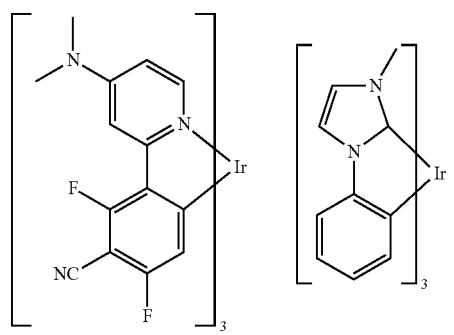
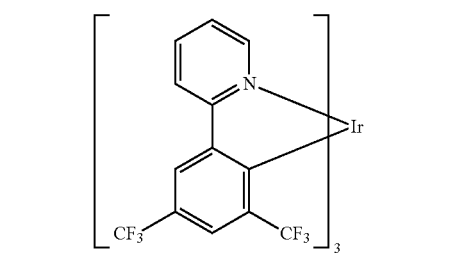
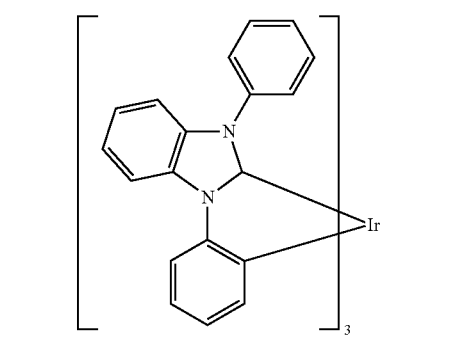
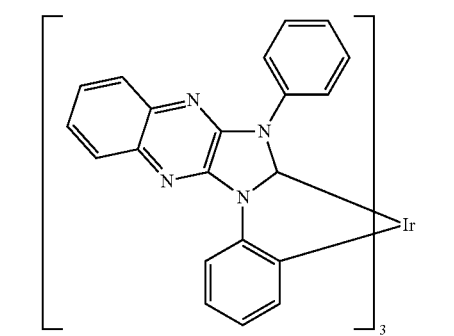

-continued
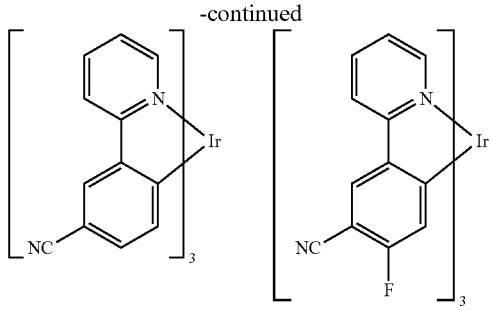
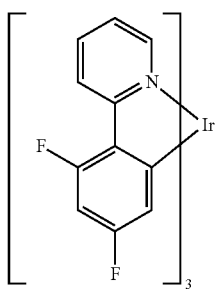
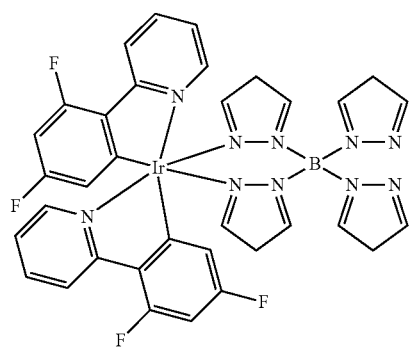
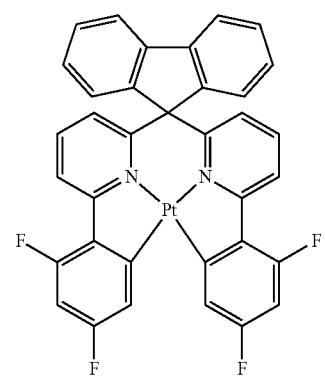
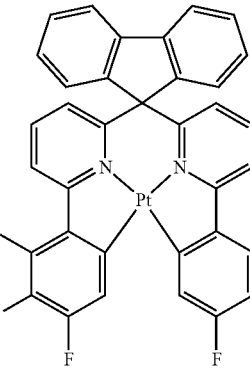
-continued
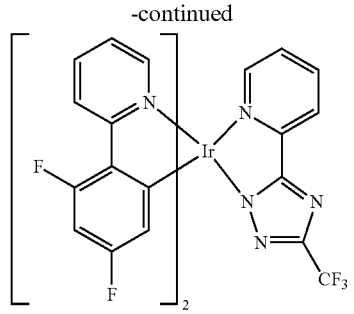
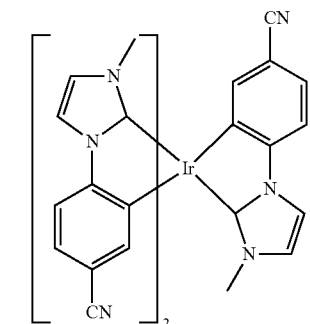
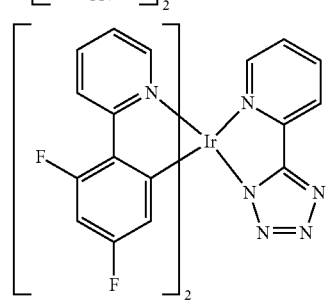
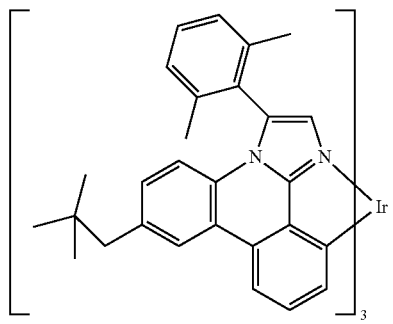
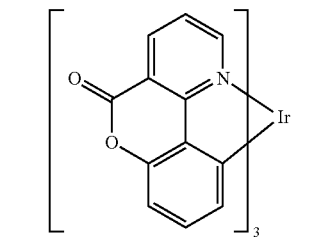
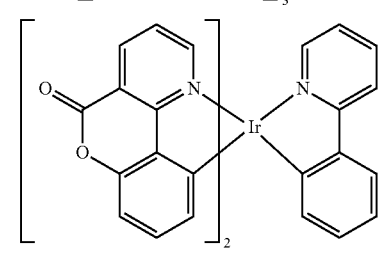

211
-continued
212
-continued
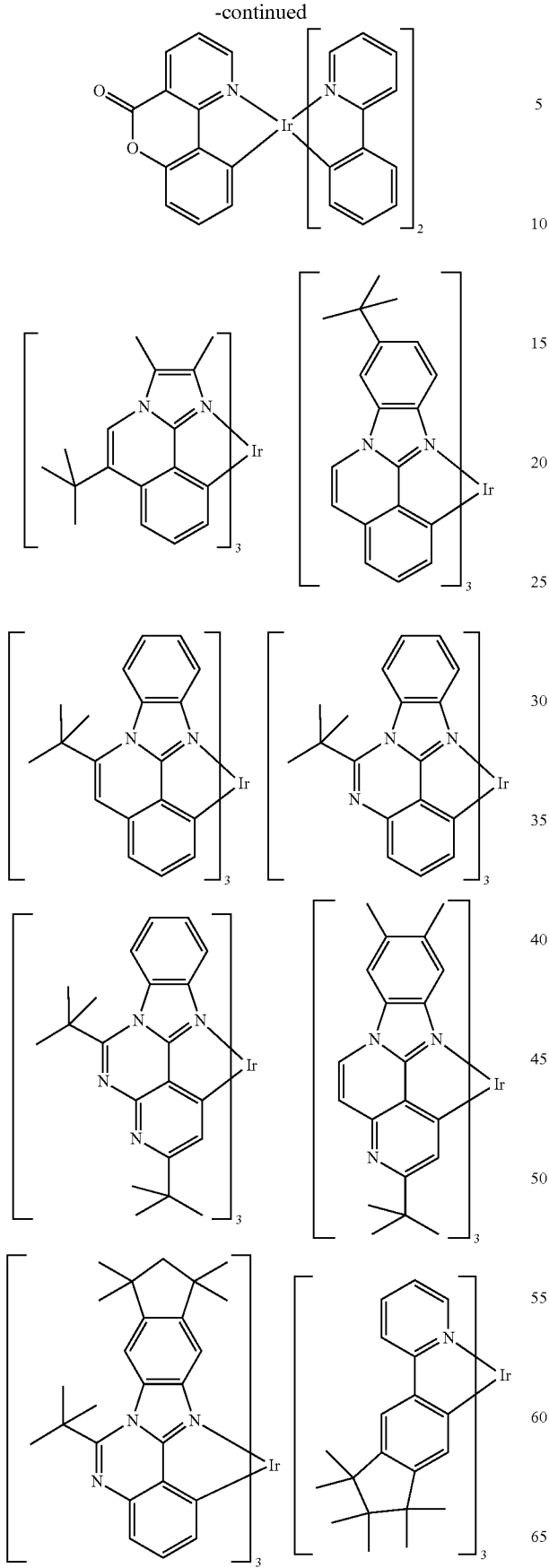
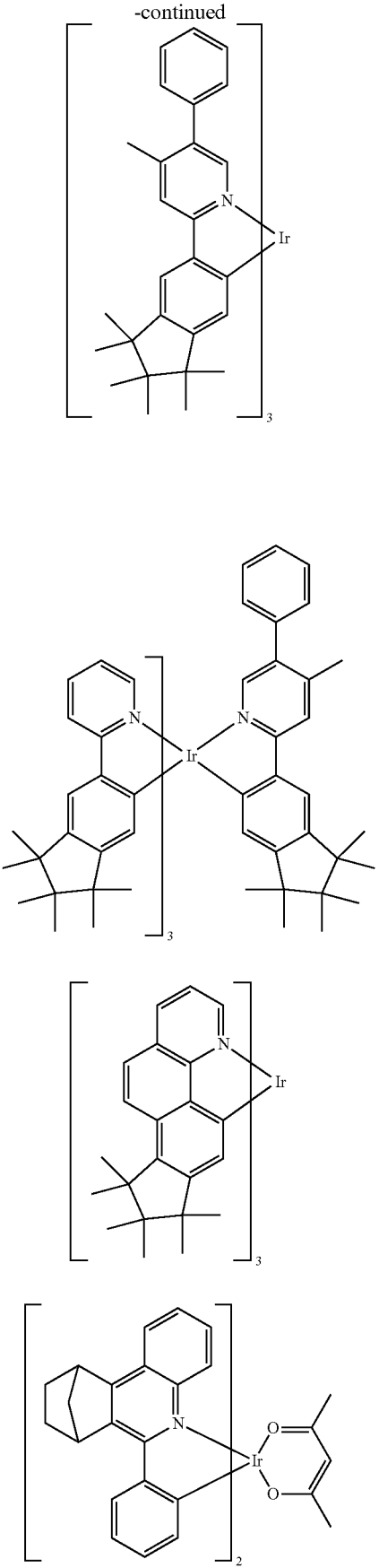

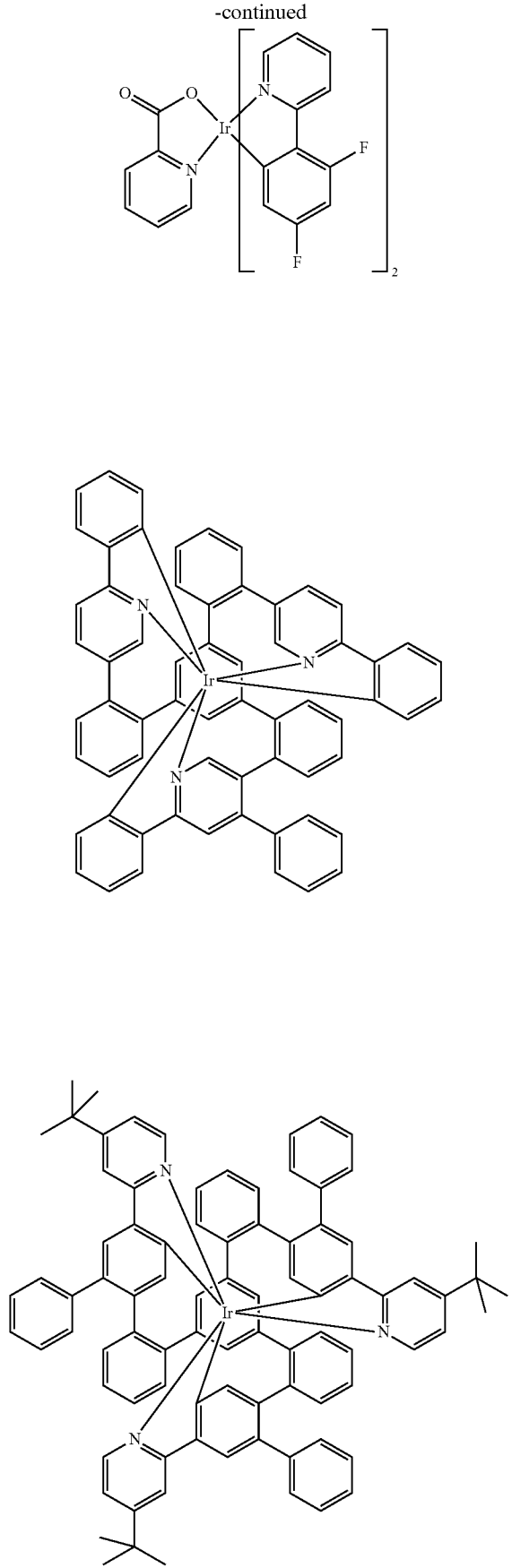

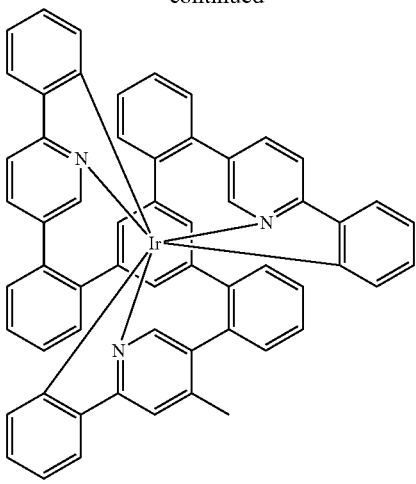

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthracenamines, aromatic anthracenediamines, aromatic pyrenamines, aromatic pyrenediamines, aromatic chrysenamines or aromatic chrysenediamines. An aromatic anthracenamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyrenamines, pyrenediamines, chrysenamines and chrysenediamines are defined analogously, where the diarylamino groups are bonded to the pyrene preferably in the 1-position or 1,6-positions. Further preferred emitting compounds are indenofluorenamines and -fluorenediamines, benzoindenofluorenamines and -fluorenediamines, dibenzoindenofluoreneamines and -diamines, and indenofluorene derivatives having fused aryl groups. Likewise preferred are pyrenearylamines. Likewise preferred are benzoindenofluorenamines, benzofluorenamines, extended benzoindenofluorenes, phenoxazines, and fluorene derivatives bonded to furan units or to thiophene units.

Useful matrix materials, preferably for fluorescent emitting compounds, include materials of various substance classes. Preferred matrix materials are selected from the classes of the oligoarylenes (e.g. 2,2',7,7'-tetraphenylspirobifluorene or dinaphthylanthracene), especially of oligoarylenes containing fused aromatic groups, oligoarylenevinylenes (e.g. DPVBi or spiro-DPVBi), polypodal metal complexes, hole-conducting compounds, electron-conducting compounds, especially ketones, phosphine oxides, and sulphoxides, and atropisomers, boronic acid derivatives or benzanthracenes. Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulphoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another.

Preferred matrix materials for phosphorescent emitting compounds are, as well as the compounds of the present application, aromatic ketones, aromatic phosphine oxides or aromatic sulphoxides or sulphones, triarylamines, carbazole derivatives, e.g. CBP (N,N-biscarbazolylbiphenyl) or carbazole derivatives, indolocarbazole derivatives, indenocarbazole derivatives, azacarbazole derivatives, bipolar matrix materials, silanes, azaboroles or boronic esters, triazine derivatives, zinc complexes, diazasilole or tetraazasilole derivatives, diazaphosphole derivatives, bridged carbazole derivatives, triphenylene derivatives, or lactams.

Suitable charge transport materials as usable in the hole injection or hole transport layer or electron blocking layer or in the electron transport layer of the electronic device of the invention are, other than the compounds of the present application, for example, the compounds disclosed in Y. Shirota et al., Chem. Rev. 2007, 107(4), 953-1010, or other materials as used in these layers according to the prior art.

Particularly preferable materials for use in a hole transporting layer in the OLED are shown below:

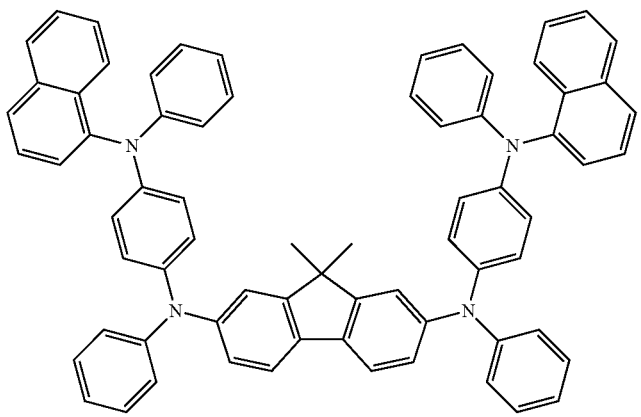

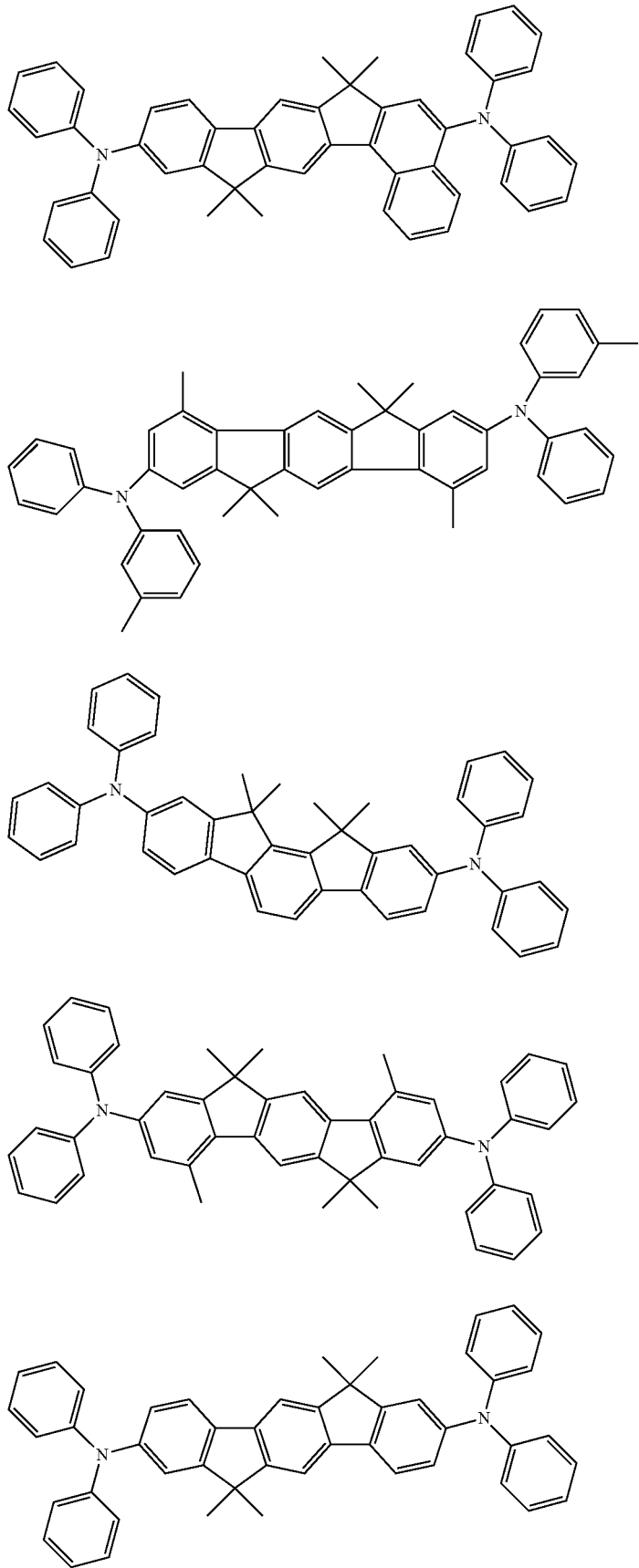

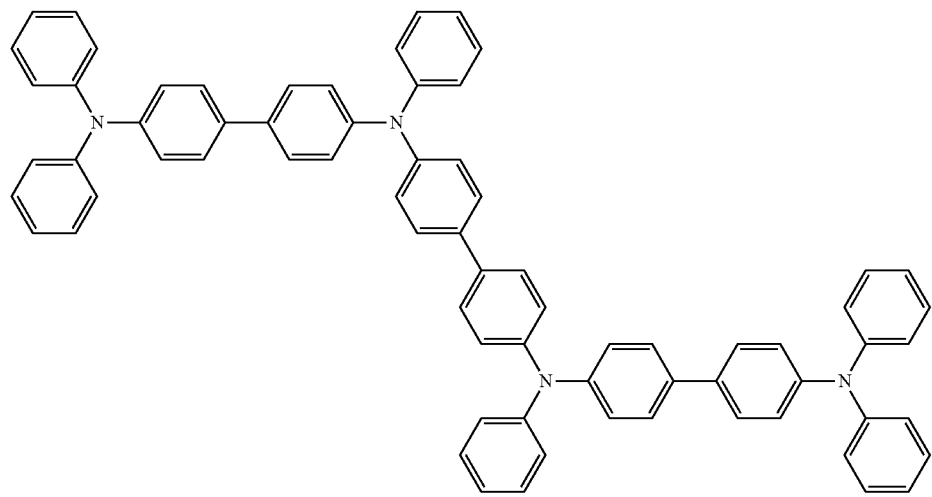
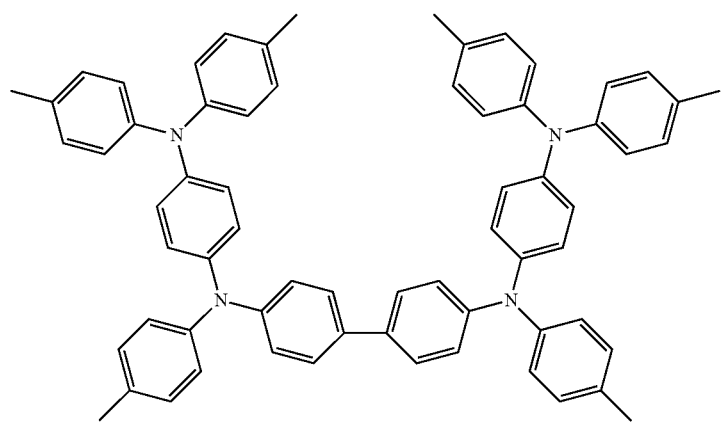
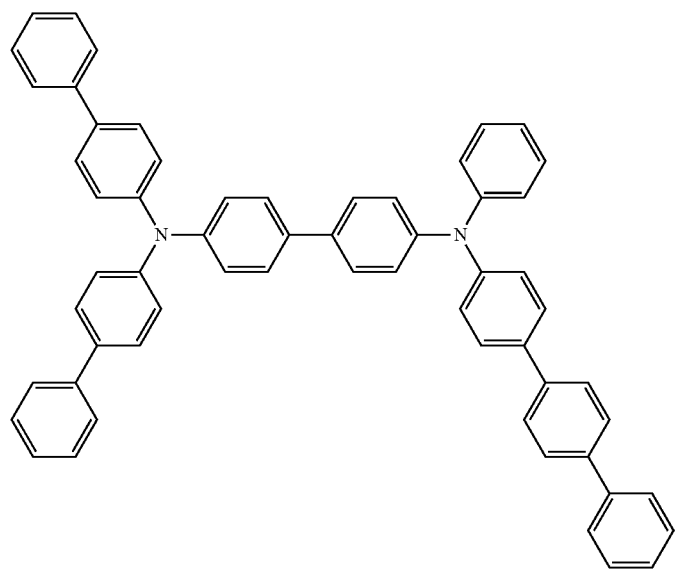

-continued
221 222
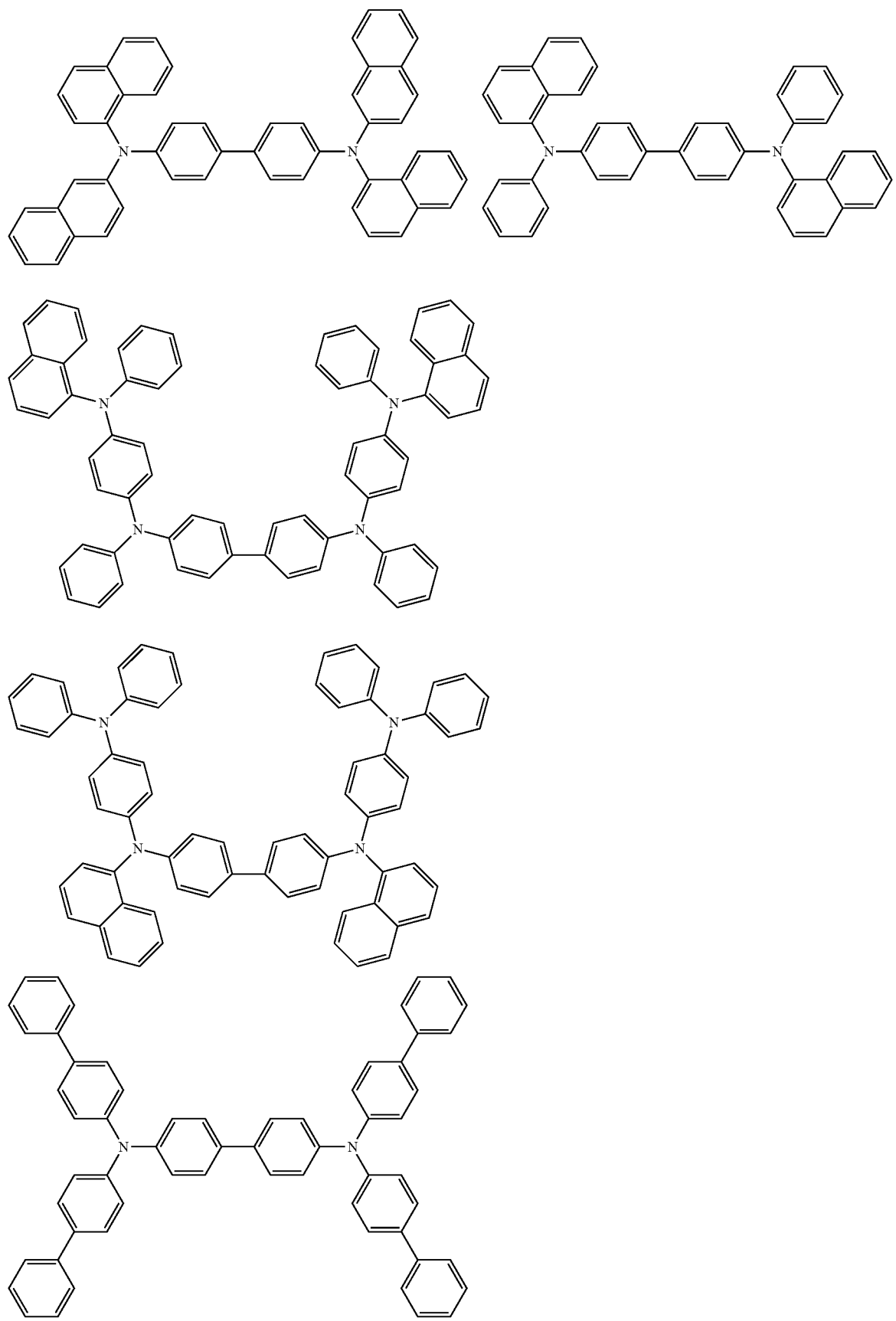

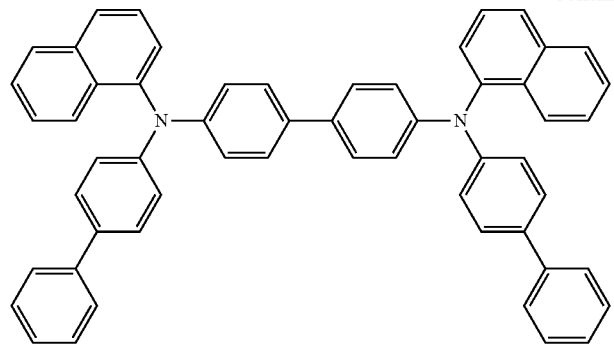
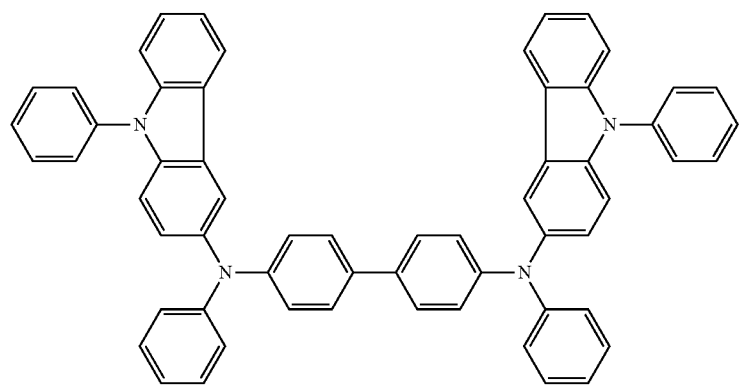
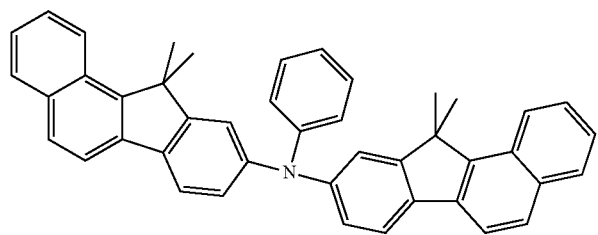
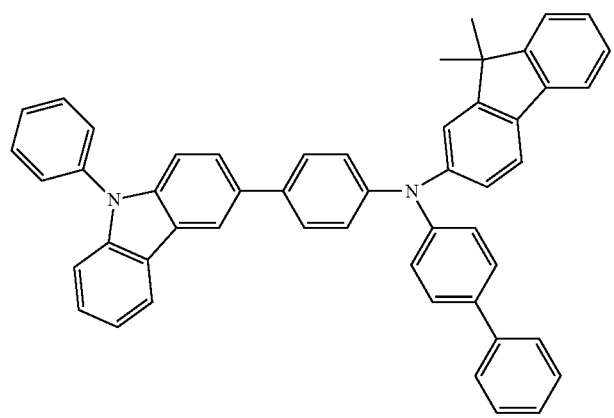

-continued

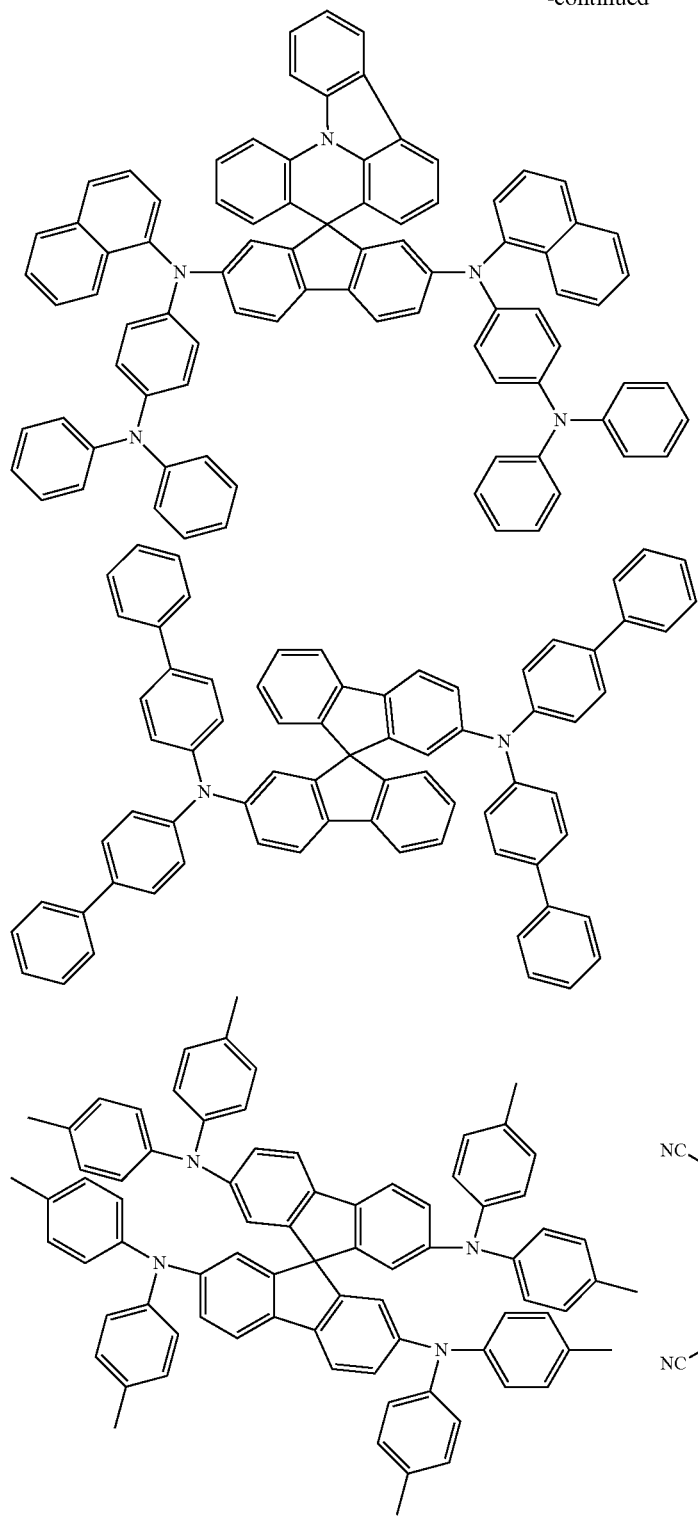

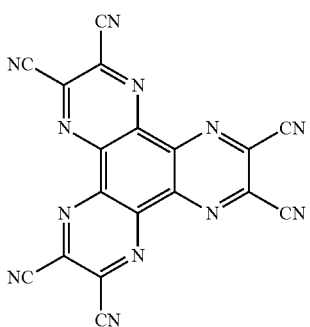

Preferably, the inventive OLED comprises two or more different hole-transporting layers. The compound of the formula (I), (II) or (III) may be used here in one or more of or in all the hole-transporting layers. In a preferred embodiment, the compound is used in exactly one or exactly two hole-transporting layers, and other compounds, preferably aromatic amine compounds, are used in the further hole-transporting layers present. Further compounds which are used alongside the compounds of the formula (I), (II) or (III), preferably in hole-transporting layers of the OLEDs of the invention, are especially indenofluorenamine derivatives, hexaazatriphenylene derivatives, amine derivatives with fused aromatics, monobenzoindenofluorenamines, dibenzoindenofluorenamines, spirobifluorenamines, fluorenamines, spirodibenzopyranamines, dihydroacridine derivatives, spirodibenzofurans and spirodibenzothiophenes, phenanthrenediarylamines, spirotribenzotropolones, spirobifluorenes with meta-phenyldiamine groups, spirobisacridines, xanthenediarylamines, and 9,10-dihydroanthracene spiro compounds with diarylamino groups.

Very particular preference is given to the use of spirobifluorenes substituted by diarylamino groups in the 4 position as hole-transporting compounds, and to the use of spirobifluorenes substituted by diarylamino groups in the 2 position as hole-transporting compounds.

Materials used for the electron transport layer may be any materials as used according to the prior art as electron transport materials in the electron transport layer. Especially suitable are aluminum complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives.

Particularly preferably electron transporting material for use in the OLEDs are shown below:

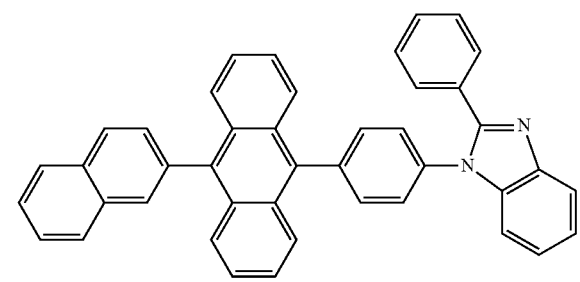

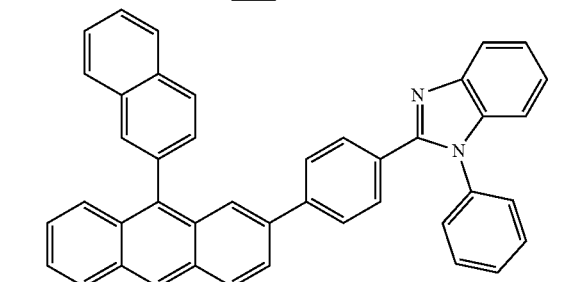

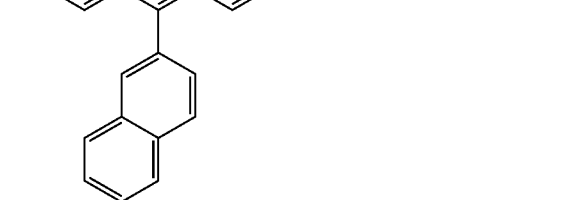

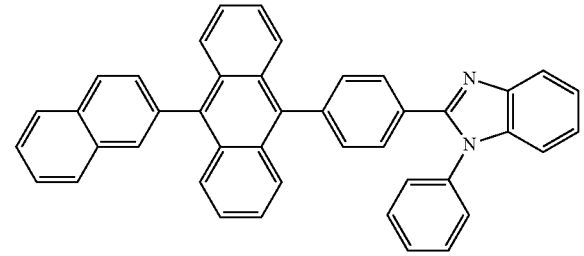

-continued

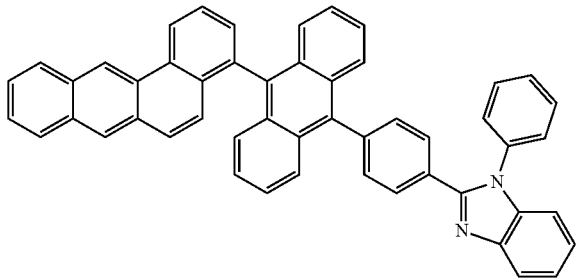

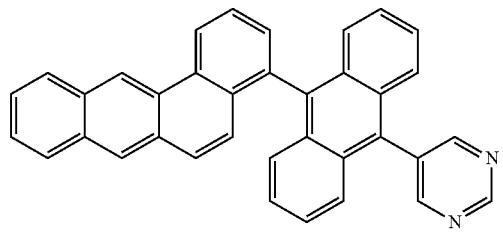

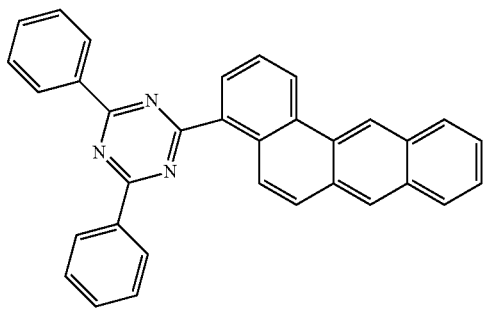

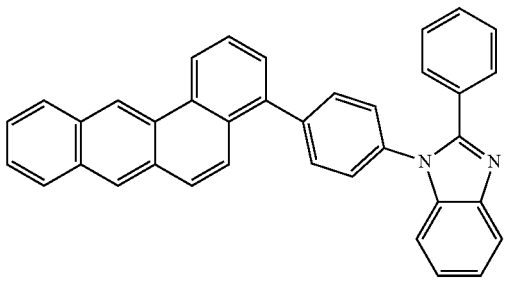

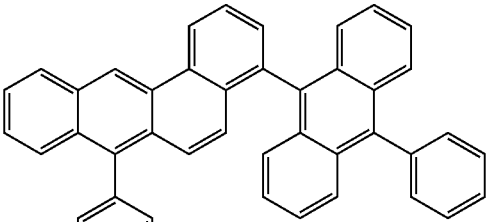

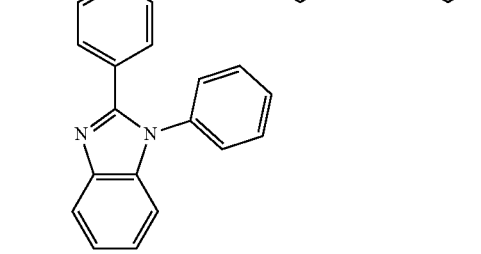

229
-continued
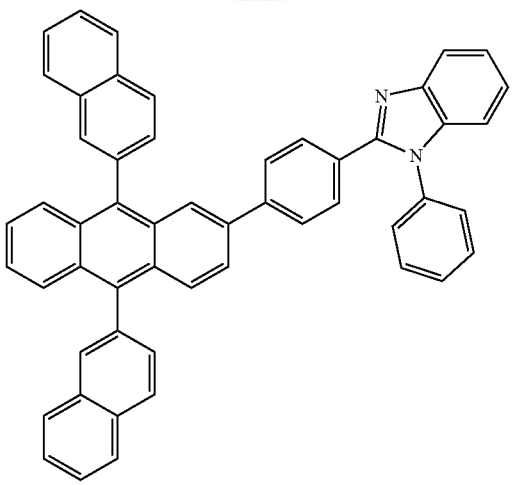
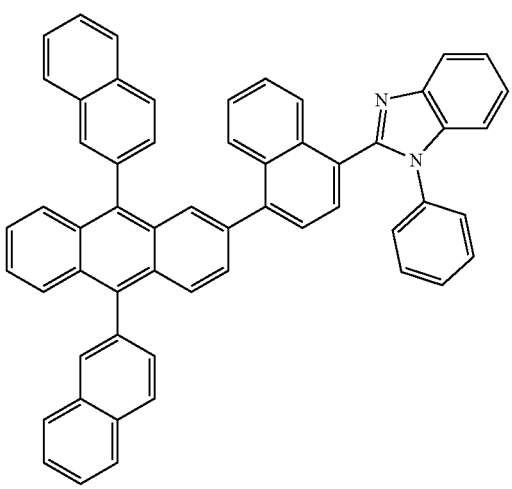
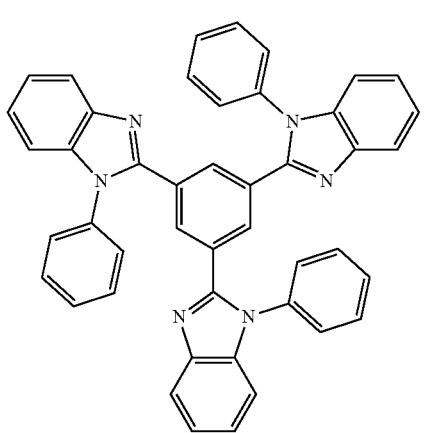
230
-continued
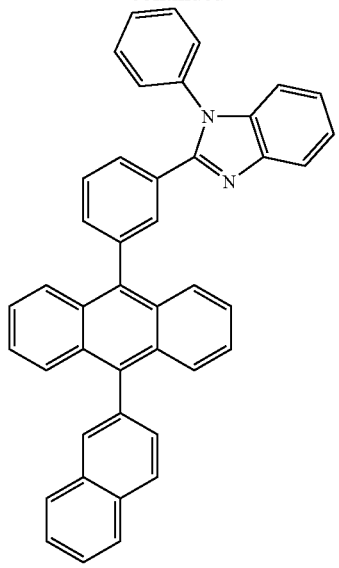
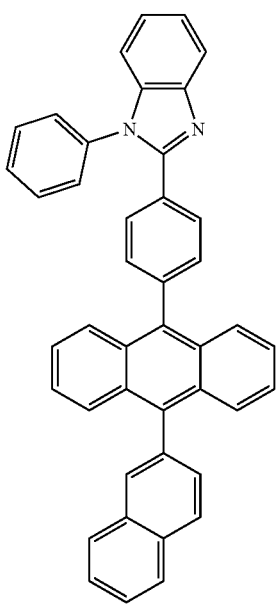
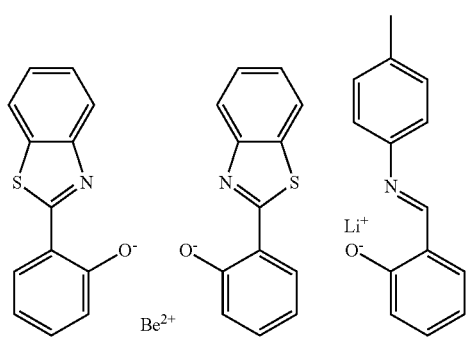

231
-continued
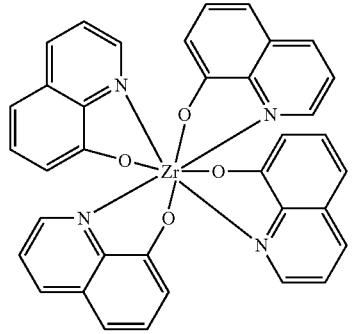
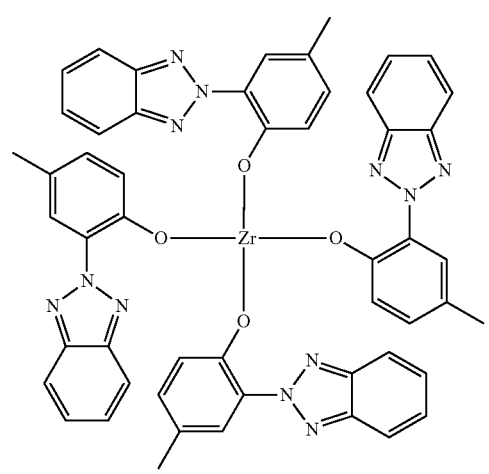
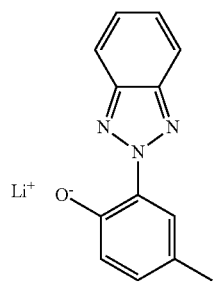
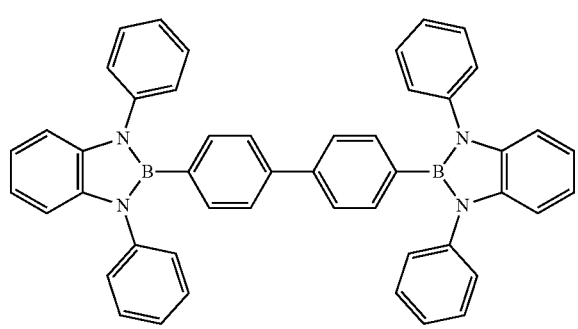
232
-continued
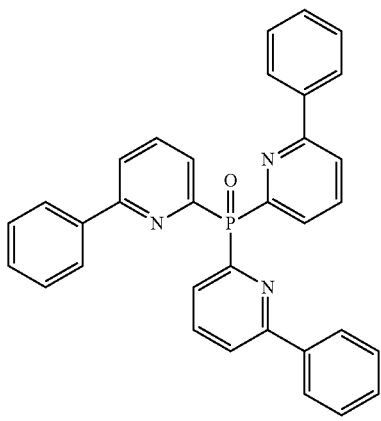
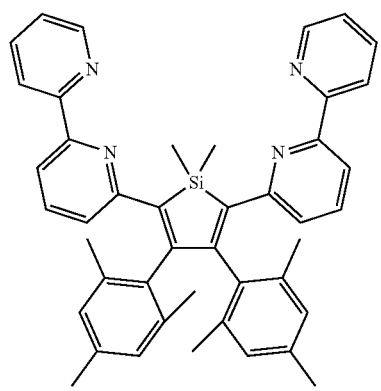
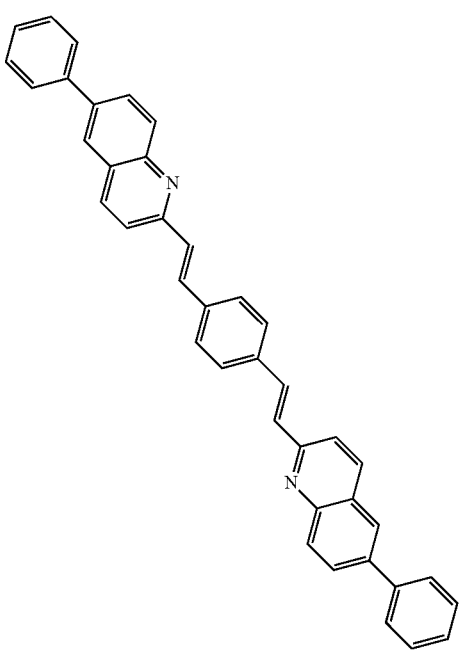

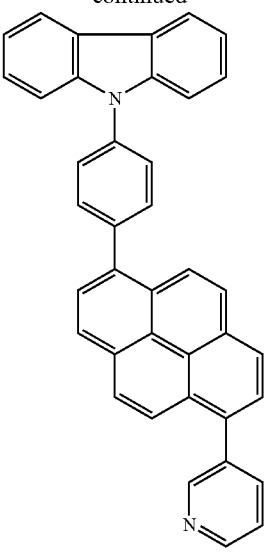

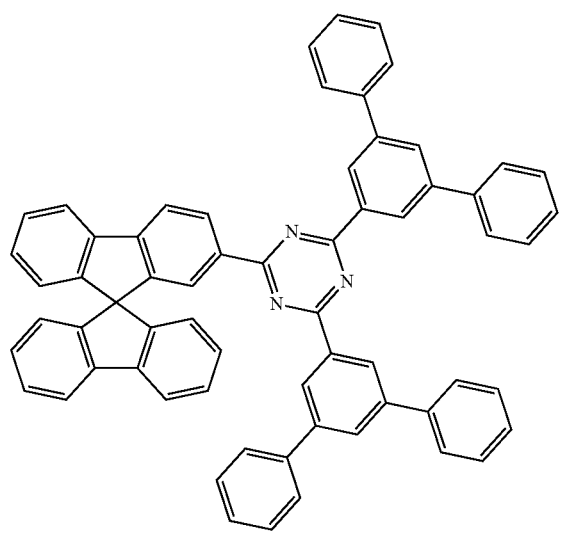

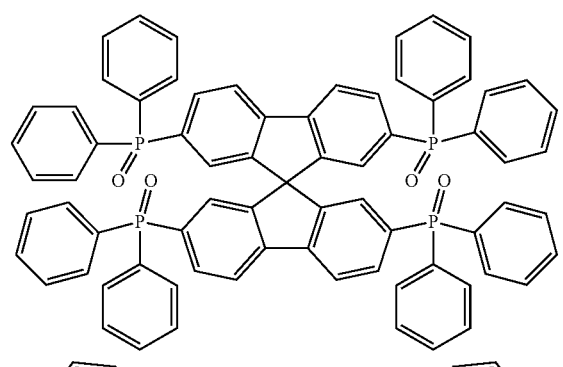

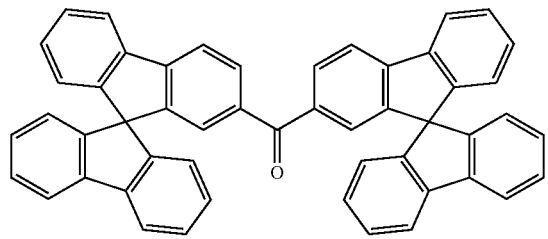

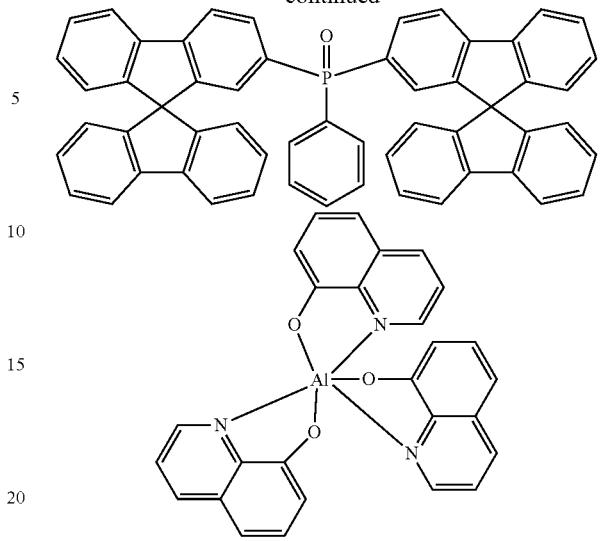

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable the irradiation of the organic material (organic solar cell) or the emission of light (OLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects by water and air.

In a preferred embodiment, the electronic device is characterized in that one or more layers are coated by a sublimation process. In this case, the materials are applied by vapour deposition in vacuum sublimation systems at an initial pressure of less than $10^{-5}$ mbar, preferably less than 10⁻⁶ mbar. In this case, however, it is also possible that the initial pressure is even lower, for example less than 10⁻⁷ mbar.

Preference is likewise given to an electronic device, characterized in that one or more layers are coated by the OVPD (organic vapour phase deposition)method or with the aid of a carrier gas sublimation. In this case, the materials are applied at a pressure between 10⁻⁵ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds are needed. High solubility can be achieved by suitable substitution of the compounds.

It is further preferable that an electronic device of the invention is produced by applying one or more layers from solution and one or more layers by a sublimation method.

According to the invention, the electronic devices comprising one or more compounds of formula (I), (II) or (III) can be used in displays, as light sources in lighting applications and as light sources in medical and/or cosmetic applications.

EXAMPLES

A) Synthesis Examples

All reactions are carried out under nitrogen and by using dried solvents unless stated otherwise.

a) 5-(4'-Bromo-[1,1'-biphenyl]-4-yl)-5H-benzo[d]benzo[4,5]imidazo[1,2-a]imidazole (1a)

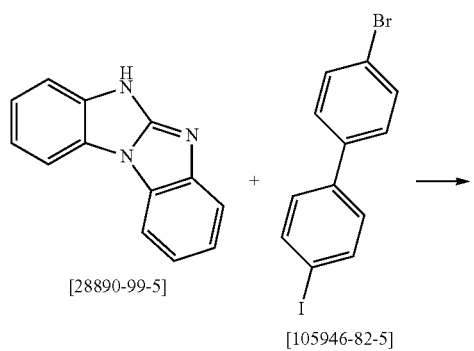

5H-Benzo[d]benzo[4,5]imidazo[1,2-a]imidazole (10.0 g, 48.3 mmol), 4-bromo-4'-iodo-1,1'-biphenyl (17.3 g, 48.3 mmol), K₃PO₄ (30.7 g, 145 mmol) and copper(I) iodide (1.84 g, 9.65 mmol) are suspended in 1,4-dioxane (600 ml) under argon. The mixture is degassed and heated up to 100° C. while stirring. trans-1,2-Diaminocyclohexane (60 ml) is added and stirring at 100° C. is continued for 24 h. Then, the reaction mixture is cooled to room temperature and 5% ammonia in water (500 ml) is added. The precipitate is filtered off. The solid is washed with 5% ammonia in water, pure water, methanol and heptane. The crude product is dried in vacuo and subsequently purified via silica column chromatography using ethyl acetate/dichloromethane as eluent. The product (7.40 g, 16.9 mmol, 35%) is obtained as solid material.

GC-MS (EI, 70 eV)=439/437 (100%, MH⁺), 359 (40%)

Synthesized accordingly are the following products using the respective starting materials (SM):

| Number | SM1 | SM2 | Product |
|---|---|---|---|
| 2a | [28890-99-5] | I—⟨⟩—Br [589-87-7] | [1401068-28-7] |

-continued

| Number | SM1 | SM2 | Product |
|---|---|---|---|
| 3a | [28890-99-5] | [583-55-1] | |
| 4a | [28890-99-5] | [130201-21-7] | |
| 5a | [28890-99-5] | [637-87-6] | [1352820-93-9] |
| 7a | [28890-99-5] | [591-18-4] | [1401068-22-1] |

-continued
| Number | SM1 | SM2 | Product |
|---|---|---|---|
| 8a | 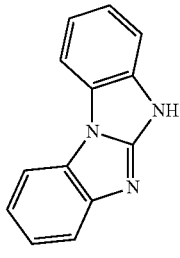 [28890-99-5] | 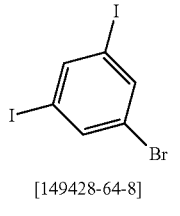 [149428-64-8] | 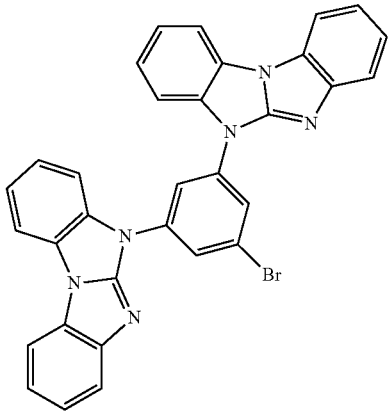 [SMILES: Brc1cc(-n2c3ccccc3n3c4ccccc4nc23)cc(-n2c3ccccc3n3c4ccccc4nc23)c1] |
| 9a | 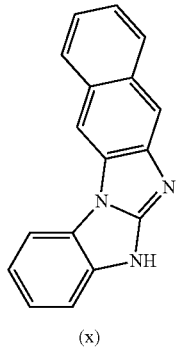 (x) | 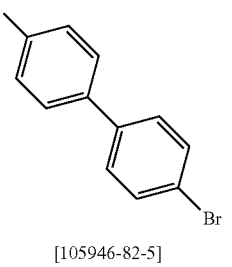 [105946-82-5] | 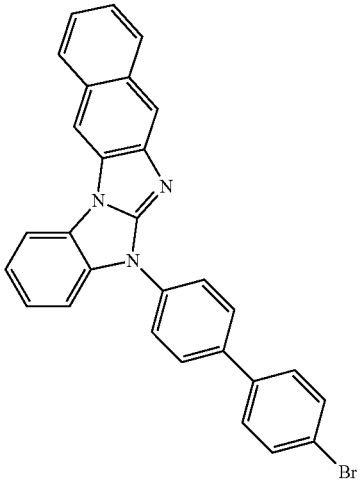 [SMILES: Brc1ccc(-c2ccc(-n3c4ccccc4n4c5cc6ccccc6cc5nc34)cc2)cc1] |

(x) Is synthesized in analogy to [28890-99-5], as described in WO17017096A1

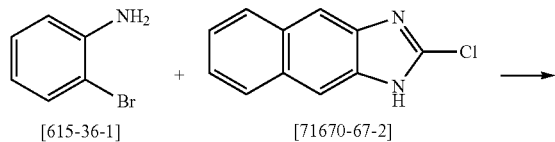

[615-36-1]     [71670-67-2]

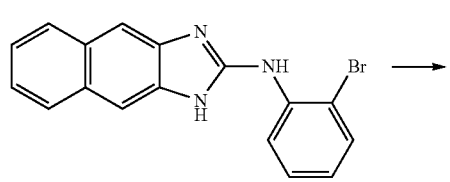

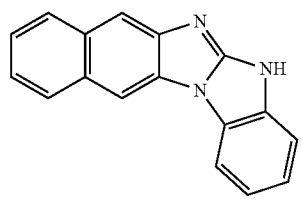

b) N,N-Di([1,1'-biphenyl]-4-yl)-4'-(5H-benzo[d]benzo[4,5]imidazo[1,2-a]imidazol-5-yl)[1,1'-biphenyl]-4-amine (1b)

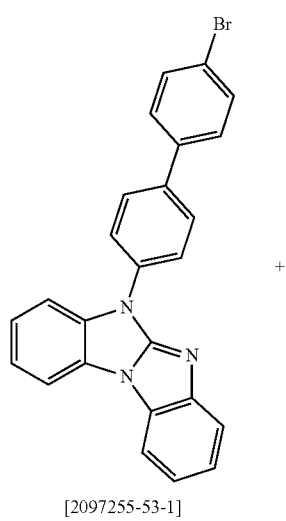

[2097255-53-1]

-continued

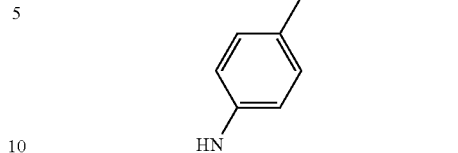

[102113-98-4]

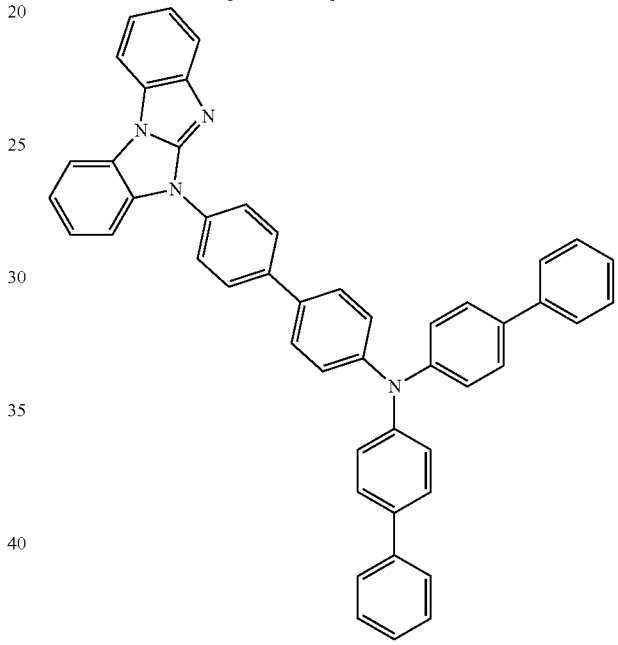

1b 5-(4'-Bromo-[1,1'-biphenyl]-4-yl)-5H-benzo[d]benzo[4,5]imidazo[1,2-a]imidazole (7.40 g, 16.9 mmol), N,N-bis(p-biphenyl)amine (5.16 g, 16.0 mmol) and sodium tert-butoxide (2.34 g, 25.3 mmol) are suspended in toluene (400 ml) under argon. The mixture is degassed. S-Phos (0.21 g, 0.51 mmol) and Pd(OAc)$_2$ (0.08 g, 0.34 mmol) are added and the mixture is stirred under reflux overnight. The reaction mixture is cooled to room temperature and is poured into aqueous solution of N-acetyl-cysteine (3%, 600 ml). After stirring the mixture vigorously for 45 min the precipitate is filtered off and is washed with water, methanol and heptane. The crude product is purified by soxhlet extraction with xylene and subsequent recrystallization from 1,4-dioxane. It is dried in vacuo and the product (8.50 g, 12.5 mmol, 74%) is obtained as white solid. The material is further purified via sublimation.

APCI-MS, m/z=679 [MH+]

Synthesized accordingly are the following products using the respective starting materials (SM):

| No. | SM1 | SM2 | Product |
|---|---|---|---|
| 2b | [2097255-53-1] | [944151-83-1] | |
| 3b | [2097255-53-1] | [955959-89-4] | |
| 4b | [1401068-28-7] | [897671-69-1] | |
| 5b | | [897671-69-1] | |

-continued

| No. | SM1 | SM2 | Product |
|---|---|---|---|
| 6b | | [102113-98-4] | |
| 7b | | [1258514-95-2] | |
| 8b | | [1933454-47-7] | |
| 9b | (y1) | [102113-98-4] | |

| No. | SM1 | SM2 | Product |
|---|---|---|---|
| 10b | (y2) | [897671-69-1] | |
| 11b | [1401068-22-1] | (y3) | |
| 12b | [2097255-53-1] | [1002762-60-8] | |

-continued

| No. | SM1 | SM2 | Product |
| --- | --- | --- | --- |
| 13b | | [102113-98-4] | |
| 14b | | [102113-98-4] | |
| 15b | [1401068-22-1] | [18628-07-4] | |

-continued
| No. | SM1 | SM2 | Product |
|---|---|---|---|
| 16b | [2097255-53-1] | [897671-69-1] | |
(y1) Is synthesized according to the following scheme:
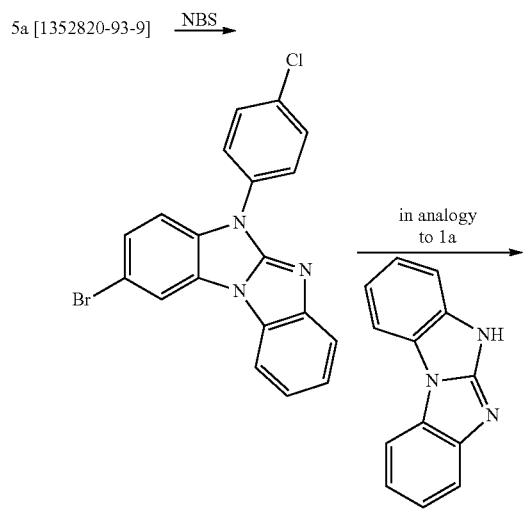
(y2) Is synthesized according to the following scheme:
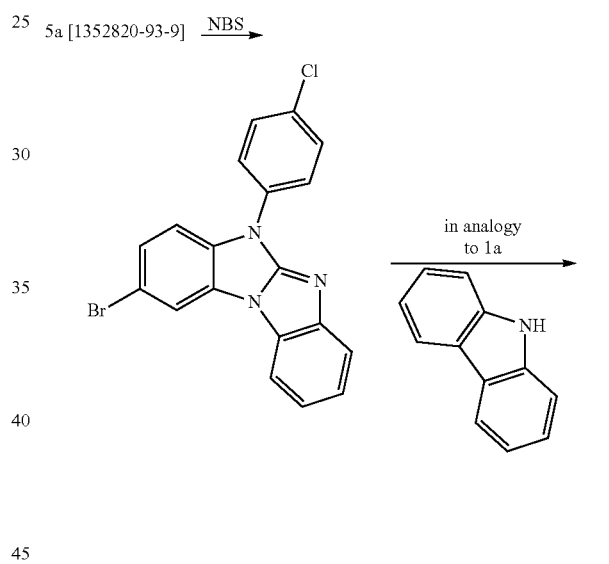
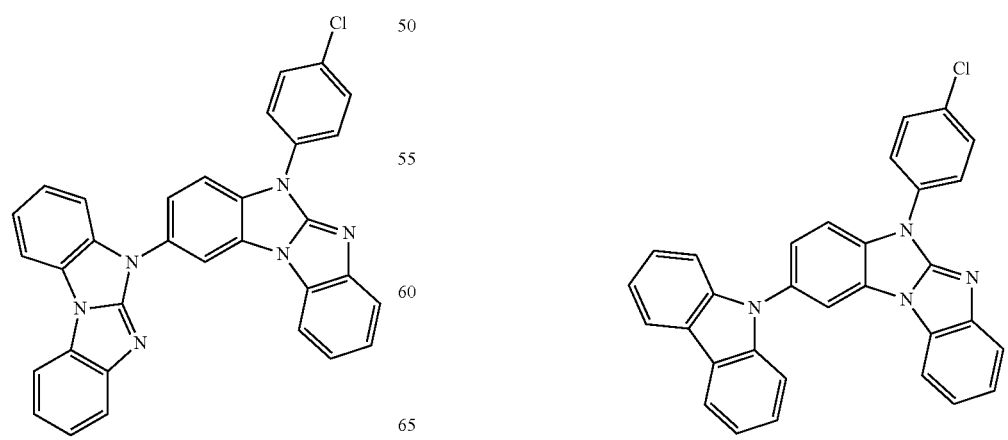

(y3) Is synthesized according to the following scheme using standard Buchwald-Hartwig conditions:

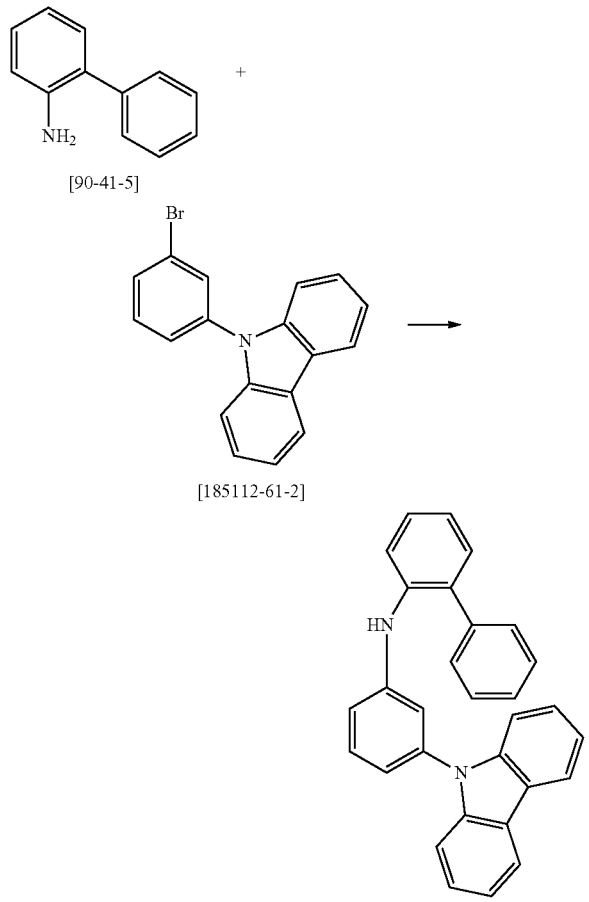

B) Device Examples

Phosphorescent green emitting OLEDs comprising HTM-1 to HTM-8, which are compounds according to this application, are prepared.

The OLEDs have the following stack structure (layer thickness in brackets):

Anode/HIM:F4TCNQ (5%) (20 nm)/HIM (180 nm)/HTM-x (10 nm)/TMM-1:TMM-2 (28%):TEG (12%) (30 nm)/ETM:LiQ (50%) (30 nm)/LiQ (1 nm)/cathode.

The anode consists of a glass plate coated with a 50 nm layer of structured ITO. The cathode is made of a 100 nm thick layer of Al. The chemical structures of the compounds which are present in the different layers are shown in Table 1. HTM-x stands for one of the compounds HTM-1 to HTM-8. The materials are deposited by thermal vapor deposition in a vacuum chamber. If two materials are present in a layer, the percentage given above is the proportion of the second material in percent by volume.

The OLEDs are characterised by standard methods. For this purpose, the electroluminescence spectra and the external quantum efficiency (EQE, measured in percent) as a function of the luminous density, calculated from current/voltage/luminous density characteristic lines (UIL characteristic lines) assuming Lambert emission characteristics and the lifetime are determined. The expression EQE @ 10 mA/cm$^2$ denotes the external quantum efficiency at an operating current density of 10 mA/cm$^2$. LT80 @ 40 mA/cm2 is the lifetime until the OLED has dropped from its initial luminance of i.e. 5000 cd/m2 to 80% of the initial intensity, i.e. to 4000 cd/m2 without using any acceleration factor.

HTM-1 features an EQE @ 10 mA/cm$^2$ of 16.7% and a LT80 @ 40 mA/cm$^2$ of 260 h (OLED 1). Bright green luminescence occurs.

HTM-3 features an EQE @ 10 mA/cm$^2$ of 16.0% and a LT80 @ 40 mA/cm$^2$ of 270 h (OLED 2). Bright green luminescence occurs.

HTM-8 features an EQE @ 10 mA/cm$^2$ of 16.6% and a LT80 @ 40 mA/cm$^2$ of 300 h (OLED 3). Bright green luminescence occurs.

TABLE 1

Materials used

TABLE 1-continued
Materials used
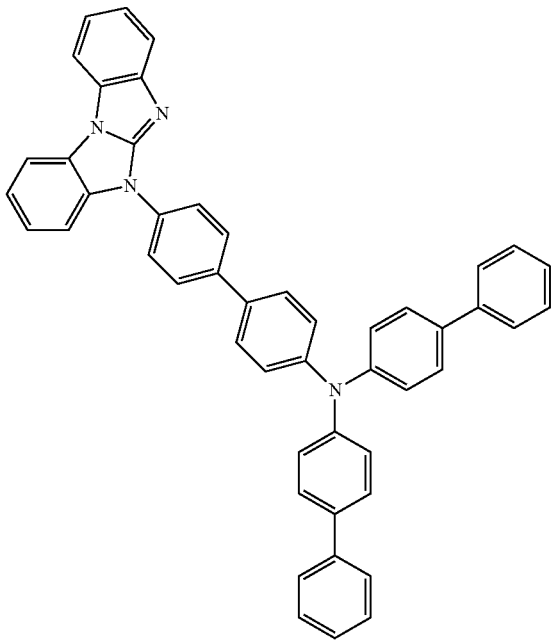 [SMILES: c1ccc(-c2ccc(N(c3ccc(-c4ccccc4)cc3)c3ccc(-c4ccc(-n5c6ccccc6n6c7ccccc7nc56)cc4)cc3)cc2)cc1]
HTM-1
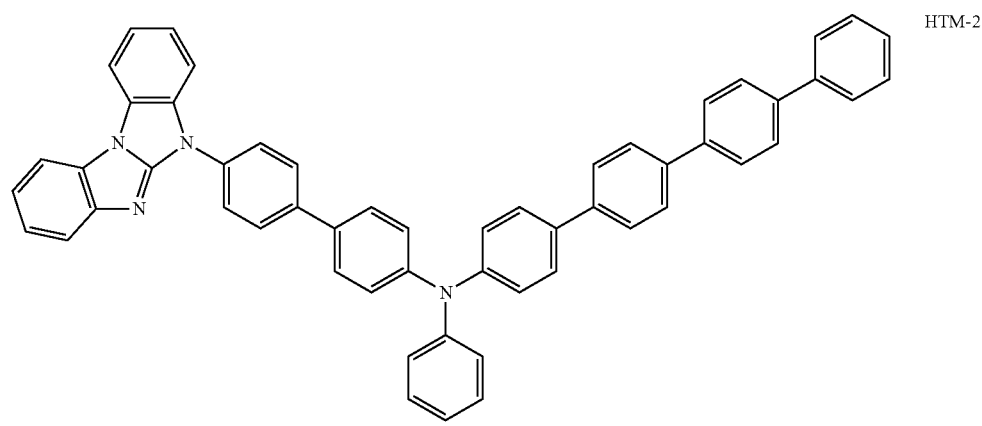
HTM-2

TABLE 1-continued
Materials used
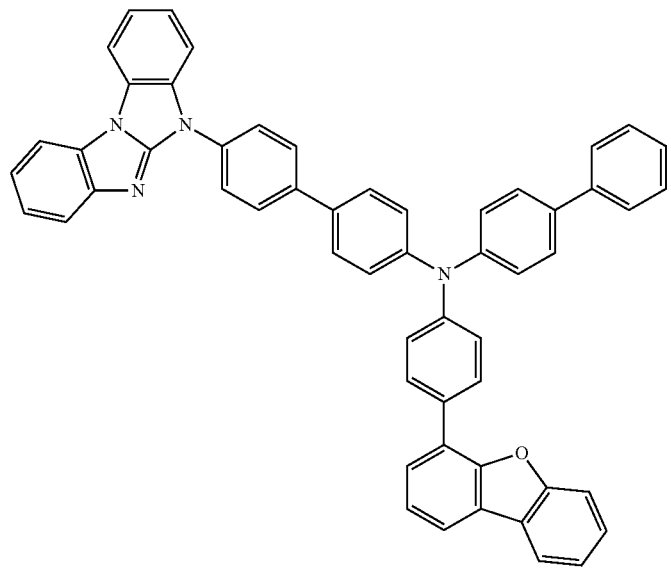 [SMILES: c1ccc(-c2ccc(N(c3ccc(-c4ccc(-n5c6ccccc6n6c7ccccc7nc56)cc4)cc3)c3ccc(-c4cccc5c4oc4ccccc45)cc3)cc2)cc1]
HTM-3
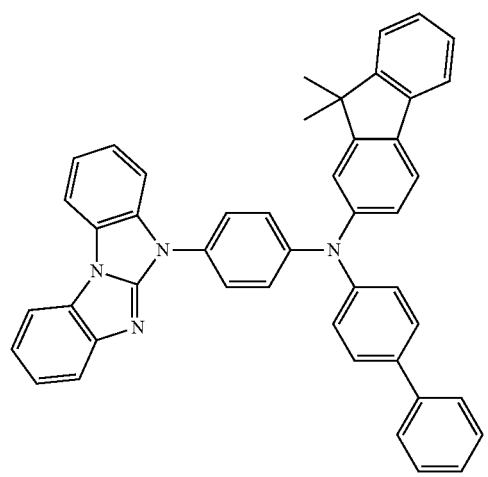 [SMILES: CC1(C)c2ccccc2-c2ccc(N(c3ccc(-c4ccccc4)cc3)c3ccc(-n4c5ccccc5n5c6ccccc6nc45)cc3)cc21]
HTM-4
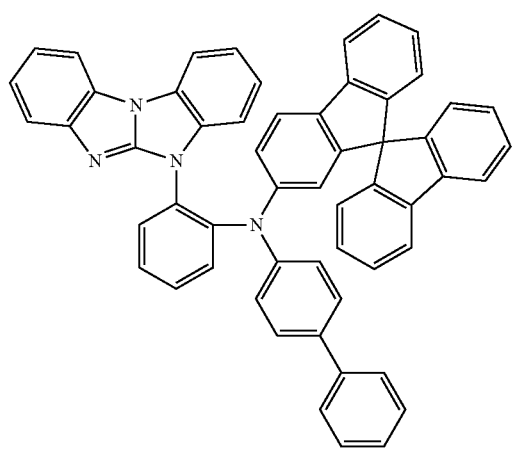 [SMILES: c1ccc(-c2ccc(N(c3ccc4c(c3)C3(c5ccccc5-c5ccccc53)c3ccccc3-4)c3ccccc3-n3c4ccccc4n4c5ccccc5nc34)cc2)cc1]
HTM-5

TABLE 1-continued
Materials used
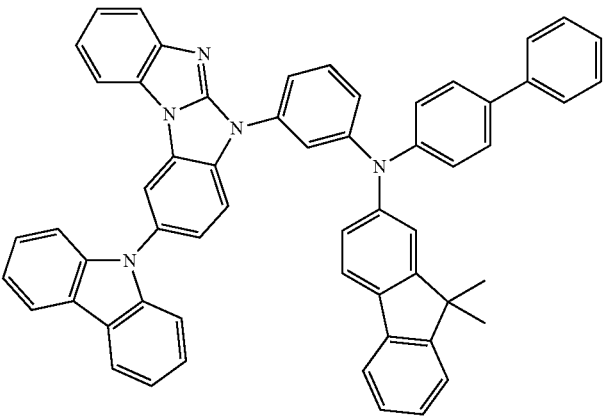 [SMILES: CC1(C)c2ccccc2-c2ccc(N(c3ccc(-c4ccccc4)cc3)c3cccc(-n4c5ccc(-n6c7ccccc7c7ccccc76)cc5n5c6ccccc6nc45)c3)cc21]
HTM-6
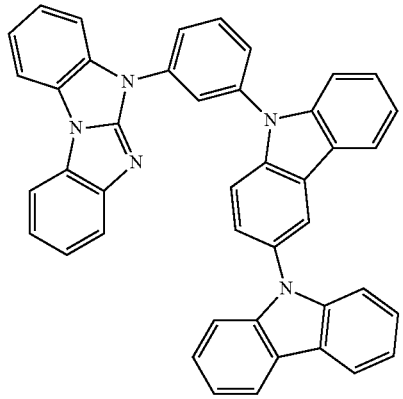 [SMILES: c1cc(-n2c3ccccc3c3cc(-n4c5ccccc5c5ccccc54)ccc32)cc(-n2c3ccccc3n3c4ccccc4nc23)c1]
HTM-7
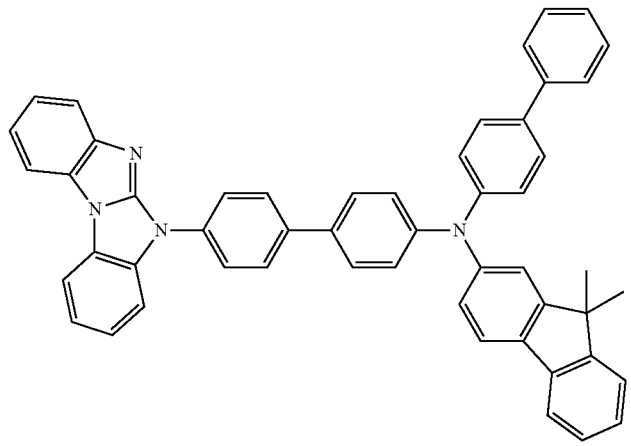 [SMILES: CC1(C)c2ccccc2-c2ccc(N(c3ccc(-c4ccccc4)cc3)c3ccc(-c4ccc(-n5c6ccccc6n6c7ccccc7nc56)cc4)cc3)cc21]
HTM-8
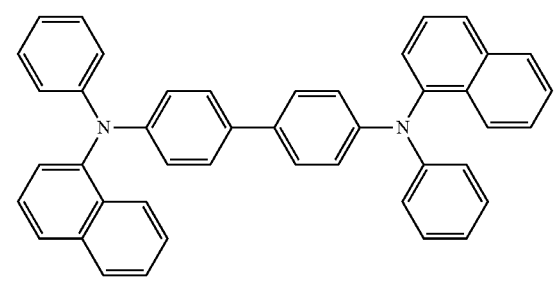 [SMILES: c1ccc(N(c2ccc(-c3ccc(N(c4ccccc4)c4cccc5ccccc45)cc3)cc2)c2cccc3ccccc23)cc1]
NPB TABLE 1-continued
Materials used
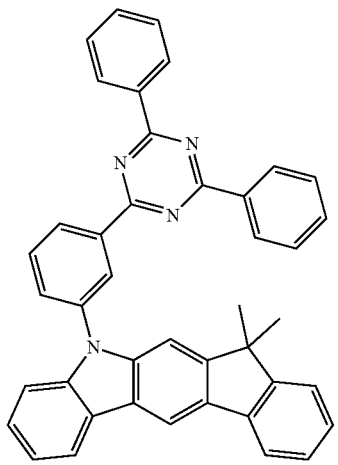 [SMILES: CC1(C)c2ccccc2-c2cc3c4ccccc4n(-c4cccc(-c5nc(-c6ccccc6)nc(-c6ccccc6)n5)c4)c3cc21]
TMM-1
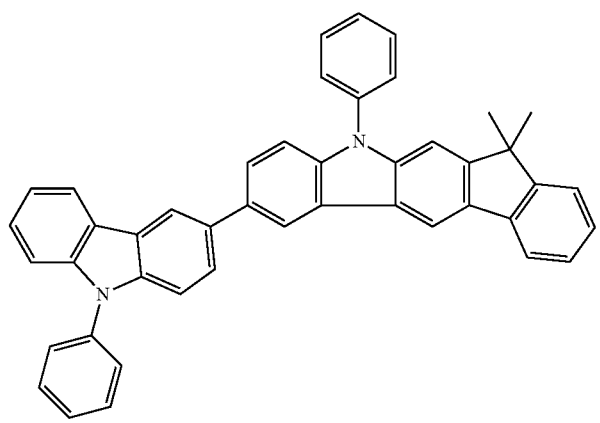 [SMILES: CC1(C)c2ccccc2-c2cc3c4cc(-c5ccc6c(c5)c5ccccc5n6-c5ccccc5)ccc4n(-c4ccccc4)c3cc21]
TMM-2
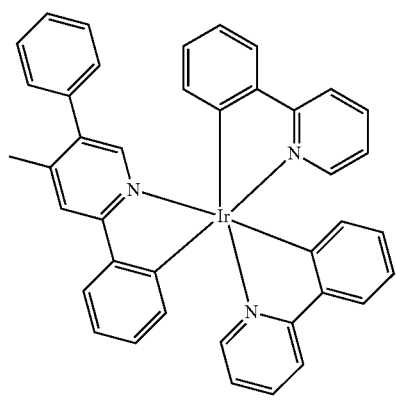
TEG TABLE 1-continued Materials used ETM (structure shown)

LIQ (structure shown)

Comparison of Performance with Compound NPB:

For OLEDs which comprise one of the compounds HTM1 to HTM8 instead of the compound NPB in the hole transporting layer of the OLED described above, an improved performance occurs, as shown in the following table:

| OLED No. | Compound of hole transporting layer | Performance |
|---|---|---|
| 1 | HTM-1 | + |
| 2 | HTM-3 | + |
| 3 | HTM-8 | + |
| 4 | HTM-2 | + |
| 5 | HTM-4 | + |
| 6 | HTM-5 | + |
| 7 | HTM-6 | + |
| 8 | HTM-7 | + |

+: Improved performance compared to NPB used in hole transporting layer

The OLEDs which contain one of compounds HTM-1 to HTM-8 according to this invention in the HTL show bright green luminescence.

The invention claimed is:

1. A compound according to formula (I) (II) or (III)

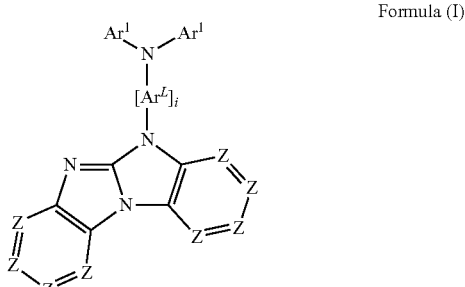

Formula (I)

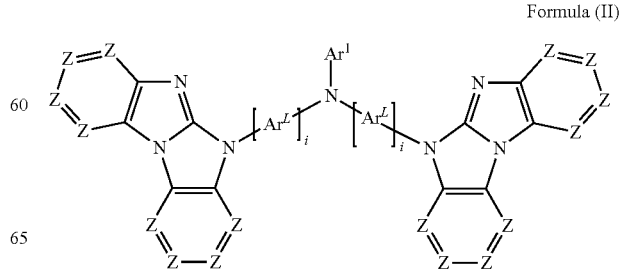

Formula (II)

-continued

Formula (III)

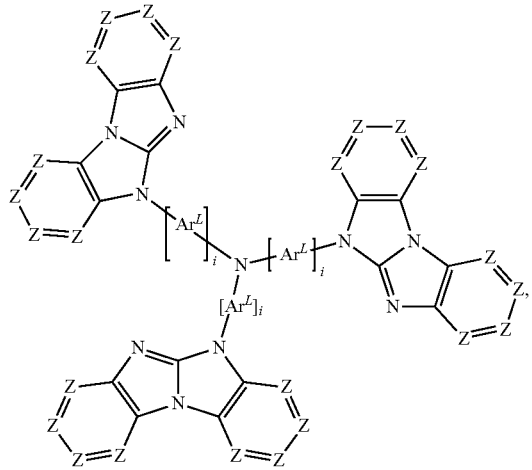

where the following applies to the variables occurring:

Z is on each occurrence, identically or differently, $CR^1$ or N;

$Ar^L$ is selected, identical or differently from benzene, biphenyl, terphenyl, and fluorene, where each of the above-mentioned groups may be substituted by one or more radicals $R^2$;

$Ar^1$ is on each occurrence, identically or differently, selected from aromatic ring systems having 6 to 40 aromatic ring atoms, which may be substituted by one or more radicals $R^3$, and heteroaromatic ring systems having 5 to 40 aromatic ring atoms, which may be substituted by one or more radicals $R^3$;

$R^1$, $R^2$, $R^3$ is selected, identically or differently at each occurrence, from H, D, F, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^1$, $R^2$ and/or $R^3$ may be connected to each other to form a ring; where the said alkyl, alkoxy, alkenyl and alkynyl groups and the said aromatic and heteroaromatic ring systems may in each case be substituted by one or more radicals $R^4$, and where one or more $CH_2$ groups in the said alkyl, alkoxy, alkenyl and alkynyl groups may in each case be replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, SO or $SO_2$;

with the proviso that in formula (I), a maximum of one group $R^3$ is $N(R^4)_2$;

$R^4$ is selected, identically or differently at each occurrence, from H, D, F, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^4$ may be connected to each other to form a ring; where the said alkyl, alkoxy, alkenyl and alkynyl groups and the said aromatic and heteroaromatic ring systems may in each case be substituted by one or more radicals $R^5$, and where one or more $CH_2$ groups in the said alkyl, alkoxy, alkenyl and alkynyl groups may in each case be replaced by $-R^5C=CR^5-$, $-C\equiv C-$, $Si(R^5)_2$, $C=O$, $C=NR^5$, $-C(=O)O-$, $-C(=O)NR^5$, $NR^5$, $P(=O)(R^5)$, $-O-$, $-S-$, SO or $SO_2$;

$R^5$ is selected, identically or differently at each occurrence, from H, D, F, CN, alkyl groups having 1 to 20 C atoms, aromatic ring systems having 6 to 40 C atoms, or heteroaromatic ring systems having 5 to 40 aromatic ring atoms; where two or more radicals $R^5$ may be connected to each other to form a ring; and where the said alkyl groups, aromatic ring systems and heteroaromatic ring systems may be substituted by one or more radicals selected from F and CN;

i is, identically or differently on each occurrence, 1, 2, 3, 4 or 5.

2. The compound according to claim 1, wherein the compound conforms to formula (I) and that it does not have $C_3$-symmetry.

3. The compound according to claim 1, wherein Z is $CR^1$.

4. The compound according to claim 1, wherein $Ar^1$ is, identically or differently, selected from phenyl, biphenyl, terphenyl, quaterphenyl, naphthyl, fluorenyl, especially 9,9'-dimethylfluorenyl and 9,9'-diphenylfluorenyl, benzofluorenyl, spirobifluorenyl, indenofluorenyl, dibenzofuranyl, dibenzothiophenyl, carbazolyl, benzofuranyl, benzothiophenyl, benzofused dibenzofuranyl, benzofused dibenzothiophenyl, naphthyl-substituted phenyl, fluorenyl-substituted phenyl, spirobifluorenyl-substituted phenyl, dibenzofuranyl-substituted phenyl, dibenzothiophenyl-substituted phenyl, carbazolyl-substituted phenyl, pyridyl-substituted phenyl, pyrimidyl-substituted phenyl, triazinyl-substituted phenyl, benzimidazole, and benzimidazobenzimidazole, each of which may optionally be substituted by one or more radicals $R^3$.

5. The compound according to claim 1, wherein $R^1$, $R^2$ and $R^3$ are selected, identically or differently at each occurrence, from H, D, F, CN, $Si(R^4)_3$, $N(R^4)_2$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems may in each case be substituted by one or more radicals $R^4$.

6. The compound according to claim 1, wherein $R^4$ is selected, identically or differently at each occurrence, from H, D, F, CN, $Si(R^5)_3$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where the said alkyl groups and the said aromatic and heteroaromatic ring systems may in each case be substituted by one or more radicals $R^5$.

7. The compound according to claim 1, wherein at least one group $R^1$ is selected from groups of the below formulae

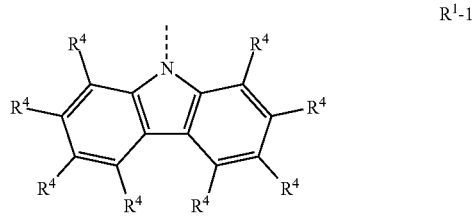

$R^1$-1

-continued

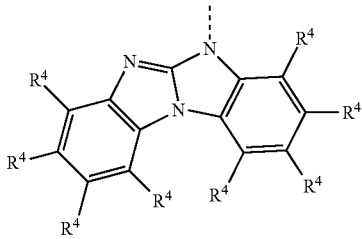
R¹-2 where the dotted bond is the bond connecting the group to the rest of formula (I).

8. The compound according to claim 1, wherein the compound conforms to one of the following Formulae

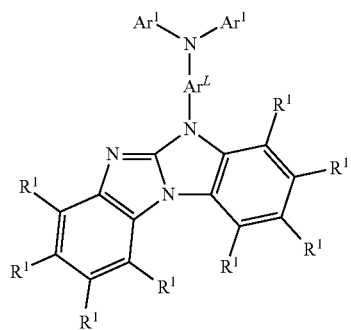
Formula (I-A)

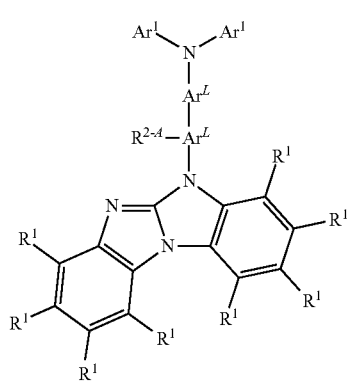
Formula (I-A-2)

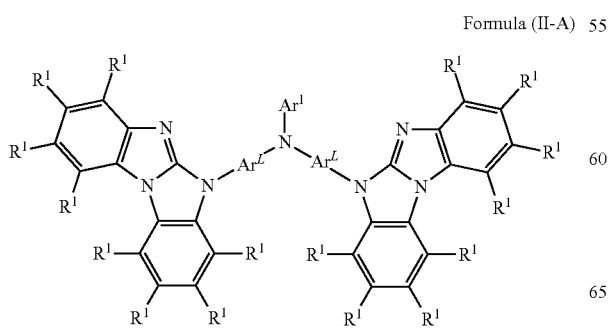
Formula (II-A)

-continued

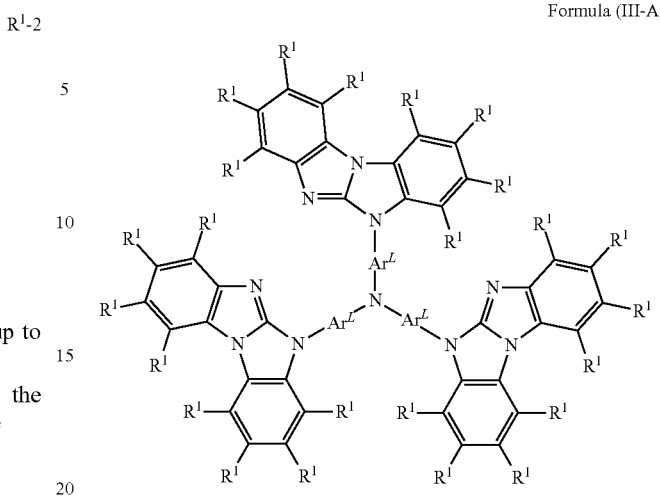
Formula (III-A)

where $R^{2-A}$ is a heteroaryl group having 5 to 20 aromatic ring atoms, which may be substituted by one or more radicals $R^4$.

9. The compound according to claim 1, wherein the compound comprises a maximum of one triarylamino group.

10. A process for preparation of the compound according to claim 1, which comprises reacting benzimidazobenzimidazole with an aromatic group having a reactive group, with a transition metal and base as reagents.

11. A formulation comprising at least one compound of formula (I), (II) or (III) according to claim 1 and at least one solvent.

12. An electronic device comprising at least one of the compounds according to claim 1.

13. An organic electroluminescent device, comprising an anode, a cathode and at least one organic layer, wherein the at least one organic layer is a hole transport layer, an electron blocking layer or a hole injection layer, comprising the at least one compound according to claim 1.

14. An oligomer, polymer or dendrimer, comprising one or more compounds of formula (I), (II) or (III) according to claim 1, where the bond(s) to the polymer, oligomer or dendrimer may be localized at any position in formula (I), (II) or (III) substituted by $R^1$, $R^2$ or $R^3$.

15. The compound according to claim 1, wherein the compound is according to formula (I).

16. The compound according to claim 1, wherein the compound is according to formula (II).

17. The compound according to claim 1, wherein the compound is according to formula (III).

18. An oligomer, polymer or dendrimer, comprising one or more compounds of formula (I), (II) or (III)

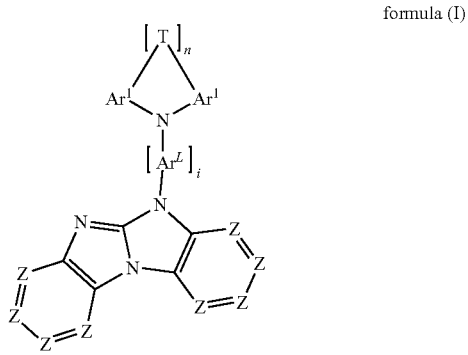
formula (I)

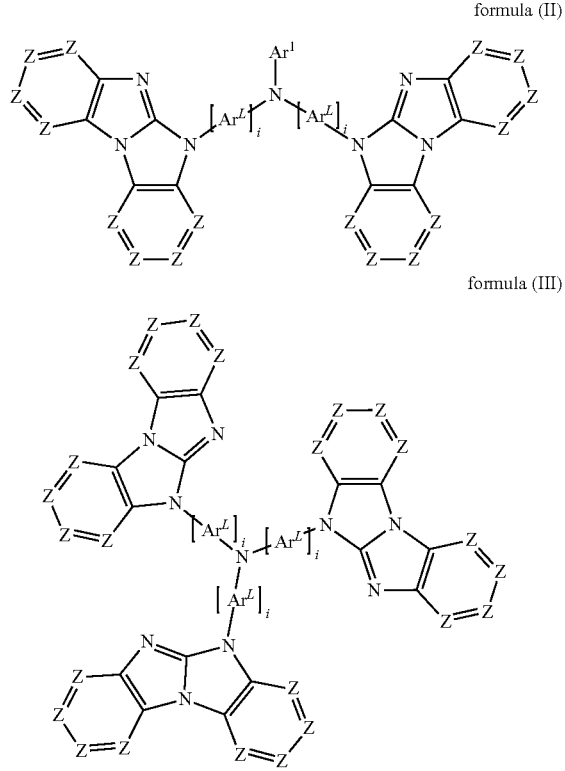

formula (II)

formula (III)

where the following applies to the variables occurring:

Z is on each occurrence, identically or differently, $CR^1$ or N;

$Ar^L$ is selected, identical or differently from benzene, biphenyl, terphenyl, naphthalene, fluorene, indenofluorene, spirobifluorene, triazine, benzoquinoline, benzoquinazole, dibenzofuran, dibenzothiophene, and carbazole, where each of the above-mentioned groups may be substituted by one or more radicals $R^2$, and where the case is excluded that $Ar^L$ is carbazole which is bonded via its N atom to the rest of formula (I);

$Ar^1$ is on each occurrence, identically or differently, selected from aromatic ring systems having 6 to 40 aromatic ring atoms, which may be substituted by one or more radicals $R^3$, and heteroaromatic ring systems having 5 to 40 aromatic ring atoms, which may be substituted by one or more radicals $R^3$;

T is a single bond;

$R^1$, $R^2$, $R^3$ is selected, identically or differently at each occurrence, from H, D, F, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^1$, $R^2$ and/or $R^3$ may be connected to each other to form a ring; where the said alkyl, alkoxy, alkenyl and alkynyl groups and the said aromatic and heteroaromatic ring systems may in each case be substituted by one or more radicals $R^4$, and where one or more $CH_2$ groups in the said alkyl, alkoxy, alkenyl and alkynyl groups may in each case be replaced by $—R^4C=CR^4—$, $—C≡C—$, $Si(R^4)_2$, $C=O$, $C=NR^4$, $—C(=O)O—$, $—C(=O)NR^4—$, $NR^4$, $P(=O)(R^4)$, $—O—$, $—S—$, SO or $SO_2$;

with the proviso that in formula (I), a maximum of one group $R^3$ is $N(R^4)_2$;

$R^4$ is selected, identically or differently at each occurrence, from H, D, F, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^4$ may be connected to each other to form a ring; where the said alkyl, alkoxy, alkenyl and alkynyl groups and the said aromatic and heteroaromatic ring systems may in each case be substituted by one or more radicals $R^5$, and where one or more $CH_2$ groups in the said alkyl, alkoxy, alkenyl and alkynyl groups may in each case be replaced by $—R^5C=CR^5—$, $—C≡C—$, $Si(R^5)_2$, $C=O$, $C=NR^5$, $—C(=O)O—$, $—C(=O)NR^5—$, $NR^5$, $P(=O)(R^5)$, $—O—$, $—S—$, SO or $SO_2$;

$R^5$ is selected, identically or differently at each occurrence, from H, D, F, CN, alkyl groups having 1 to 20 C atoms, aromatic ring systems having 6 to 40 C atoms, or heteroaromatic ring systems having 5 to 40 aromatic ring atoms; where two or more radicals $R^5$ may be connected to each other to form a ring; and where the said alkyl groups, aromatic ring systems and heteroaromatic ring systems may be substituted by one or more radicals selected from F and CN;

i is, identically or differently on each occurrence, 1, 2, 3, 4 or 5;

n is 0 or 1 and where the bond(s) to the polymer, oligomer or dendrimer may be localized at any position in formula (I), (II) or (III) substituted by $R^1$, $R^2$ or $R^3$.

19. A formulation comprising at least one polymer, oligomer or dendrimer according to claim 18 and at least one solvent.

20. An electronic device comprising at least one polymer, oligomer or dendrimer according to claim 18.

* * * * *